(12) United States Patent
Arrington et al.

(10) Patent No.: US 7,348,440 B2
(45) Date of Patent: Mar. 25, 2008

(54) MITOTIC KINESIN INHIBITORS

(75) Inventors: Kenneth L. Arrington, Philadelphia, PA (US); Paul J. Coleman, Wallingford, PA (US); Christopher D. Cox, Harleysville, PA (US); Mark E. Fraley, North Wales, PA (US); Robert M. Garbaccio, Lansdale, PA (US); George D. Hartman, Lansdale, PA (US); William F. Hoffman, Lansdale, PA (US); Edward S. Tasber, Norristown, PA (US)

(73) Assignee: Merck & Co., Inc., Rahway, NJ (US)

( * ) Notice: Subject to any disclaimer, the term of this patent is extended or adjusted under 35 U.S.C. 154(b) by 390 days.

(21) Appl. No.: 10/517,559

(22) PCT Filed: Jun. 12, 2003

(86) PCT No.: PCT/US03/18482

§ 371 (c)(1),
(2), (4) Date: Dec. 8, 2004

(87) PCT Pub. No.: WO03/105855

PCT Pub. Date: Dec. 24, 2003

(65) Prior Publication Data

US 2006/0105997 A1   May 18, 2006

Related U.S. Application Data

(60) Provisional application No. 60/458,318, filed on Mar. 28, 2003, provisional application No. 60/426,940, filed on Nov. 15, 2002, provisional application No. 60/403,830, filed on Aug. 15, 2002, provisional application No. 60/388,621, filed on Jun. 14, 2002.

(51) Int. Cl.
*C07D 207/00*    (2006.01)
*C07D 403/00*    (2006.01)
*C07D 213/00*    (2006.01)
*C07D 401/00*    (2006.01)
*C07D 271/00*    (2006.01)
*C07D 277/20*    (2006.01)
*C07D 261/06*    (2006.01)
*C07D 285/14*    (2006.01)
*C07D 249/08*    (2006.01)
*C07D 231/00*    (2006.01)
*A61K 31/535*    (2006.01)
*A61K 31/497*    (2006.01)
*A01N 43/40*    (2006.01)
*A01N 43/82*    (2006.01)
*A01N 43/80*    (2006.01)
*A01N 43/64*    (2006.01)
*A01N 43/56*    (2006.01)
*A01N 43/36*    (2006.01)

(52) U.S. Cl. ............. 548/538; 514/231.5; 514/252.13; 514/277; 514/326; 514/364; 514/372; 514/378; 514/383; 514/406; 514/423; 544/372; 546/1; 546/207; 548/125; 548/202; 548/247; 548/141; 548/266.6; 548/364.1; 548/530

(58) Field of Classification Search ................ None
See application file for complete search history.

(56) References Cited

U.S. PATENT DOCUMENTS

| | | |
|---|---|---|
| 3,644,414 A | 2/1972 | Helsey et al. |
| 6,057,342 A | 5/2000 | Fevig et al. |
| 6,440,686 B1 | 8/2002 | Sakowicz |
| 2005/0038074 A1* | 2/2005 | Coleman et al. ............ 514/326 |
| 2005/0043357 A1* | 2/2005 | Coleman et al. ............ 514/326 |
| 2006/0135594 A1* | 6/2006 | Fraley et al. ............... 514/422 |
| 2006/0234984 A1* | 10/2006 | Coleman et al. ............. 514/89 |
| 2006/0287302 A1* | 12/2006 | Coleman et al. .......... 514/227.5 |

FOREIGN PATENT DOCUMENTS

| | | |
|---|---|---|
| EP | 418 845 | 3/1991 |
| WO | WO 93/20099 | 10/1993 |
| WO | WO 98/06694 | 2/1998 |
| WO | WO 03/049527 | 6/2003 |
| WO | WO 03/106417 | 12/2003 |
| WO | WO 2004/037171 | 5/2004 |
| WO | WO 2005/019205 | 3/2005 |
| WO | WO 2005/019206 | 3/2005 |

OTHER PUBLICATIONS

Winn et al., AN:1997:568105, RN: 178607-80-2 (1 Page Only).*
Fraley et al., "Kinesin spindle protein (KSP) inhibitors. Part 2: The design, synthesis, and characterization of 2,4-diaryl-2,5-dihydropyrrole inhibitors of the mitotic kinesin KSP", Bioorganic &Medicinal Chemistry Letters, 16 (2006), 1775-1779.*
Cox et al., "Kinesin spindle protein (KSP) inhibitors. Part 1: The discovery of 3,5-diaryl-4,5-dihydropyrazoles as potent and selective inhibitors of the mitotic kinesin KSP", Bioorganic&Medicinal Chemistry Letter, 15 (2005), 2041-2045.*
Joule et al., "Heterocyclic Chemistry", 3rd edition, Chapman & Hall, p. 464 (1 Page Only).*

(Continued)

*Primary Examiner*—Rebecca Anderson
*Assistant Examiner*—Sun Jae Y Loewe
(74) *Attorney, Agent, or Firm*—Nicole M. Beeler; David A. Muthard

(57) ABSTRACT

The present invention relates to dihydropyrrole compounds that are useful for treating cellular proliferative diseases, for treating disorders associated with KSP kinesin activity, and for inhibiting KSP kinesin. The invention also related to compositions which comprise these compounds, and methods of using them to treat cancer in mammals.

13 Claims, No Drawings

OTHER PUBLICATIONS

N. Moss, et al., Journal of Medicinal Chemistry, vol. 36 (22), pp. 3005-3009 (1993).
C. Sonesson, et al., J. Org. Chem. 1996, vol. 61, p. 4756-4763.
N. Iwasawa, et al., J. Org. Chem. 1998, vol. 63, p. 3164-3165.
N. Iwasawa, et al., J. Org. Chem. 1997, vol. 62, p. 1918-1919.
R. Mison, et al., J. Chem. Research(S), 1989, 126-127.
O. Yebdri, et al., Bulletin De La Societe Chimique de France, 1983, p. 195-201.
A. Ranjon, Bulletin De La Societe Chimique de France, 1971, p. 2068-2072.
M. Bujard, et al., Tetrahedron Letters, vol. 40, 1999, p. 8785-8788.
M. Carpes, et al., Synlett, No. 7, 2000, p. 1037-1039.
A. Boukhari, et al., J. Cryst. Spect. Res., vol. 19, Iss. 3, 1989, p. 603-621.

* cited by examiner

SEQUENCE LISTING

<160> NUMBER OF SEQ ID NOS: 2

<210> SEQ ID NO 1
<211> LENGTH: 42
<212> TYPE: DNA

-continued

```
<213> ORGANISM: Artificial Sequence
<220> FEATURE:
<223> OTHER INFORMATION: Completely Synthetic Oligonucleotide

<400> SEQUENCE: 1
gcaacgatta atatggcgtc gcagccaaat tcgtctgcga ag                    42

<210> SEQ ID NO 2
<211> LENGTH: 60
<212> TYPE: DNA
<213> ORGANISM: Artificial Sequence
<220> FEATURE:
<223> OTHER INFORMATION: Completely Synthetic Oligonucleotide

<400> SEQUENCE: 2
gcaacgctcg agtcagtgat gatggtggtg atgctgattc acttcaggct tattcaatat    60
```

MITOTIC KINESIN INHIBITORS

PRIORITY CLAIM

This application is a §371 application of PCT/US03/18482 that was filed on Jun. 12, 2003, which claims priority from the U.S. Provisional Application Nos. 60/388,621, filed on Jun. 14, 2002; 60/403,830, filed on Aug. 15, 2002; 60/426,940, filed on Nov. 15, 2002; and 60/458,318, filed on Mar. 28, 2003; those provisional application which are now expired.

BACKGROUND OF THE INVENTION

This invention relates to dihydropyrrole derivatives that are inhibitors of mitotic kinesins, in particular the mitotic kinesin KSP, and are useful in the treatment of cellular proliferative diseases, for example cancer, hyperplasias, restenosis, cardiac hypertrophy, immune disorders and inflammation.

Among the therapeutic agents used to treat cancer are the taxanes and vinca alkaloids. Taxanes and vinca alkaloids act on microtubules, which are present in a variety of cellular structures. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426], and a fragment of the KSP gene (TRIP5) has been described [Lee, et al., Mol Endocrinol., 9:243-54 (1995); GenBank accession number L40372]. *Xenopus* KSP homologs (Eg5), as well as *Drosophila* K-LP61 F/KRP 130 have been reported.

Certain quinazolinones have recently been described as being inhibitors of KSP (PCT Publ. WO 01/30768, May 3, 2001).

Mitotic kinesins are attractive targets for the discovery and development of novel mitotic chemotherapeutics. Accordingly, it is an object of the present invention to provide compounds, methods and compositions useful in the inhibition of KSP, a mitotic kinesin.

SUMMARY OF THE INVENTION

The present invention relates to dihydropyrrole derivatives, that are useful for treating cellular proliferative diseases, for treating disorders associated with KSP kinesin activity, and for inhibiting KSP kinesin. The compounds of the invention may be illustrated by the Formula I:

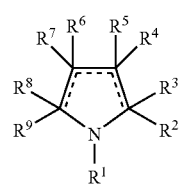

I

DETAILED DESCRIPTION OF THE INVENTION

The compounds of this invention are useful in the inhibition of mitotic kinesins and are illustrated by a compound of Formula I:

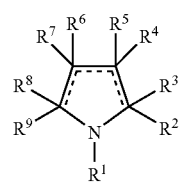

I or a pharmaceutically acceptable salt or stereoisomer thereof, wherein a is 0 or 1;
b is 0 or 1;
m is 0, 1, or 2;
n is 0 or 1;
r is 0 or 1;
s is 0 or 1;
u is 2, 3, 4 or 5;
a dashed line represents an optional double bond, provided that one and only one double bond is present in the ring;
$R^1$ is selected from:
  1) $(C_1-C_6\text{-alkylene})_n(C=X)C_1-C_{10}$ alkyl,
  2) $(C_1-C_6\text{-alkylene})_n(C=X)$aryl,
  3) $(C_1-C_6\text{-alkylene})_n(C=X)C_2-C_{10}$ alkenyl,
  4) $(C_1-C_6\text{-alkylene})_n(C=X)C_2-C_{10}$ alkynyl,
  5) $(C_1-C_6\text{-alkylene})_n(C=X)C_3-C_8$ cycloalkyl,
  6) $(C_1-C_6\text{-alkylene})_n(C=X)$heterocyclyl,
  7) $(C_1-C_6\text{-alkylene})_n(C=X)NR^cR^{c'}$,
  8) $(C_1-C_6\text{-alkylene})_nSO_2NR^cR^{c'}$,
  9) $(C_1-C_6\text{-alkylene})_nSO_2C_1-C_{10}$ alkyl,
  10) $(C_1-C_6\text{-alkylene})_nSO_2C_2-C_{10}$ alkenyl,
  11) $(C_1-C_6\text{-alkylene})_nSO_2C_2-C_{10}$ alkynyl,
  12) $(C_1-C_6\text{-alkylene})_nSO_2$-aryl,
  13) $(C_1-C_6\text{-alkylene})_nSO_2$-heterocyclyl,
  14) $(C_1-C_6\text{-alkylene})_nSO_2\text{—}C_3-C_8$ cycloalkyl,
  15) $(C_1-C_6\text{-alkylene})_nP(=O)R^dR^{d'}$,
  16) aryl;
  17) heterocyclyl; and
  18) $C_1-C_{10}$ alkyl;
said alkyl, aryl, alkenyl, alkynyl, cycloalkyl, alkylene, heteroaryl and heterocyclyl is optionally substituted with one or more substituents selected from $R^{10}$;
$R^2$ and $R^6$ are independently selected from:
  1) aryl,
  2) $C_1-C_6$ aralkyl,
  3) $C_3-C_8$ cycloalkyl, and
  4) heterocyclyl,
said aryl, cycloalkyl, aralkyl and heterocyclyl is optionally substituted with one or more substituents selected from $R^{10}$;
$R^3$, $R^4$, $R^5$, $R^7$, $R^8$, and $R^9$ are independently selected from:
  1) H,
  2) $C_1-C_{10}$ alkyl,
  3) aryl,
  4) $C_2-C_{10}$ alkenyl,
  5) $C_2-C_{10}$ alkynyl,
  6) $C_1-C_6$ perfluoroalkyl,
  7) $C_1-C_6$ aralkyl,
  8) $C_3-C_8$ cycloalkyl, and
  9) heterocyclyl,
said alkyl, aryl, alkenyl, alkynyl, cycloalkyl, aralkyl and heterocyclyl is optionally substituted with one or more substituents selected from $R^{10}$; or
$R^4$ and $R^5$, or $R^8$ and $R^9$, attached to the same carbon atom are combined to form $\text{—}(CH_2)_u\text{—}$ wherein one of the carbon atoms is optionally replaced by a moiety selected from O, $S(O)_m$, $\text{—}N(R^a)C(O)\text{—}$, $\text{—}N(R^b)\text{—}$ and $\text{—}N(COR^a)\text{—}$;
$R^{10}$ is independently selected from:
  1) $(C=O)_aO_bC_1-C_{10}$ alkyl,
  2) $(C=O)_aO_b$aryl,
  3) $C_2-C_{10}$ alkenyl,
  4) $C_2-C_{10}$ alkynyl,
  5) $(C=O)_aO_b$ heterocyclyl,
  6) $CO_2H$,
  7) halo,
  8) CN,
  9) OH,
  10) $O_bC_1-C_6$ perfluoroalkyl,
  11) $O_a(C=O)_bNR^{12}R^{13}$,
  12) $S(O)_mR^a$,
  13) $S(O)_2NR^{12}R^{13}$,
  14) oxo,
  15) CHO,
  16) $(N=O)R^{12}R^{13}$, or
  17) $(C=O)_aO_bC_3-C_8$ cycloalkyl,
said alkyl, aryl, alkenyl, alkyl, heterocyclyl, and cycloalkyl optionally substituted with one or more substituents selected from $R^{11}$;
$R^{11}$ is selected from:
  1) $(C=O)_rO_s(C_1-C_{10})$alkyl,
  2) $O_r(C_1-C_3)$perfluoroalkyl,
  3) $(C_0-C_6)$alkylene-$S(O)_mR^a$,
  4) oxo,
  5) OH,
  6) halo,
  7) CN,
  8) $(C=O)_rO_s(C_2-C_{10})$alkenyl,
  9) $(C=O)_rO_s(C_2-C_{10})$alkynyl,
  10) $(C=O)_rO_s(C_3-C_6)$cycloalkyl,
  11) $(C=O)_rO_s(C_0-C_6)$alkylene-aryl,
  12) $(C=O)_rO_s(C_0-C_6)$alkylene-heterocyclyl,
  13) $(C=O)_rO_s(C_0-C_6)$alkylene-$N(R^b)_2$,
  14) $C(O)R^a$,
  15) $(C_0-C_6)$alkylene-$CO_2R^a$,
  16) C(O)H,
  17) $(C_0-C_6)$alkylene-$CO_2H$,
  18) $C(O)N(R^b)_2$,
  19) $S(O)_mR^a$, and
  20) $S(O)_2N(R^b)_2$
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^{12}$ and $R^{13}$ are independently selected from:
  1) H,
  2) $(C=O)O_bC_1-C_{10}$ alkyl,
  3) $(C=O)O_bC_3-C_8$ cycloalkyl,
  4) $(C=O)O_b$aryl,
  5) $(C=O)O_b$heterocyclyl,
  6) $C_1-C_{10}$ alkyl,
  7) aryl,
  8) $C_2-C_{10}$ alkenyl,
  9) $C_2-C_{10}$ alkynyl,
  10) heterocyclyl,
  11) $C_3-C_8$ cycloalkyl,
  12) $SO_2R^a$, and
  13) $(C=O)NR^b_2$,
said alkyl, cycloalkyl, aryl, heterocylyl, alkenyl, and alkynyl is optionally substituted with one or more substituents selected from $R^{11}$, or
$R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{11}$;
$R^{14}$ is independently selected from:
  1) $(C=O)_aO_bC_1-C_{10}$ alkyl,
  2) $(C=O)_aO_b$aryl,
  3) $C_2-C_{10}$ alkenyl,
  4) $C_2-C_{10}$ alkynyl, 5) (C=O)$_a$O$_b$heterocyclyl,
6) CO$_2$H,
7) halo,
8) CN,
9) OH,
10) O$_b$C$_1$-C$_6$ perfluoroalkyl,
11) O$_a$(C=O)$_b$NR$^{12}$R$^{13}$,
12) S(O)$_m$R$^a$,
13) S(O)$_2$NR$^{12}$R$^{13}$,
14) oxo,
15) CHO,
16) (N=O)R$^{12}$R$^{13}$, and
17) (C=O)$_a$O$_b$C$_3$-C$_8$ cycloalkyl, said alkyl, aryl, alkenyl, alkynyl, heterocyclyl, and cycloalkyl optionally substituted with one or more substituents selected from R$^{11}$;

R$^a$ is (C$_1$-C$_6$)alkyl, (C$_3$-C$_6$)cycloalkyl, aryl, or heterocyclyl, optionally substituted with one to three substituents selected from R$^{14}$;

R$^b$ is H, (C$_1$-C$_6$)alkyl, aryl, heterocyclyl, (C$_3$-C$_6$)cycloalkyl, (C=O)OC$_1$-C$_6$ alkyl, (C=O)C$_1$-C$_6$ alkyl or S(O)$_2$R$^a$, optionally substituted with one to three substituents selected from R$^{14}$;

R$^c$ and R$^{c'}$ are independently selected from: H, (C$_1$-C$_6$)alkyl, aryl, heterocyclyl and (C$_3$-C$_6$)cycloalkyl, optionally substituted with one, two or three substituents selected from R$^{10}$, or R$^c$ and R$^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^d$ and R$^{d'}$ are independently selected from: (C$_1$-C$_6$)alkyl, (C$_1$-C$_6$)alkoxy and NR$^b_2$, or R$^d$ and R$^{d'}$ can be taken together with the phosphorous to which they are attached to form a monocyclic heterocycle with 5-7 members the ring and optionally containing, in addition to the phosphorous, one or two additional heteroatoms selected from NR$^e$, O and S, said monocyclic heterocycle optionally substituted with one, two or three substituents selected from R$^{11}$;

R$^e$ is selected from: H and (C$_1$-C$_6$)alkyl; and

X is selected from O, NR$^e$ and S.

In a second embodiment, the compounds of this invention are illustrated by a compound of Formula I:

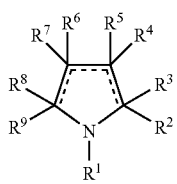

I or a pharmaceutically acceptable salt or stereoisomer thereof, wherein a is 0 or 1;
b is 0 or 1;
m is 0, 1, or 2;
n is 0 or 1;
r is 0 or 1;
s is 0 or 1;
u is 2, 3, 4 or 5;

a dashed line represents an optional double bond, provided that one and only one double bond is present in the ring;

R$^1$ is selected from:
1) (C$_1$-C$_6$-alkylene)$_n$(C=X)C$_1$-C$_{10}$ alkyl,
2) (C$_1$-C$_6$-alkylene)$_n$(C=X)aryl,
3) (C$_1$-C$_6$-alkylene)$_n$(C=X)C$_2$-C$_{10}$ alkenyl,
4) (C$_1$-C$_6$-alkylene)$_n$(C=X)C$_2$-C$_{10}$ alkynyl,
5) (C$_1$-C$_6$-alkylene)$_n$(C=X)C$_3$-C$_8$ cycloalkyl,
6) (C$_1$-C$_6$-alkylene)$_n$(C=X)heterocyclyl,
7) (C$_1$-C$_6$-alkylene)$_n$(C=X)NR$^c$R$^{c'}$,
8) (C$_1$-C$_6$-alkylene)$_n$SO$_2$NR$^c$R$^{c'}$,
9) (C$_1$-C$_6$-alkylene)$_n$SO$_2$C$_1$-C$_{10}$ alkyl,
10) (C$_1$-C$_6$-alkylene)$_n$SO$_2$C$_2$-C$_{10}$ alkenyl,
11) (C$_1$-C$_6$-alkylene)$_n$SO$_2$C$_2$-C$_{10}$ alkynyl,
12) (C$_1$-C$_6$-alkylene)$_n$SO$_2$-aryl,
13) (C$_1$-C$_6$-alkylene)$_n$SO$_2$-heterocyclyl,
14) (C$_1$-C$_6$-alkylene)$_n$SO$_2$—C$_3$-C$_8$ cycloalkyl,
15) (C$_1$-C$_6$-alkylene)$_n$P(=O)R$^d$R$^{d'}$,
16) aryl;
17) heterocyclyl; and
18) C$_1$-C$_{10}$ alkyl;

said alkyl, aryl, alkenyl, alkynyl, cycloalkyl, alkylene, heteroaryl and heterocyclyl is optionally substituted with one or more substituents selected from R$^{10}$;

R$^2$ and R$^6$ are independently selected from:
1) aryl,
2) C$_1$-C$_6$ aralkyl,
3) C$_3$-C$_8$ cycloalkyl, and
4) heterocyclyl, said aryl, cycloalkyl, aralkyl and heterocyclyl is optionally substituted with one or more substituents selected from R$^{10}$;

R$^3$, R$^4$, R$^5$, R$^7$, R$^8$, and R$^9$ are independently selected from:
1) H,
2) C$_1$-C$_{10}$ alkyl,
3) aryl,
4) C$_2$-C$_{10}$ alkenyl,
5) C$_2$-C$_{10}$ alkynyl,
6) C$_1$-C$_6$ perfluoroalkyl,
7) C$_1$-C$_6$ aralkyl,
8) C$_3$-C$_8$ cycloalkyl, and
9) heterocyclyl, said alkyl, aryl, alkenyl, alkynyl, cycloalkyl, aralkyl and heterocyclyl is optionally substituted with one or more substituents selected from R$^{10}$; or R$^4$ and R$^5$, or R$^8$ and R$^9$, attached to the same carbon atom are combined to form —(CH$_2$)$_u$— wherein one of the carbon atoms is optionally replaced by a moiety selected from O, S(O)$_m$, —N(R$^a$)C(O)—, —N(R$^b$)— and —N(COR$^a$)—;

R$^{10}$ is independently selected from:
1) (C=O)$_a$O$_b$C$_1$-C$_{10}$ alkyl,
2) (C=O)$_a$O$_b$aryl,
3) C$_2$-C$_{10}$ alkenyl,
4) C$_2$-C$_{10}$ alkynyl,
5) (C=O)$_a$O$_b$ heterocyclyl,
6) CO$_2$H,
7) halo,
8) CN,
9) OH,
10) O$_b$C$_1$-C$_6$ perfluoroalkyl,
11) O$_a$(C=O)$_b$NR$^{12}$R$^{13}$,
12) S(O)$_m$R$^a$,
13) S(O)$_2$NR$^{12}$R$^{13}$,
14) oxo,
15) CHO, 16) (N=O)R$^{12}$R$^3$, and
17) (C=O)$_a$O$_b$C$_3$-C$_8$ cycloalkyl,
said alkyl, aryl, alkenyl, alkynyl, heterocyclyl, and cycloalkyl optionally substituted with one or more substituents selected from R$^{11}$;
R$^{11}$ is selected from:
1) (C=O)$_r$O$_s$(C$_1$-C$_{10}$)alkyl,
2) O$_r$(C$_1$-C$_3$)perfluoroalkyl,
3) (C$_0$-C$_6$)alkylene-S(O)$_m$R$^a$,
4) oxo,
5) OH,
6) halo,
7) CN,
8) (C=O)$_r$O$_s$(C$_2$-C$_{10}$)alkenyl,
9) (C=O)$_r$O$_s$(C$_2$-C$_{10}$)alkynyl
10) (C=O)$_r$O$_s$(C$_3$-C$_6$)cycloalkyl,
11) (C=O)$_r$O$_s$(C$_0$-C$_6$)alkylene-aryl,
12) (C=O)$_r$O$_s$(C$_0$-C$_6$)alkylene-heterocyclyl,
13) (C=O)$_r$O$_s$(C$_0$-C$_6$)alkylene-N(R$^b$)$_2$,
14) C(O)R$^a$,
15) (C$_0$-C$_6$)alkylene-CO$_2$R$^a$,
16) C(O)H,
17) (C$_0$-C$_6$)alkylene-CO$_2$H,
18) C(O)N(R$^b$)$_2$,
19) S(O)$_m$R$^a$, and
20) S(O)$_2$N(R$^b$)$_2$
said alkyl, alkenyl, alkynyl, cycloalkyl, aryl, alkylene and heterocyclyl is optionally substituted with up to three substituents selected from R$^b$, OH, (C$_1$-C$_6$)alkoxy, halogen, CO$_2$H, CN, O(C=O)C$_1$-C$_6$ alkyl, oxo, and N(R$^b$)$_2$;
R$^{12}$ and R$^{13}$ are independently selected from:
1) H,
2) (C=O)O$_b$C$_1$-C$_{10}$ alkyl,
3) (C=O)O$_b$C$_3$-C$_8$ cycloalkyl,
4) (C=O)O$_b$aryl,
5) (C=O)O$_b$heterocyclyl,
6) C$_1$-C$_{10}$ alkyl,
7) aryl,
8) C$_2$-C$_{10}$ alkenyl,
9) C$_2$-C$_{10}$ alkynyl,
10) heterocyclyl,
11) C$_3$-C$_8$ cycloalkyl,
12) SO$_2$R$^a$, and
13) (C=O)NR$^b{}_2$,
said alkyl, cycloalkyl, aryl, heterocylyl, alkenyl, and alkynyl is optionally substituted with one or more substituents selected from R$^{11}$, or
R$^{12}$ and R$^{13}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one or more substituents selected from R$^{11}$;
R$^a$ is (C$_1$-C$_6$)alkyl, (C$_3$-C$_6$)cycloalkyl, aryl, or heterocyclyl;
R$^b$ is H, (C$_1$-C$_6$)alkyl, aryl, heterocyclyl, (C$_3$-C$_6$)cycloalkyl, (C=O)OC$_1$-C$_6$ alkyl, (C=O)C$_1$-C$_6$ alkyl or S(O)$_2$R$^a$;
R$^c$ and R$^{c'}$ are independently selected from: H, (C$_1$-C$_6$)alkyl, aryl, heterocyclyl and (C$_3$-C$_6$)cycloalkyl, optionally substituted with one, two or three substituents selected from R$^{10}$, or
R$^c$ and R$^{c'}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from R$^{11}$;
R$^d$ and R$^{d'}$ are independently selected from: (C$_1$-C$_6$)alkyl, (C$_1$-C$_6$)alkoxy and NR$^b{}_2$, or
R$^d$ and R$^{d'}$ can be taken together with the phosphorous to which they are attached to form a monocyclic heterocycle with 5-7 members the ring and optionally containing, in addition to the phosphorous, one or two additional heteroatoms selected from NR$^e$, O and S, said monocyclic heterocycle optionally substituted with one, two or three substituents selected from R$^{11}$;
R$^e$ is selected from: H and (C$_1$-C$_6$)alkyl; and
X is selected from O, NR$^e$ and S.

In another embodiment of the instant invention, the compounds are illustrated by a compound of Formula I:

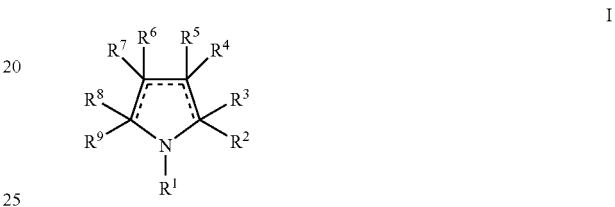

I or a pharmaceutically acceptable salt or stereoisomer thereof, wherein
a is 0 or 1;
b is 0 or 1;
m is 0, 1, or 2;
n is 0 or 1;
r is 0 or 1;
s is 0 or 1;
u is 2, 3, 4 or 5;
a dashed line represents an optional double bond, provided that one and only one double bond is present in the ring;
R$^1$ is selected from:
1) (C$_1$-C$_6$-alkylene)$_n$(C=X)C$_1$-C$_{10}$ alkyl,
2) (C$_1$-C$_6$-alkylene)$_n$(C=X)aryl,
3) (C$_1$-C$_6$-alkylene)$_n$(C=X)C$_2$-C$_{10}$ alkenyl,
4) (C$_1$-C$_6$-alkylene)$_n$(C=X)C$_2$-C$_{10}$ alkynyl,
5) (C$_1$-C$_6$-alkylene)$_n$(C=X)C$_3$-C$_8$ cycloalkyl,
6) (C$_1$-C$_6$-alkylene)$_n$(C=X)heterocyclyl,
7) (C$_1$-C$_6$-alkylene)$_n$(C=X)NR$^c$R$^{c'}$,
8) (C$_1$-C$_6$-alkylene)$_n$SO$_2$NR$^c$R$^{c'}$,
9) (C$_1$-C$_6$-alkylene)$_n$SO$_2$C$_1$-C$_{10}$ alkyl,
10) (C$_1$-C$_6$-alkylene)$_n$SO$_2$C$_2$-C$_{10}$ alkenyl,
11) (C$_1$-C$_6$-alkylene)$_n$SO$_2$C$_2$-C$_{10}$ alkynyl,
12) (C$_1$-C$_6$-alkylene)$_n$SO$_2$-aryl,
13) (C$_1$-C$_6$-alkylene)$_n$SO$_2$-heterocyclyl,
14) (C$_1$-C$_6$-alkylene)$_n$SO$_2$—C$_3$-C$_8$ cycloalkyl,
15) (C$_1$-C$_6$-alkylene)$_n$P(=O)R$^d$R$^{d'}$,
16) aryl;
17) heterocyclyl; and
18) C$_1$-C$_{10}$ alkyl;
said alkyl, aryl, alkenyl, alkynyl, cycloalkyl, alkylene, heteroaryl and heterocyclyl is optionally substituted with one or more substituents selected from R$^{10}$;
R$^2$ and R$^6$ are independently selected from:
1) aryl,
2) C$_1$-C$_6$ aralkyl,
3) C$_3$-C$_8$ cycloalkyl, and
4) heterocyclyl, said aryl, cycloalkyl, aralkyl and heterocyclyl is optionally substituted with one or more substituents selected from $R^{10}$;

$R^3$, $R^4$, $R^5$, $R^7$, $R^8$, and $R^9$ are independently selected from:
1) H,
2) $C_1$-$C_{10}$ alkyl,
3) aryl,
4) $C_2$-$C_{10}$ alkenyl,
5) $C_2$-$C_{10}$ alkynyl,
6) $C_1$-$C_6$ perfluoroalkyl,
7) $C_1$-$C_6$ aralkyl,
8) $C_3$-$C_8$ cycloalkyl, and
9) heterocyclyl, said alkyl, aryl, alkenyl, alkynyl, cycloalkyl, aralkyl and heterocyclyl is optionally substituted with one or more substituents selected from $R^{10}$; or $R^4$ and $R^5$, or $R^8$ and $R^9$, attached to the same carbon atom are combined to form —$(CH_2)_u$— wherein one of the carbon atoms is optionally replaced by a moiety selected from O, $S(O)_m$, —$N(R^a)C(O)$—, —$N(R^b)$— and —$N(COR^a)$—;

$R^{10}$ is independently selected from:
1) $(C=O)_aO_bC_1$-$C_{10}$ alkyl,
2) $(C=O)_aO_b$aryl,
3) $C_2$-$C_{10}$ alkenyl,
4) $C_2$-$C_{10}$ alkynyl,
5) $(C=O)_aO_b$ heterocyclyl,
6) $CO_2H$,
7) halo,
8) CN,
9) OH,
10) $O_bC_1$-$C_6$ perfluoroalkyl,
11) $O_a(C=O)_bNR^{12}R^{13}$,
12) $S(O)_mR^a$,
13) $S(O)_2NR^{12}R^{13}$,
14) oxo,
15) CHO,
16) $(N=O)R^{12}R^{13}$, and
17) $(C=O)_aO_bC_3$-$C_8$ cycloalkyl, said alkyl, aryl, alkenyl, alkynyl, heterocyclyl, and cycloalkyl optionally substituted with one or more substituents selected from $R^{11}$;

$R^{11}$ is selected from:
1) $(C=O)_rO_s(C_1$-$C_{10})$alkyl,
2) $O_r(C_1$-$C_3)$perfluoroalkyl,
3) $(C_0$-$C_6)$alkylene-$S(O)_mR^a$,
4) oxo,
5) OH,
6) halo,
7) CN,
8) $(C=O)_rO_s(C_2$-$C_{10})$alkenyl,
9) $(C=O)_rO_s(C_2$-$C_{10})$alkynyl,
10) $(C=O)_rO_s(C_3$-$C_6)$cycloalkyl,
11) $(C=O)_rO_s(C_0$-$C_6)$alkylene-aryl,
12) $(C=O)_rO_s(C_0$-$C_6)$alkylene-heterocyclyl,
13) $(C=O)_rO_s(C_0$-$C_6)$alkylene-$N(R^b)_2$,
14) $C(O)R^a$,
15) $(C_0$-$C_6)$alkylene-$CO_2R^a$,
16) $C(O)H$,
17) $(C_0$-$C_6)$alkylene-$CO_2H$,
18) $C(O)N(R^b)_2$,
19) $S(O)_mR^a$, and
20) $S(O)_2N(R^b)_2$ said alkyl, alkenyl, alkynyl, cycloalkyl, aryl, alkylene and heterocyclyl is optionally substituted with up to three substituents selected from $R^b$, OH, $(C_1$-$C_6)$alkoxy, halogen, $CO_2H$, CN, $O(C=O)C_1$-$C_6$ alkyl, oxo, and $N(R^b)_2$;

$R^{12}$ and $R^{13}$ are independently selected from:
1) H,
2) $(C=O)O_bC_1$-$C_{10}$ alkyl,
3) $(C=O)O_bC_3$-$C_8$ cycloalkyl,
4) $(C=O)O_b$aryl,
5) $(C=O)O_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) $(C=O)NR^b_2$, said alkyl, cycloalkyl, aryl, heterocylyl, alkenyl, and alkynyl is optionally substituted with one or more substituents selected from $R^{11}$, or $R^{12}$ and $R^{13}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one or more substituents selected from $R^{11}$;

$R^a$ is $(C_1$-$C_6)$alkyl, $(C_3$-$C_6)$cycloalkyl, aryl, or heterocyclyl;

$R^b$ is H, $(C_1$-$C_6)$alkyl, aryl, heterocyclyl, $(C_3$-$C_6)$cycloalkyl, $(C=O)OC_1$-$C_6$ alkyl, $(C=O)C_1$-$C_6$ alkyl or $S(O)_2R^a$;

$R^c$ and $R^{c'}$ are independently selected from: H, $(C_1$-$C_6)$alkyl, aryl, heterocyclyl and $(C_3$-$C_6)$cycloalkyl or $R^c$ and $R^{c'}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^d$ and $R^{d'}$ are independently selected from: $(C_1$-$C_6)$alkyl, $(C_1$-$C_6)$alkoxy and $NR^b_2$, or $R^d$ and $R^{d'}$ can be taken together with the phosphorous to which they are attached to form a monocyclic heterocycle with 5-7 members the ring and optionally containing, in addition to the phosphorous, one or two additional heteroatoms selected from $NR^e$, O and S, said monocyclic heterocycle optionally substituted with one, two or three substituents selected from $R^{11}$;

$R^e$ is selected from: H and $(C_1$-$C_6)$alkyl; and

X is selected from O, $NR^e$ and S.

A further embodiment of the present invention is illustrated by a compound of Formula II:

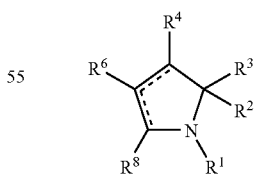

II or a pharmaceutically acceptable salt or stereoisomer thereof, wherein:
a is 0 or 1;
b is 0 or 1;
m is 0, 1, or 2;

n is 0 or 1;
r is 0 or 1;
s is 0 or 1;
a dashed line represents an optional double bond, provided that one and only one double bond is present in the ring;
$R^1$ is selected from:
1) $(C_1-C_6\text{-alkylene})_n(C=O)C_1-C_{10}$ alkyl,
2) $(C_1-C_6\text{-alkylene})_n(C=O)$aryl,
3) $(C_1-C_6\text{-alkylene})_n(C=O)C_2-C_{10}$ alkenyl,
4) $(C_1-C_6\text{-alkylene})_n(C=O)C_2-C_{10}$ alkynyl,
5) $(C_1-C_6\text{-alkylene})_n(C=O)C_3-C_8$ cycloalkyl,
6) $(C_1-C_6\text{-alkylene})_n(C=O)$heterocyclyl,
7) $(C_1-C_6\text{-alkylene})_n(C=O)NR^cR^{c'}$,
8) $(C_1-C_6\text{-alkylene})_nSO_2NR^cR^{c'}$,
9) $(C_1-C_6\text{-alkylene})_nSO_2C_1-C_{10}$ alkyl,
10) $(C_1-C_6\text{-alkylene})_nSO_2$-aryl,
11) $(C_1-C_6\text{-alkylene})_nSO_2$-heterocyclyl,
12) $(C_1-C_6\text{-alkylene})_nSO_2-C_3-C_8$ cycloalkyl,
13) $(C_1-C_6\text{-alkylene})_nP(=O)R^dR^{d'}$,
14) aryl;
15) heterocyclyl; and
16) $C_1-C_{10}$ alkyl;
said alkyl, aryl, alkenyl, alkynyl, cycloalkyl, alkylene, heteroaryl and heterocyclyl is optionally substituted with one or more substituents selected from $R^{10}$;
$R^2$ and $R^6$ are independently selected from:
1) aryl,
2) $C_1-C_6$ aralkyl,
3) $C_3-C_8$ cycloalkyl, and
4) heterocyclyl,
said aryl, cycloalkyl, aralkyl and heterocyclyl is optionally substituted with one or more substituents selected from $R^{10}$;
$R^3$, $R^4$ and $R^8$ are independently selected from:
1) H,
2) $C_1-C_{10}$ alkyl,
3) aryl,
4) $C_2-C_{10}$ alkenyl,
5) $C_2-C_{10}$ alkynyl,
6) $C_1-C_6$ perfluoroalkyl,
7) $C_1-C_6$ aralkyl,
8) $C_3-C_8$ cycloalkyl, and
9) heterocyclyl,
said alkyl, aryl, alkenyl, alkynyl, cycloalkyl, aralkyl and heterocyclyl is optionally substituted with one or more substituents selected from $R^{10}$;
$R^{10}$ is independently selected from:
1) $(C=O)_aO_bC_1-C_{10}$ alkyl,
2) $(C=O)_aO_b$aryl,
3) $C_2-C_{10}$ alkenyl,
4) $C_2-C_{10}$ alkynyl,
5) $(C=O)_aO_b$ heterocyclyl,
6) $CO_2H$,
7) halo,
8) CN,
9) OH,
10) $O_bC_1-C_6$ perfluoroalkyl,
11) $O_a(C=O)_bNR^{12}R^{13}$,
12) $S(O)_mR^a$,
13) $S(O)_2NR^{12}R^{13}$,
14) oxo,
15) CHO,
16) $(N=O)R^{12}R^{13}$, and
17) $(C=O)_aO_bC_3-C_8$ cycloalkyl,
said alkyl, aryl, alkenyl, alkynyl, heterocyclyl, and cycloalkyl optionally substituted with one, two or three substituents selected from $R^{11}$;
$R^{11}$ is selected from:
1) $(C=O)_rO_s(C_1-C_{10})$alkyl,
2) $O_r(C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_rO_s(C_3-C_6)$cycloalkyl,
10) $(C=O)_rO_s(C_0-C_6)$alkylene-aryl,
11) $(C=O)_rO_s(C_0-C_6)$alkylene-heterocyclyl,
12) $(C=O)_rO_s(C_0-C_6)$alkylene-$N(R^b)_2$,
13) $C(O)R^a$,
14) $(C_0-C_6)$alkylene-$CO_2R^a$,
15) $C(O)H$,
16) $(C_0-C_6)$alkylene-$CO_2H$,
17) $C(O)N(R^b)_2$,
18) $S(O)_mR^a$, and
19) $S(O)_2N(R^b)_2$;
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^{12}$ and $R^{13}$ are independently selected from:
1) H,
2) $(C=O)O_bC_1-C_{10}$ alkyl,
3) $(C=O)O_bC_3-C_8$ cycloalkyl,
4) $(C=O)O_b$aryl,
5) $(C=O)O_b$heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl,
12) $SO_2R^a$, and
13) $(C=O)NR^b_2$,
said alkyl, cycloalkyl, aryl, heterocylyl, alkenyl, and alkynyl is optionally substituted with one, two or three substituents selected from $R^{11}$, or
$R^{12}$ and $R^{13}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^{11}$;
$R^a$ is $(C_1-C_6)$alkyl, $(C_3-C_6)$cycloalkyl, aryl, or heterocyclyl;
$R^b$ is H, $(C_1-C_6)$alkyl, aryl, heterocyclyl, $(C_3-C_6)$cycloalkyl, $(C=O)OC_1-C_6$ alkyl, $(C=O)C_1-C_6$ alkyl or $S(O)_2R^a$;
$R^c$ and $R^{c'}$ are independently selected from:
H, $(C_1-C_6)$alkyl, aryl, heterocyclyl and $(C_3-C_6)$cycloalkyl; or
$R^c$ and $R^{c'}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^{11}$;
$R^d$ and $R^{d'}$ are independently selected from: $(C_1-C_6)$alkyl, $(C_1-C_6)$alkoxy and $NR^b_2$, or
$R^d$ and $R^{d'}$ can be taken together with the phosphorous to which they are attached to form a monocyclic heterocycle with 5-7 members the ring and optionally containing, in addition to the phosphorous, one or two additional heteroatoms selected from $NR^e$, O and S, said monocyclic heterocycle optionally substituted with one, two or three substituents selected from $R^{11}$; and $R^e$ is selected from: H and $(C_1-C_6)$alkyl.

A further embodiment of the present invention is illustrated by a compound of Formula III:

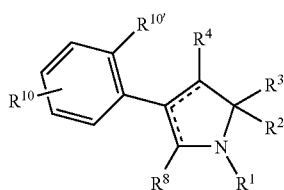

III or a pharmaceutically acceptable salt or stereoisomer thereof, wherein a is 0 or 1;
b is 0 or 1;
m is 0, 1, or 2;
r is 0 or 1;
s is 0 or 1;
a dashed line represents an optional double bond, provided that one and only one double bond is present in the ring;
$R^1$ is selected from:
  1) $(C=O)C_1-C_{10}$ alkyl,
  2) $(C=O)$aryl,
  3) $(C=O)C_2-C_{10}$ alkenyl,
  4) $(C=O)C_2-C_{10}$ alkynyl,
  5) $(C=O)C_3-C_8$ cycloalkyl,
  6) $(C=O)$heterocyclyl,
  7) $(C=O)NR^cR^{c'}$,
  8) $SO_2NR^cR^{c'}$,
  9) $SO_2C_1-C_{10}$ alkyl,
  10) $SO_2$-aryl,
  11) $SO_2$-heterocyclyl,
  12) $SO_2$—$C_3-C_8$ cycloalkyl, and
  13) $P(=O)R^dR^{d'}$,
said alkyl, aryl, alkenyl, alkynyl, cycloalkyl, heteroaryl and heterocyclyl is optionally substituted with one or more substituents selected from $R^{10}$;
$R^2$ is selected from:
  1) aryl,
  2) $C_1-C_6$ aralkyl,
  3) $C_3-C_8$ cycloalkyl, and
  4) heterocyclyl,
said aryl, cycloalkyl, aralkyl and heterocyclyl is optionally substituted with one or more substituents selected from $R^{10}$;
$R^3$, $R^4$ and $R^8$ are independently selected from:
  1) H,
  2) $C_1-C_{10}$ alkyl,
  3) aryl,
  4) $C_2-C_{10}$ alkenyl,
  5) $C_2-C_{10}$ alkynyl,
  6) $C_1-C_6$ perfluoroalkyl,
  7) $C_1-C_6$ aralkyl,
  8) $C_3-C_8$ cycloalkyl, and
  9) heterocyclyl,
said alkyl, aryl, alkenyl, alkynyl, cycloalkyl, aralkyl and heterocyclyl is optionally substituted with one or more substituents selected from $R^{10}$;
$R^{10}$ is independently selected from:
  1) $(C=O)_aO_bC_1-C_{10}$ alkyl,
  2) $(C=O)_aO_b$aryl,
  3) $C_2-C_{10}$ alkenyl,
  4) $C_2-C_{10}$ alkynyl,
  5) $(C=O)_aO_b$ heterocyclyl,
  6) $CO_2H$,
  7) halo,
  8) CN,
  9) OH,
  10) $O_bC_1-C_6$ perfluoroalkyl,
  11) $O_a(C=O)_bNR^{12}R^{13}$,
  12) $S(O)_mR^a$,
  13) $S(O)_2NR^{12}R^{13}$,
  14) oxo,
  15) CHO,
  16) $(N=O)R^{12}R^{13}$, and
  17) $(C=O)_aO_bC_3-C_8$ cycloalkyl,
said alkyl, aryl, alkenyl, alkynyl, heterocyclyl, and cycloalkyl optionally substituted with one, two or three substituents selected from $R^{11}$;
$R^{10'}$ is halogen;
$R^{11}$ is selected from:
  1) $(C=O)_rO_s(C_1-C_{10})$alkyl,
  2) $O_r(C_1-C_3)$perfluoroalkyl,
  3) oxo,
  4) OH,
  5) halo,
  6) CN,
  7) $(C_2-C_{10})$alkenyl,
  8) $(C_2-C_{10})$alkynyl,
  9) $(C=O)_rO_s(C_3-C_6)$cycloalkyl,
  10) $(C=O)_rO_s(C_0-C_6)$alkylene-aryl,
  11) $(C=O)_rO_s(C_0-C_6)$alkylene-heterocyclyl,
  12) $(C=O)_rO_s(C_0-C_6)$alkylene-$N(R^b)_2$,
  13) $C(O)R^a$,
  14) $(C_0-C_6)$alkylene-$CO_2R^a$,
  15) $C(O)H$,
  16) $(C_0-C_6)$alkylene-$CO_2H$,
  17) $C(O)N(R^b)_2$,
  18) $S(O)_mR^a$, and
  19) $S(O)_2N(R^b)_2$;
said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^{12}$ and $R^{13}$ are independently selected from:
  1) H,
  2) $(C=O)O_bC_1-C_{10}$ alkyl,
  3) $(C=O)O_bC_3-C_8$ cycloalkyl,
  4) $(C=O)O_b$aryl,
  5) $(C=O)O_b$heterocyclyl,
  6) $C_1-C_{10}$ alkyl,
  7) aryl,
  8) $C_2-C_{10}$ alkenyl,
  9) $C_2-C_{10}$ alkynyl,
  10) heterocyclyl,
  11) $C_3-C_8$ cycloalkyl,
  12) $SO_2R^a$, and
  13) $(C=O)NR^b_2$,
said alkyl, cycloalkyl, aryl, heterocylyl, alkenyl, and alkynyl is optionally substituted with one, two or three substituents selected from $R^{11}$, or
$R^{12}$ and $R^{13}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^{11}$;
$R^a$ is $(C_1-C_6)$alkyl, $(C_3-C_6)$cycloalkyl, aryl, or heterocyclyl;

$R^b$ is H, $(C_1-C_6)$alkyl, aryl, heterocyclyl, $(C_3-C_6)$cycloalkyl, $(C=O)OC_1-C_6$ alkyl, $(C=O)C_1-C_6$ alkyl or $S(O)_2R^a$;

$R^c$ and $R^{c'}$ are independently selected from: H, $(C_1-C_6)$alkyl, aryl, heterocyclyl and $(C_3-C_6)$cycloalkyl; or $R^c$ and $R^{c'}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^d$ and $R^{d'}$ are independently selected from: $(C_1-C_6)$alkyl, $(C_1-C_6)$alkoxy and $NR^b_2$, or $R^d$ and $R^{d'}$ can be taken together with the phosphorous to which they are attached to form a monocyclic heterocycle with 5-7 members the ring and optionally containing, in addition to the phosphorous, one or two additional heteroatoms selected from $NR^e$, O and S, said monocyclic heterocycle optionally substituted with one, two or three substituents selected from $R^{11}$; and $R^e$ is selected from: H and $(C_1-C_6)$alkyl.

A further embodiment of the present invention is illustrated by a compound of Formula IV:

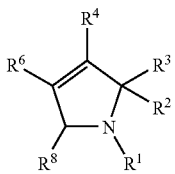

IV or a pharmaceutically acceptable salt or stereoisomer thereof, wherein a is 0 or 1;
b is 0 or 1;
m is 0, 1, or 2;
r is 0 or 1;
s is 0 or 1;

$R^1$ is selected from:
1) $(C=O)C_1-C_{10}$ alkyl,
2) $(C=O)$aryl,
3) $(C=O)C_3-C_8$ cycloalkyl,
4) $(C=O)$heterocyclyl,
5) $(C=O)NR^cR^{c'}$,
6) $(C=S)NR^cR^{c'}$,
7) $SO_2NR^cR^{c'}$,
8) $SO_2C_1-C_{10}$ alkyl,
9) $SO_2$-aryl, and
10) $SO_2$-heterocyclyl, said alkyl, aryl, cycloalkyl, and heterocyclyl is optionally substituted with one or more substituents selected from $R^{10}$; or $R^2$ is selected from:
1) aryl,
2) $C_1-C_6$ aralkyl,
3) $C_3-C_8$ cycloalkyl, and
4) heterocyclyl, said aryl, cycloalkyl, aralkyl and heterocyclyl is optionally substituted with one or more substituents selected from $R^{10}$;

$R^3$, $R^4$ and $R^8$ are independently selected from:
1) H,
2) $C_1-C_{10}$ alkyl, and
3) $C_1-C_6$ perfluoroalkyl, said alkyl is optionally substituted with one or more substituents selected from $R^{10}$;

$R^6$ is selected from:
1) aryl,
2) $C_1-C_6$ aralkyl,
3) $C_3-C_8$ cycloalkyl, and
4) heterocyclyl, said aryl, cycloalkyl, aralkyl and heterocyclyl is optionally substituted with one or more substituents selected from $R^{10}$;

$R^{10}$ is independently selected from:
1) $(C=O)_aO_bC_1-C_{10}$ alkyl,
2) $(C=O)_aO_b$aryl,
3) $C_2-C_{10}$ alkenyl,
4) $C_2-C_{10}$ alkynyl,
5) $(C=O)_aO_b$ heterocyclyl,
6) $CO_2H$,
7) halo,
8) CN,
9) OH,
10) $O_bC_1-C_6$ perfluoroalkyl,
11) $O_a(C=O)_bNR^{12}R^{13}$,
12) $S(O)_mR^a$,
13) $S(O)_2NR^{12}R^{13}$,
14) oxo,
15) CHO,
16) $(N=O)R^{12}R^{13}$, and
17) $(C=O)_aO_bC_3-C_8$ cycloalkyl, said alkyl, aryl, alkenyl, alkynyl, heterocyclyl, and cycloalkyl optionally substituted with one, two or three substituents selected from $R^{11}$;

$R^{11}$ is selected from:
1) $(C=O)_rO_s(C_1-C_{10})$alkyl,
2) $O_r(C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_rO_s(C_3-C_6)$cycloalkyl,
10) $(C=O)_rO_s(C_0-C_6)$alkylene-aryl,
11) $(C=O)_rO_s(C_0-C_6)$alkylene-heterocyclyl,
12) $(C=O)_rO_s(C_0-C_6)$alkylene-$N(R^b)_2$,
13) $C(O)R^a$,
14) $(C_0-C_6)$alkylene-$CO_2R^a$,
15) $C(O)H$,
16) $(C_0-C_6)$alkylene-$CO_2H$,
17) $C(O)N(R^b)_2$,
18) $S(O)_mR^a$, and
19) $S(O)_2N(R^b)_2$;

said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;

$R^{12}$ and $R^{13}$ are independently selected from:
1) H,
2) $(C=O)O_bC_1-C_{10}$ alkyl,
3) $(C=O)O_bC_3-C_8$ cycloalkyl,
4) $(C=O)O_b$aryl,
5) $(C=O)O_b$heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl, 12) SO$_2$R$^a$, and
13) (C=O)NR$^b_2$, said alkyl, cycloalkyl, aryl, heterocylyl, alkenyl, and alkynyl is optionally substituted with one, two or three substituents selected from R$^{11}$, or R$^{12}$ and R$^{13}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^a$ is independently selected from: (C$_1$-C$_6$)alkyl, (C$_3$-C$_6$) cycloalkyl, aryl, and heterocyclyl;

R$^b$ is independently selected from: H, (C$_1$-C$_6$)alkyl, aryl, heterocyclyl, (C$_3$-C$_6$)cycloalkyl, (C=O)OC$_1$-C$_6$ alkyl, (C=O)C$_1$-C$_6$ alkyl or S(O)$_2$R$^a$; and R$^c$ and R$^{c'}$ are independently selected from: H, (C$_1$-C$_6$)alkyl, aryl, heterocyclyl and (C$_3$-C$_6$)cycloalkyl or R$^c$ and R$^{c'}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from R$^{11}$.

Another embodiment is the compound of the Formula IV described immediately above, or a pharmaceutically acceptable salt or stereoisomer thereof, wherein:

R$^1$ is selected from:
1) (C=O)NR$^c$R$^{c'}$,
2) SO$_2$NR$^c$R$^{c'}$, and
3) SO$_2$C$_1$-C$_{10}$ alkyl, said alkyl, is optionally substituted with one, two or three substituents selected from R$^{10}$;

R$^2$ is selected from:
1) aryl, and
2) heteroaryl, said aryl and heteroaryl is optionally substituted with one or more substituents selected from R$^{10}$;

R$^3$, R$^4$ and R$^8$ are independently selected from:
1) H, and
2) C$_1$-C$_{10}$ alkyl, said alkyl is optionally substituted with one or more substituents selected from R$^{10}$, and R$^6$ is selected from:
1) aryl, and
2) heterocyclyl, said alkyl, aryl and heterocyclyl is optionally substituted with one or more substituents selected from R$^{10}$; and R$^{10}$, R$^{11}$, R$^{12}$, R$^{13}$, R$^a$, R$^b$, R$^c$ and R$^{c'}$ are as described immediately above.

In another embodiment of the compounds of Formula IV hereinabove, R$^2$ and R$^6$ are independently selected from phenyl or pyridyl, optionally substituted with one or two substituents selected from R$^{10}$.

Another embodiment is the compound of the Formula IV described immediately above, or a pharmaceutically acceptable salt or stereoisomer thereof, wherein R$^2$ is phenyl, optionally substituted with one or two substituents selected from R$^{10}$.

A further embodiment of the present invention is illustrated by a compound of Formula V, or a pharmaceutically acceptable salt or stereoisomer;

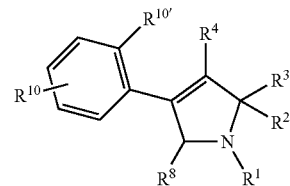

V wherein:
a is 0 or 1;
b is 0 or 1;
m is 0, 1, or 2;
r is 0 or 1;
s is 0 or 1;
R$^1$ is selected from:
1) (C=O)C$_1$-C$_{10}$ alkyl,
2) (C=O)aryl,
3) (C=O)C$_3$-C$_8$ cycloalkyl,
4) (C=O)heterocyclyl,
5) (C=O)NR$^c$R$^{c'}$,
6) (C=S)NR$^c$R$^{c'}$,
7) SO$_2$NR$^c$R$^{c'}$,
8) SO$_2$C$_1$-C$_{10}$ alkyl,
9) SO$_2$-aryl, and
10) SO$_2$-heterocyclyl, said alkyl, aryl, cycloalkyl, and heterocyclyl is optionally substituted with one or more substituents selected from R$^{10}$;

R$^2$ is selected from:
1) aryl,
2) C$_1$-C$_6$ aralkyl,
3) C$_3$-C$_8$ cycloalkyl, and
4) heterocyclyl, said aryl, cycloalkyl, aralkyl and heterocyclyl is optionally substituted with one or more substituents selected from R$^{10}$;

R$^3$, R$^4$ and R$^8$ are independently selected from:
1) H,
2) C$_1$-C$_{10}$ alkyl, and
3) C$_1$-C$_6$ perfluoroalkyl, said alkyl is optionally substituted with one or more substituents selected from R$^{10}$;

R$^{10}$ is independently selected from:
1) (C=O)$_a$O$_b$C$_1$-C$_{10}$ alkyl,
2) (C=O)$_a$O$_b$aryl,
3) C$_2$-C$_{10}$ alkenyl,
4) C$_2$-C$_{10}$ alkynyl,
5) (C=O)$_a$O$_b$ heterocyclyl,
6) CO$_2$H,
7) halo,
8) CN,
9) OH,
10) O$_b$C$_1$-C$_6$ perfluoroalkyl,
11) O$_a$(C=O)$_b$NR$^{12}$R$^{13}$,
12) S(O)$_m$R$^a$,
13) S(O)$_2$NR$^{12}$R$^{13}$,
14) oxo,
15) CHO,
16) (N=O)R$^{12}$R$^{13}$, and
17) (C=O)$_a$O$_b$C$_3$-C$_8$ cycloalkyl, said alkyl, aryl, alkenyl, alkynyl, heterocyclyl, and cycloalkyl optionally substituted with one, two or three substituents selected from R$^{11}$;

19

$R^{10'}$ is halogen;
$R^{11}$ is selected from:
1) (C=O)$_r$O$_s$(C$_1$-C$_{10}$)alkyl,
2) O$_r$(C$_1$-C$_3$)perfluoroalkyl,
3) oxo,
4) OH,
5) halo,
6) CN,
7) (C$_2$-C$_{10}$)alkenyl,
8) (C$_2$-C$_{10}$)alkynyl,
9) (C=O)$_r$O$_s$(C$_3$-C$_6$)cycloalkyl,
10) (C=O)$_r$O$_s$(C$_0$-C$_6$)alkylene-aryl,
11) (C=O)$_r$O$_s$(C$_0$-C$_6$)alkylene-heterocyclyl,
12) (C=O)$_r$O$_s$(C$_0$-C$_6$)alkylene-N(R$^b$)$_2$,
13) C(O)R$^a$,
14) (C$_0$-C$_6$)alkylene-CO$_2$R$^a$,
15) C(O)H,
16) (C$_0$-C$_6$)alkylene-CO$_2$H, and
17) C(O)N(R$^b$)$_2$,
18) S(O)$_m$R$^a$, and
19) S(O)$_2$N(R$^b$)$_2$;

said alkyl, alkenyl, alkynyl, cycloalkyl, aryl, alkylene and heterocyclyl is optionally substituted with up to three substituents selected from R$^b$, OH, (C$_1$-C$_6$)alkoxy, halogen, CO$_2$H, CN, O(C=O)C$_1$-C$_6$ alkyl, oxo, and N(R$^b$)$_2$;

$R^{12}$ and $R^{13}$ are independently selected from:
1) H,
2) (C=O)O$_b$C$_1$-C$_{10}$ alkyl,
3) (C=O)O$_b$C$_3$-C$_8$ cycloalkyl,
4) (C=O)O$_b$aryl,
5) (C=O)O$_b$heterocyclyl,
6) C$_1$-C$_{10}$ alkyl,
7) aryl,
8) C$_2$-C$_{10}$ alkenyl,
9) C$_2$-C$_{10}$ alkynyl,
10) heterocyclyl,
11) C$_3$-C$_8$ cycloalkyl,
12) SO$_2$R$^a$, and
13) (C=O)NR$^b{}_2$, said alkyl, cycloalkyl, aryl, heterocylyl, alkenyl, and alkynyl is optionally substituted with one, two or three substituents selected from R$^{11}$, or $R^{12}$ and $R^{13}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

$R^a$ is independently selected from: (C$_1$-C$_6$)alkyl, (C$_3$-C$_6$)cycloalkyl, aryl, and heterocyclyl;

$R^b$ is independently selected from: H, (C$_1$-C$_6$)alkyl, aryl, heterocyclyl, (C$_3$-C$_6$)cycloalkyl, (C=O)OC$_1$-C$_6$ alkyl, (C=O)C$_1$-C$_6$ alkyl or S(O)$_2$R$^a$; and $R^c$ and $R^{c'}$ are independently selected from: H, (C$_1$-C$_6$)alkyl, aryl, heterocyclyl and (C$_3$-C$_6$)cycloalkyl or $R^c$ and $R^{c'}$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one, two or three substituents selected from R$^{11}$.

Specific examples of the compounds of the instant invention include:
4-(2-chloro-5-fluorophenyl)-N,N-dimethyl-2-phenyl-2,5-dihydro-1H-pyrrole-1-carboxamide;

20

(+)-4-(2,5-difluorophenyl)-N,N-dimethyl-2-phenyl-2,5-dihydro-1H-pyrrole-1-carboxamide;
(−)-4-(2,5-difluorophenyl)-N,N-dimethyl-2-phenyl-2,5-dihydro-1H-pyrrole-1-carboxamide;
4-(5-chloro-2-fluorophenyl)-N,N-dimethyl-2-phenyl-2,5-dihydro-1H-pyrrole-1-carboxamide;
4-(2-fluorophenyl)-N,N-dimethyl-2-phenyl-2,5-dihydro-1H-pyrrole-1-carboxamide;
4-(2-fluoro-5-methylphenyl)-N,N-dimethyl-2-phenyl-2,5-dihydro-1H-pyrrole-1-carboxamide;
4-(5-bromo-2-fluorophenyl)-N,N-dimethyl-2-phenyl-2,5-dihydro-1H-pyrrole-1-carboxamide;
4-{[4-(5-chloro-2-fluorophenyl)-2-phenyl-2,5-dihydro-1H-pyrrol-1-yl]carbonyl}morpholine;
4-{[4-(2,5-difluorophenyl)-2-phenyl-2,5-dihydro-1H-pyrrol-1-yl]carbonyl}morpholine;
N,N-dimethyl-2,4-diphenyl-2,5-dihydro-1H-pyrrole-1-carboxamide;
3-[2-fluoro-5-(trifluoromethyl)phenyl]-N,N-dimethyl-5-phenyl-2,3-dihydro-1H-pyrrole-1-carboxamide;
2-(3-fluorophenyl)-4-(2,5-difluorophenyl)-N,N-dimethyl-2,5-dihydro-1H-pyrrole-1-carboxamide;
4-(2,5-difluorophenyl)-2-(4-fluorophenyl)-N,N-dimethyl-2,5-dihydro-1H-pyrrole-1-carboxamide;
4-(2,5-difluorophenyl)-2-(2-fluorophenyl)-N,N-dimethyl-2,5-dihydro-1H-pyrrole-1-carboxamide;
2-(3-bromophenyl)-4-(2,5-difluorophenyl)-N,N-dimethyl-2,5-dihydro-1H-pyrrole-1-carboxamide;
2-(3-aminophenyl)-4-(2,5-difluorophenyl)-N,N-dimethyl-2,5-dihydro-1H-pyrrole-1-carboxamide;
4-(2,5-difluorophenyl)-2-(3-methylphenyl)-N,N-dimethyl-2,5-dihydro-1H-pyrrole-1-carboxamide;
(2S)-4-(5-chloro-2-fluorophenyl)-N,N-dimethyl-2-phenyl-2,5-dihydro-1H-pyrrole-1-carboxamide;
4-(2,5-difluorophenyl)-1-(methylsulfonyl)-2-phenyl-2,5-dihydro-1H-pyrrole;
4-(2,5-difluorophenyl)-1-(ethylsulfonyl)-2-phenyl-2,5-dihydro-1H-pyrrole;
4-(2,5-difluorophenyl)-2-phenyl-1-(propylsulfonyl)-2,5-dihydro-1H-pyrrole;
4-(2,5-difluorophenyl)-1-(isopropylsulfonyl)-2-phenyl-2,5-dihydro-1H-pyrrole;
4-(5-chloro-2-fluorophenyl)-1-(methylsulfonyl)-2-phenyl-2,5-dihydro-1H-pyrrole;
4-(5-chloro-2-fluorophenyl)-1-(isopropylsulfonyl)-2-phenyl-2,5-dihydro-1H-pyrrole;
4-(2-fluoro-5-methylphenyl)-1-(isopropylsulfonyl)-2-phenyl-2,5-dihydro-1H-pyrrole;
2-{[4-(2,5-difluorophenyl)-2-phenyl-2,5-dihydro-1H-pyrrol-1-yl]sulfonyl}ethanamine;
2-{[4-(2,5-difluorophenyl)-2-phenyl-2,5-dihydro-1H-pyrrol-1-yl]sulfonyl}-N,N-dimethylethanamine;
1-acetyl-4-(2,5-difluorophenyl)-2-phenyl-2,5-dihydro-1H-pyrrole;
4-(2-chloro-5-fluorophenyl)-1-pivaloyl-2-phenyl-2,5-dihydro-1H-pyrrole;
4-(2-chloro-5-fluorophenyl)-1-isobutyryl-2-phenyl-2,5-dihydro-1H-pyrrole;
4-(2,5-difluorophenyl)-1-(2,2-dimethylpropanoyl)-2-phenyl-2,5-dihydro-1H-pyrrole;
1-[4-(2,5-difluorophenyl)-2-phenyl-2,5-dihydro-1H-pyrrol-1-yl]-2-methyl-1-oxopropan-2-ol;
1-[4-(5-chloro-2-fluorophenyl)-2-phenyl-2,5-dihydro-1H-pyrrol-1-yl]-2-methyl-1-oxopropan-2-ol;
1-[4-(2,5-difluorophenyl)-2-phenyl-2,5-dihydro-1H-pyrrol-1-yl]-2-methyl-1-oxopropan-2-amine;

4-(2-fluoro-5-isocyanophenyl)-N,N-dimethyl-2-phenyl-2,5-dihydro-1H-pyrrole-1-carboxamide;
4-(2,5-difluorophenyl)-2-phenyl-1-(trifluoroacetyl)-2,5-dihydro-1H-pyrrole;
4-(5-chloro-2-fluorophenyl)-2-phenyl-1-(trifluoroacetyl)-2,5-dihydro-1H-pyrrole;
(1S)-1-{[4-(2,5-difluorophenyl)-2-phenyl-2,5-dihydro-1H-pyrrol-1-yl]carbonyl}-2-methylpropylamine;
(1R)-1-{[4-(2,5-difluorophenyl)-2-phenyl-2,5-dihydro-1H-pyrrol-1-yl]carbonyl}-2-methylpropylamine;
4-(2,5-difluorophenyl)-2-phenyl-1-L-prolyl-2,5-dihydro-1H-pyrrole;
4-(2,5-difluorophenyl)-2-phenyl-1-D-prolyl-2,5-dihydro-1H-pyrrole;
(4R)-4-{[4-(2,5-difluorophenyl)-2-phenyl-2,5-dihydro-1H-pyrrol-1-yl]carbonyl}-1,3-thiazolidine;
methyl (3S)-3-amino-4-[4-(2,5-difluorophenyl)-2-phenyl-2,5-dihydro-1H-pyrrol-1-yl]-4-oxobutanoate;
(4S)-4-amino-5-[4-(2,5-difluorophenyl)-2-phenyl-2,5-dihydro-1H-pyrrol-1-yl]-5-oxopentanamide;
(1S)-1-{[4-(2,5-difluorophenyl)-2-phenyl-2,5-dihydro-1H-pyrrol-1-yl]carbonyl}-3-(methylthio)propylamine;
(1S)-1-{[4-(2,5-difluorophenyl)-2-phenyl-2,5-dihydro-1H-pyrrol-1-yl]carbonyl}-3-(methylsulfonyl)propylamine;
(2S)-2-{[4-(2,5-difluorophenyl)-2-phenyl-2,5-dihydro-1H-pyrrol-1-yl]carbonyl}piperidine;
(1S)-1-{[4-(2,5-difluorophenyl)-2-phenyl-2,5-dihydro-1H-pyrrol-1-yl]carbonyl}pentylamine;
(1S)-2-[4-(2,5-difluorophenyl)-2-phenyl-2,5-dihydro-1H-pyrrol-1-yl]-2-oxo-1-(thien-2-ylmethyl)ethylamine;
4-{[4-(2,5-difluorophenyl)-2-phenyl-2,5-dihydro-1H-pyrrol-1-yl]carbonyl}-1,1-dioxidotetrahydro-2H-thiopyran-4-ylamine;
(2S)-1-[4-(2,5-difluorophenyl)-2-phenyl-2,5-dihydro-1H-pyrrol-1-yl]-N-methyl-1-oxopropan-2-amine;
(1S)-1-{[4-(2,5-difluorophenyl)-2-phenyl-2,5-dihydro-1H-pyrrol-1-yl]carbonyl}propylamine;
(1S)-2-[4-(2,5-difluorophenyl)-2-phenyl-2,5-dihydro-1H-pyrrol-1-yl]-2-oxo-1-phenylethanamine;
(1S)-2-[4-(2,5-difluorophenyl)-2-phenyl-2,5-dihydro-1H-pyrrol-1-yl]-2-oxo-1-phenylethanamine;
(4S)-4-amino-5-[4-(2,5-difluorophenyl)-2-phenyl-2,5-dihydro-1H-pyrrol-1-yl]-5-oxopentanamide;
3-[4-(2,5-difluorophenyl)-2-phenyl-2,5-dihydro-1H-pyrrol-1-yl]-3-oxopropan-1-amine;
(1S,2S)-1-{[4-(2,5-difluorophenyl)-2-phenyl-2,5-dihydro-1H-pyrrol-1-yl]carbonyl}-2-methylbutylamine;
(1S)-1-{[4-(2,5-difluorophenyl)-2-phenyl-2,5-dihydro-1H-pyrrol-1-yl]carbonyl}butylamine;
(1S)-1-cyclopropyl-2-[4-(2,5-difluorophenyl)-2-phenyl-2,5-dihydro-1H-pyrrol-1-yl]-2-oxoethanamine;
1-{[4-(2,5-difluorophenyl)-2-phenyl-2,5-dihydro-1H-pyrrol-1-yl]carbonyl}cyclopropanamine;
1-[4-(2,5-difluorophenyl)-2-phenyl-2,5-dihydro-1H-pyrrol-1-yl]-1-oxopropan-2-amine;
(1S)-2-[4-(2,5-difluorophenyl)-2-phenyl-2,5-dihydro-1H-pyrrol-1-yl]-1-methyl-2-oxoethylamine;
(1S)-2-[4-(2,5-difluorophenyl)-2-phenyl-2,5-dihydro-1H-pyrrol-1-yl]-2-oxo-1-(pyridin-2-ylmethyl)ethylamine;
(1S)-1-cyclohexyl-2-[4-(2,5-difluorophenyl)-2-phenyl-2,5-dihydro-1H-pyrrol-1-yl]-2-oxoethanamine;
(1S)-2-[4-(2,5-difluorophenyl)-2-phenyl-2,5-dihydro-1H-pyrrol-1-yl]-1-(4-iodobenzyl)-2-oxoethylamine;
(1S)-1-benzyl-2-[4-(2,5-difluorophenyl)-2-phenyl-2,5-dihydro-1H-pyrrol-1-yl]-2-oxoethylamine;
4-{(2S)-2-amino-3-[4-(2,5-difluorophenyl)-2-phenyl-2,5-dihydro-1H-pyrrol-1-yl]-3-oxopropyl}phenol;
(3S)-3-{[4-(2,5-difluorophenyl)-2-phenyl-2,5-dihydro-1H-pyrrol-1-yl]carbonyl}-1,2,3,4-tetrahydroisoquinoline;
(1S)-1-{[4-(2,5-difluorophenyl)-2-phenyl-2,5-dihydro-1H-pyrrol-1-yl]carbonyl}-3-phenylpropylamine;
(1S)-1-{[4-(2,5-difluorophenyl)-2-phenyl-2,5-dihydro-1H-pyrrol-1-yl]carbonyl}-3-methylbutylamine;
(1S)-2-[4-(2,5-difluorophenyl)-2-phenyl-2,5-dihydro-1H-pyrrol-1-yl]-2-oxo-1-(pyridin-3-ylmethyl)ethylamine;
1-[(2S)-azetidin-2-ylcarbonyl]-4-(2,5-difluorophenyl)-2-phenyl-2,5-dihydro-1H-pyrrole;
(3S)-3-amino-4-[4-(2,5-difluorophenyl)-2-phenyl-2,5-dihydro-1H-pyrrol-1-yl]-4-oxobutanamide;
4-(2,5-difluorophenyl)-1-[(2S)-2,5-dihydro-1H-pyrrol-2-ylcarbonyl]-2-phenyl-2,5-dihydro-1H-pyrrole;
4-(2,5-difluorophenyl)-1-[(2-methylazetidin-2-yl)carbonyl]-2-phenyl-2,5-dihydro-1H-pyrrole;
(1S)-1-{[4-(2,5-difluorophenyl)-2-phenyl-2,5-dihydro-1H-pyrrol-1-yl]carbonyl}-2,2-dimethylpropylamine;
methyl(4S)-4-amino-5-[4-(2,5-difluorophenyl)-2-phenyl-2,5-dihydro-1H-pyrrol-1-yl]-5-oxopentanoate;
4-(2,5-difluorophenyl)-2-phenyl-1-{[(2S,3S)-2-phenylpyrrolidin-3-yl]carbonyl}-2,5-dihydro-1H-pyrrole;
4-(2,5-difluorophenyl)-2-phenyl-4-[(5-phenylpyrrolidin-3-yl)carbonyl]-2,5-dihydro-1H-pyrrole;
(2S)-2-amino-3-[4-(2,5-difluorophenyl)-2-phenyl-2,5-dihydro-1H-pyrrol-1-yl]-3-oxopropan-1-ol;
(2R,3S)-3-amino-4-[4-(2,5-difluorophenyl)-2-phenyl-2,5-dihydro-1H-pyrrol-1-yl]-4-oxobutan-2-ol;
(1S)-2-[4-(2,5-difluorophenyl)-2-phenyl-2,5-dihydro-1H-pyrrol-1-yl]-1-(methoxymethyl)-2-oxoethylamine;
4-(2,5-difluorophenyl)-2-phenyl-1-(pyrrolidin-3-ylcarbonyl)-2,5-dihydro-1H-pyrrole;
4-(2,5-difluorophenyl)-2-phenyl-1-[(3-phenylpyrrolidin-3-yl)acetyl]-2,5-dihydro-1H-pyrrole;
(1S)-1-{[4-(2,5-difluorophenyl)-2-phenyl-2,5-dihydro-1H-pyrrol-1-yl]carbonyl}-3,3-difluoropropylamine;
(1S)-3-[4-(2,5-difluorophenyl)-2-phenyl-2,5-dihydro-1H-pyrrol-1-yl]-3-oxo-1-phenylpropan-1-amine;
4-(2,5-difluorophenyl)-2-phenyl-1-[(4S)-4-phenyl-L-prolyl]-2,5-dihydro-1H-pyrrole;
1-{2-[4-(2,5-difluorophenyl)-2-phenyl-2,5-dihydro-1H-pyrrol-1-yl]-2-oxoethyl}cyclohexanamine;
2-[4-(2,5-difluorophenyl)-2-phenyl-2,5-dihydro-1H-pyrrol-1-yl]-2-oxoethanamine;
4-{[4-(2,5-difluorophenyl)-2-phenyl-2,5-dihydro-1H-pyrrol-1-yl]carbonyl}piperidin-4-amine;
(1S,3R)-3-{[4-(2,5-difluorophenyl)-2-phenyl-2,5-dihydro-1H-pyrrol-1-yl]carbonyl}cyclopentanamine;
(1R,4S)-4-{[4-(2,5-difluorophenyl)-2-phenyl-2,5-dihydro-1H-pyrrol-1-yl]carbonyl}cyclopent-2-en-1-amine;
(1S,4R)-4-{[4-(2,5-difluorophenyl)-2-phenyl-2,5-dihydro-1H-pyrrol-1-yl]carbonyl}cyclopent-2-en-1-amine;
(1S)-1-{[4-(2,5-difluorophenyl)-2-phenyl-2,5-dihydro-1H-pyrrol-1-yl]carbonyl}but-3-ynylamine;
(1R)-3-[4-(2,5-difluorophenyl)-2-phenyl-2,5-dihydro-1H-pyrrol-1-yl]-3-oxo-1-phenylpropan-1-amine;
3-{[4-(2,5-difluorophenyl)-2-phenyl-2,5-dihydro-1H-pyrrol-1-yl]carbonyl}-2-phenylpiperidine;
(1S)-1-{[4-(2,5-difluorophenyl)-2-phenyl-2,5-dihydro-1H-pyrrol-1-yl]carbonyl}but-3-enylamine;
(2S)-3-[4-(2,5-difluorophenyl)-2-phenyl-2,5-dihydro-1H-pyrrol-1-yl]-2-(methylamino)-3-oxopropan-1-ol;
(3R,5S)-5-{[4-(2,5-difluorophenyl)-2-phenyl-2,5-dihydro-1H-pyrrol-1-yl]carbonyl}pyrrolidin-3-ol;
(1S)-2-[4-(2,5-difluorophenyl)-2-phenyl-2,5-dihydro-1H-pyrrol-1-yl]-2-oxo-1-(1,3-thiazol-4-ylmethyl)ethylamine;

(1R)-1-{[4-(2,5-difluorophenyl)-2-phenyl-2,5-dihydro-1H-pyrrol-1-yl]carbonyl}but-3-enylamine;

(2S)-1-[4-(2,5-difluorophenyl)-2-phenyl-2,5-dihydro-1H-pyrrol-1-yl]-N,3-dimethyl-1-oxobutan-2-amine;

(2S)-1-[4-(2,5-difluorophenyl)-2-phenyl-2,5-dihydro-1H-pyrrol-1-yl]-N,4-dimethyl-1-oxopentan-2-amine;

(1S)-2-[4-(2,5-difluorophenyl)-2-phenyl-2,5-dihydro-1H-pyrrol-1-yl]-1-[(1-methyl-1H-imidazol-4-yl)methyl]-2-oxoethylamine;

4-(2,5-difluorophenyl)-1-(N~6~-formyl-L-lysyl)-2-phenyl-2,5-dihydro-1H-pyrrole;

(2S,3S)-1-[4-(2,5-difluorophenyl)-2-phenyl-2,5-dihydro-1H-pyrrol-1-yl]-N,3-dimethyl-1-oxopentan-2-amine;

(1S)-1-(cyclohexylmethyl)-2-[4-(2,5-difluorophenyl)-2-phenyl-2,5-dihydro-1H-pyrrol-1-yl]-2-oxoethylamine;

(1S)-2-[4-(2,5-difluorophenyl)-2-phenyl-2,5-dihydro-1H-pyrrol-1-yl]-1-(1H-indol-3-ylmethyl)-2-oxoethylamine;

(1S)-2-[4-(2,5-difluorophenyl)-2-phenyl-2,5-dihydro-1H-pyrrol-1-yl]-1-(isocyanomethyl)-2-oxoethylamine;

(1S)-1-{[4-(2,5-difluorophenyl)-2-phenyl-2,5-dihydro-1H-pyrrol-3-yl]carbonyl}-3,3-dimethylbutylamine;

1-[4-(2,5-difluorophenyl)-2-phenyl-2,5-dihydro-1H-pyrrol-1-yl]-2,3-dimethyl-1-oxobutan-2-amine;

1-{[4-(2,5-difluorophenyl)-2-phenyl-2,5-dihydro-1H-pyrrol-1-yl]carbonyl}cyclohexanamine;

1-{[4-(2,5-difluorophenyl)-2-phenyl-2,5-dihydro-1H-pyrrol-1-yl]carbonyl}cyclopentanamine;

(1S)-3-(benzyloxy)-1-{[4-(2,5-difluorophenyl)-2-phenyl-2,5-dihydro-1H-pyrrol-1-yl]carbonyl}propylamine;

1-[4-(2,5-difluorophenyl)-2-phenyl-2,5-dihydro-1H-pyrrol-1-yl]-2,3-dimethyl-1-oxobutan-2-amine;

1-{[4-(2,5-difluorophenyl)-2-phenyl-2,5-dihydro-1H-pyrrol-1-yl]carbonyl}cyclopent-3-en-1-amine;

(1S)-1-cyclopentyl-2-[4-(2,5-difluorophenyl)-2-phenyl-2,5-dihydro-1H-pyrrol-1-yl]-2-oxoethanamine;

4-(2,5-difluorophenyl)-1-(2-methylprolyl)-2-phenyl-2,5-dihydro-1H-pyrrole;

1-[4-(5-chloro-2-fluorophenyl)-2-phenyl-2,5-dihydro-1H-pyrrol-1-yl]-2-methyl-1-oxopropan-2-amine;

(1S)-1-{[4-(5-chloro-2-fluorophenyl)-2-phenyl-2,5-dihydro-1H-pyrrol-1-yl]carbonyl}-2-methylpropylamine;

(1S)-2-[4-(5-chloro-2-fluorophenyl)-2-phenyl-2,5-dihydro-1H-pyrrol-1-yl]-1-cyclopropyl-2-oxoethanamine;

(1S,2S)-1-{[4-(5-chloro-2-fluorophenyl)-2-phenyl-2,5-dihydro-1H-pyrrol-1-yl]carbonyl}-2-methylbutylamine;

(1S)-1-{[4-(5-chloro-2-fluorophenyl)-2-phenyl-2,5-dihydro-1H-pyrrol-1-yl]carbonyl}pentylamine;

(1S)-1-{[4-(5-chloro-2-fluorophenyl)-2-phenyl-2,5-dihydro-1H-pyrrol-1-yl]carbonyl}-3,3-dimethylbutylamine;

(1S)-1-{[(2S)-4-(2,5-difluorophenyl)-2-phenyl-2,5 dihydro-1H-pyrrol-1-yl]carbonyl}-2,2-dimethylpropylamine;

(1S)-1-{[(2S)-4-(2,5-difluorophenyl)-2-phenyl-2,5-dihydro-1H-pyrrol-1-yl]carbonyl}-2-methylpropylamine;

(1S)-1-cyclohexyl-2-[(2S)-4-(2,5-difluorophenyl)-2-phenyl-2,5-dihydro-1H-pyrrol-1-yl]-2-oxoethanamine;

(1S)-1-{[(2S)-4-(2,5-difluorophenyl)-2-phenyl-2,5-dihydro-1H-pyrrol-1-yl]carbonyl}but-3-enylamine;

(1S)-1-{[(2S)-4-(2,5-difluorophenyl)-2-phenyl-2,5-dihydro-1H-pyrrol-1-yl]carbonyl}but-3-ynylamine;

(1S)-1-benzyl-2-[(2S)-4-(2,5-difluorophenyl)-2-phenyl-2,5-dihydro-1H-pyrrol-1-yl]-2-oxoethylamine;

(1S)-1-cyclopropyl-2-[(2S)-4-(2,5-difluorophenyl)-2-phenyl-2,5-dihydro-1H-pyrrol-1-yl]-2-oxoethanamine;

1-[(2S)-4-(2,5-difluorophenyl)-2-phenyl-2,5-dihydro-1H-pyrrol-1-yl]-2-methyl-1-oxopropan-2-amine;

(1S)-1-{[(2S)-4-(5-chloro-2-fluorophenyl)-2-phenyl-2,5-dihydro-1H-pyrrol-1-yl]carbonyl}-2,2-dimethylpropylamine;

(1S)-1-{[(2S)-4-(2,5-difluorophenyl)-2-phenyl-2,5-dihydro-1H-pyrrol-1-yl]carbonyl}pentylamine;

(1S)-1-{[(2S)-4-(2,5-difluorophenyl)-2-phenyl-2,5-dihydro-1H-pyrrol-1-yl]carbonyl}-3-methylbutylamine;

(1S)-1-{[(2S)-4-(2,5-difluorophenyl)-2-phenyl-2,5-dihydro-1H-pyrrol-1-yl]carbonyl}-3,3-dimethylbutylamine;

1-cyclopropyl-3-[(2S)-4-(2,5-difluorophenyl)-2-phenyl-2,5-dihydro-1H-pyrrol-1-yl]-3-oxopropan-1-amine;

(1S)-2-[(2S)-4-(5-chloro-2-fluorophenyl)-2-phenyl-2,5-dihydro-1H-pyrrol-1-yl]-1-cyclopropyl-2-oxoethanamine;

(1S)-1-{[(2S)-4-(5-chloro-2-fluorophenyl)-2-phenyl-2,5-dihydro-1H-pyrrol-1-yl]carbonyl}-2-methylpropylamine;

(1S,2S)-1-{[(2S)-4-(2,5-difluorophenyl)-2-phenyl-2,5-dihydro-1H-pyrrol-1-yl]carbonyl}-2-methylbutylamine;

4-(5-chloro-2-fluorophenyl)-2-(3-hydroxyphenyl)-1-(2-methylalanyl)-2,5-dihydro-1H-pyrrole;

(2S)-4-(5-chloro-2-fluorophenyl)-2-(3-hydroxyphenyl)-1-(2-methylalanyl)-2,5-dihydro-1H-pyrrole;

4-(2,5-difluorophenyl)-2-(3-hydroxyphenyl)-1-L-valyl-2,5-dihydro-1H-pyrrole;

4-(5-chloro-2-fluorophenyl)-2-(3-hydroxyphenyl)-1-L-valyl-2,5-dihydro-1H-pyrrole;

(2S)-4-(5-chloro-2-fluorophenyl)-2-(3-hydroxyphenyl)-1-L-valyl-2,5-dihydro-1H-pyrrole;

4-(2,5-difluorophenyl)-2-(3-hydroxyphenyl)-1-(2-methylalanyl)-2,5-dihydro-1H-pyrrole;

3-[1-[(2S)-2-amino-2-cyclopropylethanoyl]-4-(5-chloro-2-fluorophenyl)-2,5-dihydro-1H-pyrrol-2-yl]phenol;

4-(5-chloro-2-fluorophenyl)-2-(3-hydroxyphenyl)-1-L-isoleucyl-2,5-dihydro-1H-pyrrole;

4-(5-chloro-2-fluorophenyl)-2-(3-hydroxyphenyl)-1-L-norleucyl-2,5-dihydro-1H-pyrrole;

(2S)-4-(5-chloro-2-fluorophenyl)-2-(3-hydroxyphenyl)-1-(3-methyl-1-valyl)-2,5-dihydro-1H-pyrrole;

(2S)-4-(2,5-Difluorophenyl)-N-methyl-2-phenyl-N-piperidin-4-yl-2,5-dihydro-1H-pyrrole-1-carboxamide;

(2S)-4-(2,5-Difluorophenyl)-N-methyl-2-phenyl-N-(piperidin-4-ylmethyl)-2,5-dihydro-1H-pyrrole-1-carboxamide;

(2S)-4-(5-Chloro-2-fluorophenyl)-N-methyl-2-phenyl-N-[(3R)-pyrrolidin-3-yl]-2,5-dihydro-1H-pyrrole-1-carboxamide;

(2S)-4-(5-chloro-2-fluorophenyl)-N-methyl-2-phenyl-N-piperidin-4-yl-2,5-dihydro-1H-pyrrole-1-carboxamide;

(2S)-4-(5-chloro-2-fluorophenyl)-N-methyl-2-phenyl-N-[(3S)-pyrrolidin-3-yl]-2,5-dihydro-1H-pyrrole-1-carboxamide;

(2S)-4-(2,5-difluorophenyl)-N-methyl-2-phenyl-N-pyrrolidin-3-yl-2,5-dihydro-1H-pyrrole-1-carboxamide;

(2S)-4-(2,5-difluorophenyl)-N-methyl-N-[(3S)-1-methylpyrrolidin-3-yl]-2-phenyl-2,5-dihydro-1H-pyrrole-1-carboxamide;

(2S)-4-(2,5-difluorophenyl)-N-methyl-N-[(3R)-1-methylpyrrolidin-3-yl]-2-phenyl-2,5-dihydro-1H-pyrrole-1-carboxamide;

(2S)-4-(2,5-difluorophenyl)-N-methyl-N-[(1-methyl-5-oxopyrrolidin-2-yl)methyl]-2-phenyl-2,5-dihydro-1H-pyrrole-1-carboxamide;

(2S)-4-(2,5-difluorophenyl)-N-(1,3-dioxolan-2-ylmethyl)-N-methyl-2-phenyl-2,5-dihydro-1H-pyrrole-1-carboxamide;

(2S)-4-(2,5-difluorophenyl)-N-methyl-2-phenyl-N-tetrahydrofuran-3-yl-2,5-dihydro-1H-pyrrole-1-carboxamide;

(2S)-N-(1-allylpiperidin-4-yl)-4-(2,5-difluorophenyl)-N-methyl-2-phenyl-2,5-dihydro-1H-pyrrole-1-carboxamide;

allyl 4-[{[(2S)-4-(2,5-difluorophenyl)-2-phenyl-2,5-dihydro-1H-pyrrol-1-yl]carbonyl}(methyl)amino]piperidine-1-carboxylate;

allyl 4-{[{[(2S)-4-(2,5-difluorophenyl)-2-phenyl-2,5-dihydro-1H-pyrrol-1-yl]arbonyl}(methyl)amino]methyl}piperidine-1-carboxylate;

(2S)-4-(2,5-difluorophenyl)-N-methyl-N-(1-methylpiperidin-4-yl)-2-phenyl-2,5-dihydro-1H-pyrrole-1-carboxamide;

4-(2,5-Difluorophenyl)-N-methyl-N-[(1-methylpiperidin-3-yl)methyl]-2-phenyl-2,5-dihydro-1H-pyrrole-1-carboxamide;

4-(2,5-difluorophenyl)-N-methyl-2-phenyl-N-(pyridin-3-ylmethyl)-2,5-dihydro-1H-pyrrole-1-carboxamide;

N-benzyl-4-(2,5-difluorophenyl)-N-methyl-2-phenyl-2,5-dihydro-1H-pyrrole-1-carboxamide;

4-(2,5-difluorophenyl)-N-methyl-N-[(1-methyl-1H-pyrazol-4-yl)methyl]-2-phenyl-2,5-dihydro-1H-pyrrole-1-carboxamide;

4-(2,5-difluorophenyl)-N-[2-(dimethylamino)ethyl]-N-methyl-2-phenyl-2,5-dihydro-1H-pyrrole-1-carboxamide;

4-(2,5-difluorophenyl)-N-(2-hydroxyethyl)-N-methyl-2-phenyl-2,5-dihydro-1H-pyrrole-1-carboxamide;

4-(2,5-difluorophenyl)-N-isobutyl-N-methyl-2-phenyl-2,5-dihydro-1H-pyrrole-1-carboxamide;

4-(2,5-difluorophenyl)-N-methyl-2-phenyl-N-(2-pyridin-2-ylethyl)-2,5-dihydro-1H-pyrrole-1-carboxamide;

4-(2,5-difluorophenyl)-N-(2-methoxyethyl)-N-methyl-2-phenyl-2,5-dihydro-1H-pyrrole-1-carboxamide;

4-(2,5-difluorophenyl)-N-(2,3-dihydroxypropyl)-N-methyl-2-phenyl-2,5-dihydro-1H-pyrrole-1-carboxamide;

4-(2,5-difluorophenyl)-N-methyl-2-phenyl-N-(2-phenylethyl)-2,5-dihydro-1H-pyrrole-1-carboxamide;

4-(2,5-difluorophenyl)-2-phenyl-N-propyl-2,5-dihydro-1H-pyrrole-1-carboxamide;

4-(5-chloro-2-fluorophenyl)-2-(3-hydroxyphenyl)-N-methyl-N-piperidin-4-yl-2,5-dihydro-1H-pyrrole-1-carboxamide;

4-(2,5-difluorophenyl)-2-(3-hydroxyphenyl)-N-methyl-N-piperidin-4-yl-2,5-dihydro-1H-pyrrole-1-carboxamide;

1-Acetyl-4-(2,5-difluorophenyl)-2-methyl-2-phenyl-2,5-dihydro-1H-pyrrole;

(2S)-1-[4-(2,5-difluorophenyl)-2-methyl-2-phenyl-2,5-dihydro-1H-pyrrol-1-yl]-3-methyl-1-oxobutan-2-amine;

(2S)-4-(2,5-difluorophenyl)-N,N,2-trimethyl-2-phenyl-2,5-dihydro-1H-pyrrole-1-carboxamide;

(2S)-4-(5-chloro-2-fluorophenyl)-N,N,2-trimethyl-2-phenyl-2,5-dihydro-1H-pyrrole-1-carboxamide;

(2S)-4-(5-chloro-2-fluorophenyl)-2-methyl-2-phenyl-2,5-dihydro-1H-pyrrole-1-carboxamide;

(2S)-4-(5-chloro-2-fluorophenyl)-N-ethyl-2-methyl-2-phenyl-2,5-dihydro-1H-pyrrole-1-carboxamide;

(2S)-1-[(2S)-4-(2,5-difluorophenyl)-2-phenyl-2,5-dihydro-1H-pyrrol-1-yl]-3,3-dimethyl-1-oxobutan-2-ol;

(2S)-1-[(2S)-4-(2,5-difluorophenyl)-2-phenyl-2,5-dihydro-1H-pyrrol-1-yl]-3-methyl-1-oxobutan-2-ol;

(2S,3S)-1-[(2S)-4-(2,5-difluorophenyl)-2-phenyl-2,5-dihydro-1H-pyrrol-1-yl]-3-methyl-1-oxopentan-2-ol;

1-[(2S)-4-(2,5-difluorophenyl)-2-phenyl-2,5-dihydro-1H-pyrrol-1-yl]-1-oxohexan-2-ol;

(2S)-1-[4-(2,5-difluorophenyl)-2-phenyl-2,5-dihydro-1H-pyrrol-1-yl]-1-oxo-3-phenylpropan-2-ol;

(2S)-1-[4-(2,5-difluorophenyl)-2-phenyl-2,5-dihydro-1H-pyrrol-1-yl]-4-methyl-1-oxopentan-2-ol;

(1S)-1-cyclohexyl-2-[4-(2,5-difluorophenyl)-2-phenyl-2,5-dihydro-1H-pyrrol-1-yl]-2-oxoethanol;

(2S)-1-[4-(2,5-difluorophenyl)-2-phenyl-2,5-dihydro-1H-pyrrol-1-yl]-3,3-dimethyl-1-oxobutan-2-ol;

N-1-{(1S)-1-cyclopropyl-2-[(2S)-4-(2,5-difluorophenyl)-2-phenyl-2,5-dihydro-1H-pyrrol-1-yl]-2-oxoethyl}-N-2,N-2-dimethylglycinamide;

N-1-{(1S)-1-cyclopropyl-2-[(2S)-4-(2,5-difluorophenyl)-2-phenyl-2,5-dihydro-1H-pyrrol-1-yl]-2-oxoethyl}-N-2-methylglycinamide;

N-1-{(1S)-1-cyclopropyl-2-[(2S)-4-(2,5-difluorophenyl)-2-phenyl-2,5-dihydro-1H-pyrrol-1-yl]-2-oxoethyl}glycinamide;

N-1-{(1S)-1-cyclopropyl-2-[(2S)-4-(2,5-difluorophenyl)-2-phenyl-2,5-dihydro-1H-pyrrol-1-yl]-2-oxoethyl}-2-methylalaninamide;

N-1-{(1S)-1-tert-butyl-2-[(2S)-4-(2,5-difluorophenyl)-2-phenyl-2,5-dihydro-1H-pyrrol-1-yl]-2-oxoethyl}glycinamide;

N-1-{(1S)-1-tert-butyl-2-[(2S)-4-(2,5-difluorophenyl)-2-phenyl-2,5-dihydro-1H-pyrrol-1-yl]-2-oxoethyl}-N-2,N-2-dimethylglycinamide;

N-1-{(1S)-1-tert-butyl-2-[(2S)-4-(2,5-difluorophenyl)-2-phenyl-2,5-dihydro-1H-pyrrol-1-yl]-2-oxoethyl}-N-2,N-2-dimethylglycinamide, N-oxide;

N-1-{(1S)-1-tert-butyl-2-[(2S)-4-(2,5-difluorophenyl)-2-phenyl-2,5-dihydro-1H-pyrrol-1-yl]-2-oxoethyl}-2-methylalaninamide;

N-1-{(1S)-1-cyclopropyl-2-[(2S)-4-(2,5-difluorophenyl)-2-phenyl-2,5-dihydro-1H-pyrrol-1-yl]-2-oxoethyl}-N-2-,N-2-dimethylglycinamide n-oxide;

N-{(1S)-1-cyclopropyl-2-[(2S)-4-(2,5-difluorophenyl)-2-phenyl-2,5-dihydro-1H-pyrrol-1-yl]-2-oxoethyl}-2-pyrrolidin-1-ylacetamide;

2-azetidin-1-yl-N-{(1S)-1-cyclopropyl-2-[(2S)-4-(2,5-difluorophenyl)-2-phenyl-2,5-dihydro-1H-pyrrol-1-yl]-2-oxoethyl}acetamide;

N-{(1S)-1-cyclopropyl-2-[(2S)-4-(2,5-difluorophenyl)-2-phenyl-2,5-dihydro-1H-pyrrol-1-yl]-2-oxoethyl}-2-morpholin-4-ylacetamide;

N-{(1S)-1-cyclopropyl-2-[(2S)-4-(2,5-difluorophenyl)-2-phenyl-2,5-dihydro-1H-pyrrol-1-yl]-2-oxoethyl}-2-piperazin-1-ylacetamide;

N-{(1S)-1-cyclopropyl-2-[(2S)-4-(2,5-difluorophenyl)-2-phenyl-2,5-dihydro-1H-pyrrol-1-yl]-2-oxoethyl}-2-(4-methylpiperazin-1-yl)acetamide;

2-azetidin-1-yl-N-{(1S)-1-tert-butyl-2-[(2S)-4-(2,5-difluorophenyl)-2-phenyl-2,5-dihydro-1H-pyrrol-1-yl]-2-oxoethyl}acetamide;

N-{(1S)-1-tert-butyl-2-[(2S)-4-(2,5-difluorophenyl)-2-phenyl-2,5-dihydro-1H-pyrrol-1-yl]-2-oxoethyl}-2-pyrrolidin-1-ylacetamide;

N-{(1S)-1-tert-butyl-2-[(2S)-4-(2,5-difluorophenyl)-2-phenyl-2,5-dihydro-1H-pyrrol-1-yl]-2-oxoethyl}-2-piperidin-1-ylacetamide;

N-{(1S)-1-tert-butyl-2-[(2S)-4-(2,5-difluorophenyl)-2-phenyl-2,5-dihydro-1H-pyrrol-1-yl]-2-oxoethyl}-2-morpholin-4-ylacetamide;

N-1-{(1S)-1-tert-butyl-2-[(2S)-4-(2,5-difluorophenyl)-2-phenyl-2,5-dihydro-1H-pyrrol-1-yl]-2-oxoethyl}-N-2-(2-hydroxyethyl)glycinamide;

N-{(1S)-1-tert-butyl-2-[(2S)-4-(2,5-difluorophenyl)-2-phenyl-2,5-dihydro-1H-pyrrol-1-yl]-2-oxoethyl}-2-(4-methylpiperazin-1-yl)acetamide;

N-1-{(1S)-1-cyclopropyl-2-[(2S)-4-(2,5-difluorophenyl)-2-phenyl-2,5-dihydro-1H-pyrrol-1-yl]-2-oxoethyl}-N-2-isopropylglycinamide;

N-{(1S)-1-cyclopropyl-2-[(2S)-4-(2,5-difluorophenyl)-2-phenyl-2,5-dihydro-1H-pyrrol-1-yl]-2-oxoethyl}acetamide;

N-1-{(1S)-1-tert-butyl-2-[(2S)-4-(2,5-difluorophenyl)-2-phenyl-2,5-dihydro-1H-pyrrol-1-yl]-2-oxoethyl}-N-2-ethylglycinamide;

N-{(1S)-1-cyclopropyl-2-[(2S)-4-(2,5-difluorophenyl)-2-phenyl-2,5-dihydro-1H-pyrrol-1-yl]-2-oxoethyl}-2-hydroxyacetamide;

N-{(S)-1-cyclopropyl-2-[(2S)-4-(2,5-difluorophenyl)-2-phenyl-2,5-dihydro-1H-pyrrol-1-yl]-2-oxoethyl}piperazine-1-carboxamide;

N-{(1S)-1-cyclopropyl-2-[(2S)-4-(2,5-difluorophenyl)-2-phenyl-2,5-dihydro-1H-pyrrol-1-yl]-2-oxoethyl}-N'-piperidin-4-ylurea;

4-amino-N-{(1S)-1-cyclopropyl-2-[(2S)-4-(2,5-difluorophenyl)-2-phenyl-2,5-dihydro-1H-pyrrol-1-yl]-2-oxoethyl}piperidine-1-carboxamide;

N-(2-aminoethyl)-N'-{(1S)-1-cyclopropyl-2-[(2S)-4-(2,5-difluorophenyl)-2-phenyl-2,5-dihydro-1H-pyrrol-1-yl]-2-oxoethyl}urea;

N-{(1S)-1-cyclopropyl-2-[(2S)-4-(2,5-difluorophenyl)-2-phenyl-2,5-dihydro-1H-pyrrol-1-yl]-2-oxoethyl}-N'-(3-morpholin-4-ylpropyl)urea;

N-{(1S)-1-cyclopropyl-2-[(2S)-4-(2,5-difluorophenyl)-2-phenyl-2,5-dihydro-1H-pyrrol-1-yl]-2-oxoethyl}-N'-[2-(dimethylamino)ethyl]urea;

2-azetidin-1-yl-N-{(1S)-1-cyclopropyl-2-[(2S)-4-(2,5-difluorophenyl)-2-phenyl-2,5-dihydro-1H-pyrrol-1-yl]-2-oxoethyl}ethanesulfonamide N-{(1S)-1-cyclopropyl-2-[(2S)-4-(2,5-difluorophenyl)-2-phenyl-2,5-dihydro-1H-pyrrol-1-yl]-2-oxoethyl}-2-(isopropylamino)ethanesulfonamide;

N-{(1S)-1-cyclopropyl-2-[(2S)-4-(2,5-difluorophenyl)-2-phenyl-2,5-dihydro-1H-pyrrol-1-yl]-2-oxoethyl}-2-pyrrolidin-1-ylethanesulfonamide;

N-{(1S)-1-cyclopropyl-2-[(2S)-4-(2,5-difluorophenyl)-2-phenyl-2,5-dihydro-1H-pyrrol-1-yl]-2-oxoethyl}-2-morpholin-ylethanesulfonamide;

N-{(1S)-1-cyclopropyl-2-[(2S)-4-(2,5-difluorophenyl)-2-phenyl-2,5-dihydro-1H-pyrrol-1-yl]-2-oxoethyl}-2-piperazin-1-ylethanesulfonamide;

N-{(1S)-1-cyclopropyl-2-[(2S)-4-(2,5-difluorophenyl)-2-phenyl-2,5-dihydro-1H-pyrrol-1-yl]-2-oxoethyl}-2-(4-methylpiperazin-1-yl)ethanesulfonamide;

N-(tert-butyl)-2-[(2S)-4-(2,5-difluorophenyl)-2-phenyl-2,5-dihydro-1H-pyrrol-1-yl]acetamide;

2-[(2S)-4-(2,5-difluorophenyl)-2-phenyl-2,5-dihydro-1H-pyrrol-1-yl]-N-isopropylacetamide;

(2S)-1-(2-azetidin-1-yl-2-oxoethyl)-4-(2,5-difluorophenyl)-2-phenyl-2,5-dihydro-1H-pyrrole;

(2S)-4-(2,5-difluorophenyl)-1-(2-oxo-2-pyrrolidin-1-ylethyl)-2-phenyl-2,5-dihydro-1H-pyrrole;

4-{[(2S)-4-(2,5-difluorophenyl)-2-phenyl-2,5-dihydro-1H-pyrrol-1-yl]acetyl}morpholine;

1-{[(2S)-4-(2,5-difluorophenyl)-2-phenyl-2,5-dihydro-1H-pyrrol-1-yl]acetyl}piperazine;

1-{[(2S)-4-(2,5-difluorophenyl)-2-phenyl-2,5-dihydro-1H-pyrrol-1-yl]acetyl}-4-methylpiperazine;

2-[(2S)-4-(2,5-difluorophenyl)-2-phenyl-2,5-dihydro-1H-pyrrol-1-yl]-N-isopropylbutanamide;

4-{2-[(2S)-4-(2,5-difluorophenyl)-2-phenyl-2,5-dihydro-1H-pyrrol-1-yl]butanoyl}morpholine;

2-[(2S)-4-(2,5-difluorophenyl)-2-phenyl-2,5-dihydro-1H-pyrrol-1-yl]-N-ethylacetamide;

N-cyclobutyl-2-[(2S)-4-(2,5-difluorophenyl)-2-phenyl-2,5-dihydro-1H-pyrrol-1-yl]acetamide;

2-[(2S)-4-(2,5-difluorophenyl)-2-phenyl-2,5-dihydro-1H-pyrrol-1-yl]-N-ethylpropanamide;

N-cyclobutyl-2-[(2S)-4-(2,5-difluorophenyl)-2-phenyl-2,5-dihydro-1H-pyrrol-1-yl]propanamide;

2-[(2S)-4-(2,5-difluorophenyl)-2-phenyl-2,5-dihydro-1H-pyrrol-1-yl]-N-methylpropanamide;

2-[(2S)-4-(2,5-difluorophenyl)-2-phenyl-2,5-dihydro-1H-pyrrol-1-yl]-N-isopropylpropanamide;

N-(tert-butyl)-2-[(2S)-4-(2,5-difluorophenyl)-2-phenyl-2,5-dihydro-1H-pyrrol-1-yl]propanamide;

4-{2-[(2S)-4-(2,5-difluorophenyl)-2-phenyl-2,5-dihydro-1H-pyrrol-1-yl]propanoyl}morpholine;

(3S)-3-amino-4-[(2S)-4-(2,5-difluorophenyl)-2-phenyl-2,5-dihydro-1H-pyrrol-1-yl]-N-ethyl-2,2-dimethyl-4-oxobutanamide;

(3S)-3-amino-4-[(2S)-4-(2,5-difluorophenyl)-2-phenyl-2,5-dihydro-1H-pyrrol-1-yl]-2,2-dimethyl-4-oxo-N-piperidin-4-ylbutanamide;

(3S)-3-amino-4-[(2S)-4-(2,5-difluorophenyl)-2-phenyl-2,5-dihydro-1H-pyrrol-1-yl]-2,2-dimethyl-4-oxobutanoic acid;

(3S)-3-amino-4-[(2S)-4-(2,5-difluorophenyl)-2-phenyl-2,5-dihydro-1H-pyrrol-1-yl]-N,N,2,2-tetramethyl-4-oxobutanamide;

(1S)-1-{[(2S)-4-(2,5-difluorophenyl)-2-phenyl-2,5-dihydro-1H-pyrrol-1-yl]carbonyl}-2,2-dimethyl-3-oxo-3-piperazin-1-ylpropylamine;

(3S)-3-amino-4-[(2S)-4-(2,5-difluorophenyl)-2-phenyl-2,5-dihydro-1H-pyrrol-1-yl]-N-isopropyl-2,2-dimethyl-4-oxobutanamide;

(3S)-3-amino-4-[(2S)-4-(2,5-difluorophenyl)-2-phenyl-2,5-dihydro-1H-pyrrol-1-yl]-N,2,2-trimethyl-4-oxobutanamide;

(3R)-3-amino-4-[(2S)-4-(2,5-difluorophenyl)-2-phenyl-2,5-dihydro-1H-pyrrol-1-yl]-N,N,2,2-tetramethyl-4-oxobutanamide;

(3R)-3-amino-4-[(2S)-4-(2,5-difluorophenyl)-2-phenyl-2,5-dihydro-1H-pyrrol-1-yl]-2,2-dimethyl-4-oxobutanoic acid;

(1R)-1-{[(2S)-4-(2,5-difluorophenyl)-2-phenyl-2,5-dihydro-1H-pyrrol-1-yl]carbonyl}-2,2-dimethyl-3-oxo-3-piperazin-1-ylpropylamine;

2-({(1S)-1-tert-butyl-2-[(2S)-4-(2,5-difluorophenyl)-2-phenyl-2,5-dihydro-1H-pyrrol-1-yl]-2-oxoethyl}amino)-N-ethylacetamide;

2-({(1S)-1-tert-butyl-2-[(2S)-4-(2,5-difluorophenyl)-2-phenyl-2,5-dihydro-1H-pyrrol-1-yl]-2-oxoethyl}amino)-N-methylacetamide;

2-({(1S)-1-tert-butyl-2-[(2S)-4-(2,5-difluorophenyl)-2-phenyl-2,5-dihydro-1H-pyrrol-1-yl]-2-oxoethyl}amino)-N,N-dimethylacetamide;

2-({(1S)-1-tert-butyl-2-[(2S)-4-(2,5-difluorophenyl)-2-phenyl-2,5-dihydro-1H-pyrrol-1-yl]-2-oxoethyl}amino)-N-methyl-N-ethylacetamide;

2-({(1S)-1-cyclopropyl-2-[(2S)-4-(2,5-difluorophenyl)-2-phenyl-2,5-dihydro-1H-pyrrol-1-yl]-2-oxoethyl}amino)-N-methylacetamide;

2-({(1S)-1-cyclopropyl-2-[(2S)-4-(2,5-difluorophenyl)-2-phenyl-2,5-dihydro-1H-pyrrol-1-yl]-2-oxoethyl}amino)-N-ethylacetamide;

2-({(1S)-1-cyclopropyl-2-[(2S)-4-(2,5-difluorophenyl)-2-phenyl-2,5-dihydro-1H-pyrrol-1-yl]-2-oxoethyl}amino)-N,N-dimethylacetamide;

2-({(1S)-1-cyclopropyl-2-[(2S)-4-(2,5-difluorophenyl)-2-phenyl-2,5-dihydro-1H-pyrrol-1-yl]-2-oxoethyl}amino)-N-isopropylacetamide;

2-({(1S)-1-cyclopropyl-2-[(2S)-4-(2,5-difluorophenyl)-2-phenyl-2,5-dihydro-1H-pyrrol-1-yl]-2-oxoethyl}amino)-N-ethyl-N-methylacetamide;
2-({(1S)-1-cyclopropyl-2-[(2S)-4-(2,5-difluorophenyl)-2-phenyl-2,5-dihydro-1H-pyrrol-1-yl]-2-oxoethyl}amino)-N,N-diethylacetamide;
(1S)-1-cyclopropyl-2-[(2S)-4-(2,5-difluorophenyl)-2-phenyl-2,5-dihydro-1H-pyrrol-1-yl]-2-oxo-N-(2-oxo-2-pyrrolidin-1-ylethyl)ethanamine;
(1S)-1-cyclopropyl-2-[(2S)-4-(2,5-difluorophenyl)-2-phenyl-2,5-dihydro-1H-pyrrol-1-yl]-N-(2-morpholin-4-yl-2-oxoethyl)-2-oxoethanamine;
1-[({(1S)-1-cyclopropyl-2-[(2S)-4-(2,5-difluorophenyl)-2-phenyl-2,5-dihydro-1H-pyrrol-1-yl]-2-oxoethyl}amino)acetyl]piperidin-4-ol;
(1S)-1-cyclopropyl-2-[(2S)-4-(2,5-difluorophenyl)-2-phenyl-2,5-dihydro-1H-pyrrol-1-yl]-N-[2-(4-methylpiperazin-1-yl)-2-oxoethyl]-2-oxoethanamine;
(1S)-N-(2-azetidin-1-yl-2-oxoethyl)-1-cyclopropyl-2-[(2S)-4-(2,5-difluorophenyl)-2-phenyl-2,5-dihydro-1H-pyrrol-1-yl]-2-oxoethanamine;
(1S)-1-cyclopropyl-2-[(2S)-4-(2,5-difluorophenyl)-2-phenyl-2,5-dihydro-1H-pyrrol-1-yl]-N-[2-(1,1-dioxidothiomorpholin-4-yl)-2-oxoethyl]-2-oxoethanamine;
(1S)-N-[2-(4-acetylpiperazin-1-yl)-2-oxoethyl]-1-cyclopropyl-2-[(2S)-4-(2,5-difluorophenyl)-2-phenyl-2,5-dihydro-1H-pyrrol-1-yl]-2-oxoethanamine;
(1S)-1-tert-butyl-2-[(2S)-4-(2,5-difluorophenyl)-2-phenyl-2,5-dihydro-1H-pyrrol-1-yl]-N-(2-morpholinyl-2-oxoethyl)-2-oxoethanamine;
(1S)-1-tert-butyl-2-[(2S)-4-(2,5-difluorophenyl)-2-phenyl-2,5-dihydro-1H-pyrrol-1-yl]-2-oxo-N-(2-oxo-2-pyrrolidin-1-ylethyl)ethanamine;
2-({(1S)-1-tert-butyl-2-[(2S)-4-(2,5-difluorophenyl)-2-phenyl-2,5-dihydro-1H-pyrrol-1-yl]-2-oxoethyl}amino)-N-isopropylacetamide;
2-(dimethylamino)ethyl(1S)-1-cyclopropyl-2-[(2S)-4-(2,5-difluorophenyl)-2-phenyl-2,5-dihydro-1H-pyrrol-1-yl]-2-oxoethylcarbamate;
1-methylpiperidin-4-yl(1S)-1-cyclopropyl-2-[(2S)-4-(2,5-difluorophenyl)-2-phenyl-2,5-dihydro-1H-pyrrol-1-yl]-2-oxoethylcarbamate;
(2S)-4-cyclopropyl-N,N-dimethyl-2-phenyl-2,5-dihydro-1H-pyrrole-1-carboxamide;
(2S)-4-cyclopentyl-N,N-dimethyl-2-phenyl-2,5-dihydro-1H-pyrrole-1-carboxamide;
(1S)-1-cyclopropyl-2-[(2S)-4-(2,5-difluorophenyl)-2-phenyl-2,5-dihydro-1H-pyrrol-1-yl]-2-oxoethyl 4-methylpiperazine-1-carboxylate;
1-cyclopropyl-2-[(2S)-4-(2,5-difluorophenyl)-2-phenyl-2,5-dihydro-1H-pyrrol-1-yl]-2-oxoethyl-2-morpholin-4-ylethylcarbamate;
N-[({(1S)-1-cyclopropyl-2-[(2S)-4-(2,5-difluorophenyl)-2-phenyl-2,5-dihydro-1H-pyrrol-1-yl]-2-oxoethyl}oxy)carbonyl]glycine;
(1S)-1-cyclopropyl-2-[(2S)-4-(2,5-difluorophenyl)-2-phenyl-2,5-dihydro-1H-pyrrol-1-yl]-2-oxoethyl 1-methylpiperidin-4-ylcarbamate;
(1S)-1-cyclopropyl-2-[(2S)-4-(2,5-difluorophenyl)-2-phenyl-2,5-dihydro-1H-pyrrol-1-yl]-2-oxoethylmethyl(1-methylpiperidin-4-yl)carbamate;
(1S)-1-cyclopropyl-2-[(2S)-4-(2,5-difluorophenyl)-2-phenyl-2,5-dihydro-1H-pyrrol-1-yl]-2-oxoethyl-4-dimethylamino)piperidine-1-carboxylate;
tert-butyl (2S)-4-(2-chloro-5-fluoropyrimidin-4-yl)-2-phenyl-2,5-dihydro-1H-pyrrole-1-carboxylate;

(2S)-4-(5-fluoro-2-methylpyrimidin-4-yl)-N,N-dimethyl-2-phenyl-2,5-dihydro-1H-pyrrole-1-carboxamide;
(2S)-4-(2-chloro-5-fluoropyrimidin-4-yl)-N,N-dimethyl-2-phenyl-2,5-dihydro-1H-pyrrole-1-carboxamide;
(2S)-4-(4-chloro-5-methylpyrimidin-2-yl)-N,N-dimethyl-2-phenyl-2,5-dihydro-1H-pyrrole-1-carboxamide;
(2S)-4-(6-chloropyrimidin-4-yl)-N,N-dimethyl-2-phenyl-2,5-dihydro-1H-pyrrole-1-carboxamide;
(2S)-4-(2-chloropyrimidin-4-yl)-N,N-dimethyl-2-phenyl-2,5-dihydro-1H-pyrrole-1-carboxamide;
(2S)-N,N-dimethyl-4-(4-methylpyridin-3-yl)-2-phenyl-2,5-dihydro-1H-pyrrole-1-carboxamide;
(2S)-N,N-dimethyl-2-phenyl-4-(1,3-thiazol-2-yl)-2,5-dihydro-1H-pyrrole-1-carboxamide;
(2S)-N,N-dimethyl-2-phenyl-4-(1,3-thiazol-4-yl)-2,5-dihydro-1H-pyrrole-1-carboxamide;
(2S)-N,N-dimethyl-2-phenyl-4-(1,2-thiazol-5-yl)-2,5-dihydro-1H-pyrrole-1-carboxamide;
4-(2,5-difluorophenyl)-2-(3-hydroxyphenyl)-N,N-dimethyl-2,5-dihydro-1H-pyrrole-1-carboxamide;
(2S)-4-(2,5-difluorophenyl)-2-(3-hydroxyphenyl)-N,N-dimethyl-2,5-dihydro-1H-pyrrole-1-carboxamide;
(2S)-4-(2,5-difluorophenyl)-N-(2-hydroxyethyl)-N-methyl-2-phenyl-2,5-dihydro-1H-pyrrole-1-carboxamide;
N-{[4-(2,5-difluorophenyl)-2-(3-hydroxyphenyl)-2,5-dihydro-1H-pyrrol-1-yl]carbonyl}-N-methyl-beta-alanine;
methyl N-{[4-(2,5-difluorophenyl)-2-(3-hydroxyphenyl)-2,5-dihydro-1H-pyrrol-1-yl]carbonyl}-N-methyl-beta-alaninate;
4-{[4-(2,5-difluorophenyl)-2-(3-hydroxyphenyl)-2,5-dihydro-1H-pyrrol-1-yl]acetyl}morpholin-4-ium;
3-[(2S)-4-(2,5-difluorophenyl)-1-(2-hydroxy-2-methylpropanoyl)-2,5-dihydro-1H-pyrrol-2-yl]phenol;
4-(2,5-difuorophenyl)-2-(3-hydroxyphenyl)-N,N-dimethyl-2,5-dihydro-1H-pyrrole-1-sulfonamide;
3-[4-(2,5-difluorophenyl)-1-(methylsulfonyl)-2,5-dihydro-1H-pyrrol-2-yl]phenol;
3-[4-(2,5-difluorophenyl)-1-(morpholin-4-ylcarbonyl)-2,5-dihydro-1H-pyrrol-2-yl]phenol;
3-[4-(2,5-difluorophenyl)-1-(2,2-dimethylpropanoyl)-2,5-dihydro-1H-pyrrol-2-yl]phenol;
(2S)-4-(2,5-difluorophenyl)-1-[(methylsulfonyl)acetyl]-2-phenyl-2,5-dihydro-1H-pyrrole;
(2S)-4-(2,5-difluorophenyl)-2-phenyl-1-[(phenylsulfonyl)acetyl]-2,5-dihydro-1H-pyrrole;
3-[(2S)-1-[(2S)-2-cyclopropyl-2-hydroxyethanoyl]-4-(2,5-difluorophenyl)-2,5-dihydro-1H-pyrrol-2-yl]phenol;
3-{(2S)-4-(2,5-difluorophenyl)-1-[(2S)-2-hydroxy-3,3-dimethylbutanoyl]-2,5-dihydro-1H-pyrrol-2-yl}phenol;
(1S)-1-cyclopropyl-2-[(2S)-4-(2,5-difluorophenyl)-2-phenyl-2,5-dihydro-1H-pyrrol-1-yl]-2-oxoethanol;
(2S)-4-(2,5-difluorophenyl)-2-(3-hydroxyphenyl)-N-methyl-N-tetrahydrofuran-3-yl-2,5-dihydro-1H-pyrrole-1-carboxamide;
(2S)-4-(2,5-difluorophenyl)-2-(3-hydroxyphenyl)-N-(2-methoxyethyl)-N-methyl-2,5-dihydro-1H-pyrrole-1-carboxamide;
(2S)-4-(2,5-difluorophenyl)-2-(3-hydroxyphenyl)-N-methyl-N-tetrahydro-2H-pyran-4-yl-2,5-dihydro-1H-pyrrole-1-carboxamide;
3-[(2S)-4-(2,5-difluorophenyl)-1-(piperidin-1-ylcarbonyl)-2,5-dihydro-1H-pyrrol-2-yl]phenol;
4-(2,5-difluorophenyl)-N-[1-(2-fluoroethyl)piperidin-4-yl]-2-(3-hydroxyphenyl)-N-methyl-2,5-dihydro-1H-pyrrole-1-carboxamide;

4-[{[4-(2,5-difluorophenyl)-2-(3-hydroxyphenyl)-2,5-dihydro-1H-pyrrol-1-yl]carbonyl}(methyl)amino]piperidinium trifluoroacetate;

2-[{[4-(2,5-difluorophenyl)-2-(3-hydroxyphenyl)-2,5-dihydro-1H-pyrrol-1-yl]carbonyl}(methyl)amino]ethyl 4-methylpiperazine-1-carboxylate;

3-{4-(2,5-difluorophenyl)-1-[(4-methylpiperazin-1-yl)carbonyl]-2,5-dihydro-1H-pyrrol-2-yl}phenol;

2-[{[4-(2,5-difluorophenyl)-2-(3-hydroxyphenyl)-2,5-dihydro-1H-pyrrol-1-yl]carbonyl}(methyl)amino]ethyl morpholine-4-carboxylate;

4-(2,5-difluorophenyl)-2-(3-hydroxyphenyl)-N-methyl-N-[(1-methyl-1H-pyrazol-4-yl)methyl]-2,5-dihydro-1H-pyrrole-1-carboxamide;

4-(2,5-difluorophenyl)-2-(3-hydroxyphenyl)-N-(isoxazol-5-ylmethyl)-N-methyl-2,5-dihydro-1H-pyrrole-1-carboxamide;

2-[{[4-(2,5-difluorophenyl)-2-(3-hydroxyphenyl)-2,5-dihydro-1H-pyrrol-1-yl]carbonyl}(methyl)amino]ethyl dimethylaminocarboxylate;

2-[{[4-(2,5-difluorophenyl)-2-(3-hydroxyphenyl)-2,5-dihydro-1H-pyrrol-1-yl]carbonyl}(methyl)amino]ethyl piperidine-1-carboxylate;

4-(2,5-difluorophenyl)-2-(3-hydroxyphenyl)-N-methyl-N-[2-(2-oxopyrrolidin-1-yl)ethyl]-2,5-dihydro-1H-pyrrole-1-carboxamide;

4-(2,5-difluorophenyl)-2-(3-hydroxyphenyl)-N-methyl-N-[(5-oxo-4,5-dihydro-1H-1,2,4-triazol-3-yl)methyl]-2,5-dihydro-1H-pyrrole-1-carboxamide;

4-(2,5-difluorophenyl)-2-(3-hydroxyphenyl)-N-methyl-N-(tetrahydro-2H-pyran-4-ylmethyl)-2,5-dihydro-1H-pyrrole-1-carboxamide;

4-(2,5-difluorophenyl)-2-(3-hydroxyphenyl)-N-{[5-(methoxymethyl)-1H-pyrazol-3-yl]methyl}-N-methyl-2,5-dihydro-1H-pyrrole-1-carboxamide;

4-(2,5-difluorophenyl)-2-(3-hydroxyphenyl)-N-methyl-N-(1,3-thiazol-4-ylmethyl)-2,5-dihydro-1H-pyrrole-1-carboxamide;

4-(2,5-difluorophenyl)-2-(3-hydroxyphenyl)-N-methyl-N-[(4-methyl-1,2,5-oxadiazol-3-yl)methyl]-2,5-dihydro-1H-pyrrole-1-carboxamide;

4-(2,5-difluorophenyl)-2-(3-hydroxyphenyl)-N-methyl-N-(1,3-thiazol-2-ylmethyl)-2,5-dihydro-1H-pyrrole-1-carboxamide;

4-(2,5-difluorophenyl)-2-(3-hydroxyphenyl)-N-(isoxazol-3-ylmethyl)-N-methyl-2,5-dihydro-1H-pyrrole-1-carboxamide;

4-(2,5-difluorophenyl)-2-(3-hydroxyphenyl)-N-methyl-N-[2-(1H-1,2,4-triazol-1-yl)ethyl]-2,5-dihydro-1H-pyrrole-1-carboxamide;

4-(2,5-difluorophenyl)-2-(3-hydroxyphenyl)-N-methyl-N-[2-(1H-pyrazol-1-yl)ethyl]-2,5-dihydro-1H-pyrrole-1-carboxamide;

4-(2,5-difluorophenyl)-2-(3-hydroxyphenyl)-N-methyl-N-[(1-methyl-5-oxopyrrolidin-2-yl)methyl]-2,5-dihydro-1H-pyrrole-1-carboxamide;

4-(2,5-difluorophenyl)-2-(3-hydroxyphenyl)-N-(1-isoxazol-3-ylethyl)-N-methyl-2,5-dihydro-1H-pyrrole-1-carboxamide;

4-(2,5-difluorophenyl)-N-(1,3-dioxolan-2-ylmethyl)-2-(3-hydroxyphenyl)-N-methyl-2,5-dihydro-1H-pyrrole-1-carboxamide;

4-(2,5-difluorophenyl)-N-(1,4-dioxan-2-ylmethyl)-2-(3-hydroxyphenyl)-N-methyl-2,5-dihydro-1H-pyrrole-1-carboxamide;

4-(2,5-difluorophenyl)-2-(3-hydroxyphenyl)-N-methyl-N-[(5-methyl-1,3,4-oxadiazol-2-yl)methyl]-2,5-dihydro-1H-pyrrole-1-carboxamide;

4-(2,5-difluorophenyl)-2-(3-hydroxyphenyl)-N-methyl-N-[2-(methylsulfonyl)ethyl]-2,5-dihydro-1H-pyrrole-1-carboxamide;

2-[{[4-(2,5-difluorophenyl)-2-(3-hydroxyphenyl)-2,5-dihydro-1H-pyrrol-1-yl]carbonyl}(methyl)amino]ethanesulfonic acid;

2-hydroxyethyl(1S)-1-{[(2S) (2,5-difluorophenyl)-2-phenyl-2,5-dihydro-1H-pyrrol-1-yl]carbonyl}-2,2-dimethylpropylcarbamate;

3-hydroxypropyl(1S)-1-{[(2S)-4-(2,5-difluorophenyl)-2-phenyl-2,5-dihydro-1H-pyrrol-1-yl]carbonyl}-2,2-dimethylpropylcarbamate;

2-hydroxyethyl {(1S)-1-isopropyl-2-[(2S)-4-(2,5-difluorophenyl)-2-phenyl-2,5-dihydro-1H-pyrrol-1-yl]-2-oxoethyl}carbamate;

2-hydroxyethyl {(1S)-1-cyclopropyl-2-[(2S)-4-(2,5-difluorophenyl)-2-phenyl-2,5-dihydro-1H-pyrrol-1-yl]-2-oxoethyl}carbamate;

4-hydroxybutyl(1S)-1-{[(2S)-4-(2,5-difluorophenyl)-2-phenyl-2,5-dihydro-1H-pyrrol-1-yl]carbonyl}-2,2-dimethylpropylcarbamate;

(2S)-4-(2,5-difluorophenyl)-1-[2-(methylsulfonyl)ethyl]-2-phenyl-2,5-dihydro-1H-pyrrole;

(2S)-4-(2,5-difluorophenyl)-1-[2-(ethylsulfonyl)ethyl]-2-phenyl-2,5-dihydro-1H-pyrrole;

1-[(2S)-4-(2,5-difluorophenyl)-2-phenyl-2,5-dihydro-1H-pyrrol-1-yl]pentan-3-one;

4-[(2S)-4-(2,5-difluorophenyl)-2-phenyl-2,5-dihydro-1H-pyrrol-1-yl]butan-2-one;

4-[(2S)-4-(2,5-difluorophenyl)-2-phenyl-2,5-dihydro-1H-pyrrol-1-yl]-3-methylbutan-2-one;

2-[(2S)-4-(2,5-difluorophenyl)-2-phenyl-2,5-dihydro-1H-pyrrol-1-yl]-N,N-dimethylethanesulfonamide;

3-{(2S)-4-(2,5-difluorophenyl)-1-[2-(methylsulfonyl)ethyl]-2,5-dihydro-1H-pyrrol-2-yl}phenol;

(2S)-4-(2,5-difluorophenyl)-1-[2-(ethylsulfonyl)propyl]-2-phenyl-2,5-dihydro-1H-pyrrole;

3-[(2S)-4-(2,5-difluorophenyl)-2-phenyl-2,5-dihydro-1H-pyrrol-1-yl]-N-methylpropanamide;

3-[(2S)-4-(2,5-difluorophenyl)-2-phenyl-2,5-dihydro-1H-pyrrol-1-yl]-N,N-dimethylpropanamide;

3-[(2S)-4-(2,5-difluorophenyl)-2-phenyl-2,5-dihydro-1H-pyrrol-1-yl]-N,N,2-trimethylpropanamide;

4-{3-[(2S)-4-(2,5-difluorophenyl)-2-phenyl-2,5-dihydro-1H-pyrrol-1-yl]propanoyl}morpholine;

1-{3-[(2S)-4-(2,5-difluorophenyl)-2-phenyl-2,5-dihydro-1H-pyrrol-1-yl]propanoyl}4-(methylsulfonyl)piperazine;

1-{3-[(2S)-4-(2,5-difluorophenyl)-2-phenyl-2,5-dihydro-1H-pyrrol-1-yl]propanoyl}piperidin-4-ol;

methyl 3-[(2S)-4-(2,5-difluorophenyl)-2-phenyl-2,5-dihydro-1H-pyrrol-1-yl]propanoate;

2-({(1S)-1-cyclopropyl-2-[(2S)-4-(2,5-difluorophenyl)-2-phenyl-2,5-dihydro-1H-pyrrol-1-yl]-2-oxoethyl}oxy)-N-ethylacetamide;

4-({(1S)-1-cyclopropyl-2-[(2S)-4-(2,5-difluorophenyl)-2-phenyl-2,5-dihydro-1H-pyrrol-1-yl]-2-oxoethoxy}acetyl)morpholine;

2-{(1S)-1-cyclopropyl-2-[(2S)-4-(2,5-difluorophenyl)-2-phenyl-2,5-dihydro-1H-pyrrol-1-yl]-2-oxoethoxy}-N-(2-hydroxyethyl)acetamide;

1-({(1S)-1-cyclopropyl-2-[(2S)-4-(2,5-difluorophenyl)-2-phenyl-2,5-dihydro-1H-pyrrol-1-yl]-2-oxoethoxy}acetyl)-4-methylpiperazine;

1-({(1S)-1-cyclopropyl-2-[(2S)-4-(2,5-difluorophenyl)-2-phenyl-2,5-dihydro-1H-pyrrol-1-yl]-2-oxoethoxy}acetyl) piperazine;
2-{(1S)-1-cyclopropyl-2-[(2S)-4-(2,5-difluorophenyl)-2-phenyl-2,5-dihydro-1H-pyrrol-1-yl]-2-oxoethoxy}-N-piperidin-4-ylacetamide;
1-({(1S)-1-cyclopropyl-2-[(2S)-4-(2,5-difluorophenyl)-2-phenyl-2,5-dihydro-1H-pyrrol-1-yl]-2-oxoethoxy}acetyl) piperidin-4-amine;
N-{(1S)-1-cyclopropyl-2-[(2S)-4-(2,5-difluorophenyl)-2-phenyl-2,5-dihydro-1H-pyrrol-1-yl]-2-oxoethyl}-3-morpholin-4-yl-3-oxopropan-1-amine;
$N^3$-{(1S)-1-cyclopropyl-2-[(2S)-4-(2,5-difluorophenyl)-2-phenyl-2,5-dihydro-1H-pyrrol-1-yl]-2-oxoethyl}-$N^1,N^1$-dimethyl-β-alaninamide;
((1S)-1-{[(2S)-4-(2,5-difluorophenyl)-2-phenyl-2,5-dihydro-1H-pyrrol-1-yl]carbonyl}-2,2-dimethylpropyl)(3-morpholinyl-3-oxopropyl)amine;

or a pharmaceutically acceptable salt or stereoisomer thereof.

Particular examples of the compounds of the instant invention are:
(−)-4-(2,5-difluorophenyl)-N,N-dimethyl-2-phenyl-2,5-dihydro-1H-pyrrole-1-carboxamide;
4-(5-chloro-2-fluorophenyl)-N,N-dimethyl-2-phenyl-2,5-dihydro-1H-pyrrole-1-carboxamide;
4-(2,5-difluorophenyl)-1-(isopropylsulfonyl)-2-phenyl-2,5-dihydro-1H-pyrrole;
1-[4-(2,5-difluorophenyl)-2-phenyl-2,5-dihydro-1H-pyrrol-1-yl]-2-methyl-1-oxopropan-2-ol;
1-[4-(2,5-difluorophenyl)-2-phenyl-2,5-dihydro-1H-pyrrol-1-yl]-2-methyl-1-oxopropan-2-amine;
(1S)-1-{[(2S)-4-(2,5-difluorophenyl)-2-phenyl-2,5-dihydro-1H-pyrrol-1-yl]carbonyl}-2,2-dimethylpropylamine;
(2S)-4-(2,5-difluorophenyl)-N-methyl-2-phenyl-N-piperidin-4-yl-2,5-dihydro-1H-pyrrole-1-carboxamide;

or a pharmaceutically acceptable salt or stereoisomer thereof.

In another embodiment, particular examples of the compounds of the instant invention are:
(1S)-1-cyclopropyl-2-[(2S)-4-(2,5-difluorophenyl)-2-phenyl-2,5-dihydro-1H-pyrrol-1-yl]-2-oxoethanamine;
(2S)-4-(2,5-difluorophenyl)-N-methyl-2-phenyl-N-piperidin-4-yl-2,5-dihydro-1H-pyrrole-1-carboxamide;
(1S)-1-{[(2S)-4-(2,5-difluorophenyl)-2-phenyl-2,5-dihydro-1H-pyrrol-1-yl]carbonyl}-2,2-dimethylpropylamine;
2-({(1S)-1-tert-butyl-2-[(2S)-4-(2,5-difluorophenyl)-2-phenyl-2,5-dihydro-1H-pyrrol-1-yl]-2-oxoethyl}amino)-N-ethylacetamide;
(2S)-4-(2,5-difluorophenyl)-2-(3-hydroxyphenyl)-N,N-dimethyl-2,5-dihydro-1H-pyrrole-1-carboxamide;
(2S)-4-(2,5-difluorophenyl)-N-methyl-N-(1-methylpiperidin-4-yl)-2-phenyl-2,5-dihydro-1H-pyrrole-1-carboxamide; and
(2S)-4-(2,5-difluorophenyl)-2-(3-hydroxyphenyl)-1-L-valyl-2,5-dihydro-1H-pyrrole or a pharmaceutically acceptable salt or stereoisomer thereof.

Further examples of the compounds of the instant invention are the TFA salts of:
2-{[4-(2,5-difluorophenyl)-2-phenyl-2,5-dihydro-1H-pyrrol-1-yl]sulfonyl}-N,N-dimethylethanamine;
1-[4-(2,5-difluorophenyl)-2-phenyl-2,5-dihydro-1H-pyrrol-1-yl]-2-methyl-1-oxopropan-2-amine;
4-(5-chloro-2-fluorophenyl)-2-phenyl-1-(trifluoroacetyl)-2,5-dihydro-1H-pyrrole;
(1S)-1-{[4-(2,5-difluorophenyl)-2-phenyl-2,5-dihydro-1H-pyrrol-1-yl]carbonyl}-2-methylpropylamine;
(1R)-1-{[4-(2,5-difluorophenyl)-2-phenyl-2,5-dihydro-1H-pyrrol-1-yl]carbonyl}-2-methylpropylamine;
4-(2,5-difluorophenyl)-2-phenyl-1-L-prolyl-2,5-dihydro-1H-pyrrole;
4-(2,5-difluorophenyl)-2-phenyl-1-D-prolyl-2,5-dihydro-1H-pyrrole;
(4R)-4-{[4-(2,5-difluorophenyl)-2-phenyl-2,5-dihydro-1H-pyrrol-1-yl]carbonyl}-1,3-thiazolidine;
methyl(3S)-3-amino-4-[4-(2,5-difluorophenyl)-2-phenyl-2,5-dihydro-1H-pyrrol-1-yl]-4-oxobutanoate;
(4S)-4-amino-5-[4-(2,5-difluorophenyl)-2-phenyl-2,5-dihydro-1H-pyrrol-1-yl]-5-oxopentanamide;
(1S)-1-{[4-(2,5-difluorophenyl)-2-phenyl-2,5-dihydro-1H-pyrrol-1-yl]carbonyl}-3-(methylthio)propylamine;
(1S)-1-{[4-(2,5-difluorophenyl)-2-phenyl-2,5-dihydro-1H-pyrrol-1-yl]carbonyl}-3-(methylsulfonyl)propylamine;
(2S)-2-{[4-(2,5-difluorophenyl)-2-phenyl-2,5-dihydro-1H-pyrrol-1-yl]carbonyl}piperidine;
(1S)-1-{[4-(2,5-difluorophenyl)-2-phenyl-2,5-dihydro-1H-pyrrol-1-yl]carbonyl}pentylamine;
(1S)-2-[4-(2,5-difluorophenyl)-2-phenyl-2,5-dihydro-1H-pyrrol-1-yl]-2-oxo-1-(thien-2-ylmethyl)ethylamine;
4-{[4-(2,5-difluorophenyl)-2-phenyl-2,5-dihydro-1H-pyrrol-1-yl]carbonyl}-1,1-dioxidotetrahydro-2H-thiopyran-4-ylamine;
(2S)-1-[4-(2,5-difluorophenyl)-2-phenyl-2,5-dihydro-1H-pyrrol-1-yl]-N-methyl-1-oxopropan-2-amine;
(1S)-1-{[4-(2,5-difluorophenyl)-2-phenyl-2,5-dihydro-1H-pyrrol-1-yl]carbonyl}propylamine;
(1S)-2-[4-(2,5-difluorophenyl)-2-phenyl-2,5-dihydro-1H-pyrrol-1-yl]-2-oxo-1-phenylethanamine;
(1S)-2-[4-(2,5-difluorophenyl)-2-phenyl-2,5-dihydro-1H-pyrrol-1-yl]-2-oxo-1-phenylethanamine;
(4S)-4-amino-5-[4-(2,5-difluorophenyl)-2-phenyl-2,5-dihydro-1H-pyrrol-1-yl]-5-oxopentanamide
3-[4-(2,5-difluorophenyl)-2-phenyl-2,5-dihydro-1H-pyrrol-1-yl]-3-oxopropan-1-amine;
(1S,2S)-1-{[4-(2,5-difluorophenyl)-2-phenyl-2,5-dihydro-1H-pyrrol-1-yl]carbonyl}-2-methylbutylamine;
(1S)-1-{[4-(2,5-difluorophenyl)-2-phenyl-2,5-dihydro-1H-pyrrol-1-yl]carbonyl}butylamine;
(1S)-1-cyclopropyl-2-[4-(2,5-difluorophenyl)-2-phenyl-2,5-dihydro-1H-pyrrol-1-yl]-2-oxoethanamine;
1-{[4-(2,5-difluorophenyl)-2-phenyl-2,5-dihydro-1H-pyrrol-1-yl]carbonyl}cyclopropanamine;
1-[4-(2,5-difluorophenyl)-2-phenyl-2,5-dihydro-1H-pyrrol-1-yl]-1-oxopropan-2-amine;
(1S)-2-[4-(2,5-difluorophenyl)-2-phenyl-2,5-dihydro-1H-pyrrol-1-yl]-1-methyl-2-oxoethylamine;
(1S)-2-[4-(2,5-difluorophenyl)-2-phenyl-2,5-dihydro-1H-pyrrol-1-yl]-2-oxo-1-(pyridin-2-ylmethyl)ethylamine;
(1S)-1-cyclohexyl-2-[4-(2,5-difluorophenyl)-2-phenyl-2,5-dihydro-1H-pyrrol-1-yl]-2-oxoethanamine;
(1S)-2-[4-(2,5-difluorophenyl)-2-phenyl-2,5-dihydro-1H-pyrrol-1-yl]-1-(4-iodobenzyl)-2-oxoethylamine;
(1S)-1-benzyl-2-[4-(2,5-difluorophenyl)-2-phenyl-2,5-dihydro-1H-pyrrol-1-yl]-2-oxoethylamine;
4-{(2S)-2-amino-3-[4-(2,5-difluorophenyl)-2-phenyl-2,5-dihydro-1H-pyrrol-1-yl]-3-oxopropyl}phenol;
(3S)-3-{[4-(2,5-difluorophenyl)-2-phenyl-2,5-dihydro-1H-pyrrol-1-yl]carbonyl}-1,2,3,4-tetrahydroisoquinoline;
(1S)-1-{[4-(2,5-difluorophenyl)-2-phenyl-2,5-dihydro-1H-pyrrol-1-yl]carbonyl}-3-phenylpropylamine;

(1S)-1-{[4-(2,5-difluorophenyl)-2-phenyl-2,5-dihydro-1H-pyrrol-1-yl]carbonyl}-3-methylbutylamine;

(1S)-2-[4-(2,5-difluorophenyl)-2-phenyl-2,5-dihydro-1H-pyrrol-1-yl]-2-oxo-1-(pyridin-3-ylmethyl)ethylamine;

1-[(2S)-azetidin-2-ylcarbonyl]-4-(2,5-difluorophenyl)-2-phenyl-2,5-dihydro-1H-pyrrole;

(3S)-3-amino-4-[4-(2,5-difluorophenyl)-2-phenyl-2,5-dihydro-1H-pyrrol-1-yl]-4-oxobutanamide;

4-(2,5-difluorophenyl)-1-[(2-methylazetidin-2-yl)carbonyl]-2-phenyl-2,5-dihydro-1H-pyrrole;

(1S)-1-{[4-(2,5-difluorophenyl)-2-phenyl-2,5-dihydro-1H-pyrrol-1-yl]carbonyl}-2,2-dimethylpropylamine;

methyl(4S)-4-amino-5-[4-(2,5-difluorophenyl)-2-phenyl-2,5-dihydro-1H-pyrrol-1-yl]-5-oxopentanoate;

4-(2,5-difluorophenyl)-2-phenyl-1-{[(2S,3S)-2-phenylpyrrolidin-3-yl]carbonyl}-2,5-dihydro-1H-pyrrole;

4-(2,5-difluorophenyl)-2-phenyl-1-[(5-phenylpyrrolidin-3-yl)carbonyl]-2,5-dihydro-1H-pyrrole;

(2S)-2-amino-3-[4-(2,5-difluorophenyl)-2-phenyl-2,5-dihydro-1H-pyrrol-1-yl]-3-oxopropan-1-ol;

(2R,3S)-3-amino-4-[4-(2,5-difluorophenyl)-2-phenyl-2,5-dihydro-1H-pyrrol-1-yl]-4-oxobutan-2-ol;

(1S)-2-[4-(2,5-difluorophenyl)-2-phenyl-2,5-dihydro-1H-pyrrol-1-yl]-1-(methoxymethyl)-2-oxoethylamine;

4-(2,5-difluorophenyl)-2-phenyl-1-(pyrrolidin-3-ylcarbonyl)-2,5-dihydro-1H-pyrrole;

4-(2,5-difluorophenyl)-2-phenyl-1-[(3-phenylpyrrolidin-3-yl)acetyl]-2,5-dihydro-1H-pyrrole;

(1S)-1-{[4-(2,5-difluorophenyl)-2-phenyl-2,5-dihydro-1H-pyrrol-1-yl]carbonyl}-3,3-difluoropropylamine;

(1S)-3-[4-(2,5-difluorophenyl)-2-phenyl-2,5-dihydro-1H-pyrrol-1-yl]-3-oxo-1-phenylpropan-1-amine;

4-(2,5-difluorophenyl)-2-phenyl-1-[(4S)-4-phenyl-1-prolyl]-2,5-dihydro-1H-pyrrole;

1-{2-[4-(2,5-difluorophenyl)-2-phenyl-2,5-dihydro-1H-pyrrol-1-yl]-2-oxoethyl}cyclohexanamine;

2-[4-(2,5-difluorophenyl)-2-phenyl-2,5-dihydro-1H-pyrrol-1-yl]-2-oxoethanamine;

4-{[4-(2,5-difluorophenyl)-2-phenyl-2,5-dihydro-1H-pyrrol-1-yl]carbonyl}piperidin-4-amine;

(1S,3R)-3-{[4-(2,5-difluorophenyl)-2-phenyl-2,5-dihydro-1H-pyrrol-1-yl]carbonyl}cyclopentanamine;

(1R,4S)-4-{[4-(2,5-difluorophenyl)-2-phenyl-2,5-dihydro-1H-pyrrol-}-yl]carbonyl) cyclopent-2-en-1-amine;

(1S,4R)-4-{[4-(2,5-difluorophenyl)-2-phenyl-2,5-dihydro-1H-pyrrol-1-yl]carbonyl}cyclopent-2-en-1-amine;

(1S)-1-{[4-(2,5-difluorophenyl)-2-phenyl-2,5-dihydro-1H-pyrrol-1-yl]carbonyl}but-3-ynylamine;

(1R)-3-[4-(2,5-difluorophenyl)-2-phenyl-2,5-dihydro-1H-pyrrol-1-yl]-3-oxo-1-phenylpropan-1-amine;

3-{[4-(2,5-difluorophenyl)-2-phenyl-2,5-dihydro-1H-pyrrol-1-yl]carbonyl}-2-phenylpiperidine;

(1S)-1-{[4-(2,5-difluorophenyl)-2-phenyl-2,5-dihydro-1H-pyrrol-1-yl]carbonyl}-but-3-enylamine;

(2S)-3-[4-(2,5-difluorophenyl)-2-phenyl-2,5-dihydro-1H-pyrrol-1-yl]-2-(methylamino)-3-oxopropan-1-ol;

(3R,5S)-5-{[4-(2,5-difluorophenyl)-2-phenyl-2,5-dihydro-1H-pyrrol-1-yl]carbonyl}pyrrolidin-3-ol;

(1S)-2-[4-(2,5-difluorophenyl)-2-phenyl-2,5-dihydro-1H-pyrrol-1-yl]-2-oxo-1-(1,3-thiazol-ylmethyl)ethylamine;

(1R)-1-{[4-(2,5-difluorophenyl)-2-phenyl-2,5-dihydro-1H-pyrrol-1-yl]carbonyl}but-3-enylamine;

(2S)-1-[4-(2,5-difluorophenyl)-2-phenyl-2,5-dihydro-1H-pyrrol-1-yl]-N,3-dimethyl-1-oxobutan-2-amine;

(2S)-1-[4-(2,5-difluorophenyl)-2-phenyl-2,5-dihydro-1H-pyrrol-1-yl]-N,4-dimethyl-1-oxopentan-2-amine;

(1S)-2-[4-(2,5-difluorophenyl)-2-phenyl-2,5-dihydro-1H-pyrrol-1-yl]-1-[(1-methyl-1H-imidazol-4-yl)methyl]-2-oxoethylamine;

4-(2,5-difluorophenyl)-1-(N~6~-formyl-L-lysyl)-2-phenyl-2,5-dihydro-1H-pyrrole;

(2S,3S)-1-[4-(2,5-difluorophenyl)-2-phenyl-2,5-dihydro-1H-pyrrol-1-yl]-N,3-dimethyl-1-oxopentan-2-amine;

(1S)-1-(cyclohexylmethyl)-2-[4-(2,5-difluorophenyl)-2-phenyl-2,5-dihydro-1H-pyrrol-1-yl]-2-oxoethylamine;

(1S)-2-[4-(2,5-difluorophenyl)-2-phenyl-2,5-dihydro-1H-pyrrol-1-yl]-1-(1H-indol-3-ylmethyl)-2-oxoethylamine;

(1S)-2-[4-(2,5-difluorophenyl)-2-phenyl-2,5-dihydro-1H-pyrrol-1-yl]-1-(isocyanomethyl)-2-oxoethylamine;

(1S)-1-{[4-(2,5-difluorophenyl)-2-phenyl-2,5-dihydro-1H-pyrrol-1-yl]carbonyl}-3,3-dimethylbutylamine;

1-[4-(2,5-difluorophenyl)-2-phenyl-2,5-dihydro-1H-pyrrol-1-yl]-2,3-dimethyl-1-oxobutan-2-amine;

1-{[4-(2,5-difluorophenyl)-2-phenyl-2,5-dihydro-1H-pyrrol-1-yl]carbonyl}cyclohexanamine;

1-{[4-(2,5-difluorophenyl)-2-phenyl-2,5-dihydro-1H-pyrrol-1-yl]carbonyl}cyclopentanamine;

(1S)-3-(benzyloxy)-1-{[4-(2,5-difluorophenyl)-2-phenyl-2,5-dihydro-1H-pyrrol-1-yl]carbonyl}propylamine;

1-[4-(2,5-difluorophenyl)-2-phenyl-2,5-dihydro-1H-pyrrol-1-yl]-2,3-dimethyl-1-oxobutan-2-amine;

1-{[4-(2,5-difluorophenyl)-2-phenyl-2,5-dihydro-1H-pyrrol-1-yl]carbonyl}cyclopent-3-en-1-amine;

(1S)-1-cyclopentyl-2-[4-(2,5-difluorophenyl)-2-phenyl-2,5-dihydro-1H-pyrrol-1-yl]-2-oxoethanamine;

4-(2,5-difluorophenyl)-1-(2-methylprolyl)-2-phenyl-2,5-dihydro-1H-pyrrole;

(1S)-2-[4-(5-chloro-2-fluorophenyl)-2-phenyl-2,5-dihydro-1H-pyrrol-1-yl]-1-cyclopropyl-2-oxoethanamine;

(1S,2S)-1-{[4-(5-chloro-2-fluorophenyl)-2-phenyl-2,5-dihydro-1H-pyrrol-1-yl]carbonyl}-2-methylbutylamine;

(1S)-1-{[(2S)-4-(2,5-difluorophenyl)-2-phenyl-2,5-dihydro-1H-pyrrol-1-yl]carbonyl}but-3-enylamine;

(1S)-1-{[(2S)-4-(2,5-difluorophenyl)-2-phenyl-2,5-dihydro-1H-pyrrol-1-yl]carbonyl}but-3-ynylamine;

(1S)-1-cyclopropyl-2-[(2S)-4-(2,5-difluorophenyl)-2-phenyl-2,5-dihydro-1H-pyrrol-1-yl]-2-oxoethanamine;

1-cyclopropyl-3-[(2S)-4-(2,5-difluorophenyl)-2-phenyl-2,5-dihydro-1H-pyrrol-1-yl]-3-oxopropan-1-amine;

(1S,2S)-1-{[(2S)-4-(2,5-difluorophenyl)-2-phenyl-2,5-dihydro-1H-pyrrol-1-yl]carbonyl}-2-methylbutylamine;

4-(2,5-difluorophenyl)-2-(3-hydroxyphenyl)-1-L-valyl-2,5-dihydro-1H-pyrrole;

4-(2,5-difluorophenyl)-2-(3-hydroxyphenyl)-1-(2-methylalanyl)-2,5-dihydro-1H-pyrrole;

3-[1-[(2S)-2-amino-2-cyclopropylethanoyl]-4-(5-chloro-2-fluorophenyl)-2,5-dihydro-1H-pyrrol-2-yl]phenol;

4-(5-chloro-2-fluorophenyl)-2-(3-hydroxyphenyl)-1-L-isoleucyl-2,5-dihydro-1H-pyrrole;

(2S)-4-(2,5-Difluorophenyl)-N-methyl-2-phenyl-N-(piperidin-4-ylmethyl)-2,5-dihydro-1H-pyrrole-1-carboxamide;

(2S)-4-(5-Chloro-2-fluorophenyl)-N-methyl-2-phenyl-N-[(3R)-pyrrolidin-3-yl]-2,5-dihydro-1H-pyrrole-1-carboxamide;

(2S)-4-(5-chloro-2-fluorophenyl)-N-methyl-2-phenyl-N-piperidin-4-yl-2,5-dihydro-1H-pyrrole-1-carboxamide;

(2S)-4-(5-chloro-2-fluorophenyl)-N-methyl-2-phenyl-N-[(3S)-pyrrolidin-3-yl]-2,5-dihydro-1H-pyrrole-1-carboxamide;

(2S)-4-(2,5 difuorophenyl)-N-methyl-2-phenyl-N-pyrrolidin-3-yl-2,5-dihydro-1H-pyrrole-1-carboxamide;

(2S)-N-(1-allylpiperidin-4-yl)-4-(2,5-difluorophenyl)-N-methyl-2-phenyl-2,5-dihydro-1H-pyrrole-1-carboxamide;
4-(2,5-Difluorophenyl)-N-methyl-N-[(1-methylpiperidin-3-yl)methyl]-2-phenyl-2,5-dihydro-1H-pyrrole-1-carboxamide;
4-(2,5-difluorophenyl)-N-methyl-2-phenyl-N-(pyridin-3-ylmethyl)-2,5-dihydro-1H-pyrrole-1-carboxamide;
4-(2,5-difluorophenyl)-N-methyl-N-[(1-methyl-1H-pyrazol-4-yl)methyl]-2-phenyl-2,5-dihydro-1H-pyrrole-1-carboxamide;
4-(2,5-difluorophenyl)-N-[2-(dimethylamino)ethyl]-N-methyl-2-phenyl-2,5-dihydro-1H-pyrrole-1-carboxamide;
4-(2,5-difluorophenyl)-N-methyl-2-phenyl-N-(2-pyridin-2-ylethyl)-2,5-dihydro-1H-pyrrole-1-carboxamide;
4-(5-chloro-2-fluorophenyl)-2-(3-hydroxyphenyl)-N-methyl-N-piperidin-4-yl-2,5-dihydro-1H-pyrrole-1-carboxamide;
4-(2,5-difluorophenyl)-2-(3-hydroxyphenyl)-N-methyl-N-piperidin-4-yl-2,5-dihydro-1H-pyrrole-1-carboxamide;
(2S)-1-[4-(2,5-difluorophenyl)-2-methyl-2-phenyl-2,5-dihydro-1H-pyrrol-1-yl]-3-methyl-1-oxobutan-2-amine;
N-1-{(1S)-1-cyclopropyl-2-[(2S)-4-(2,5-difluorophenyl)-2-phenyl-2,5-dihydro-1H-pyrrol-1-yl]-2-oxoethyl}-N-2,N-2-dimethylglycinamide;
N-1-{(1S)-1-cyclopropyl-2-[(2S)-4-(2,5-difluorophenyl)-2-phenyl-2,5-dihydro-1H-pyrrol-1-yl]-2-oxoethyl}-N-2-methylglycinamide;
N-1-{(1S)-1-cyclopropyl-2-[(2S)-4-(2,5-difluorophenyl)-2-phenyl-2,5-dihydro-1H-pyrrol-1-yl]-2-oxoethyl}glycinamide;
N-1-{(1S)-1-cyclopropyl-2-[(2S)-4-(2,5-difluorophenyl)-2-phenyl-2,5-dihydro-1H-pyrrol-1-yl]-2-oxoethyl}-2-methylalaninamide;
N-{(1S)-1-cyclopropyl-2-[(2S)-4-(2,5-difluorophenyl)-2-phenyl-2,5-dihydro-1H-pyrrol-1-yl]-2-oxoethyl}-2-pyrrolidin-1-ylacetamide;
2-azetidin-1-yl-N-{(1S)-1-cyclopropyl-2-[(2S)-4-(2,5-difluorophenyl)-2-phenyl-2,5-dihydro-1H-pyrrol-1-yl]-2-oxoethyl}acetamide;
N-{(1S)-1-cyclopropyl-2-[(2S)-4-(2,5-difluorophenyl)-2-phenyl-2,5-dihydro-1H-pyrrol-1-yl]-2-oxoethyl}-2-morpholin-4-ylacetamide;
N-{(1S)-1-cyclopropyl-2-[(2S)-4-(2,5-difluorophenyl)-2-phenyl-2,5-dihydro-1H-pyrrol-1-yl]-2-oxoethyl}-2-piperazin-1-ylacetamide;
N-{(1S)-1-cyclopropyl-2-[(2S)-4-(2,5-difluorophenyl)-2-phenyl-2,5-dihydro-1H-pyrrol-1-yl]-2-oxoethyl}-2-(4-methylpiperazin-1-yl)acetamide;
N-1-{(1S)-1-cyclopropyl-2-[(2S)-4-(2,5-difluorophenyl)-2-phenyl-2,5-dihydro-1H-pyrrol-1-yl]-2-oxoethyl}-N-2-isopropylglycinamide;
N-{(1S)-1-cyclopropyl-2-[(2S)-4-(2,5-difluorophenyl)-2-phenyl-2,5-dihydro-1H-pyrrol-1-yl]-2-oxoethyl}piperazine-1-carboxamide;
N-{(1S)-1-cyclopropyl-2-[(2S)-4-(2,5-difluorophenyl)-2-phenyl-2,5-dihydro-1H-pyrrol-1-yl]-2-oxoethyl}-N'-piperidin-4-ylurea;
4-amino-N-{(1S)-1-cyclopropyl-2-[(2S)-4-(2,5-difluorophenyl)-2-phenyl-2,5-dihydro-1H-pyrrol-1-yl]-2-oxoethyl}piperidine-1-carboxamide;
N-(2-aminoethyl)-N'-{(1S)-1-cyclopropyl-2-[(2S)-4-(2,5-difluorophenyl)-2-phenyl-2,5-dihydro-1H-pyrrol-1-yl]-2-oxoethyl}urea;
N-{(1S)-1-cyclopropyl-2-[(2S)-4-(2,5-difluorophenyl)-2-phenyl-2,5-dihydro-1H-pyrrol-1-yl]-2-oxoethyl}-N'-(3-morpholin-4-ylpropyl)urea;
N-{(1S)-1-cyclopropyl-2-[(2S)-4-(2,5-difluorophenyl)-2-phenyl-2,5-dihydro-1H-pyrrol-1-yl]-2-oxoethyl}-N'-[2-(dimethylamino)ethyl]urea;
2-azetidin-1-yl-N-{(1S)-1-cyclopropyl-2-[(2S)-4-(2,5-difluorophenyl)-2-phenyl-2,5-dihydro-1H-pyrrol-1-yl]-2-oxoethyl}ethanesulfonamide
N-{(1S)-1-cyclopropyl-2-[(2S)-4-(2,5-difluorophenyl)-2-phenyl-2,5-dihydro-1H-pyrrol-1-yl]-2-oxoethyl}-2-(isopropylamino)ethanesulfonamide;
N-{(1S)-1-cyclopropyl-2-[(2S)-4-(2,5-difluorophenyl)-2-phenyl-2,5-dihydro-1H-pyrrol-1-yl]-2-oxoethyl}-2-pyrrolidin-1-ylethanesulfonamide;
N-{(1S)-1-cyclopropyl-2-[(2S)-4-(2,5-difluorophenyl)-2-phenyl-2,5-dihydro-1H-pyrrol-1-yl]-2-oxoethyl}-2-morpholin-4-ylethanesulfonamide;
N-{(1S)-1-cyclopropyl-2-[(2S)-4-(2,5-difluorophenyl)-2-phenyl-2,5-dihydro-1H-pyrrol-1-yl]-2-oxoethyl}-2-piperazin-1-ylethanesulfonamide;
N-{(1S)-1-cyclopropyl-2-[(2S)-4-(2,5-difluorophenyl)-2-phenyl-2,5-dihydro-1H-pyrrol-1-yl]-2-oxoethyl}-2-(4-methylpiperazin-1-yl)ethanesulfonamide;
N-(tert-butyl)-2-[(2S)-4-(2,5-difluorophenyl)-2-phenyl-2,5-dihydro-1H-pyrrol-1-yl]acetamide;
2-[(2S)-4-(2,5-difluorophenyl)-2-phenyl-2,5-dihydro-1H-pyrrol-1-yl]-N-isopropylacetamide;
(2S)-1-(2-azetidin-1-yl-2-oxoethyl)-4-(2,5-difluorophenyl)-2-phenyl-2,5-dihydro-1H-pyrrole;
(2S)-4-(2,5-difluorophenyl)-1-(2-oxo-2-pyrrolidin-1-ylethyl)-2-phenyl-2,5-dihydro-1H-pyrrole;
4-{[(2S)-4-(2,5-difluorophenyl)-2-phenyl-2,5-dihydro-1H-pyrrol-1-yl]acetyl}morpholine;
1-{[(2S)-4-(2,5-difluorophenyl)-2-phenyl-2,5-dihydro-1H-pyrrol-1-yl]acetyl}piperazine;
1-{[(2S)-4-(2,5-difluorophenyl)-2-phenyl-2,5-dihydro-1H-pyrrol-1-yl]acetyl}methylpiperazine;
2-[(2S)-4-(2,5-difluorophenyl)-2-phenyl-2,5-dihydro-1H-pyrrol-1-yl]-N-isopropylbutanamide;
4-{2-[(2S)-4-(2,5-difluorophenyl)-2-phenyl-2,5-dihydro-1H-pyrrol-1-yl]butanoyl}morpholine;
2-[(2S)-4-(2,5-difluorophenyl)-2-phenyl-2,5-dihydro-1H-pyrrol-1-yl]-N-ethylacetamide;
N-cyclobutyl-2-[(2S)-4-(2,5-difluorophenyl)-2-phenyl-2,5-dihydro-1H-pyrrol-1-yl]acetamide;
2-[(2S) (2,5-difluorophenyl)-2-phenyl-2,5-dihydro-1H-pyrrol-1-yl]-N-ethylpropanamide;
N-cyclobutyl-2-[(2S)-4-(2,5-difluorophenyl)-2-phenyl-2,5-dihydro-1H-pyrrol-1-yl]propanamide;
2-[(2S)-4-(2,5-difluorophenyl)-2-phenyl-2,5-dihydro-1H-pyrrol-1-yl]-N-methylpropanamide;
2-[(2S)-4-(2,5-difluorophenyl)-2-phenyl-2,5-dihydro-1H-pyrrol-1-yl]-N-isopropylpropanamide;
N-(tert-butyl)-2-[(2S)-4-(2,5-difluorophenyl)-2-phenyl-2,5-dihydro-1H-pyrrol-1-yl]propanamide;
4-{2-[(2S)-4-(2,5-difluorophenyl)-2-phenyl-2,5-dihydro-1H-pyrrol-1-yl]propanoyl}morpholine;
(3S)-3-amino-4-[(2S)-4-(2,5-difluorophenyl)-2-phenyl-2,5-dihydro-1H-pyrrol-1-yl]-N-ethyl-2,2-dimethyl-4-oxobutanamide;
(3S)-3-amino-4-[(2S)-4-(2,5-difluorophenyl)-2-phenyl-2,5-dihydro-1H-pyrrol-1-yl]-2,2-dimethyl-4-oxo-N-piperidin-4-ylbutanamide;
(3S)-3-amino-4-[(2S)-4-(2,5-difluorophenyl)-2-phenyl-2,5-dihydro-1H-pyrrol-1-yl]-2,2-dimethyl-4-oxobutanoic acid;
(3S)-3-amino-4-[(2S)-4-(2,5-difluorophenyl)-2-phenyl-2,5-dihydro-1H-pyrrol-1-yl]-N,N,2,2-tetramethyl-4-oxobutanamide;

(1S)-1-{[(2S)-4-(2,5-difluorophenyl)-2-phenyl-2,5-dihydro-1H-pyrrol-1-yl]carbonyl}-2,2-dimethyl-3-oxo-3-piperazin-1-ylpropylamine;

(3S)-3-amino-4-[(2S)-4-(2,5-difluorophenyl)-2-phenyl-2,5-dihydro-1H-pyrrol-1-yl]-N-isopropyl-2,2-dimethyl-4-oxobutanamide;

(3S)-3-amino-4-[(2S)-4-(2,5-difluorophenyl)-2-phenyl-2,5-dihydro-1H-pyrrol-1-yl]-N,2,2-trimethyl-4-oxobutanamide;

(3R)-3-amino-4-[(2S)-4-(2,5-difluorophenyl)-2-phenyl-2,5-dihydro-1H-pyrrol-1-yl]-N,N,2,2-tetramethyl-4-oxobutanamide;

(3R)-3-amino-4-[(2S)-4-(2,5-difluorophenyl)-2-phenyl-2,5-dihydro-1H-pyrrol-1-yl]-2,2-dimethyl-4-oxobutanoic acid;

(1R)-1-{[(2S)-4-(2,5-difluorophenyl)-2-phenyl-2,5-dihydro-1H-pyrrol-1-yl]carbonyl}-2,2-dimethyl-3-oxo-3-piperazin-1-ylpropylamine (1S)-1-cyclopropyl-2-[(2S)-4-(2,5-difluorophenyl)-2-phenyl-2,5-dihydro-1H-pyrrol-1-yl]-2-oxoethyl 4-methylpiperazine-1-carboxylate;

(1S)-1-cyclopropyl-2-[(2S)-4-(2,5-difluorophenyl)-2-phenyl-2,5-dihydro-1H-pyrrol-1-yl]-2-oxoethyl 1-methylpiperidin-4-ylcarbamate;

(1S)-1-cyclopropyl-2-[(2S)-4-(2,5-difluorophenyl)-2-phenyl-2,5-dihydro-1H-pyrrol-1-yl]-2-oxoethylmethyl(1-methylpiperidin-4-yl)carbamate;

(1S)-1-cyclopropyl-2-[(2S)-4-(2,5-difluorophenyl)-2-phenyl-2,5-dihydro-1H-pyrrol-1-yl]-2-oxoethyl-4-dimethylamino)piperidine-1-carboxylate;

(2S)-N,N-dimethyl-4-(4-methylpyridin-3-yl)-2-phenyl-2,5-dihydro-1H-pyrrole-1-carboxamide;

4-{[4-(2,5-difluorophenyl)-2-(3-hydroxyphenyl)-2,5-dihydro-1H-pyrrol-1-yl]acetyl}morpholin-4-ium;

4-(2,5-difluorophenyl)-2-(3-hydroxyphenyl)-N-methyl-N-piperidin-4-yl-2,5-dihydro-1H-pyrrole-1-carboxamide;

2-[{[4-(2,5-difluorophenyl)-2-(3-hydroxyphenyl)-2,5-dihydro-1H-pyrrol-1-yl]carbonyl}(methyl)amino]ethyl-4-methylpiperazine-1-carboxylate;

3-{4-(2,5-difluorophenyl)-1-[(4-methylpiperazin-1-yl)carbonyl]-2,5-dihydro-1H-pyrrol-2-yl}phenol;

4-(2,5-difluorophenyl)-2-(3-hydroxyphenyl)-N-methyl-N-[(1-methyl-1H-pyrazol-4-yl)methyl]-2,5-dihydro-1H-pyrrole-1-carboxamide;

4-(2,5-difluorophenyl)-2,5-dihydro-2-(3-hydroxyphenyl)-N-methyl-N-[2-(4-methyl-1-piperazinyl)-2-oxoethyl]-H-pyrrole-1-carboxamide;

4-(2,5-difluorophenyl)-2-(3-hydroxyphenyl)-N-methyl-N-[(5-oxo-4,5-dihydro-1H-1,2,4-triazol-3-yl)methyl]-2,5-dihydro-1H-pyrrole-1-carboxamide;

4-(2,5-difluorophenyl)-2-(3-hydroxyphenyl)-N-{[5-(methoxymethyl)-1H-pyrazol-3-yl]methyl}-N-methyl-2,5-dihydro-1H-pyrrole-1-carboxamide;

4-(2,5-difluorophenyl)-2-(3-hydroxyphenyl)-N-methyl-N-(1,3-thiazol-4-ylmethyl)-2,5-dihydro-1H-pyrrole-1-carboxamide;

4-(2,5-difluorophenyl)-2-(3-hydroxyphenyl)-N-methyl-N-(1,3-thiazol-2-ylmethyl)-2,5-dihydro-1H-pyrrole-1-carboxamide;

4-(2,5-difluorophenyl)-2-(3-hydroxyphenyl)-N-methyl-N-[2-(1H-1,2,4-triazol-1-yl)ethyl]-2,5-dihydro-1H-pyrrole-1-carboxamide;

4-(2,5-difluorophenyl)-2-(3-hydroxyphenyl)-N-methyl-N-[2-(1H-pyrazol-1-yl)ethyl]-2,5-dihydro-1H-pyrrole-1-carboxamide;

4-[(2S)-4-(2,5-difluorophenyl)-2-phenyl-2,5-dihydro-1H-pyrrol-1-yl]butan-2-one;

4-[(2S)-4-(2,5-difluorophenyl)-2-phenyl-2,5-dihydro-1H-pyrrol-1-yl]-3-methylbutan-2-one;

3-[(2S)-4-(2,5-difluorophenyl)-2-phenyl-2,5-dihydro-1H-pyrrol-1-yl]-N-methylpropanamide;

3-[(2S)-4-(2,5-difluorophenyl)-2-phenyl-2,5-dihydro-1H-pyrrol-1-yl]-N,N-dimethylpropanamide;

3-[(2S)-4-(2,5-difluorophenyl)-2-phenyl-2,5-dihydro-1H-pyrrol-1-yl]-N,N,2-trimethylpropanamide;

4-{3-[(2S)-4-(2,5-difluorophenyl)-2-phenyl-2,5-dihydro-1H-pyrrol-1-yl]propanoyl}morpholine;

1-{3-[(2S)-4-(2,5-difluorophenyl)-2-phenyl-2,5-dihydro-1H-pyrrol-1-yl]propanoyl}-4-(methylsulfonyl)piperazine;

1-{3-[(2S)-4-(2,5-difluorophenyl)-2-phenyl-2,5-dihydro-1H-pyrrol-1-yl]propanoyl}piperidin-4-ol; and methyl 3-[(2S)-4-(2,5-difluorophenyl)-2-phenyl-2,5-dihydro-1H-pyrrol-1-yl]propanoate.

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

When any variable (e.g. $R^{10}$, $R^{11}$, $R^{12}$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —$CH_2$—, —$CH_2CH_2$— and the like.

When used in the phrases "$C_1$-$C_6$ aralkyl" and "$C_1$-$C_6$ heteroaralkyl" the term "$C_1$-$C_6$" refers to the alkyl portion of the moiety and does not describe the number of atoms in the aryl and heteroaryl portion of the moiety.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, the term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" in this embodiment therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In another embodiment, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a $(C_1-C_6)$alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C=O) $CH_2CH(OH)CH_3$, —(C=O)OH, —$CH_2(OH)CH_2CH(O)$, and so on.

The moiety formed when, in the definition of $R^4$ and $R^5$ and $R^8$ and $R^9$ on the same carbon atom are combined to form —$(CH_2)_u$— is illustrated by the following:

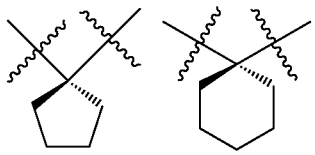

In addition, such cyclic moieties may optionally include a heteroatom(s). Examples of such heteroatom-containing cyclic moieties include, but are not limited to:

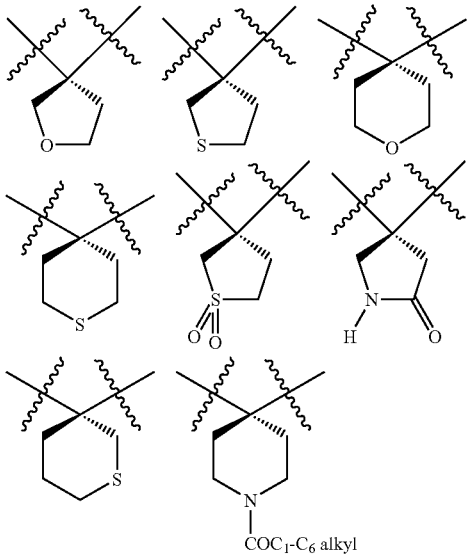

In certain instances, $R^{12}$ and $R^{13}$ and $R^c$ and $R^{c'}$ are defined such that they can be taken together with the nitrogen to which they are attached to form a monocyclic or bicyclic heterocycle with 5-7 members in each ring and optionally containing, in addition to the nitrogen, one or two additional heteroatoms selected from N, O and S, said heterocycle optionally substituted with one or more substituents selected from $R^{11}$. Examples of the heterocycles that can thus be formed include, but are not limited to the following, keeping in mind that the heterocycle is optionally substituted with one or more (and preferably one, two or three) substituents chosen from $R^{11}$:

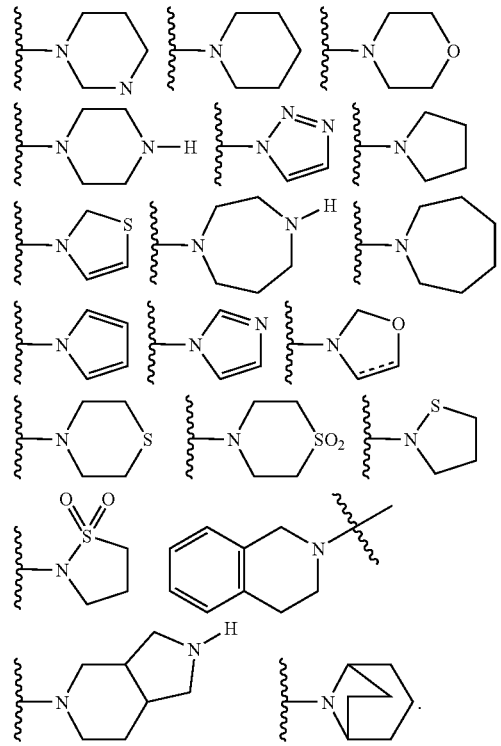

In certain instances, $R^d$ and $R^{d'}$ are defined such that they can be taken together with the phosphorous to which they are attached to form a monocyclic heterocycle with 5-7 members in the ring and optionally containing, in addition to the nitrogen, one or two additional heteroatoms selected from $NR^e$, O and S, said heterocycle optionally substituted with one or more substituents selected from $R^{11}$. Examples of the heterocycles that can thus be formed include, but are not limited to the following, keeping in mind that the heterocycle is optionally substituted with one or more (and preferably one or two) substituents chosen from $R^{11}$:

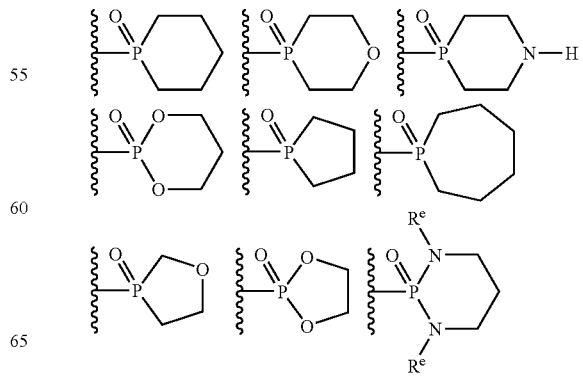

-continued

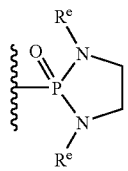

In an embodiment, $R^1$ is selected from (C=O)$NR^cR^{c'}$ and —$SO_2C_1$-$C_6$ alkyl, optionally substituted with one to three substituents selected from $R^{10}$. In another aspect of this embodiment, $R^1$ is aminocarbonyl, N,N-dimethylaminocarbonyl, methylsulfonyl or ethylsulfonyl.

In another embodiment, $R^1$ is selected from (C=O)$NR^cR^{c'}$ and (C=O)$C_1$-$C_6$ alkyl, optionally substituted with one to three substituents selected from $R^{10}$. In another aspect of this embodiment, $R^1$ is selected from:
a) 1-cyclopropyl-2-oxoethanamine or 1-t-butyl-2-oxoethanamine, wherein the amine nitrogen is optionally substituted with $R^{12}$ and $R^{13}$,
b) N,N-dimethylcarboxamide, and
c) N-methyl-N-(1-methylpiperidin-4-yl)carboxamide.

In an embodiment, $R^2$ is selected from aryl, optionally substituted with one to three substituents selected from $R^{10}$. In another aspect of this embodiment, $R^2$ is phenyl, optionally substituted with one to three substituents selected from halo.

In another embodiment, $R^2$ is selected from aryl, optionally substituted with one to three substituents selected from $R^{10}$. In another aspect of this embodiment, $R^2$ is phenyl and 3-hydrophenyl, optionally substituted with one to three substituents selected from halo.

In an embodiment, $R^4$, $R^5$, $R^7$, $R^8$ and $R^9$ are H.

In an embodiment, $R^3$ is selected from H and $C_1$-$C_6$ alkyl, optionally substituted with one to two substituents selected from $R^{10}$. In another aspect of this embodiment, $R^3$ is selected from H and methyl.

In an embodiment, $R^6$ is selected from aryl, optionally substituted with one to three substituents selected from $R^{10}$. More preferably, $R^6$ is phenyl, optionally substituted with one to three substituents selected from halo.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. When the compound of the present invention is acidic, the term "free form" refers to the compound in its non-salt form, such that the acidic functionality is still protonated.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom. An isolated compound having internally balance charges, and thus not associated with a intermolecular counterion, may also be considered the "free form" of a compound.

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

SCHEMES

As shown in Scheme A, key dihydropyrrole intermediate A-4 may be obtained from readily available suitably substituted anilines and N-protected dihydropyrrole. Subsequent deprotection of the ring nitrogen allows functionallization with appropriately substituted electrophiles, such as the dialkylcarbamoyl chloride illustrated to give the instant compound A-6. Scheme A-1 shows an alternative synthesis of the A-4 intermediate.

As shown in Scheme B, use of a single phenyl pyrrole enantiomer having a suitably located hydroxyl moiety allows for the preparation of the enantiomerically pure intermediate B-5, which may then be deprotected and functionalized in a method analogous to that shown in Scheme A.

Scheme C illustrates attachment of a suitably substituted amino acid residue to the intermediate A-5. The group $R^{sc}$ represents a substituent sidechain, preferably a sidechain of an amino acid.

As illustrated in Schemes D and F, attachment of an amino carbonyl moiety to the dihydropyrrole ring nitrogen can also be accoplished by a two step synthesis, thereby allowing incorporation of a wide variety of substituted amines into the instant compounds.

Scheme E illustrates the syntheses of compounds of the instant invention that incorporate both a phenylmoiety and an alkyl moiety on the 2-position of the dihydropyrrole ring.

As illustrated in Scheme G, suitably substituted hydroxyalkylamides may also be prepared.

Other $R^6$ substituents may be incorporated into the instant compound as shown in Scheme H. Thus a suitable Grignard reagent may replace the aryl boronic acid that is utilized in Scheme B.

A Suzuki coupling may also be employed to incorporate an $R^6$ heteroaryl substituent, as illustrated in Scheme I.

SCHEME A

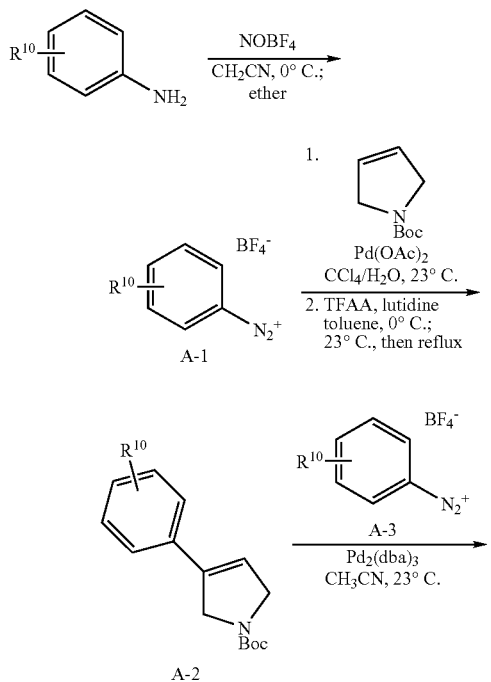

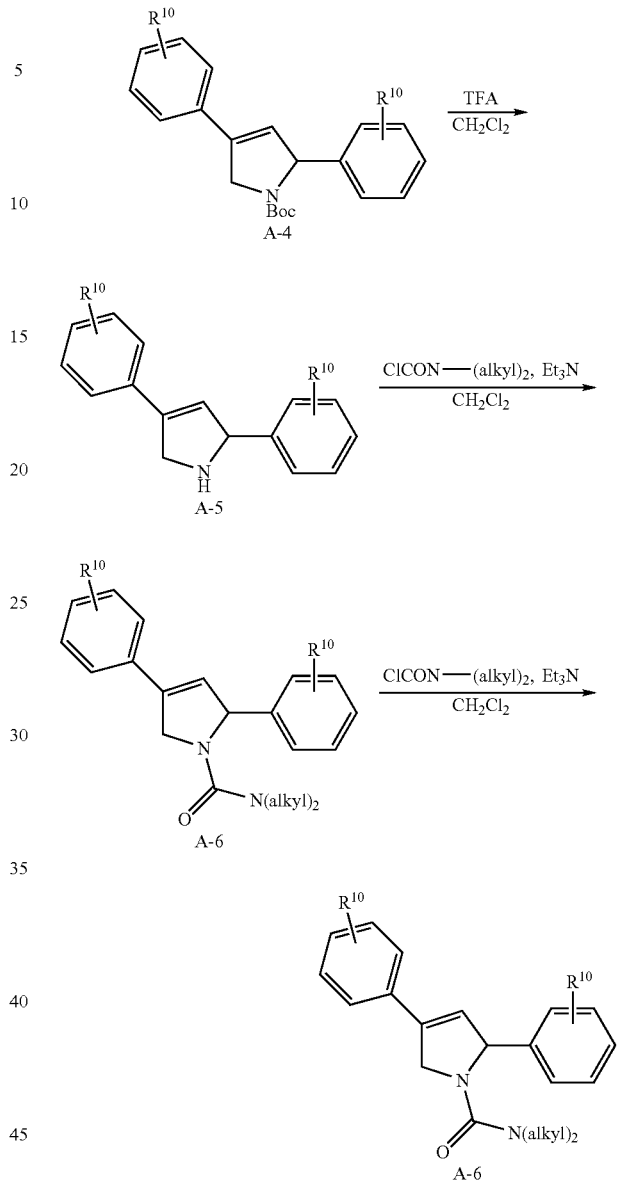

SCHEME A-1

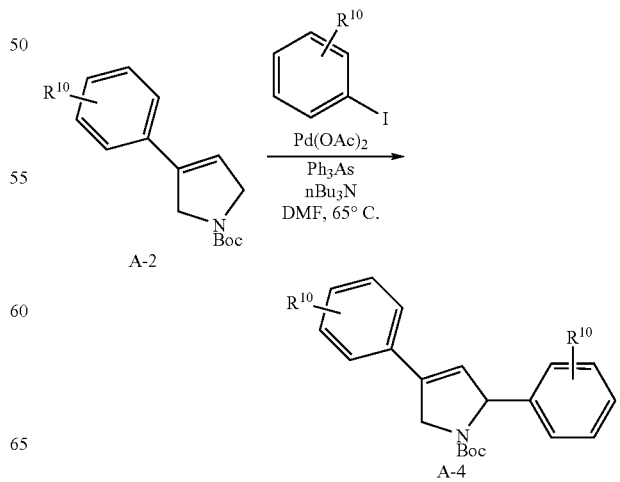

SCHEME B
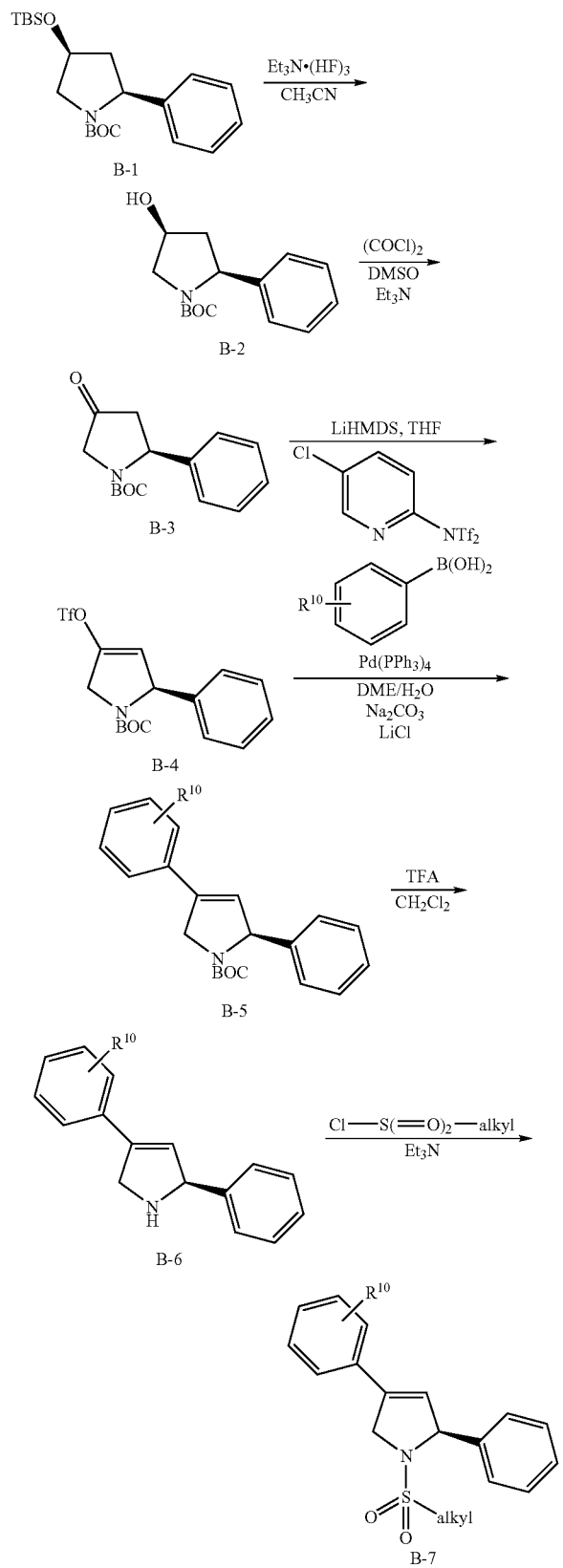
SCHEME C
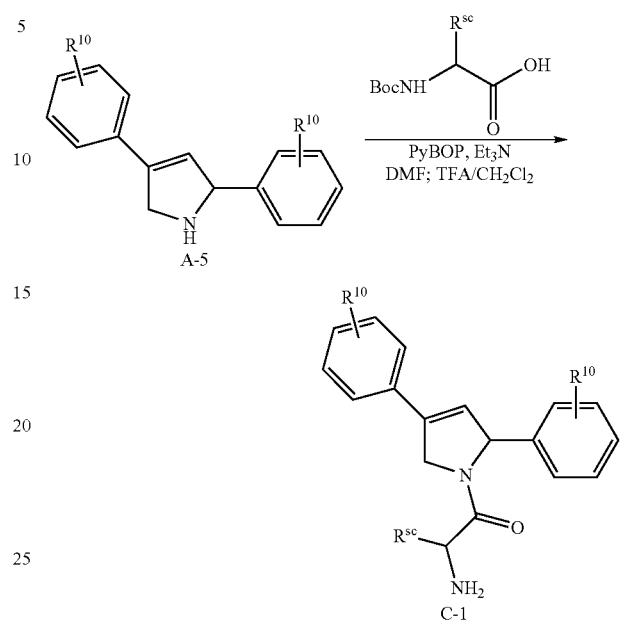
SCHEME D
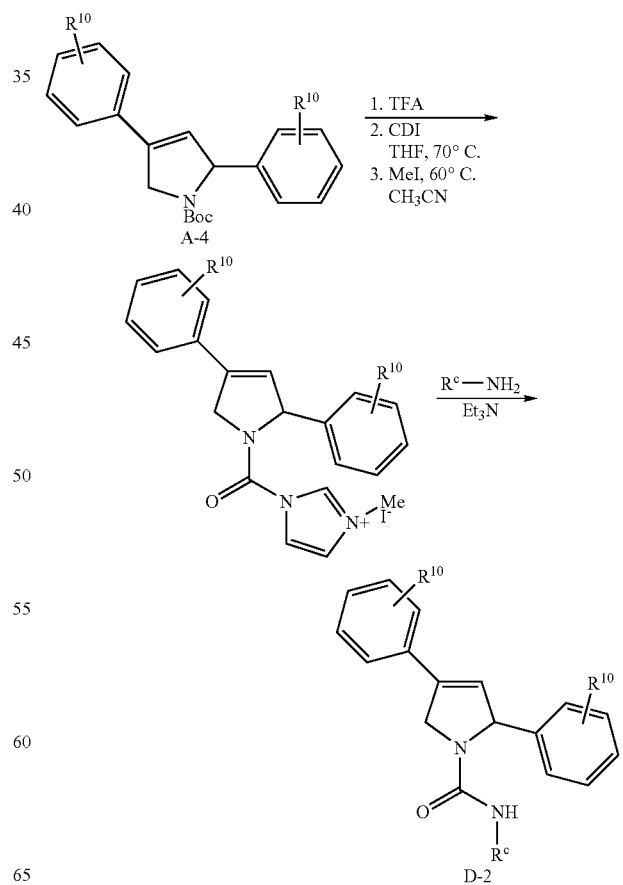

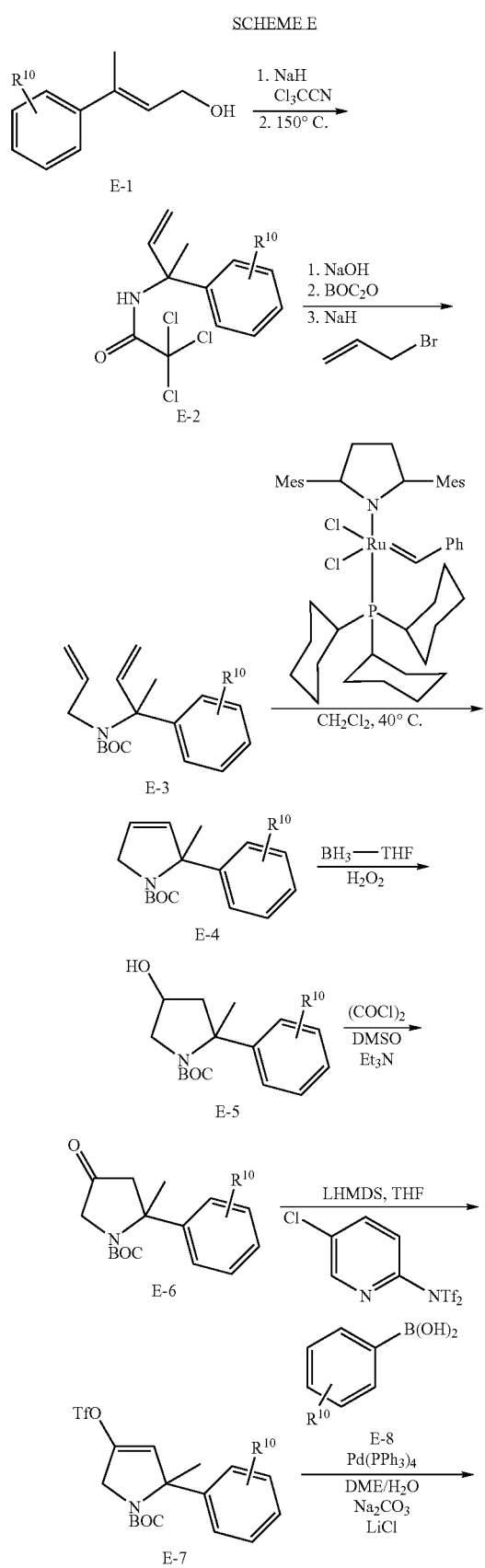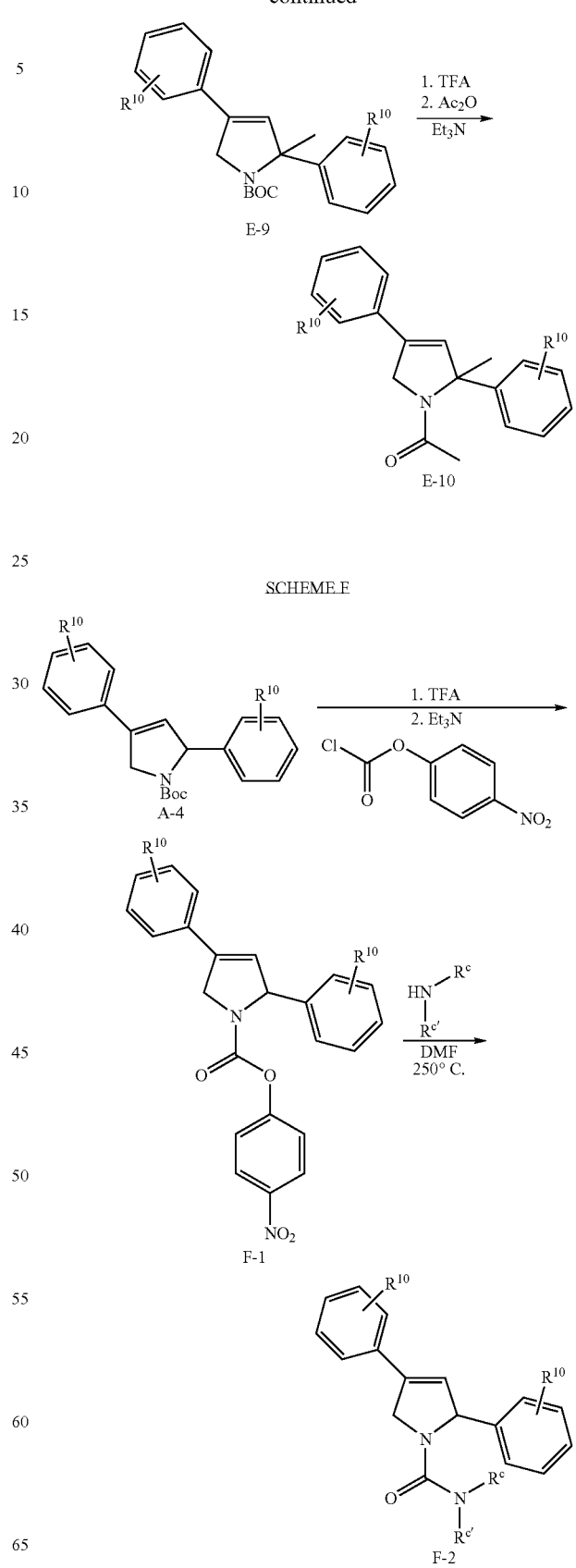

SCHEME G

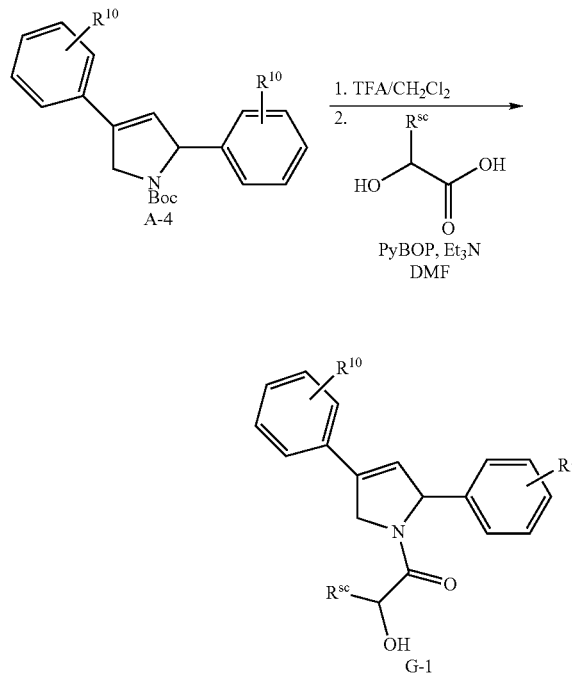

SCHEME H

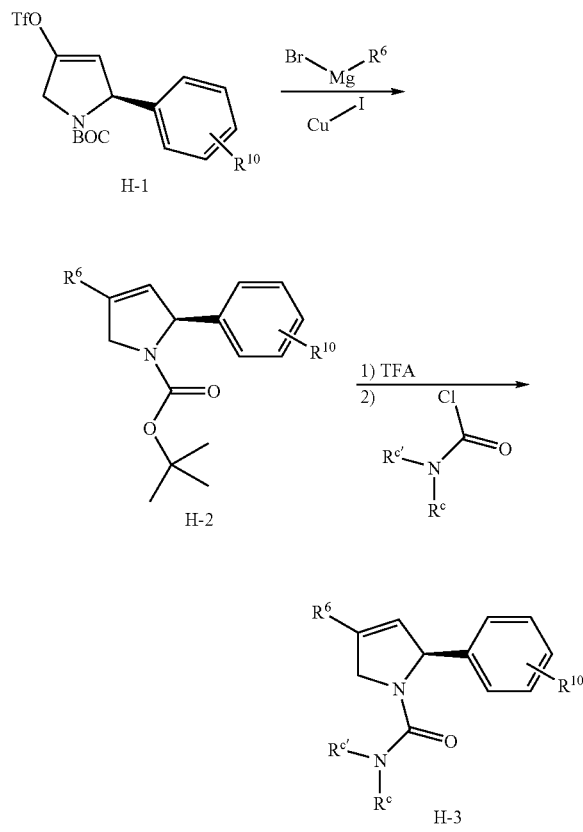

SCHEME I

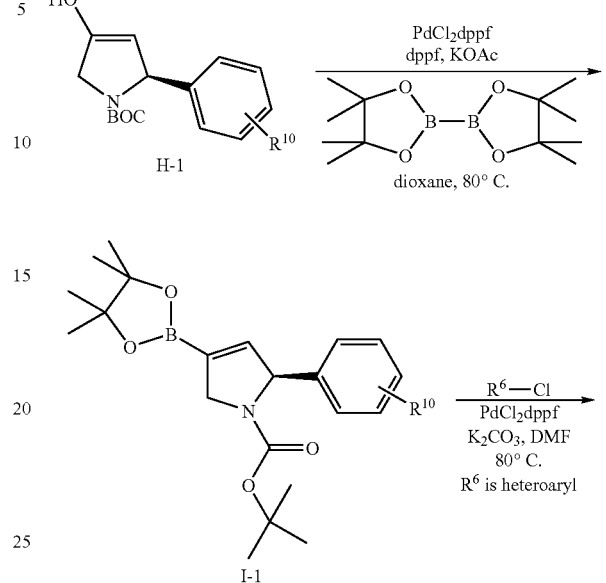

Utilities

The compounds of the invention find use in a variety of applications. As will be appreciated by those in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a preferred embodiment, the compounds of the invention are used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to and/or modulate the activity of a mitotic kinesin. In a preferred embodiment, the mitotic kinesin is a member of the bimC subfamily of mitotic kinesins (as described in U.S. Pat. No. 6,284,480, column 5). In a further preferred embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See PCT Publ. WO 01/31335: "Methods of Screening for Modulators of Cell Proliferation and Methods of Diagnosing Cell Proliferation States", filed Oct. 27, 1999, hereby incorporated by reference in its entirety. In addition, other mitotic kinesins may be inhibited by the compounds of the present invention.

The compounds of the invention are used to treat cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple mycloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

The compounds of the instant invention may also be useful as antifungal agents, by modulating the activity of the fungal members of the bimC kinesin subgroup, as is described in U.S. Pat. No. 6,284,480.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteosome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-1-valyl-1-valyl-N-methyl-1-valyl-1-prolyl-1-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768 and WO 01/98278, and pending U.S. Ser. Nos. 60/338,779 (filed Dec. 6, 2001), 60/338,344 (filed Dec. 6, 2001), 60/338,383 (filed Dec. 6, 2001), 60/338,380 (filed Dec. 6, 2001), 60/338,379 (filed Dec. 6, 2001) and 60/344,453 (filed Nov. 7, 2001). In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-1-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (1MIEVA-COR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAY-CHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

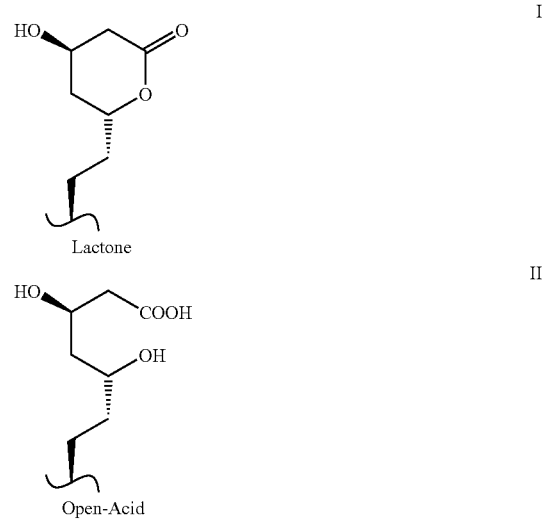

Lactone

Open-Acid

In HMG-CoA reductase inhibitors where an open-acid form can exist, salt and ester forms may be formed from the open-acid, and all such forms are included within the meaning of the term "HMG-CoA reductase inhibitor" as used herein. In an embodiment, the HMG-CoA reductase inhibitor is selected from lovastatin and simvastatin, and in a further embodiment, simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane.

Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazolylmethyl}benzonitrile, 18,19-dihydro-19-oxo-5H, 17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo [d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins, GPIIb/IIIa antagonists (such as tirofiban), warfarin, thrombin inhibitors and carboxypeptidase U inhibitors (also known as inhibitors of active thrombin activatable fibrinolysis inhibitor [TAPIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140 and WO 02/083138), inhibitors of Raf kinase (for example BAY43-9006), inhibitors of MEK (for example CI-1040 and PD-098059), inhibitors of mTOR (for example Wyeth CCI-779), and inhibitors of PI3K (for example LY294002).

The combinations with NSAID's are directed to the use of NSAID's which are potent COX-2 inhibiting agents. For purposes of this specification an NSAID is potent if it possess an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone; and

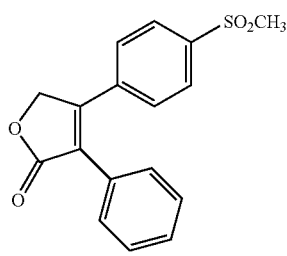

5-chloro-3-(4-methylsulfonyl)phenyl-2-(2-methyl-5-pyridinyl)pyridine;

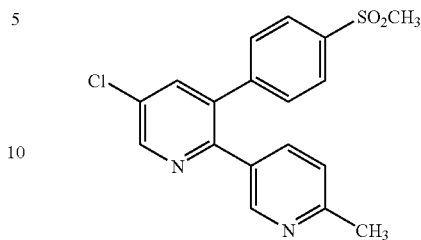

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

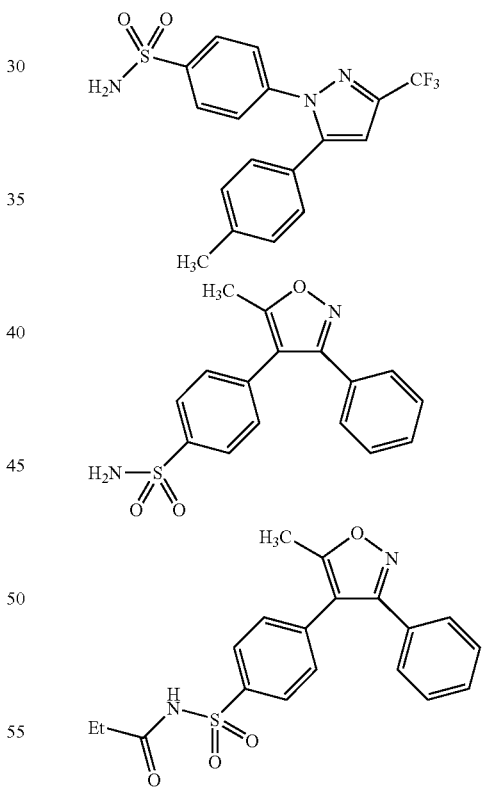

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No.

5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_1$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999;274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine*, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990;401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. For the treatment or prevention of emesis that may result upon administration of the instant compounds, conjunctive therapy with an anti-emesis agent selected from a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

Thus, the scope of the instant invention encompasses the use of the instantly claimed compounds in combination with a second compound selected from:
1) an estrogen receptor modulator,
2) an androgen receptor modulator,
3) retinoid receptor modulator,
4) a cytotoxic/cytostatic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) a PPAR-γ agonists,
12) a PPAR-δ agonists,
13) an inhibitor of inherent multidrug resistance,
14) an anti-emetic agent,
15) an agent useful in the treatment of anemia,
16) an agent useful in the treatment of neutropenia,
17) an immunologic-enhancing drug,
18) an inhibitor of cell proliferation and survival signaling, and
19) an agent that interfers with a cell cycle checkpoint.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from:
1) an estrogen receptor modulator,
2) an androgen receptor modulator,
3) a retinoid receptor modulator,
4) a cytotoxic/cytostatic agent,
5) an antiproliferative agent,
6) a prenyl-protein transferase inhibitor,
7) an HMNG-CoA reductase inhibitor, 8) an HIV protease inhibitor,
9) a reverse transcriptase inhibitor,
10) an angiogenesis inhibitor,
11) PPAR-γ agonists,
12) PPAR-δ agonists,
13) an inhibitor of inherent multidrug resistance,
14) an anti-emetic agent,
15) an agent useful in the treatment of anemia,
16) an agent useful in the treatment of neutropenia,
17) an immunologic-enhancing drug,
18) an inhibitor of cell proliferation and survival signaling, and
19) an agent that interfers with a cell cycle checkpoint.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from:
1) an estrogen receptor modulator,
2) an androgen receptor modulator,
3) a retinoid receptor modulator,
4) a cytotoxic/cytostatic agent,
5) an antiproliferative agent,
6) a prenyl-protein transferase inhibitor,
7) an HMG-CoA reductase inhibitor,
8) an IRV protease inhibitor,
9) a reverse transcriptase inhibitor,
10) an angiogenesis inhibitor, and
11) a PPAR-γ agonist,
12) a PPAR-δ agonists;
13) an inhibitor of cell proliferation and survival signaling, and
14) an agent that interfers with a cell cycle checkpoint.

The invention further comprises the use of the instant compounds in a method to screen for other compounds that bind to KSP. To employ the compounds of the invention in a method of screening for compounds that bind to KSP kinesin, the KSP is bound to a support, and a compound of the invention (which is a mitotic agent) is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a preferred embodiment, the mitotic agent (the compound of the invention) is labeled, for example, with a fluorescent or radioactive moiety and binding determined directly. For example, this may be done by attaching all or a portion of KSP to a solid support, adding a labeled mitotic agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific-binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the mitotic agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays may be done by combining KSP and a drug candidate in a first sample. A second sample comprises a mitotic agent, KSP and a drug candidate. This may be performed in either the presence or absence of microtubules. The binding of the drug candidate is determined for both samples, and a change, or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a preferred embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between about 4 and about 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the mitotic agent, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

These and other aspects of the invention will be apparent from the teachings contained herein.

ASSAYS

The compounds of the instant invention described in the Examples were tested by the assays described below and were found to have kinesin inhibitory activity. Other assays are known in the literature and could be readily performed by those of skill in the art (see, for example, PCT Publication WO 01/30768, May 3, 2001, pages 18-22).

I. Kinesin ATPase In Vitro Assay

Cloning and Expression of Human Poly-histidine Tagged KSP Motor Domain (KSP(367H))

Plasmids for the expression of the human KSP motor domain construct were cloned by PCR using a pBluescript full length human KSP construct (Blangy et al., Cell, vol. 83, pp1159-1169, 1995) as a template. The N-terminal primer 5'-GCAACGATTAATATGGCGTCGCAGC-CAAATTCGTCTGCGAAG (SEQ.ID.NO.: 1) and the C-terminal primer 5'-GCAACGCTCGAGTCAGTGAT GATGGTGGTGATGCTGATTCACTTTCAG-GCTTATTCAAATAT (SEQ.ID.NO.: 2) were used to amplify the motor domain and the neck linker region. The PCR products were digested with AseI and XhoI, ligated into the NdeI/XhoI digestion product of pRSETa (Invitrogen) and transformed into *E. coli* BL21 (DE3).

Cells were grown at 37° C. to an $OD_{600}$ of 0.5. After cooling the culture to room temperature expression of KSP was induced with 100 µM IPTG and incubation was continued overnight. Cells were pelleted by centrifugation and washed once with ice-cold PBS. Pellets were flash-frozen and stored −80° C.

Protein Purification

Cell pellets were thawed on ice and resuspended in lysis buffer (50 mM K-HEPES, pH 8.0, 250 mM KCl, 0.1% Tween, 10 mM imidazole, 0.5 mM Mg-ATP, 1 mM PMSF, 2 mM benzimidine, 1× complete protease inhibitor cocktail (Roche)). Cell suspensions were incubated with 1 mg/ml lysozyme and 5 mM β-mercaptoethanol on ice for 10 minutes, followed by sonication (3×30 sec). All subsequent procedures were performed at 4° C. Lysates were centrifuged at 40,000×g for 40 minutes. Supernatants were diluted and loaded onto an SP Sepharose column (Pharmacia, 5 ml cartridge) in buffer A (50 mM K-HEPES, pH 6.8, 1 mM MgCl$_2$, 1 mM EGTA, 10 μM Mg-ATP, 1 mM DTT) and eluted with a 0 to 750 mM KCl gradient in buffer A. Fractions containing KSP were pooled and incubated with Ni-NTA resin (Qiagen) for one hour. The resin was washed three times with buffer B (Lysis buffer minus PMSF and protease inhibitor cocktail), followed by three 15-minute incubations and washes with buffer B. Finally, the resin was incubated and washed for 15 minutes three times with buffer C (same as buffer B except for pH 6.0) and poured into a column. KSP was eluted with elution buffer (identical to buffer B except for 150 mM KCl and 250 mM imidazole). KSP-containing fractions were pooled, made 10% in sucrose, and stored at −80° C.

Microtubules are prepared from tubulin isolated from bovine brain. Purified tubulin (>97% MAP-free) at 1 mg/ml is polymerized at 37° C. in the presence of 10 μM paclitaxel, 1 mM DTT, 1 mM GTP in BRB80 buffer (80 mM K-PIPES, 1 mM EGTA, 1 mM MgCl$_2$ at pH 6.8). The resulting microtubules are separated from non-polymerized tubulin by ultracentrifugation and removal of the supernatant. The pellet, containing the microtubules, is gently resuspended in 10 μM paclitaxel, 1 mM DTT, 50 μg/ml ampicillin, and 5 μg/ml chloramphenicol in BRB80.

The kinesin motor domain is incubated with microtubules, 1 mM ATP (1:1 MgCl$_2$: Na-ATP), and compound at 23° C. in buffer containing 80 mM K-HEPES (pH 7.0), 1 mM EGTA, 1 mM DTT, 1 mM MgCl$_2$, and 50 mM KCl. The reaction is terminated by a 2-10 fold dilution with a final buffer composition of 80 mM HEPES and 50 mM EDTA (or, alternately, with a 1:1 addition of reaction volume to stop buffer(1.8M KCl and 50 mM EDTA)). Free phosphate from the ATP hydrolysis reaction is measured via a quinaldine red/ammonium molybdate assay by adding a 1.5 times volume of quench C (e.g., to a mixture of 40 μl reaction volume+40 μl stop buffer is then added 120 μl quench C). Quench A contains 0.1 mg/ml quinaldine red and 0.14% polyvinyl alcohol; quench B contains 12.3 mM ammonium molybdate tetrahydrate in 1.15 M sulfuric acid. Quench C is a 2:1 ratio of quench A:quench B The reaction is incubated for 5-10 minutes at 23° C., and the absorbance of the phospho-molybdate complex is measured at 540 nm.

The compounds 1-6,2-6 to 2-14, 3-2, 42 to 4-7, 54, 6-1 to 6-7,7-2, 8-2,9-1, 10-1 to 10-3, 11-1, 12-1, 13-1, 14-1 to 14-2, 15-1 to 15-86, 16-1 to 16-16, 17-5 to 17-13, 18-4, 18a-6, 18b-8, 18-5 to 18-16, 19-2 to 19-15, 20-10 to 20-11, 21-4 to 21-7, 22-1 to 22-8, 24-1 to 24-9, 25-2 to 25-16, 26-2 to 26-7, 27-2 to 27-7, 28-2 to 28-18, 29-5 to 29-14, 30-2 to 30-21, 31-2 to 31-3, 32-3 to 32-3, 33-1 to 33-6, 334-2 to 34-11, 35-2 to 35-11, 36-2 to 36-6, 37-1 to 37-8, 38-1, 39-2 to 39-8, 40-2 to 40-8 and 41-2 to 41-4 in the Examples were tested in the above assay and found to have an IC$_{50}$≦50 μM.

II. Cell Proliferation Assay

Cells are plated in 96-well tissue culture dishes at densities that allow for logarithmic growth over the course of 24, 48, and 72 hours and allowed to adhere overnight. The following day, compounds are added in a 10-point, one-half log titration to all plates. Each titration series is performed in triplicate, and a constant DMSO concentration of 0.1% is maintained throughout the assay. Controls of 0.1% DMSO alone are also included. Each compound dilution series is made in media without serum. The final concentration of serum in the assay is 5% in a 200 μL volume of media. Twenty microliters of Alamar blue staining reagent is added to each sample and control well on the titration plate at 24, 48, or 72 hours following the addition of drug and returned to incubation at 37° C. Alamar blue fluorescence is analyzed 6-12 hours later on a CytoFluor II plate reader using 530-560 nanometer wavelength excitation, 590 nanometer emission.

A cytotoxic EC$_{50}$ is derived by plotting compound concentration on the x-axis and average percent inhibition of cell growth for each titration point on the y-axis. Growth of cells in control wells that have been treated with vehicle alone is defined as 100% growth for the assay, and the growth of cells treated with compounds is compared to this value. Proprietary in-house software is used to calculate percent cytotoxicity values and inflection points using logistic 4-parameter curve fitting.

Percent cytotoxicity is defined as:

% cytotoxicity: (Fluorescence$_{control}$)− (Flourescence$_{sample}$)×100×(Fluorescence$_{control}$)$^{-1}$ The inflection point is reported as the cytotoxic EC$_{50}$.

III. Evaluation of Mitotic Arrest and Apoptosis by FACS

FACS analysis is used to evaluate the ability of a compound to arrest cells in mitosis and to induce apoptosis by measuring DNA content in a treated population of cells. Cells are seeded at a density of 1.4×10$^6$ cells per 6 cm$^2$ tissue culture dish and allowed to adhere overnight. Cells are then treated with vehicle (0.1% DMSO) or a titration series of compound for 8-16 hours. Following treatment, cells are harvested by trypsinization at the indicated times and pelleted by centrifugation. Cell pellets are rinsed in PBS and fixed in 70% ethanol and stored at 4° C. overnight or longer.

For FACS analysis, at least 500,000 fixed cells are pelleted and the 70% ethanol is removed by aspiration. Cells are then incubated for 30 min at 4° C. with RNase A (50 Kunitz units/ml) and propidium iodide (50 μg/ml), and analyzed using a Becton Dickinson FACSCaliber. Data (from 10,000 cells) is analyzed using the Modfit cell cycle analysis modeling software (Verity Inc.).

An EC$_{50}$ for mitotic arrest is derived by plotting compound concentration on the x-axis and percentage of cells in the G2/M phase of the cell cycle for each titration point (as measured by propidium iodide fluorescence) on the y-axis. Data analysis is performed using the SigmaPlot program to calculate an inflection point using logistic 4-parameter curve fitting. The inflection point is reported as the EC$_{50}$ for mitotic arrest. A similar method is used to determine the compound EC$_{50}$ for apoptosis. Here, the percentage of apoptotic cells at each titration point (as determined by propidium iodide fluorescence) is plotted on the y-axis, and a similar analysis is carried out as described above.

VI. Immunofluorescence Microscopy to Detect Monopolar Spindles

Methods for immunofluorescence staining of DNA, tubulin, and pericentrin are essentially as described in Kapoor et al. (2000) J. Cell Biol. 150: 975-988. For cell culture studies, cells are plated on tissue culture treated glass chamber slides and allowed to adhere overnight. Cells are then incubated with the compound of interest for 4 to 16 hours. After incubation is complete, media and drug are aspirated and the chamber and gasket are removed from the glass slide. Cells are then permeabilized, fixed, washed, and blocked for nonspecific antibody binding according to the referenced protocol. Paraffin-embedded tumor sections are deparaffinized with xylene and rehydrated through an ethanol series prior to blocking. Slides are incubated in primary antibodies (mouse monoclonal anti-α-tubulin antibody, clone DM1A from Sigma diluted 1:500; rabbit polyclonal anti-pericentrin antibody from Covance, diluted 1:2000) overnight at 4° C. After washing, slides are incubated with conjugated secondary antibodies (FITC-conjugated donkey anti-mouse IgG for tubulin; Texas red-conjugated donkey anti-rabbit IgG for pericentrin) diluted to 15 μg/ml for one hour at room temperature. Slides are then washed and counterstained with Hoechst 33342 to visualize DNA. Immunostained samples are imaged with a 100× oil immersion objective on a Nikon epifluorescence microscope using Metamorph deconvolution and imaging software.

EXAMPLES

Examples provided are intended to assist in a further understanding of the invention. Particular materials employed, species and conditions are intended to be illustrative of the invention and not limiting of the reasonable scope thereof.

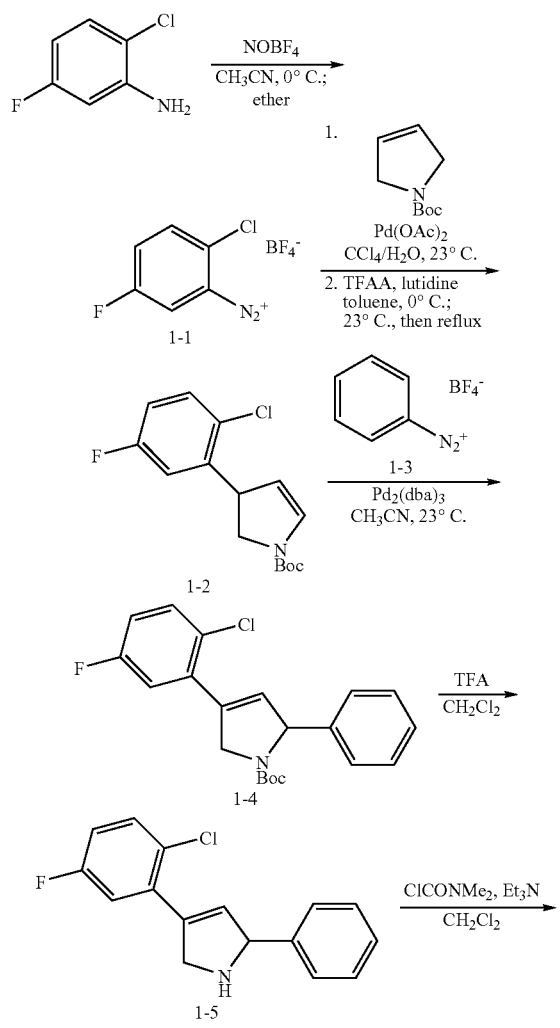

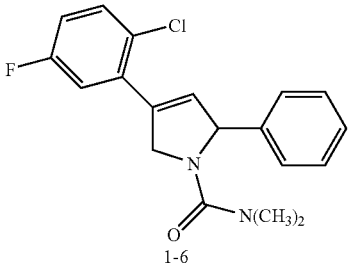

Step 1: 2-chloro-5-fluorobenzenediazonium tetrafluoroborate (1-1)

Nitrosonium tetrafluoroborate (802 mg, 6.87 mmol) was added to a solution of 2-chloro-5-fluoroaniline (1.00 g, 6.87 mmol) in acetonitrile (50 mL) at 0° C. The resulting mixture was stirred for 1 hour, then diluted with ethyl ether (150 mL). The precipitate was filtered and air-dried to give 2-chloro-5-fluorobenzenediazonium tetrafluoroborate (1-1) as an off-white solid. $^1$H NMR (300 MHz, CD$_3$OD) δ 8.66 (ddd, 1H, J=6.7, 2.1, 1.0 Hz), 8.16 (m, 2H).

Step 2: tert-butyl 3-(2-chloro-5-fluorophenyl)-2,3-dihydro-1H-pyrrole-1-carboxylate (1-2)

Palladium(II) acetate (24 mg, 0.11 mmol, 0.020 equiv) was added to a vigourously stirred, deoxygenated mixture of tert-butyl 2,5-dihydro-1H-pyrrole-1-carboxylate (900 mg, 5.32 mmol) and 2-chloro-5-fluorobenzenediazonium tetrafluoroborate (1-1, 1.30 g, 5.32 mmol) in water and carbon tetrachloride (1:1, 50 mL) at 23° C., and the resulting mixture was stirred for 20 hours. The reaction mixture was partitioned between saturated aqueous sodium bicarbonate solution (150 mL) and ethyl acetate (2×150 mL). The combined organic layers were dried over sodium sulfate and concentrated. The residue was dissolved in toluene (100 mL), and the resulting solution concentrated in vacuo to facilitate azeotropic removal of residual water. 2,6-Lutidine (1.24 mL, 10.6 mmol, 2.00 equiv) and trifluoroacetic anhydride (0.558 mL, 2.66 mmol, 0.500 equiv) were then sequentially added to a solution of the residue in toluene (100 mL) at 0° C. The resulting mixture was stirred at 0° C. for 8 hours, then warmed to 23° C. and stirred an additional 8 hours. The reaction mixture was heated at reflux for 1 hour, then cooled to 23° C. and concentrated. The residue was partitioned between ethyl acetate (100 mL) and saturated aqueous sodium bicarbonate solution (100 mL). The organic layer was dried over sodium sulfate and concentrated. The residue was purified by flash column chromatography (hexanes initially, grading to 60% EtOAc in hexanes) to give tert-butyl 3-(2-chloro-5-fluorophenyl)-2,3-dihydro-1H-pyrrole-1-carboxylate (1-2) as an orange oil. LRMS m/z (M+H—CH$_3$) 283.0 found, 283.1 required.

Step 3: tert-butyl 4-(2-chloro-5-fluorophenyl)-2-phenyl-2,5-dihydro-1H-pyrrole-1-carboxylate (1-4)

Tris(dibenzylideneacetone)dipalladium(0) (20 mg, 022 mmol, 0.020 equiv) was added to a deoxygenated mixture of tert-butyl 3-(2-chloro-5-fluorophenyl)-2,3-dihydro-1H-pyrrole-1-carboxylate (1-2, 330 mg, 1.11 mmol, 1 equiv), benzenediazonium tetrafluoroborate (1-3, prepared from aniline by the method described for 1-1, 213 mg, 1.11 mmol, 1.00 equiv), and sodium acetate trihydrate (459 mg, 3.32 mmol, 3.00 equiv) in acetonitrile (20 mL) at 23° C. The reaction mixture was stirred for 16 hours, then partitioned between saturated aqueous sodium bicarbonate solution (50 mL) and ethyl acetate (2×70 mL). The combined organic layers were dried over sodium sulfate and concentrated. The residue was purified by flash column chromatography (hexanes initially, grading to 40% hexanes in EtOAc) to provide tert-butyl 4-(2-chloro-5-fluorophenyl)-2-phenyl-2,5-dihydro-1H-pyrrole-1-carboxylate (14) as a dark orange oil. LRMS m/z (M+H—CH$_3$) 359.0 found, 359.1 required.

Step 4: 4-(2-chloro-5-fluorophenyl)-2-phenyl-2,5-dihydro-1H-pyrrole (1-5)

Trifluoroacetic acid (10 mL) was added to a solution of tert-butyl 4-(2-chloro-5-fluorophenyl)-2-phenyl-2,5-dihydro-1H-pyrrole-1-carboxylate (14, 320 mg, 0.856 mmol, 1 equiv) in dichloromethane (40 mL) at 23° C., and the resulting mixture was stirred for 30 min, then concentrated to give 4-(2-chloro-5-fluorophenyl)-2-phenyl-2,5-dihydro-1H-pyrrole (1-5) as a TFA salt (brown oil). LRMS m/z (M+H) 274.1 found, 274.1 required.

Step 5: 4-(2-chloro-5-fluorophenyl)-N,N-dimethyl-2-phenyl-2,5-dihydro-1H-pyrrole-1-carboxamide (1-6)

Triethylamine (0.600 mL, 4.28 mmol, 5.00 equiv) and dimethylcarbamoyl chloride (0.080 mL, 0.86 mmol, 1.00 equiv) were added to a solution of 4-(2-chloro-5-fluorophenyl)-2-phenyl-2,5-dihydro-1H-pyrrole (1-5, TPA salt, 0.856 mmol, 1 equiv) in dichloromethane (50 mL) at 23° C., and the resulting mixture was stirred for 2 hours, then concentrated. The residue was partitioned between saturated aqueous sodium bicarbonate solution (75 mL) and ethyl acetate (100 mL). The organic layer was dried over sodium sulfate and concentrated. The residue was suspended in ethyl ether (2 mL) and the precipitate filtered to provide 4-(2-chloro-5-fluorophenyl)-N,N-dimethyl-2-phenyl-2,5-dihydro-1H-pyrrole-1-carboxamide (1-6) as an off-white solid. $^1$H NMR (500 MHz, CDCl$_3$) δ 7.40-7.30 (m, 5H), 7.26 (m, 1H), 7.03 (dd, 1H, J=9.0, 2.9 Hz), 6.97 (m, 1H), 6.24 (m, 1H), 6.15 (m, 1H), 4.86 (ddd, 1H, J=13.9, 5.6, 2.2 Hz), 4.49 (dt, 1H, J=13.9, 2.0 Hz), 2.86 (s, 6H). LRMS m/z (M+H) 345.0 found, 345.1 required.

SCHEME 2

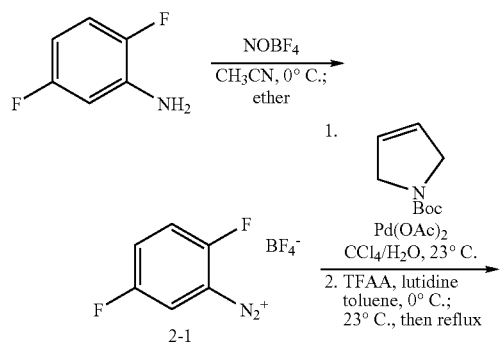

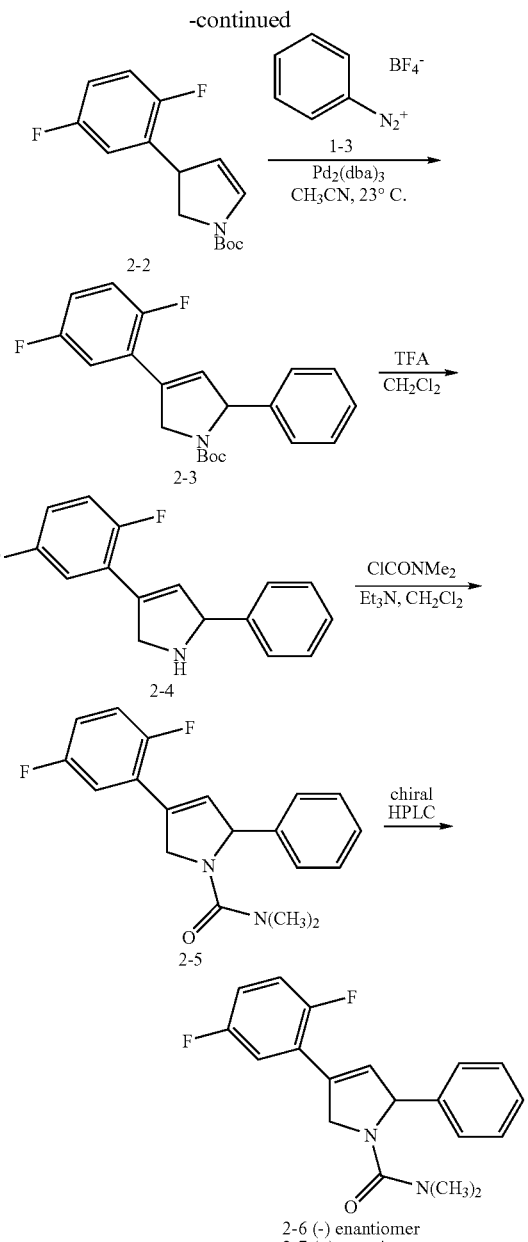

2-6 (−) enantiomer
2-7 (+) enantiomer

Step 1: 2,5-difluorobenzenediazonium tetrafluoroborate (2-1)

Nitrosonium tetrafluoroborate (905 mg, 7.75 mmol, 1.00 equiv) was added to a solution of 2,5-difluoroaniline (0.780 mL, 7.75 mmol, 1 equiv) in acetonitrile (50 mL) at 0° C. The resulting mixture was stirred for 1 hour, then diluted with ethyl ether (150 mL). The precipitate was filtered and air dried to give 2,5-difluorobenzenediazonium tetrafluoroborate (2-1) as a tan solid. $^1$H NMR (300 MHz, CD$_3$OD) δ 8.54 (m, 1H), 8.24 (m, 1H), 7.95 (m, 1H).

Step 2: tert-butyl 3-(2,5-difluorophenyl)-2,3-dihydro-1H-pyrrole-1-carboxylate (2-2)

Palladium(II) acetate (67 mg, 0.30 mmol, 0.020 equiv) was added to a vigorously stirred, deoxygenated mixture of tert-butyl 2,5-dihydro-1H-pyrrole-1-carboxylate (2.59 mL, 15.0 mmol, 1 equiv) and 2,5-difluorobenzenediazonium tetrafluoroborate (2-1, 3.42 g, 15.0 mmol, 1.00 equiv) in water and carbon tetrachloride (1:1, 150 mL) at 23° C., and the resulting mixture was stirred for 20 hours. The reaction mixture was concentrated, and the residue partitioned between ethyl acetate (300 mL) and saturated aqueous sodium bicarbonate solution (75 mL). The organic layer was washed with brine, then dried over sodium sulfate and concentrated. The residue was dissolved in toluene (200 mL), and the resulting solution concentrated in vacuo to facilitate azeotropic removal of residual water. 2,6-Lutidine (3.50 mL, 30.0 mmol, 2.00 equiv) and trifluoroacetic anhydride (1.48 mL, 10.5 mmol, 0.700 equiv) were then sequentially added to a solution of the residue in toluene (100 mL) at −10° C. The resulting mixture was allowed to warm to 10° C. over 16 hours, then heated at reflux for 1 hour. The reaction mixture was allowed to cool to 23° C., then concentrated. The residue was partitioned between ethyl acetate (300 mL) and saturated aqueous sodium bicarbonate solution (150 mL). The organic layer was dried over sodium sulfate and concentrated. The residue was purified by flash column chromatography (hexanes initially, grading to 20% EtOAc in hexanes) to give tert-butyl 3-(2,5-difluorophenyl)-2,3-dihydro-1H-pyrrole-1-carboxylate (2-2) as a red oil. $^1$H NMR (500 MHz, CDCl$_3$) major rotamer: δ 7.03-6.84 (m, 3H), 6.70 (br s, 1H), 5.01 (br s, 1H), 4.42 (m, 1H), 4.13 (m, 1H), 3.60 (m, 1H), 1.50 (s, 9H).

Step 3: tert-butyl 4-(2,5-difluorophenyl)-2-phenyl-2,5-dihydro-1H-pyrrole-1-carboxylate (2-3)

Tris(dibenzylideneacetone)dipalladium(0) (59 mg, 064 mmol, 0.020 equiv) was added to a deoxygenated mixture of tert-butyl 3-(2,5-difluorophenyl)-2,3-dihydro-1H-pyrrole-1-carboxylate (2-2, 900 mg, 3.20 mmol, 1 equiv), benzenediazonium tetrafluoroborate (1-3, prepared by the method described above for 1-1, 614 mg, 3.20 mmol, 1.00 equiv), and sodium acetate trihydrate (1.32 g, 9.60 mmol, 3.00 equiv) in acetonitrile (70 mL) at 23° C. The reaction mixture was stirred for 16 h, then partitioned between saturated aqueous sodium bicarbonate solution and ethyl acetate (2×70 mL). The combined organic layers were dried over sodium sulfate and concentrated. The residue was purified by flash column chromatography (hexanes initially, grading to 40% hexanes in EtOAc) to provide tert-butyl 4-(2,5-difluorophenyl)-2-phenyl-2,5-dihydro-1H-pyrrole-1-carboxylate (2-3) as an orange oil. LRMS m/z (M+H—CH$_3$) 343.0 found, 343.1 required.

Step 4: 4-(2,5-difluorophenyl)-2-phenyl-2,5-dihydro-1H-pyrrole (2-4)

Trifluoroacetic acid (20 mL) was added to a solution of tert-butyl 4-(2,5-difluorophenyl)-2-phenyl-2,5-dihydro-1H-pyrrole-1-carboxylate (2-3,700 mg, 1.96 mmol, 1 equiv) in dichloromethane (50 mL) at 23° C., and the resulting mixture was stirred for 30 minutes, then concentrated to give 4-(2,5-difluorophenyl)-2-phenyl-2,5-dihydro-1H-pyrrole (24) as a TFA salt (brown oil). LRMS m/z (M+H) 258.1 found, 258.1 required.

Step 5: 4-(2,5-difluorophenyl)-N,N-dimethyl-2-phenyl-2,5-dihydro-1H-pyrrole-1-carboxamide (2-5)

Triethylamine (1.37 mL, 9.79 mmol, 5.00 equiv) and dimethylcarbamoyl chloride (0.180 mL, 1.96 mmol, 1.00 equiv) were added to a solution of 4-(2,5-difluorophenyl)-2-phenyl-2,5-dihydro-1H-pyrrole (24, 1.96 mmol) in dichloromethane (50 mL) at 23° C., and the resulting mixture was stirred for 2 hours, then concentrated. The residue was partitioned between saturated aqueous sodium bicarbonate solution (75 ml) and ethyl acetate (100 mL). The organic layer was dried over sodium sulfate and concentrated. The residue was purified by reverse-phase LC (H$_2$O/CH$_3$CN gradient w/0.1% TPA present) to provide 4-(2,5-difluorophenyl)-N,N-dimethyl-2-phenyl-2,5-dihydro-1H-pyrrole-1-carboxamide (2-5) as an off-white solid. $^1$H NMR (500 MHz, CDCl$_3$) δ 7.35-7.29 (m, 4H), 7.25 (m, 1H), 7.05 (m, 1H), 7.00 (m, 1H), 6.96 (m, 1H), 6.40 (br s, 1H), 6.13 (m, 1H), 4.88 (ddd, 1H, J=13.7, 5.6, 2.0 Hz), 4.52 (d, 1H, J=13.7 Hz), 2.88 (s, 6H). LRMS m/z (M+H) 329.1 found, 329.1 required.

Step 6: Enantiomers of 4-(2,5-difluorophenyl)-N,N-dimethyl-2-phenyl-2,5-dihydro-1H-pyrrole-1-carboxamide (2-6 and 2-7)

Resolution of enantiomers of racemic 4-(2,5-difluorophenyl)-N,N-dimethyl-2-phenyl-2,5-dihydro-1H-pyrrole-1-carboxamide (2-5) by chiral normal-phase HPLC (Chiralcel OD column: 0.1% diethylamine in 40% ethanol in hexanes) provided in order of elution 2-6 (−) and 2-7 (+).

The following compounds were prepared by using appropriately substituted anilines in place of 2,5-difluoroaniline in Step 1 and simple modifications of the above procedure.

| Cmpd | Structure | Name | $^1$H NMR/LRMS m/z (M + H) |
|---|---|---|---|
| 2-8 | (structure with Cl, F, N(CH$_3$)$_2$ substituents) | 4-(5-chloro-2-fluorophenyl)-N,N-dimethyl-2-phenyl-2,5-dihydro-1H-pyrrole-1-carboxamide | $^1$H NMR (500 MHz, CDCl$_3$) δ 7.36-7.20 (m, 7H), 7.04 (dd, 1H, J=10.7, 8.8 Hz), 6.40 (br s, 1H), 6.13 (m, 1H), 4.87 (ddd, 1H, J=13.7, 5.6, 2.0 Hz), 4.52 (d, 1H, J = 13.7 Hz), 2.88 (s, 6H). LRMS m/z (M+H) 345.0 found, 345.1 required. |

-continued

| Cmpd | Structure | Name | ¹H NMR/LRMS m/z (M + H) |
|---|---|---|---|
| 2-9 | 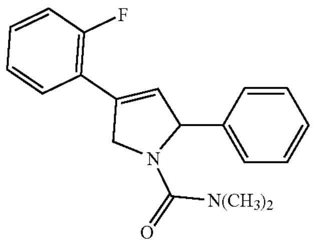 | 4-(2-fluorophenyl)-N,N-dimethyl-2-phenyl-2,5-dihydro-1H-pyrrole-1-carboxamide | ¹H NMR (300 MHz, CDCl₃) δ 7.38-7.20 (m, 8H), 7.18-7.05 (m, 2H), 6.36 (br s, 1H), 6.12 (m, 1H), 4.92 (ddd, 1H, J= 13.7, 5.6, 2.0 Hz), 4.56 (d, 1H, J = 13.7 Hz), 2.88 (s, 6H). LRMS m/z (M+H) 311.0 found, 311.1 required. |
| 2-10 | 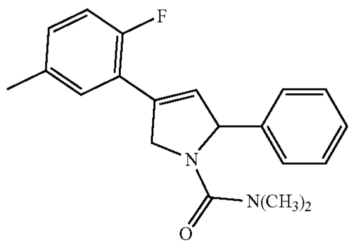 | 4-(2-fluoro-5-methylphenyl)-N,N-dimethyl-2-phenyl-2,5-dihydro-1H-pyrrole-1-carboxamide | ¹H NMR (500 MHz, CDCl₃) δ 7.36-7.29 (m, 4H), 7.24 (m, 1H), 7.11 (dd, 1H, J=7.3, 2.0 Hz), 7.05 (m, 1H), 6.97 (dd, 1H, J=11.2, 8.3 Hz), 6.33 (br s, 1H), 6.11 (m, 1H), 4.89 (ddd, 1H, J = 13.7, 5.6, 2.0 Hz), 4.54 (d, 1H, J = 13.9 Hz), 2.88 (s, 6H), 2.32 (s, 3H). LRMS m/z (M + H) 325.0 found, 325.2 required. |
| 2-11 | 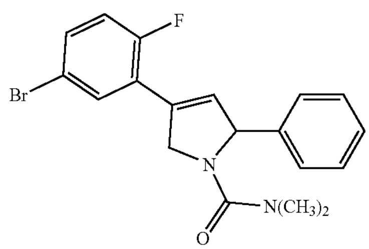 | 4-(5-bromo-2-fluorophenyl)-N,N-dimethyl-2-phenyl-2,5-dihydro-1H-pyrrole-1-carboxamide | ¹H NMR (500 MHz, CDCl₃) δ 7.42 (dd, 1H, J=6.6, 2.4 Hz), 7.37 (ddd, 1H, J=6.8, 4.4, 2.4 Hz), 7.34-7.23 (m, 5H), 6.99 (dd, 1H, J=11.0, 8.8 Hz), 6.40 (br s, 1H), 6.13 (m, 1H), 4.87 (ddd, 1H, J = 13.7, 5.6, 2.0 Hz), 4.52 (d, 1H, J= 13.7 Hz), 2.88 (s, 6H). LRMS m/z (M + H) 390.9 found, 391.1 required. |
| 2-12 | 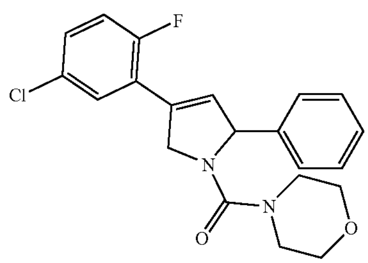 | 4-{[4-(5-chloro-2-fluoro-phenyl)-2-phenyl-2,5-dihydro-1H-pyrrol-1-yl]carbonyl}morpholine | ¹H NMR (500 MHz, CD₃OD) δ 7.33 (m, 3H), 7.25 (m, 2H), 7.14 (m, 1H), 7.07 (m, 1H), 6.42 (br s, 1H), 6.07 (m, 1H), 4.99 (ddd, 1H, J = 13.9, 5.6, 2.0 Hz), 4.62 (br d, 1H, J= 13.9 Hz), 3.68 (m, 2H), 3.58 (m, 2H), 3.46 (m, 2H), 3.21 (m, 2H). LRMS m/z (M + H) 387.1 found, 387.1 required. |
| 2-13 | 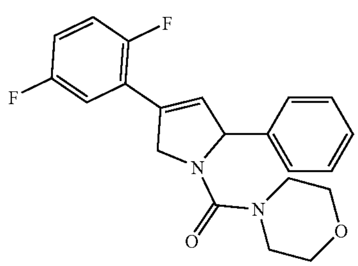 | 4-{[4-(2,5-difluorophenyl)-2-phenyl-2,5-dihydro-1H-pyrrol-1-yl]carbonyl}morpholine | ¹H NMR (500 MHz, CD₃OD) δ 7.46 (dd, 1H, J = 8.8, 5.1 Hz), 7.35 (m, 3H), 7.27 (tt, 1H, J = 6.8, 2.2 Hz), 7.23 (dd, 1H, J = 8.8, 6.4, 3.2 Hz), 7.09 (dd, 1H, J=4.9, 3.2 Hz), 6.26 (m, 1H), 6.08 (m, 1H), 4.97 (ddd, 1H, J=13.9, 5.6, 2.0 Hz), 4.58 (dt, 1H, J = 10.3, 1.9 Hz), 3.65 (m, 2H), 3.57 (m, 2H), 3.43 (m, 2H), 3.19 (m, 2H). LRMS m/z (M + H) 371.0 found, 370.1 required. |
| 2-14 | 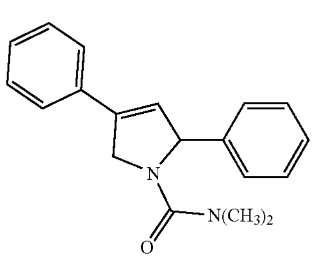 | N,N-dimethyl-2,4-diphenyl-2,5-dihydro-1H-pyrrole-1-carboxamide | ¹H NMR (500 MHz, CDCl₃) δ 7.42 (br d, 2H, J = 7.6 Hz), 7.36 (br t, 2H, J = 7.1 Hz), 7.33-7.28 (m, 5H), 7.24 (m, 1H), 6.18 (m, 1H), 6.09 (m, 1H), 4.90 (ddd, 1H, J=13.7, 5.6, 2.0Hz), 4.52 (dt, 1H, J= 13.7, 2.0 Hz), 2.88 (s, 6H). LRMS m/z (M + H) 293.15 found, 293.16 required. |

SCHEME 3

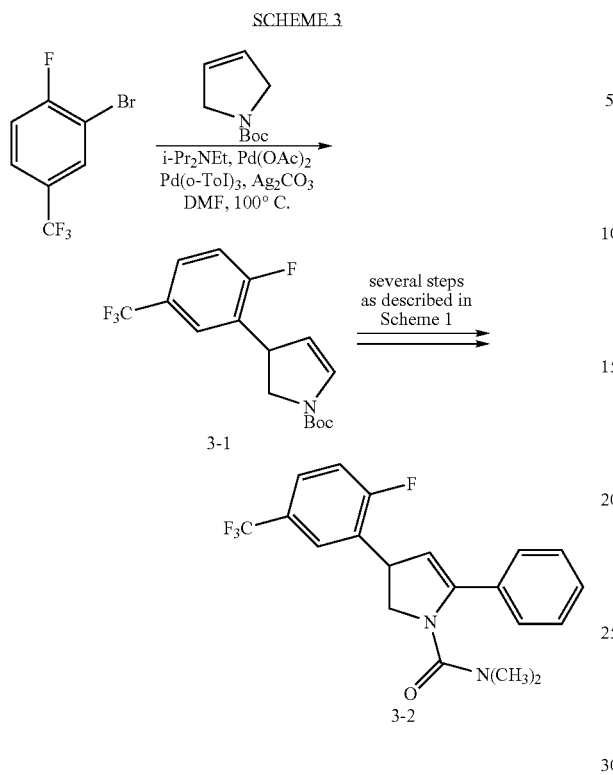

SCHEME 4

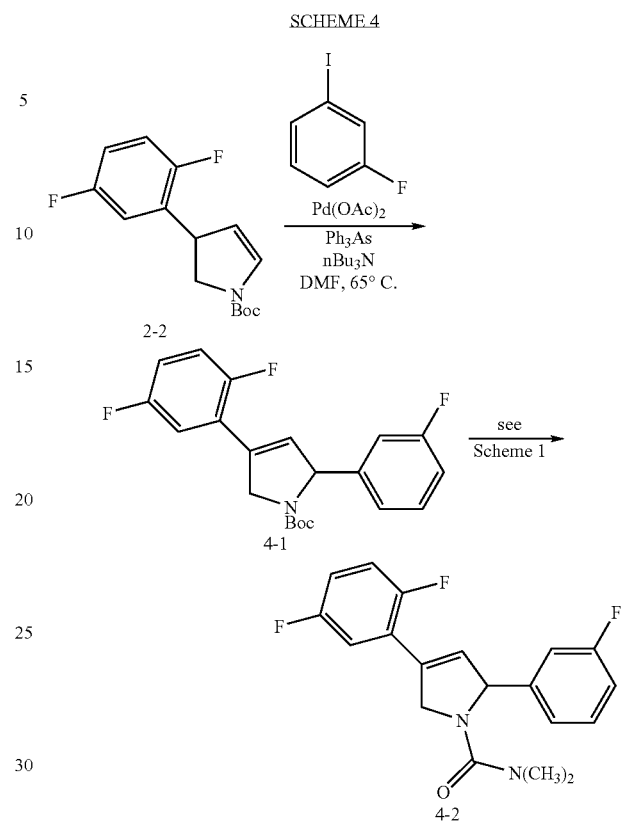

Step 1: tert-butyl 3-[2-fluoro-5-(trifluoromethyl) phenyl]-2,3-dihydro-1H-pyrrole-1-carboxylate (3-1)

A deoxygenated solution of tert-butyl 2,5-dihydro-1H-pyrrole-1-carboxylate (3.38 g, 20.0 mmol, 10.0 equiv), 2-bromo-1-fluoro-4-(trifluoromethyl)benzene (486 mg, 2.00 mmol, 1 equiv), N,N-diisopropylethylamine (1.39 mL, 8.00 mmol, 4.00 equiv), tri-o-tolylphosphine (67 mg, 0.22 mmol, 0.11 equiv), palladium(II) acetate (22 mg, 0.10 mmol, 0.050 equiv), and silver carbonate (386 mg, 1.40 mmol, 0.700 equiv) in DMF (8.0 mL) was heated under nitrogen at 100° C. for 20 h. The reaction mixture was partitioned between saturated aqueous sodium bicarbonate solution (50 mL) and ethyl acetate (50 mL). The organic layer was washed with brine, dried over magnesium sulfate, and concentrated. The residue was purified by flash column chromatography (20% $CH_2Cl_2$ in hexanes, grading to 50% $CH_2Cl_2$ in hexanes) to give tert-butyl 3-[2-fluoro-5-(trifluoromethyl)phenyl]-2,3-dihydro-1H-pyrrole-1-carboxylate (3-1) as a colorless gum. $^1$H NMR (500 MHz, $CDCl_3$) major rotamer: δ 7.51 (m, 2H), 7.15 (t, 1H, J=9.1 Hz), 6.74 (br s, 1H), 5.03 (br s, 1H), 4.48 (m, 1H), 4.17 (m, 1H), 3.61 (m, 1H), 1.50 (s, 9H).

Step 2: 3-[2-fluoro-5-(trifluoromethyl)phenyl]-N,N-dimethyl-5-phenyl-2,3-dihydro-1H-pyrrole-1-carboxamide (3-2)

3-[2-fluoro-5-(trifluoromethyl)phenyl]-N,N-dimethyl-5-phenyl-2,3-dihydro-1H-pyrrole-1-carboxamide (3-2) was prepared from tert-butyl 3-[2-fluoro-5-(trifluoromethyl)phenyl]-2,3-dihydro-1H-pyrrole-1-carboxylate (3-1) following the method of Scheme 1. $^1$H NMR (500 MHz, $CDCl_3$) δ 7.56 (m, 2H), 7.33 (m, 3H), 7.26 (m, 1H), 7.21 (dd, 1H, J=10.7, 8.8 Hz), 6.46 (br s, 1H), 6.15 (m, 1H), 4.93 (ddd, 1H, J=13.7, 5.6, 2.0 Hz), 4.58 (d, 1H, J=13.7 Hz), 2.89 (s, 6H). LRMS m/z (M+H) 379.0 found, 379.1 required.

Step 1: tert-butyl 4-(2,5-difluorophenyl)-2-(3-fluorophenyl)-2,5-dihydro-1H-pyrrole-1-carboxylate (4-1)

To a flame dried flask equipped with stir bar was added tert-butyl 3-(2,5-difluorophenyl)-2,3-dihydro-1H-pyrrole-1-carboxylate (2-2, 0.088 g, 0.31 mmol), 3-fluoro-1-iodobenzene (0.070 g, 0.31 mmol), triphenylarsine (0.038 g, 0.13 mmol), tributylamine (0.15 mL, 0.62 mmol) and anhydrous DMF (2.0 mL). The resulting solution was purged, and filled with a nitrogen atmosphere. Palladium acetate (0.014 g, 0.06 mmol) was added in one portion, and the reaction was carefully returned to a nitrogen atmosphere. The reaction stirred under nitrogen for 24 h at 65° C. The reaction was then diluted with EtOAc (10 mL) and poured into 5% aq. $NaHCO_3$ in a separatory funnel. The organic layer was washed with brine, separated and dried over magnesium sulfate. The organic layer was then filtered and concentrated to provide crude product. Purification by flash column chromatography ($SiO_2$, 0-20% EtOAc/hexanes gradient) provided tert-butyl 4-(2,5-difluorophenyl)-2-(3-fluorophenyl)-2,5-dihydro-1H-pyrrole-1-carboxylate (4-1). LRMS m/z (M+H) 361.0 found, 361.1 required (M−15). Further transformations followed those described in Scheme 1.

Step 2: 2-(3-fluorophenyl)-4-(2,5-difluorophenyl)-N,N-dimethyl-2,5-dihydro-1H-pyrrole-1-carboxamide (4-2)

Using the procedures described in Steps 4 and 5 of Scheme 1, but substituting intermediate 4-1 for intermediate 1-4 provided the title compound. $^1$H NMR (400 MHz, $CDCl_3$) δ 7.29 (m, 1H), 7.14-6.90 (m, 6H), 6.37 (m, 1H), 6.14 (m, 1H), 4.86 (ddd, J=13.7, 5.5, 1.2 Hz, 1H), 4.51 (d, J=13.7 Hz, 1H), 2.91 (s, 6H). LRMS m/z (M+H) 347.0 found, 347.1 required.

The following compounds were prepared by simple modifications of the above procedures.

| Cmpd | Structure | Name | $^1$H NMR/LRMS m/z (M + H) |
|---|---|---|---|
| 4-3 | 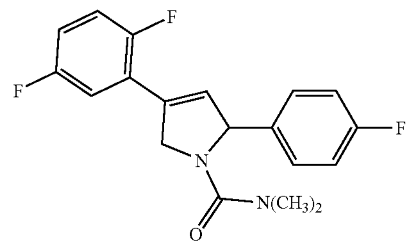 | 4-(2,5-difluorophenyl)-2-(4-fluorophenyl)-N,N-dimethyl-2,5-dihydro-1H-pyrrole-1-carboxamide | $^1$H NMR (500 MHz, CDCl$_3$) δ 7.33-7.29 (m, 2H), 7.09-6.94 (m, 5H), 6.37 (s, 1H), 6.13 (m, 1H), 4.85 (ddd, J=13.5, 5.5, 2.0 Hz, 1H), 4.50 (d, J = 13.5 Hz, 1H), 2.88 (s, 6H). LRMS m/z (M + H) 347.0 found, 347.1 required. |
| 4-4 | 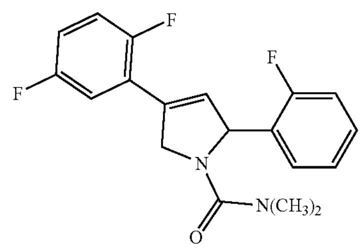 | 4-(2,5-difluorophenyl)-2-(2-fluorophenyl)-N,N-dimethyl-2,5-dihydro-1H-pyrrole-1-carboxamide | $^1$H NMR (500 MHz, CDCl$_3$) δ 7.31-7.20 (m, 2H), 7.12-6.93 (m, 5H), 6.40 (s, 1H), 6.37 (m, 1H), 4.89 (ddd, J = 13.5, 5.5, 2.0 Hz, 1H), 4.56 (d, J = 13.5 Hz, 1H), 2.92 (s, 6H). LRMS m/z (M + H) 346.9 found, 347.1 required. |
| 4-5 | 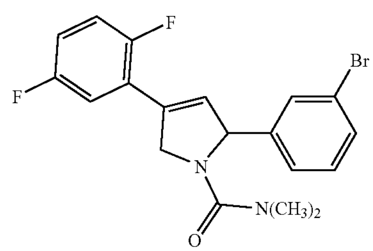 | 2-(3-bromophenyl)-4-(2,5-difluorophenyl)-N,N-dimethyl-2,5-dihydro-1H-pyrrole-1-carboxamide | $^1$H NMR (500 MHz, CDCl$_3$) δ 7.45 (s, 1H), 7.38 (d, J = 7.5 Hz, 1H), 7.29 (d, J = 7.5 Hz, 1H), 7.19 (t, J = 7.5 Hz, 1H), 7.09-7.04 (m, 1H), 7.02-6.95 (m, 2H), 6.36 (s, 1H), 6.13 (t, J=3.0 Hz, 1H), 4.85 (ddd, J=13.0, 5.5, 1.5 Hz, 1H), 4.51 (d, J=13.5, 1H), 2.91 (s, 6H). LRMS m/z (M + H) 408.9 found, 409.1 required. |
| 4-6 | 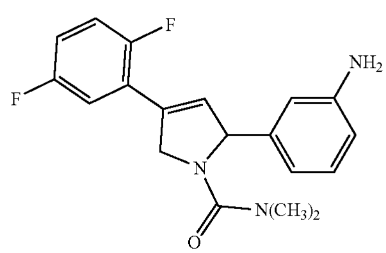 | 2-(3-aminophenyl)-4-(2,5-difluorophenyl)-N,N-dimethyl-2,5-dihydro-1H-pyrrole-1-carboxamide | $^1$H NMR (500 MHz, CDCl$_3$) δ 8.06 (br s, 3H), 7.43 (s, 1H), 7.32 (t, J = 7.5 Hz, 1H), 7.27 (d, J=4 Hz, 1H), 7.22 (d, J = 7.5 Hz, 1H), 7.07-7.02 (m, 1H), 6.98-6.94 (m, 2H), 6.31 (s, 1H), 6.07 (m, 1H), 4.86 (dd, J = 13.5, 4.0 Hz, 1H), 4.47 (d, J = 13.5 Hz, 1H), 2.82 (s, 6H). LRMS m/z (M + H) 344.0 found, 344.1 required. |
| 4-7 | 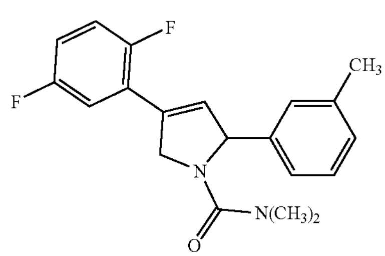 | 4-(2,5-difluorophenyl)-2-(3-methylphenyl)-N,N-dimethyl-2,5-dihydro-1H-pyrrole-1-carboxamide | $^1$NMR (500 MHz, CDCl$_3$) δ 7.21 (t, J= 7.5 Hz, 1H), 7.12-6.94 (m, 6H), 6.38 (s, 1H), 6.08 (m, 1H), 4.90 (ddd, J = 14.0, 5.5, 2.0 Hz, 1H), 4.53 (d, J = 14.0 Hz, 1H), 2.89 (s, 6H), 2.33 (s, 3H). LRMS m/z (M + H) 343.1 found, 343.2 required. |

SCHEME 5

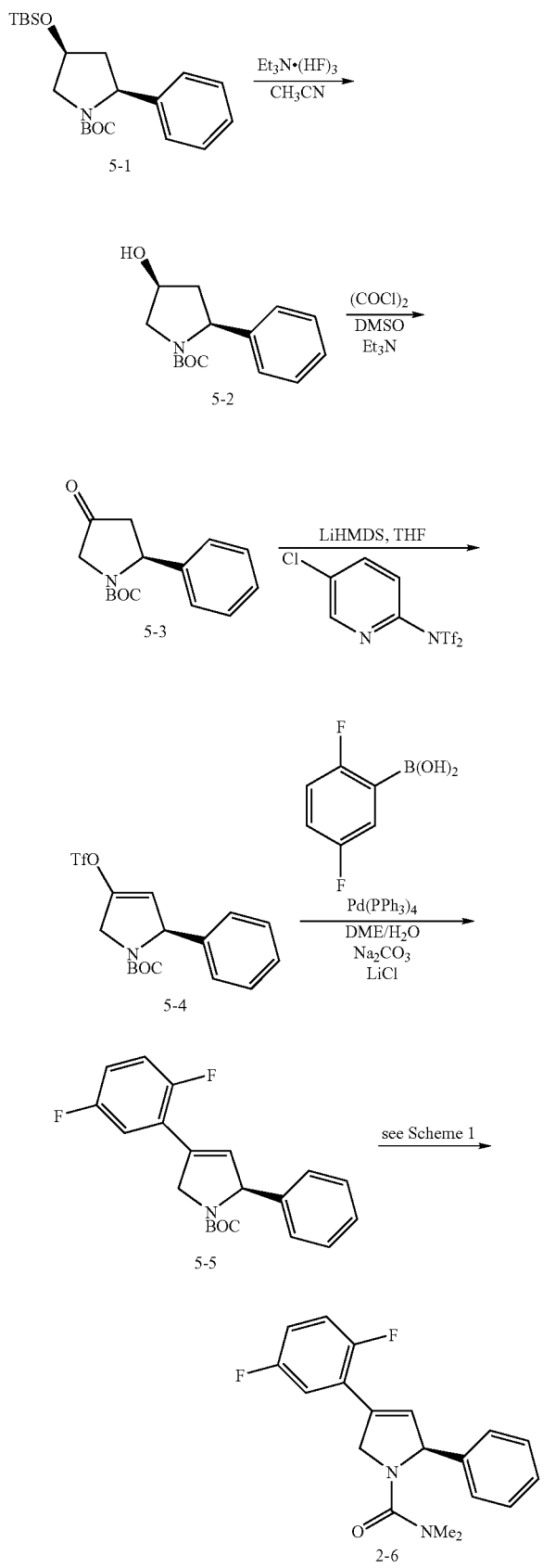

Step 1: (2S,4S)-tert-Butyl 4-hydroxy-2-phenylpyrrolidine-1-carboxylate (5-2)

To a flame dried flask equipped with stir bar was added tert-butyl (2S,4S)-4-{[tert-butyl(dimethyl)silyl]oxy}-2-phenylpyrrolidine-1-carboxylate (5-1, prepared from (S)-(−)-4-chloro-3-hydroxybutyronotrile by the method of Maeda, et al *Synlett* 2001, 1808-1810, 7.8 g, 20.7 mmol) and anhydrous acetonitrile (20.0 mL). The resulting solution was treated with triethylamine trihydrofluoride (10.1 mL, 62.0 mmol) while stirring under $N_2$. The reaction stirred 12 hours at 40° C. The reaction was then diluted with EtOAc (100 mL) and poured into 5% aq. $NaHCO_3$. Following cessation of gas evolution, the organic layer was washed three addition times with 5% aq. $NaHCO_3$. The organic layer was dried over magnesium sulfate, filtered and concentrated to provide crude product. Recrystallization was effected from EtOAc/hexanes to provide (2S,4S)-tert-butyl 4-hydroxy-2-phenylpyrrolidine-1-carboxylate (5-2) as a white crystalline solid. $^1$H NMR (300 MHz, $CDCl_3$) rotamers δ 7.38-7.18 (m, 5H), 4.90 (m, 1H), 4.42 (m, 1H), 3.88 (m, 1H), 3.56 (dd, J=11.5, 4.0 Hz, 1H), 2.60 (m, 1H), 2.03 (m, 1H), 1.50 and 1.20 (br s, 9H); MS 208.0 found, 208.1 (M-C(CH$_3$)$_3$) required.

Step 2: (2S)-tert-butyl 4-oxo-2-phenylpyrrolidine-1-carboxylate (5-3)

To a flame dried flask equipped with stir bar was added 150 mL anhydrous dichloromethane which was cooled to −78° C. Oxalyl chloride (3.8 mL, 44 mmol) and DMSO (4.8 mL, 61 mmol) were added sequentially and the reaction stirred for 10 minutes. (2S,4S)-tert-Butyl 4-hydroxy-2-phenylpyrrolidine-1-carboxylate (5-2, 2.28 g, 8.73 mmol) in 10 mL anhydrous dichloromethane was added dropwise and stirred 1 hour at −78° C. Triethylamine (12 mL, 87 mmol) was added and the reaction was warmed to 0° C. over 1 hour. Upon completion, the reaction was washed with 5% NaHCO$_3$, brine and dried over MgSO$_4$. The organic layer was concentrated to provide crude (2S)-tert-butyl 4-oxo-2-phenylpyrrolidine-1-carboxylate (5-3). Recrystallization was effected with EtOAc/hexanes. $^1$H NMR (300 MHz, CDCl$_3$) δ 7.35 (m, 3H), 7.17 (m, 2H), 5.38 (m, 1H), 4.08 (d, J=19.5 Hz, 1H), 3.90 (d, J=19.3 Hz, 1H), 3.13 (dd, J=18.8, 9.8 Hz, 1H), 2.58 (dd, J=18.6, 2.4 Hz, 1H), 1.40 (br s, 9H); MS 206.0 found, 206.1 (M-C(CH$_3$)$_3$) required.

Step 3: (2S)-tert-butyl 2-phenyl-4-([[(trifluoromethyl)sulfonyl]oxy}-2,5-dihydro-1H-pyrrole-1-carboxylate (5-4)

To a flame dried flask equipped with stir bar was added ketone (2S)-tert-butyl 4-oxo-2-phenylpyrrolidine-1-carboxylate (5-3, 0.16 g, 0.62 mmol) and anhydrous THF (2 mL). The resulting solution was cooled to −78° C., and treated dropwise with lithium hexamethyldisilylamide (LH-MDS, 0.68 mL, 1M in THF, 0.68 mmoL). The reaction stirred 1 hour at −78° C., and N-(5-chloropyridin-2-yl)-1,1,1-trifluoro-N-[(trifluoromethyl)sulfonyl]methanesulfonamide (0.27 g, 068 mmol) was added neat in one portion. The reaction was allowed to warm to 0° C. and stirred 4 hours total. The reaction was diluted with Et₂O (10 mL) and washed successively with H₂O (10 mL) and brine (10 mL). The organic layer was dried over MgSO₄, filtered and concentrated. The crude residue was purified by flash column choromatography (0-20% EtOAc/hexanes gradient, 15 min) to provide (2S)-tert-butyl 2-phenyl-4-{[(trifluoromethyl)sulfonyl]oxy}-2,5-dihydro-1H-pyrrole-1-carboxylate (54). ¹H NMR (300 MD, CDCl₃) major rotamer: δ 7.30 (m, 5H), 5.72 (m, 1H), 5.48 (m, 1H), 4.42 (m, 2H), 1.18 (s, 9H); MS 379.0 found 379.1 (M-CH₃) required.

Step 4: (2S)-4-(2,5-difluorophenyl)-2-phenyl-N,N-dimethyl-2,5-dihydro-1H-pyrrole-1-carboxamide (2-6)

To a flame dried flask equipped with stir bar was added (2S)-tert-butyl 2-phenyl-4-{[(trifluoromethyl)sulfonyl]oxy}-2,5-dihydro-1H-pyrrole-1-carboxylate (5-4, 0.250 g, 0.636 mmol), 2,5-difluorophenyl boronic acid (0.251 g, 1.59 mmol), Na₂CO₃ (0.202 g, 1.91 mmol), and LiCl (0.081 g, 1.91 mmol). The solids were dissolved in 20 mL 4:1 DME/H₂O and degassed with nitrogen. Pd(PPh₃)₄ (0.037 g, 0.032 mmol) was added and the reaction was sealed under nitrogen and heated to 90° C. for 2 hours. Upon completion, the reaction was partitioned between 5% aq. NaHCO₃ and EtOAc (3×50 m]L), and the combined organic layers were dried over MgSO₄. Following filtration, the organic layer was concentrated and purified via flash column chromatography (SiO₂, 0-20% EtOAc/hexanes gradient) to provide (2S)-tert-butyl 4-(2,5-difluorophenyl)-2-phenyl-2,5-dihydro-1H-pyrrole-1-carboxylate (5-5). Further transformations followed those described in Scheme 1 to provide compound 2-6.

The following compounds were prepared by simple modifications of the above procedures.

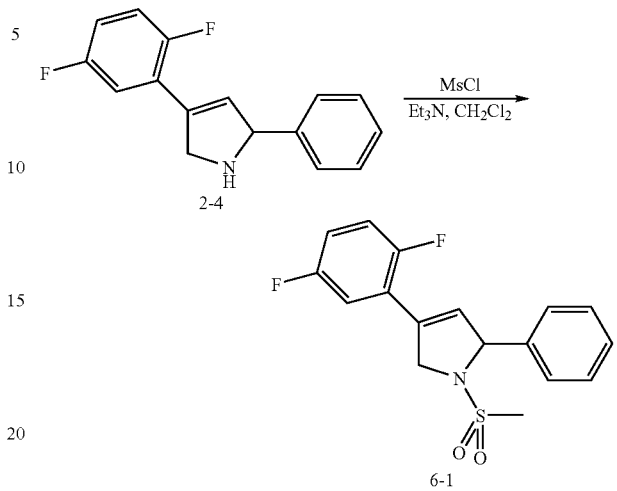

SCHEME 6

4-(2,5-difluorophenyl)-1-(methylsulfonyl)-2-phenyl-2,5-dihydro-1H-pyrrole (6-1)

Methanesulfonyl chloride (40 μL, 0.51 mmol, 1.00 equiv) was added to a solution of 4-(2,5-difluorophenyl)-2-phenyl-2,5-dihydro-1H-pyrrole (2-4, 130 mg, 0.505 mmol, 1 equiv) and triethylamine (350 μL, 2.52 mmol, 5.00 equiv) in dichloromethane (30 mL) at 23° C., and the resulting reaction mixture was stirred for 16 hours. The reaction mixture was partitioned between saturated aqueous sodium bicarbonate solution (50 mL) and ethyl acetate (3×50 mL). The combined organic layers were dried over sodium sulfate and concentrated. The residue was purified by reverse-phase LC (H₂O/CH₃CN gradient w/0.1% TFA present) to provide 4-(2,5-difluorophenyl)-1-(methylsulfonyl)-2-phenyl-2,5-dihydro-1H-pyrrole (6-1) as a tan solid. ¹H NMR (300 MHz, CDCl₃) δ 7.39-7.30 (m, 5H), 7.09 (td, 1H, J=9.8, 4.6 Hz), 7.01 (m, 2H), 6.36 (br s, 1H), 5.76 (m, 1H), 4.84 (br d, 1H, J=13.2 Hz), 4.64 (ddd, 1H, J=13.2, 5.6, 2.0 Hz), 2.55 (s, 3H). LRMS m/z (M+H) 336.0 found, 336.1 required.-

| Cmpd | Structure | Name | ¹H NMR/LRMS m/z (M + H) |
|---|---|---|---|
| 5-6 | (structure with F, F, N-C(O)-N(CH₃)₂, phenyl) | (2S)-4-(5-chloro-2-fluorophenyl)-N,N-dimethyl-2-phenyl-2,5-dihydro-1H-pyrrole-1-carboxamide | ¹H NMR (300 MHz, CDCl₃) δ 7.34-7.22 (m, 6H), 6.92-6.82 (m, 2H), 6.29 (m, 1H), 6.10 (m, 1H), 4.88 (ddd, 1H, J = 13.7, 5.6, 2.0 Hz), 4.53 (d, 1H, J = 13.7 Hz), 2.87 (s, 6H). LRMS m/z (M + H) 329.0 found, 329.1 required. |

The following compounds were prepared by simple modifications of the above procedure.

| Cmpd | Structure | Name | ¹H NMR/LRMS m/z (M + H) |
|---|---|---|---|
| 6-2 | 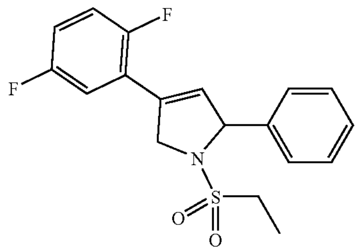 | 4-(2,5-difluorophenyl)-1-(ethylsulfonyl)-2-phenyl-2,5-dihydro-1H-pyrrole | ¹H NMR (300 MHz, CDCl₃) δ 7.40-7.30 (m, 5H), 7.08 (td, 1H, J = 9.8, 4.6 Hz), 7.00 (m, 2H), 6.35 (br s, 1H), 5.81 (m, 1H), 4.95 (br d, 1H, J = 13.2 Hz), 4.62 (ddd, 1H, J = 13.2, 5.6, 2.0 Hz), 2.65 (m, 1H), 2.57 (m, 1H), 1.16 (t, 3H, J= 7.3 Hz) LRMS m/z (M +H) 350.0 found, 350.1 required. |
| 6-3 | 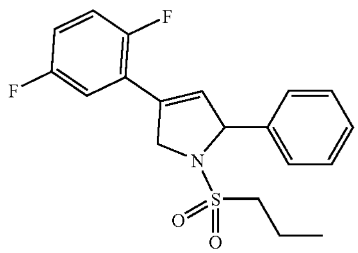 | 4-(2,5-difluorophenyl)-2-phenyl-1-(propylsulfonyl)-2,5-dihydro-1H-pyrrole | ¹H NMR (300 MHz, CDCl₃) δ 7.40-7.30 (m, 5H), 7.08 (td, 1H, J=9.8, 4.6 Hz), 6.98 (m, 2H), 6.35 (br s, 1H), 5.80 (m, 1H), 4.92 (br d, 1H, J = 13.2 Hz), 4.61 (ddd, 1H, J=13.2, 5.6, 2.0 Hz), 2.59 (m, 1H), 2.48 (m, 1H), 1.67 (m, 2H), 0.82 (t, 3H, 7.3 Hz) LRMS m/z (M + H) 364.0 found, 364.1 required. |
| 6-4 | 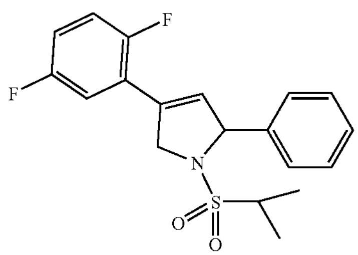 | 4-(2,5-difluorophenyl)-1-(isopropylsulfonyl)-2-phenyl-2,5-dihydro-1H-pyrrole | ¹H NMR (300 MHz, CDCl₃) δ 7.40-7.30 (m, 5H), 7.08 (td, 1H, J=9.8, 4.6 Hz), 6.98 (m, 2H), 6.35 (br s, 1H), 5.87 (m, 1H), 5.01 (br d, 1H, J=13.2 Hz), 4.58 (ddd, 1H, J=13.2, 5.6, 2.0 Hz), 2.57 (pentet, 1H, J=6.7 Hz), 1.18 (d, 3H, J= 7.0 Hz), 1.13 (d, 3H, J=6.7 Hz) LRMS m/z (M + H) 364.0 found, 364.1 required. |
| 6-5 | 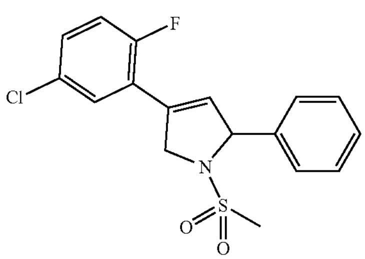 | 4-(5-chloro-2-fluorophenyl)-1-(methylsulfonyl)-2-phenyl-2,5-dihydro-1H-pyrrole | ¹H NMR (500 MHz, CD₃OD) δ 7.49 (dd, 1H, J=8.8, 5.1 Hz), 7.45 (br d, 2H, J = 7.3 Hz), 7.38 (br t, 2H, J=7.3 Hz), 7.32 (br t, 1H, J = 7.1 Hz), 7.26 (dd, 1H, J = 9.3, 2.9 Hz), 7.12 (td, 1H, J = 8.6, 2.9 Hz), 6.22 (m, 1H), 5.75 (m, 1H), 4.74 (dt, 1H, J = 14.2, 2.0 Hz), 4.68 (ddd, 1H, J= 14.2, 5.4, 2.0 Hz), 2.74 (s, 3H). LRMS m/z (M + H) 352.0 found, 352.05 required. |
| 6-6 | 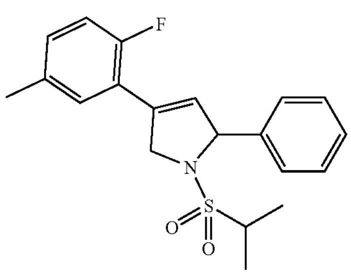 | 4-(2-fluoro-5-methylphenyl)-1-(isopropylsulfonyl)-2-phenyl-2,5-dihydro-1H-pyrrole | LRMS m/z (M + H) 360.1 found, 360.1 required. |

| Cmpd | Structure | Name | ¹H NMR/LRMS m/z (M + H) |
|---|---|---|---|
| 6-7 | 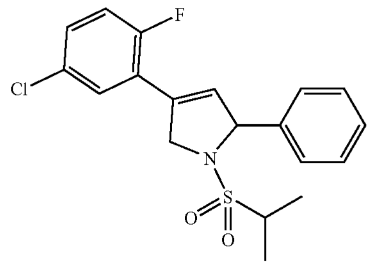 | 4-(5-chloro-2-fluorophenyl)-1-(isopropylsulfonyl)-2-phenyl-2,5-dihydro-1H-pyrrole | ¹H NMR (500 MHz, CD₃OD) δ 7.49 (dd, 1H, J=8.8, 5.1 Hz), 7.44 (br d, 2H, J = 7.3 Hz), 7.39 (br t, 2H, J=7.3 Hz), 7.32 (br t, 1H, J=7.1 Hz), 7.24 (dd, 1H, J = 9.3, 2.9 Hz), 7.11 (td, 1H, J=8.6, 2.9 Hz), 6.19 (m, 1H), 5.84 (m, 1H), 4.89 (dt, 1H, J = 14.2, 2.0 Hz), 4.64 (ddd, 1H, J= 14.2, 5.4, 2.0 Hz), 2.76 (m, 1H), 1.15 (d, 3H, J=6.8 Hz), 1.14 (d, 3H, J=6.8 Hz). LRMS m/z (M + H) 379.9 found, 380.1 required. |

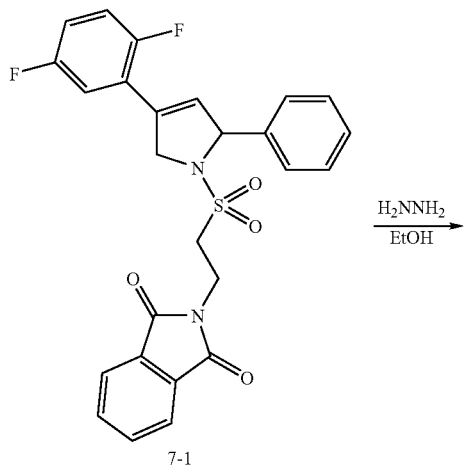

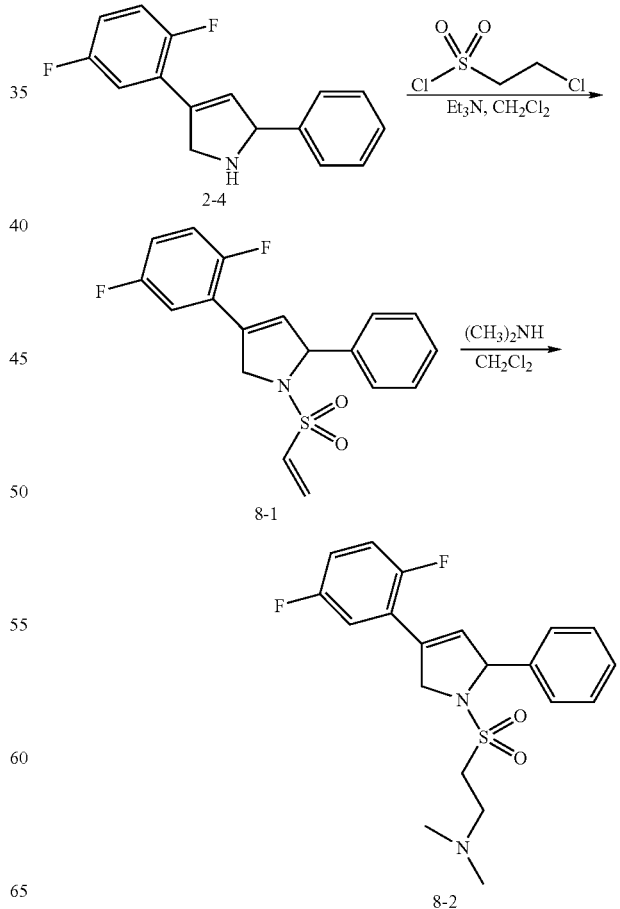

2-{[4-(2,5-difluorophenyl)-2-phenyl-2,5-dihydro-1H-pyrrol-1-yl]sulfonyl}ethanamine (7-2)

A solution of hydrazine hydrate (20 μL, 0.35 mmol, 4.0 equiv) and 2-(2-{[4-(2,5-difluorophenyl)-2-phenyl-2,5-dihydro-1H-pyrrol-1-yl]sulfonyl}ethyl)-1H-isoindole-1,3 (2H)-dione (7-1, prepared by the method of Scheme 6 from the corresponding sulfonyl chloride, 43 mg, 0.087 mmol, 1 equiv) in ethanol (5 mL) was heated at reflux for 5 hours. The reaction mixture was partitioned between saturated aqueous sodium bicarbonate solution (50 mL) and ethyl acetate (3×50 mL). The combined organic layers were dried over sodium sulfate and concentrated. The residue was purified by reverse-phase LC (H₂O/CH₃CN gradient w/0.1% TFA present) to provide 2-{[4-(2,5-difluorophenyl)-2-phenyl-2,5-dihydro-1H-pyrrol-1-yl]sulfonyl}ethanamine (7-2) as a TFA salt (white solid). ¹H NMR (300 MHz, CD₃OD) δ 7.42 (m, 5H), 7.30-7.05 (br m, 3H), 6.42 (br s, 1H), 5.93 (m, 1H), 4.83 (m, 2H), 3.35-3.02 (br m, 4H). LRMS m/z (M+H) 365.0 found, 365.1 required.

Step 1: 4-(2,5-difluorophenyl)-2-phenyl-1-(vinylsulfonyl)-2,5-dihydro-1H-pyrrole (8-1)

Triethylamine (122 µL, 0.874 mmol, 5.00 equiv) and 2-chloroethanesulfonyl chloride (29 mg, 0.175 mmol, 1.00 equiv) were added sequentially to a solution of 4-(2,5-difluorophenyl)-2-phenyl-2,5-dihydro-1H-pyrrole (2-4, 45 mg, 0.175 mmol, 1 equiv) in dichloromethane (10 mL) at 23° C., and the resulting mixture was stirred for 1 hour. The reaction mixture was partitioned between saturated aqueous sodium bicarbonate solution (50 mL) and ethyl acetate (2×50 mL). The combined organic layers were dried over sodium sulfate and were concentrated to provide 4-(2,5-difluorophenyl)-2-phenyl-1-(vinylsulfonyl)-2,5-dihydro-1H-pyrrole (8-1) as a brown oil. LRMS m/z (M+H) 348.0 found, 348.1 required.

Step 2: 2-{[4-(2,5-difluorophenyl)-2-phenyl-2,5-dihydro-1H-pyrrol-1-yl]sulfonyl}-N,N-dimethylethanamine (8-2)

Dimethylamine hydrochloride (7.0 mg, 0.086 mmol, 1.0 equiv) was added to a solution of 4-(2,5-difluorophenyl)-2-phenyl-1-(vinylsulfonyl)-2,5-dihydro-1H-pyrrole (8-1, 30 mg, 0.086 mmol, 1 equiv) and N,N-diisopropylethylamine (75 µL, 0.43 mmol, 5.0 equiv) in dichloromethane (5 mL) at 23° C., and the resulting mixture was stirred for 16 hours. Additional dimethylamine hydrochloride (21 mg, 0.26 mmol, 3.0 equiv) was added the and reaction mixture was stirred for 3 hours, then partitioned between saturated aqueous sodium bicarbonate solution (50 mL) and ethyl acetate (3×50 mL). The combined organic layers were dried over sodium sulfate and concentrated. The residue was purified by reverse-phase LC (H₂O/CH₃CN gradient w/0.1% TFA present) to provide 2-{[4-(2,5-difluorophenyl)-2-phenyl-2,5-dihydro-1H-pyrrol-1-yl]sulfonyl}-N,N-dimethylethanamine (8-2) as a TFA salt (white solid). $^1$H NMR (300 MHz, CD₃OD) δ 7.43 (m, 5H), 7.30-7.10 (br m, 3H), 6.42 (br s, 1H), 5.86 (m, 1H), 4.94-4.74 (br m, 2H), 3.46-3.14 (br m, 4H), 2.78 (s, 6H). LRMS m/z (M+H) 393.0 found, 393.1 required.

1-acetyl-4-(2,5-difluorophenyl)-2-phenyl-2,5-dihydro-1H-pyrrole (9-1)

Acetic anhydride (44 µL, 0.47 mmol, 2.0 equiv) and triethylamine (163 µL, 1.17 mmol, 5.00 equiv) were added sequentially to a solution of 4-(2-chloro-5-fluorophenyl)-2-phenyl-2,5-dihydro-1H-pyrrole (2-4, 60 mg, 0.233 mmol, 1 equiv) in dichloromethane (10 mL) at 23° C., and the resulting mixture was stirred for 1 hour. The reaction mixture was concentrated and the residue purified by reverse-phase LC (H₂O/CH₃CN gradient w/0.1% TFA present) to provide 1-acetyl-4-(2,5-difluorophenyl)-2-phenyl-2,5-dihydro-1H-pyrrole (9-1) as a colorless oil. $^1$H NMR (500 MHz, CDCl₃) major rotamer: δ 7.40-7.24 (m, 5H), 7.11-6.94 (m, 3H), 6.38 (br s, 1H), 5.69 (br s, 1H), 4.91 (d, 1H, J=15.9 Hz), 4.79 (dd, 1H, J=15.9, 4.4 Hz), 1.89 (s, 3H). LRMS m/z (M+H) 300.0 found, 300.1 required.

SCHEME 10

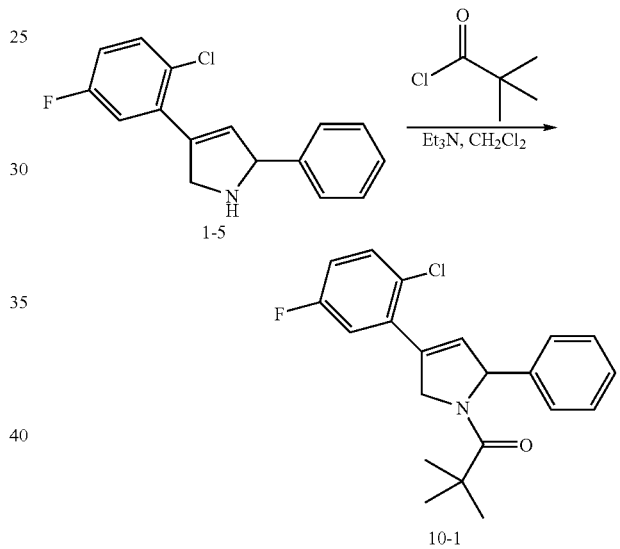

4-(2-chloro-5-fluorophenyl)-1-pivaloyl-2-phenyl-2,5-dihydro-1H-pyrrole (10-1)

Triethylamine (149 µL, 1.07 mmol, 10.00 equiv) and pivaloyl chloride (26 µL, 0.214 mmol, 2.00 equiv) were added sequentially to a solution of 4-(2-chloro-5-fluorophenyl)-2-phenyl-2,5-dihydro-1H-pyrrole (1-5, 0.107 mmol, 1 equiv) in dichloromethane (10 mL) at 23° C., and the resulting mixture was stirred for 20 minutes. The reaction mixture was concentrated and the residue purified by reverse-phase LC (H₂O/CH₃CN gradient w/0.1% TFA present) to provide 4-(2-chloro-5-fluorophenyl)-1-(2,2-dimethylpropanoyl)-2-phenyl-2,5-dihydro-1H-pyrrole (10-1) as a tan solid. $^1$H NMR (300 MHz, CDCl₃) δ 7.39 (dd, 1H, J=8.8, 5.2 Hz), 7.33 (m, 4H), 7.26 (m, 1H), 7.05 (dd, 1H, J=9.2, 3.1 Hz), 6.99 (m, 1H), 6.20 (m, 1H), 5.98 (m, 1H), 5.00 (m, 2H), 1.28 (s, 9H). LRMS m/z (M+H) 358.0 found, 358.1 required.

SCHEME 9

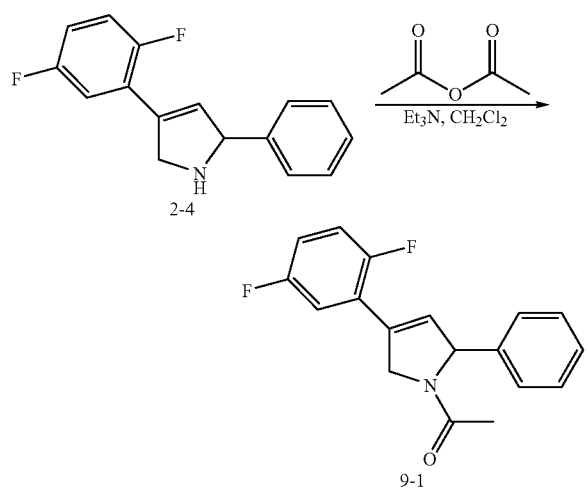

The following compounds were prepared by simple modifications of the above procedure.

| Cmpd | Structure | Name | $^1$H NMR/LRMS m/z (M + H) |
|---|---|---|---|
| 10-2 | 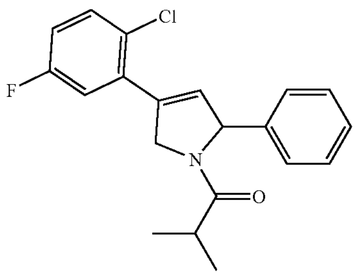 | 4-(2-chloro-5-fluorophenyl)-1-isobutyryl-2-phenyl-2,5-dihydro-1H-pyrrole | LRMS m/z (M + H) 344.0 found, 344.1 required. |
| 10-3 | 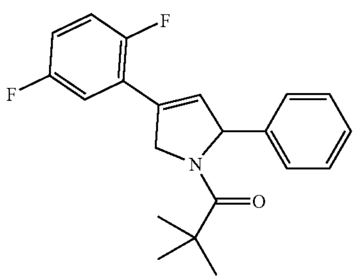 | 4-(2,5-difluorophenyl)-1-(2,2-dimethyl-propanoyl)-2-phenyl-2,5-dihydro-1H-pyrrole | LRMS m/z (M + H) 342.1 found, 342.2 required. |

SCHEME 11

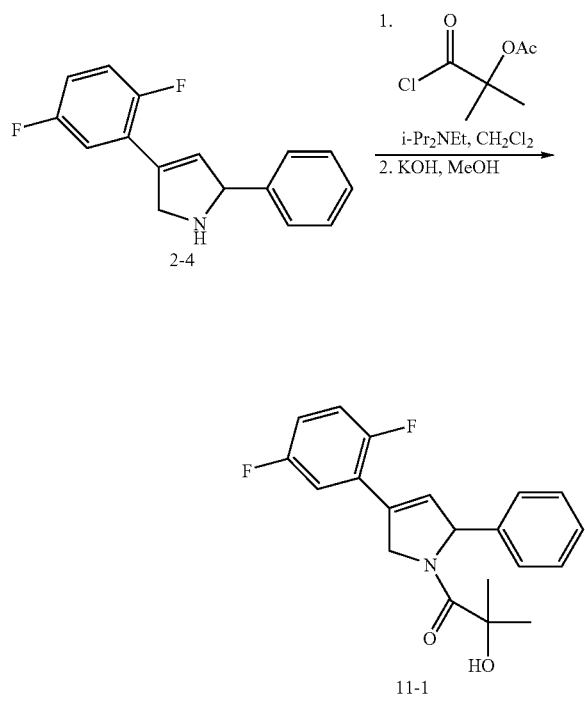

1-[4-(2,5-difluorophenyl)-2-phenyl-2,5-dihydro-1H-pyrrol-1-yl]-2-methyl-1-oxopropan-2-ol (11-1)

N,N-Diisopropylethylamine (200 μL, 1.2 mmol, 5.0 equiv) and 2-chloro-1,1-dimethyl-2-oxoethyl acetate (50 μL, 0.35 mmol, 1.5 equiv) were added sequentially to a solution of 4-(2,5-difluorophenyl)-2-phenyl-2,5-dihydro-1H-pyrrole (2-4, 60 mg, 0.23 mmol, 1 equiv) in dichloromethane (12 mL) at 23° C., and the resulting mixture was stirred for 35 minutes. The reaction mixture was partitioned between saturated aqueous sodium bicarbonate solution (40 mL) and dichloromethane (2×35 mL). The combined organic layers were dried over sodium sulfate and concentrated. Potassium hydroxide (65 mg, 1.2 mmol, 5.0 equiv) was added to a solution of the residue in 4:1 mixture of methanol and water (20 mL) and the resulting mixture was stirred at 23° C. for 20 hours. The reaction mixture was partitioned between half-saturated aqueous sodium chloride solution (55 mL) and ethyl acetate (50 mL). The organic layer was dried over sodium sulfate and concentrated. The residue was purified by reverse-phase LC (H$_2$O/CH$_3$CN gradient w/0.1% TFA present) to provide 1-[4-(2,5-difluorophenyl)-2-phenyl-2,5-dihydro-1H-pyrrol-1-yl]-2-methyl-1-oxopropan-2-ol (11-1) as an off-white solid. $^1$H NMR (500 MHz, CD$_3$OD) δ 7.30 (m, 4H), 7.22 (m, 2H), 7.14 (m, 1H), 7.08 (m, 1H), 6.40 (m, 1H), 5.91 (m, 1H), 5.27 (d, 1H, J=14.9 Hz), 5.19 (br d, 1H, J=14.9 Hz), 1.43 (s, 3H), 1.41 (s, 3H). LRMS m/z (M+H) 344.1 found, 344.1 required.-

The following compounds were prepared by simple modifications of the above procedure.

| Cmpd | Structure | Name | $^1$H NMR/LRMS m/z (M + H) |
|---|---|---|---|
| 11-2 | (structure shown) | 1-[4-(5-chloro-2-fluorophenyl)-2-phenyl-2,5-dihydro-1H-pyrrol-1-yl]-2-methyl-1-oxopropan-2-ol | $^1$H NMR (500 MHz, CD$_3$OD) δ 7.46 (dd, 1H, J = 8.8, 5.1 Hz), 7.36 (br d, 2H, J = 7.6 Hz), 7.32 (br t, 2H, J=7.3 Hz), 7.22 (m, 2H), 7.09 (td, 1H, J=8.6, 2.9 Hz), 6.21 (m, 1H), 5.91 (m, 1H), 5.24 (d, 1H, J=14.9 Hz), 5.19 (ddd, 1H, J=14.9, 5.6, 2.0 Hz), 1.42 (s, 3H), 1.38 (s, 3H). LRMS m/z (M + H) 360.0 found, 360.1 required. |

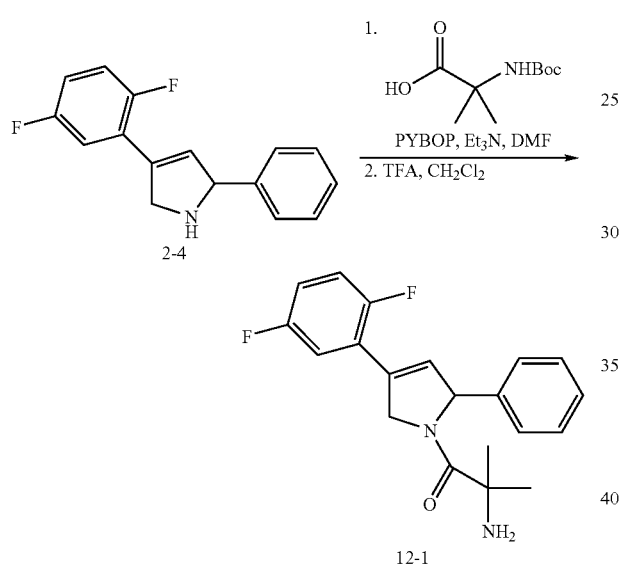

SCHEME 12

1-[4-(2,5-difluorophenyl)-2-phenyl-2,5-dihydro-1H-pyrrol-1-yl]-2-methyl-1-oxopropan-2-amine (12-1)

A solution of N-(tert-butoxycarbonyl)-2-methylalanine (65 mg, 0.32 mmol, 1.5 equiv), 4-(2,5-difluorophenyl)-2-phenyl-2,5-dihydro-1H-pyrrole (2-4, 55 mg, 0.21 mmol, 1 equiv), triethylamine (75 μL, 0.54 mmol, 2.5 equiv), and PYBOP (145 mg, 0.279 mmol, 1.30 equiv) in DMF (15 mL) was stirred at 23° C. for 20 hours. Additional triethylamine (75 μL, 0.54 mmol, 2.5 equiv), and PYBOP (145 mg, 0.279 mmol, 1.30 equiv) were added and the resulting mixture stirred for 5 hours. The reaction mixture was partitioned between water (50 mL) and dichloromethane (2×50 mL). The combined organic layers were dried over sodium sulfate and concentrated. A solution of the residue in a 1:1 mixture (10 mL) of TFA and dichloromethane was stirred for 1.5 hours, then concentrated. The residue was purified by reverse-phase LC (H$_2$O/CH$_3$CN gradient w/0.1% TFA present) to provide 1-[4-(2,5-difluorophenyl)-2-phenyl-2,5-dihydro-1H-pyrrol-1-yl]-2-methyl-1-oxopropan-2-amine (12-1) as a TFA salt (light yellow oil). $^1$H NMR (500 MHz, CDCl$_3$) δ 7.28-6.98 (m, 8H), 6.33 (br s, 1H), 5.90 (m, 1H), 4.89 (m, 4H), 1.66 (s, 3H), 1.61 (s, 3H). LRMS m/z (M+H) 343.1 found, 343.15 required.

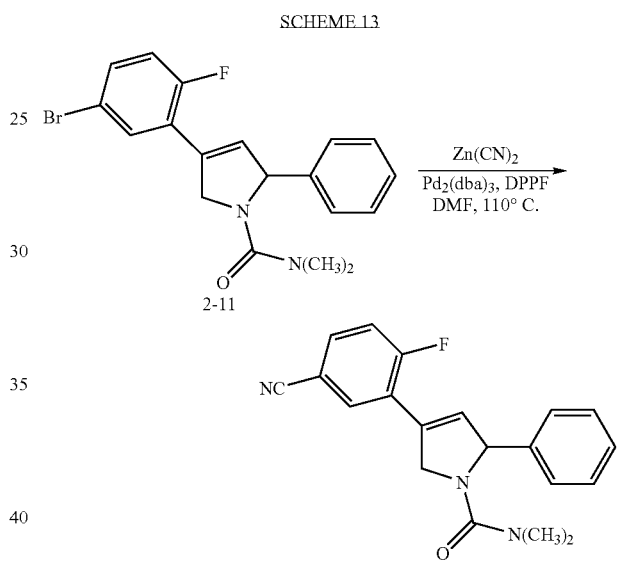

SCHEME 13

4-(2-fluoro-5-isocyanophenyl)-N,N-dimethyl-2-phenyl-2,5-dihydro-1H-pyrrole-1-carboxamide (13-1)

A deoxygenated solution of 4-(5-bromo-2-fluorophenyl)-N,N-dimethyl-2-phenyl-2,5-dihydro-1H-pyrrole-1-carboxamide (2-11, 50 mg, 0.13 mmol, 1 equiv), zinc cyanide (10 mg, 0.85 mmol, 0.66 equiv), tris(dibenzylideneacetone)-dipalladium (12 mg, 0.013 mmol, 0.10 equiv), and 1,1'-bis (diphenylphosphino)-ferrocene (17 mg, 0.031 mmol, 0.24 equiv) in DMF (3 mL) was heated at 110° C. for 3 hours. The reaction mixture was partitioned between brine (50 mL) and ethyl acetate (50 mL). The organic layer was dried over sodium sulfate and concentrated. The residue was purified by flash column chromatography (CH$_2$Cl$_2$ initially, grading to 10% EtOAc in CH$_2$Cl$_2$) to provide 4-(2-fluoro-5-isocyanophenyl)-N,N-dimethyl-2-phenyl-2,5-dihydro-1H-pyrrole-1-carboxamide (13-1) as a pale yellow solid. $^1$H NMR (500 MHz, CDCl$_3$) δ 7.62 (dd, 1H, j=6.8, 2.0 Hz), 7.59 (m, 1H), 7.33 (m, 4H), 7.26 (m, 1H), 7.22 (dd, 1H, J=10.7, 8.8 Hz), 6.49 (br s, 1H), 6.16 (m, 1H), 4.89 (ddd, 1H, J=13.7, 5.6, 2.0 Hz), 4.55 (d, 1H, J=13.7 Hz), 2.89 (s, 6H). LRMS m/z (M+H) 336.05 found, 336.14 required.

SCHEME 14

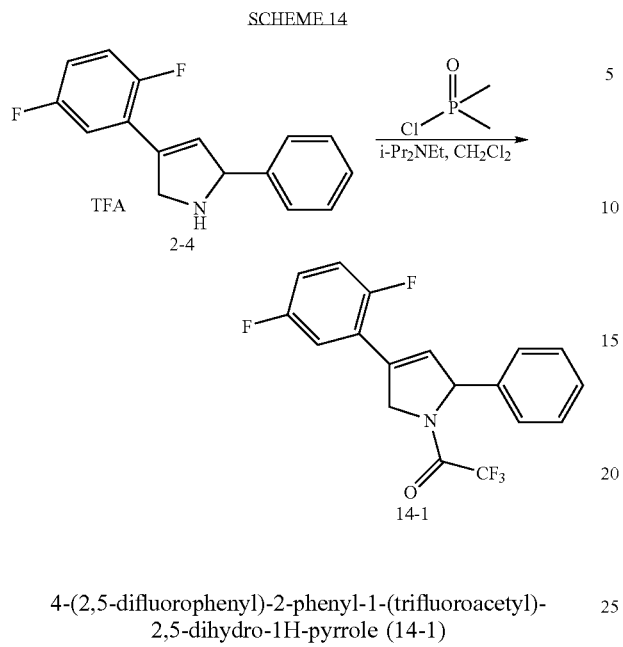

4-(2,5-difluorophenyl)-2-phenyl-1-(trifluoroacetyl)-
2,5-dihydro-1H-pyrrole (14-1)

N,N-Diisopropylethylamine (190 μL, 1.1 mmol, 5.0 equiv) and dimethylphosphinic chloride (36 mg, 0.32 mmol, 1.5 equiv) were added sequentially to a solution of the TFA salt of 4-(2,5-difluorophenyl)-2-phenyl-2,5-dihydro-1H-pyrrole (2-4, 55 mg, 0.21 mmol, 1 equiv) in dichloromethane (10 mL) at 23° C., and the resulting mixture was stirred for 20 hours. The reaction mixture was then partitioned between saturated aqueous sodium bicarbonate solution (40 mL) and dichloromethane (2×35 mL). The combined organic layers were dried over sodium sulfate and concentrated. The residue was purified by reverse-phase LC ($H_2O/CH_3CN$ gradient w/0.1% TPA present) to provide 4-(2,5-difluorophenyl)-2-phenyl-1-(trifluoroacetyl)-2,5-dihydro-1H-pyrrole (14-1) as an off-white solid. $^1$H NMR (500 MHz, $CD_3OD$) major rotamer: δ 7.33 (m, 4H), 7.28 (m, 2H), 7.20 (m, 1H), 7.12 (m, 1H), 6.45 (m, 1H), 5.96 (m, 1H), 5.14 (br d, 1H, J=14.9 Hz), 5.05 (br d, 1H, J=14.9 Hz). LRMS m/z (M+H) 354.0 found, 354.1 required.

The following compounds were prepared by simple modifications of the above procedure.

SCHEME 15

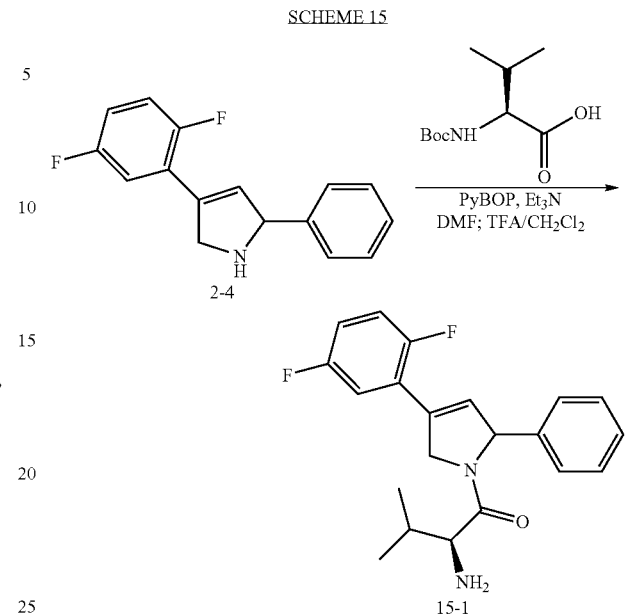

(1S)-1-{[4-(2,5-difluorophenyl)-2-phenyl-2,5-dihydro-1H-pyrrol-1-yl]carbonyl}-2-methylpropylamine
(15-1)

N-(tert-butoxycarbonyl)-L-valine (101 mg, 0.464 mmol, 2.00 equiv), PYBOP (243 mg, 0.467 mmol, 2.00 equiv), and triethylamine (0.163 mL, 1.17 mmol, 5.00 equiv) were added to a solution of 4-(2,5-difluorophenyl)-2-phenyl-2,5-dihydro-1H-pyrrole (24, 0.233 mmol, 1 equiv) in DMF (10 mL) at 23° C., and the resulting mixture was stirred for 20 hours. The reaction mixture was partitioned between a 3:1 mixture of saturated aqueous sodium bicarbonate solution and brine (50 mL) and ethyl acetate (50 mL). The organic layer was dried over sodium sulfate and concentrated. The residue was dissolved in a 1:1 mixture of trifluoroacetic acid and dichloromethane (10 mL), and the resulting solution was allowed to stand for 45 minutes, then concentrated. The residue was purified by reverse-phase LC ($H_2O/CH_3CN$ gradient w/0.1% TPA present) to provide (1S)-1-{[4-(2,5-difluorophenyl)-2-phenyl-2,5-dihydro-1H-pyrrol-1-yl]car-

| Cmpd | Structure | Name | $^1$H NMR/LRMS m/z (M + H) |
|---|---|---|---|
| 14-2 | ![structure] | 4-(5-chloro-2-fluorophenyl)-2-phenyl-1-(trifluoroacetyl)-2,5-dihydro-1H-pyrrole | $^1$H NMR (500 MHz, $CD_3OD$) major rotamer: δ 7.49 (dd, 1H, J=8.8, 5.1 Hz), 7.39 (br d, 2H, J= 7.3 Hz), 7.35 (br t, 2H, J= 7.3 Hz), 7.32 (br t, 1H, J= 7.1 Hz), 7.25 (dd, 1H, J= 9.3, 2.9 Hz), 7.11 (td, 1H, J=8.6,2.9 Hz), 6.25 (m, 1H), 5.96 (m, 1H), 5.12 (br d, 1H, J=14.9 Hz), 4.99 (br d, 1H, J = 14.9 Hz). LRMS m/z (M + H) 370.0 found, 370.05 required. | bonyl}-2-methylpropylamine (15-1) as a 1:1 mixture of diastereomers (tan gum) (isolated as the TFA salt). LRMS m/z (M+H) 357.2 found, 357.2 required.

The following compounds were prepared by simple modifications of the above procedure. Unless otherwise indicated, the compounds in the table were isolated as the TEA salt.

| Cmpd | Structure | Name | LRMS m/z (M + H) |
|---|---|---|---|
| 15-2 | 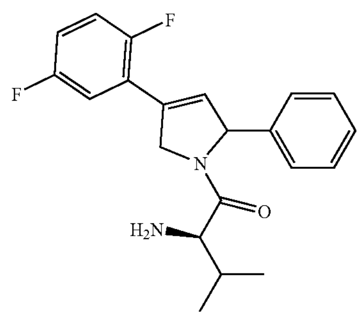 | (1R)-1-{[4-(2,5-difluorophenyl)-2-phenyl-2,5-dihydro-1H-pyrrol-1-yl]carbonyl}-2-methylpropylamine | LRMS m/z (M + H) 357.2 found, 357.2 required. |
| 15-3 | 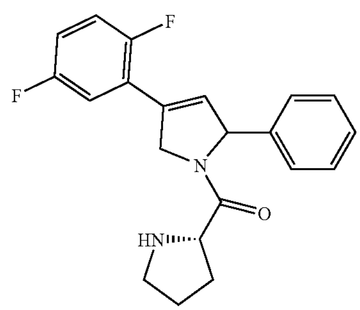 | 4-(2,5-difluorophenyl)-2-phenyl-1-L-prolyl-2,5-dihydro-1H-pyrrole. | LRMS m/z (M + H) 355.2 found, 355.2 required |
| 15-4 | 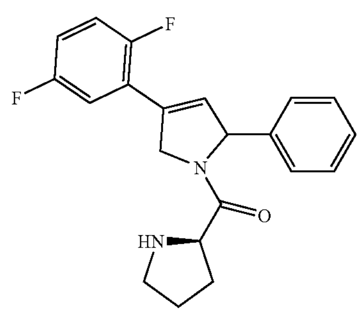 | 4-(2,5-difluorophenyl)-2-phenyl-1-D-prolyl-2,5-dihydro-1H-pyrrole | LRMS m/z (M + H) 355.2 found, 355.2 required |
| 15-5 | 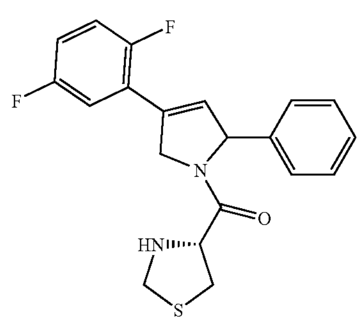 | (4R)-4-{[4-(2,5-difluorophenyl)-2-phenyl-2,5-dihydro-1H-pyrrol-1-yl]carbonyl}-1,3-thiazolidine | LRMS m/z (M + H) 373.1 found, 373.1 required |

| Cmpd | Structure | Name | LRMS m/z (M + H) |
|---|---|---|---|
| 15-6 | 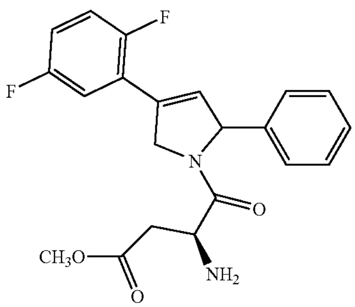 | methyl (3S)-3-amino-4-[4-(2,5-difluorophenyl)-2-phenyl-2,5-dihydro-1H-pyrrol-1-yl]-4-oxobutanoate | LRMS m/z (M + H) 387.2 found, 387.1 required |
| 15-7 | 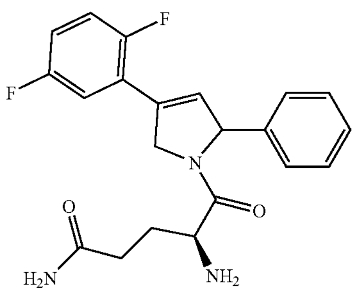 | (4S)-4-amino-5-[4-(2,5-difluorophenyl)-2-phenyl-2,5-dihydro-1H-pyrrol-1-yl]-5-oxopentanamide | LRMS m/z (M + H) 386.1 found, 386.2 required |
| 15-8 | 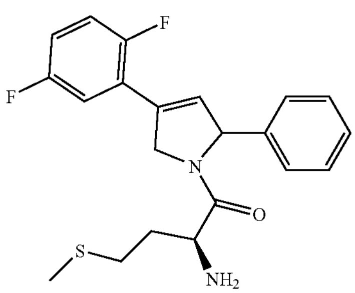 | (1S)-1-{[4-(2,5-difluorophenyl)-2-phenyl-2,5-dihydro-1H-pyrrol-1-yl]carbonyl}-3-(methylthio)propylamine | LRMS m/z (M + H) 389.2 found, 389.1 required |
| 15-9 | 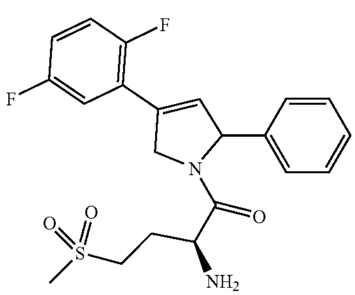 | (1S)-1-{[4-(2,5-difluorophenyl)-2-phenyl-2,5-dihydro-1H-pyrrol-1-yl]carbonyl)-3-(methylsulfonyl)propylamine | LRMS m/z (M + H) 421.1 found, 421.1 required |
| 15-10 | 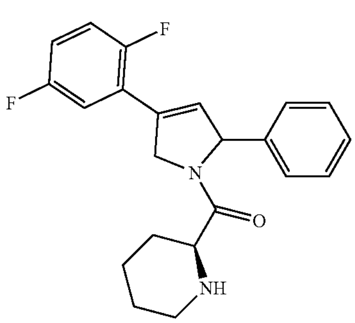 | (2S)-2-{[4-(2,5-difluorophenyl)-2-phenyl-2,5-dihydro-1H-pyrrol-1-yl]carbonyl}piperidine | LRMS m/z (M + H) 369.2 found, 369.2 required |

-continued

| Cmpd | Structure | Name | LRMS m/z (M + H) |
|---|---|---|---|
| 15-11 | 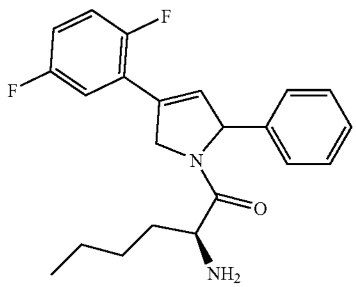 | (1S)-1-{[4-(2,5-difluorophenyl)-2-phenyl-2,5-dihydro-1H-pyrrol-1-yl]cabonyl}pentylamine | LRMS m/z (M + H) 371.1 found, 371.2 required |
| 15-12 | 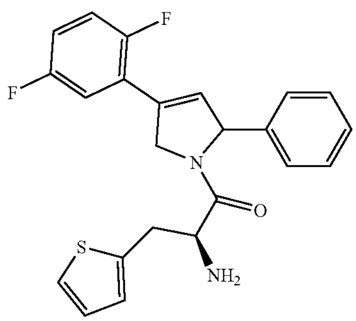 | (1S)-2-[4-(2,5-difluorophenyl)-2-phenyl-2,5-dihydro-1H-pyrrol-1-yl]-2-oxo-1-thien-2-ylmethyl)ethylamine | LRMS m/z (M + H) 411.1 found, 411.1 required |
| 15-13 | 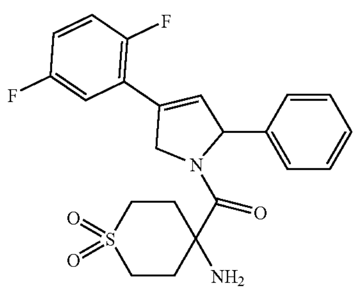 | 4-{[4-(2,5-difluorophenyl)-2-phenyl-2,5-dihydro-1H-pyrrol-1-yl]carbonyl}-1,1-dioxidotetrahydro-2H-thiopyran-4-ylamine | LRMS m/z (M + H) 433.1 found, 433.1 required |
| 15-14 | 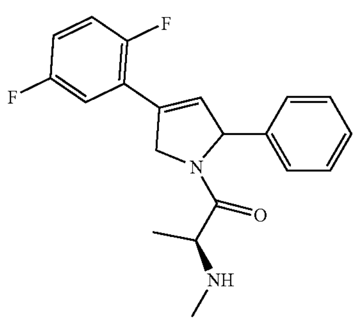 | (2S)-1-[4-(2,5-difluorophenyl)-2-phenyl-2,5-dihydro-1H-pyrrol-1-yl]-N-methyl-1-oxopropan-2-amine | LRMS m/z (M + H) 343.1 found, 343.2 required |
| 15-15 | 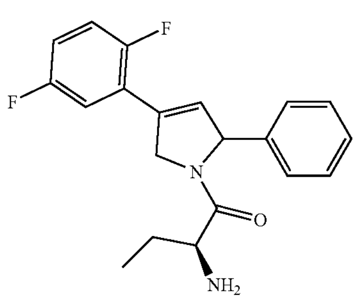 | (1S)-1-{[4-(2,5-difluorophenyl)-2-phenyl-2,5-dihydro-1H-pyrrol-1-yl]carbonyl}propylamine | LRMS m/z (M + H) 343.1 found, 343.2 required |

-continued

| Cmpd | Structure | Name | LRMS m/z (M + H) |
|---|---|---|---|
| 15-16 | 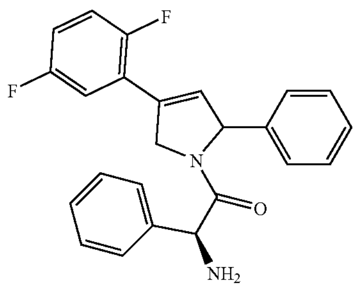 | (1S)-2-[4-(2,5-difluorophenyl)-2-phenyl-2,5-dihydro-1H-pyrrol-1-yl]-2-oxo-1-phenylethanamine | LRMS m/z (M + H) 391.0 found, 391.2 required |
| 15-17 | 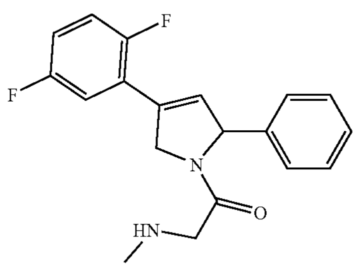 | 2-[4-(2,5-difluorophenyl)-2-phenyl-2,5-dihydro-1H-pyrrol-1-yl]-N-methyl-2-oxoethanamine | LRMS m/z (M + H) 329.1 found, 329.1 required |
| 15-18 | 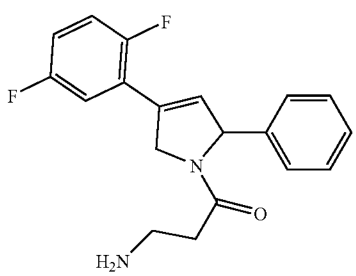 | 3-[4-(2,5-difluorophenyl)-2-phenyl-2,5-dihydro-1H-pyrrol-1-yl]-3-oxopropan-1-amine | LRMS m/z (M + H) 329.1 found, 329.1 required |
| 15-19 | 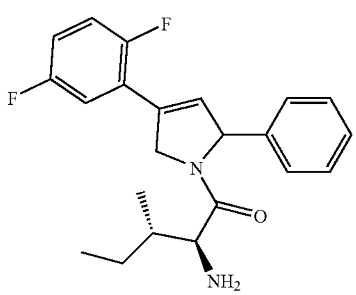 | (1S,2S)-1-{[4-(2,5-difluorophenyl)-2-phenyl-2,5-dihydro-1H-pyrrol-1-yl]carbonyl}-2-methylbutylamine | LRMS m/z (M + H) 371.1 found, 371.2 required |
| 15-20 | 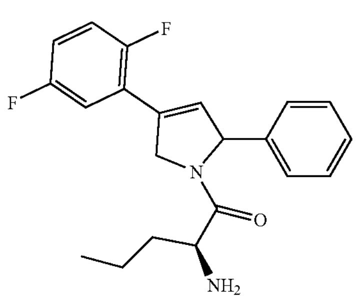 | (1S)-1-{[4-(2,5-difluorophenyl)-2-phenyl-2,5-dihydro-1H-pyrrol-1-yl]carbonyl}butylamine | LRMS m/z (M + H) 357.1 found, 357.2 required |

| Cmpd | Structure | Name | LRMS m/z (M + H) |
|---|---|---|---|
| 15-21 | 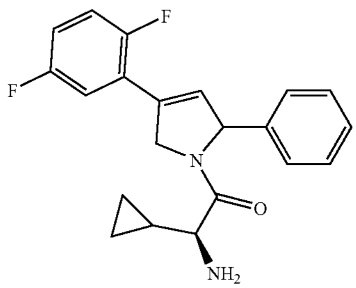 | (1S)-1-cyclopropyl-2-[4-(2,5-difluorophenyl)-2-phenyl-2,5-dihydro-1H-pyrrol-1-yl]-2-oxoethanamine | LRMS m/z (M + H) 355.1 found, 355.2 required |
| 15-22 | 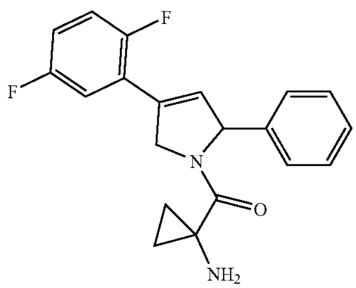 | 1-{[4-(2,5-difluorophenyl)-2-phenyl-2,5-dihydro-1H-pyrrol-1-yl]carbonyl}cyclopropanamine | LRMS m/z (M + H) 340.9 found, 341.1 required |
| 15-23 | 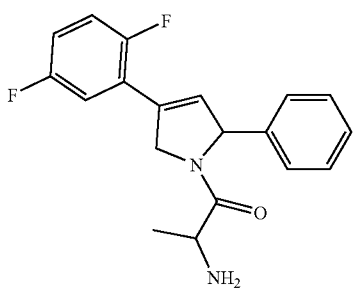 | 1-[4-(2,5-difluorophenyl)-2-phenyl-2,5-dihydro-1H-pyrrol-1-yl]-1-oxopropan-2-amine | LRMS m/z (M + H) 329.2 found, 329.1 required |
| 15-24 | 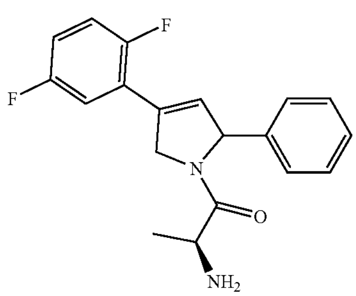 | (1S)-2-[4-(2,5-difluorophenyl)-2-phenyl-2,5-dihydro-1H-pyrrol-1-yl]-1-methyl-2-oxoethylamine | LRMS m/z (M + H) 329.1 found, 329.1 required |
| 15-25 | 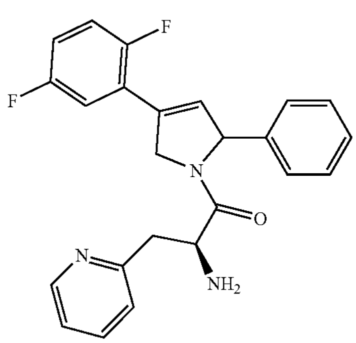 | (1S)-2-[4-(2,5-difluorophenyl)-2-phenyl-2,5-dihydro-1H-pyrrol-1-yl]-2-oxo-1-(pyridin-2-ylmethyl)ethylamine | LRMS m/z (M + H) 406.1 found, 406.2 required |

| Cmpd | Structure | Name | LRMS m/z (M + H) |
|---|---|---|---|
| 15-26 | 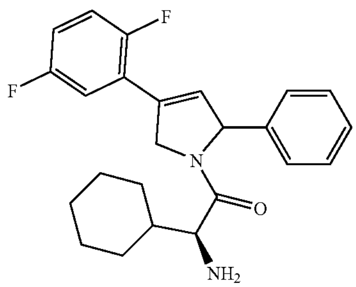 | (1S)-1-cyclohexyl-2-[4-(2,5-difluorophenyl)-2-phenyl-2,5-dihydro-1H-pyrrol-1-yl]-2-oxoethanamine | LRMS m/z (M + H) 397.2 found, 397.2 required |
| 15-27 | 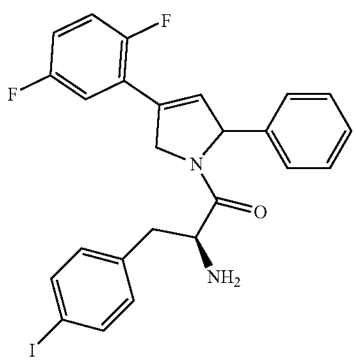 | (1S)-2-[4-(2,5-difluorophenyl)-2-phenyl-2,5-dihydro-1H-pyrrol-1-yl]-1-(4-iodobenzyl)-2-oxoethylamine | LRMS m/z (M + H) 531.0 found, 531.1 required |
| 15-28 | 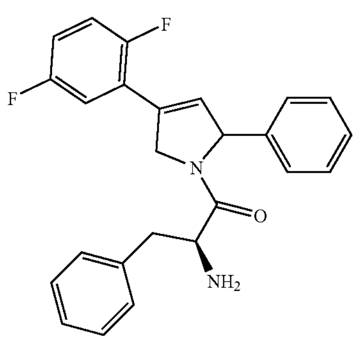 | (1S)-1-benzyl-2-[4-(2,5-difluorophenyl)-2-phenyl-2,5-dihydro-1H-pyrrol-1-yl]-2-oxoethylamine | LRMS m/z (M + H) 405.2 found, 405.2 required |
| 15-29 | 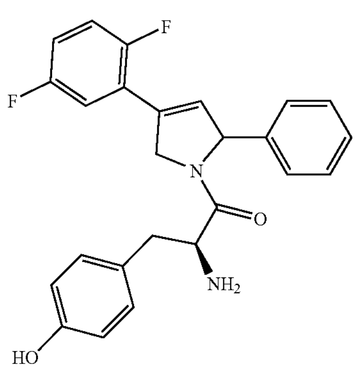 | 4-{(2S)-2-amino-3-[4-(2,5-difluorophenyl)-2-phenyl-2,5-dihydro-1H-pyrrol-1-yl]-3-oxopropyl}phenol | LRMS m/z (M + H) 421.1 found, 421.2 required |

-continued

| Cmpd | Structure | Name | LRMS m/z (M + H) |
|---|---|---|---|
| 15-30 | 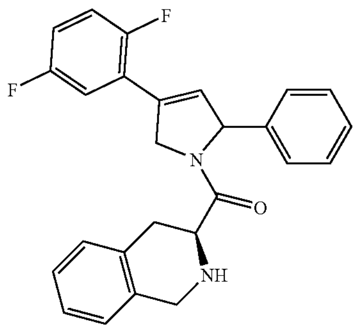 | (3S)-3-{[4-(2,5-difluorophenyl)-2-phenyl-2,5-dihydro-1H-pyrrol-1-yl]carbonyl}-1,2,3,4-tetrahydroisoquinoline | LRMS m/z (M + H) 417.2 found, 417.2 required |
| 15-31 | 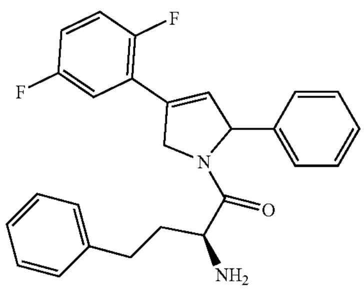 | (1S)-1-{[4-(2,5-difluorophenyl)-2-phenyl-2,5-dihydro-1H-pyrrol-1-yl]carbonyl}-3-phenylpropylamine | LRMS m/z (M + H) 419.2 found, 419.2 required |
| 15-32 | 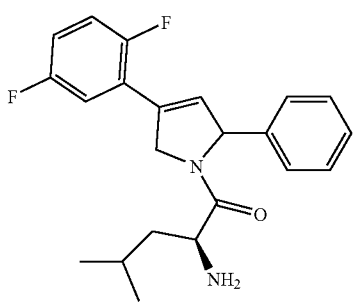 | (1S)-1-{[4-(2,5-difluorophenyl)-2-phenyl-2,5-dihydro-1H-pyrrol-1-yl]carbonyl}-3-methylbutylamine | LRMS m/z (M + H) 371.2 found, 371.2 required |
| 15-33 | 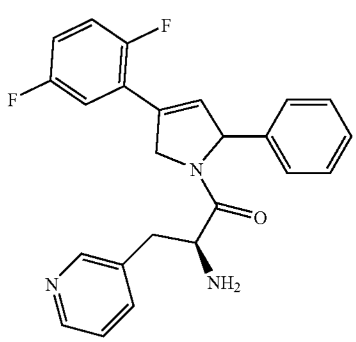 | (1S)-2-[4-(2,5-difluorophenyl)-2-phenyl-2,5-dihydro-1H-pyrrol-1-yl]-2-oxo-1-(pyridin-3-ylmethyl)ethylamine | LRMS m/z (M + H) 406.1 found, 406.2 required |
| 15-34 | 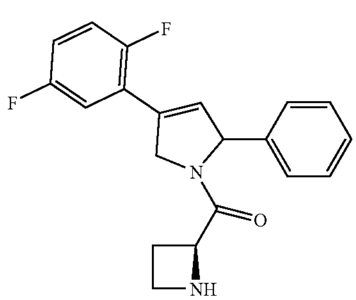 | 1-[(2S)-azetidin-2-ylcarbonyl]-4-(2,5-difluorophenyl)-2-phenyl-2,5-dihydro-1H-pyrrole | LRMS m/z (M + H) 341.1 found, 341.1 required |

-continued

| Cmpd | Structure | Name | LRMS m/z (M + H) |
|---|---|---|---|
| 15-35 | 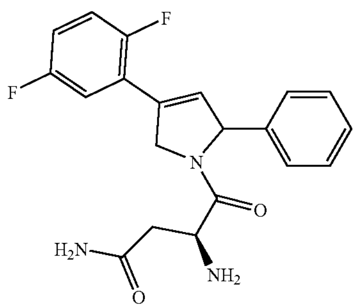 | (3S)-3-amino-4-[4-(2,5-difluorophenyl)-2-phenyl-2,5-dihydro-1H-pyrrol-1-yl]-4-oxobutanamide | LRMS m/z (M + H) 372.1 found, 372.1 required |
| 15-36 | 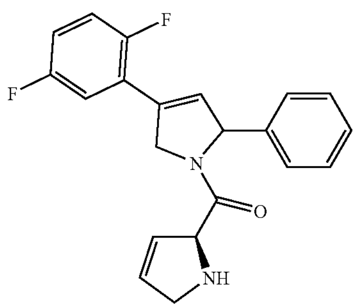 | 4-(2,5-difluorophenyl)-1-[(2S)-2,5-dihydro-1H-pyrrol-2-ylcarbonyl]-2-phenyl-2,5-dihydro-1H-pyrrole | LRMS m/z (M + H) 353.1 found, 353.1 required |
| 15-37 | 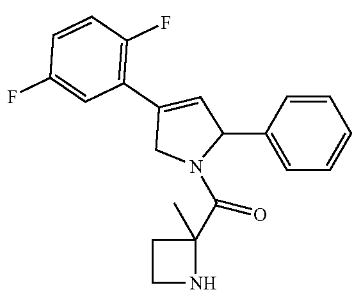 | 4-(2,5-difluorophenyl)-1-[(2-methylazetidin-2-yl)carbonyl]-2-phenyl-2,5-dihydro-1H-pyrrole | LRMS m/z (M + H) 355.1 found, 355.2 required |
| 15-38 | 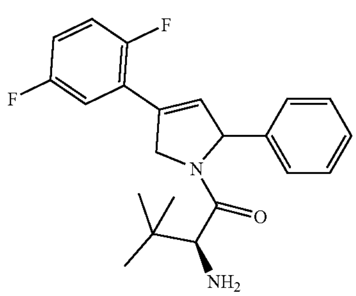 | (1S)-1-{[4-(2,5-difluorophenyl)-2-phenyl-2,5-dihydro-1H-pyrrol-1-yl]carbonyl}-2,2-dimethylpropylamine | LRMS m/z (M + H) 371.2 found, 371.2 required |
| 15-39 | 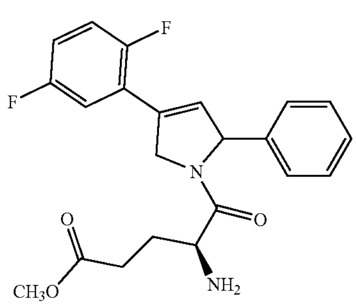 | methyl (4S)-4-amino-5-[4-(2,5-difluorophenyl)-2-phenyl-2,5-dihydro-1H-pyrrol-1-yl]-5-oxopentanoate | LRMS m/z (M + H) 401.1 found, 401.2 required |

| Cmpd | Structure | Name | LRMS m/z (M + H) |
|---|---|---|---|
| 15-40 | 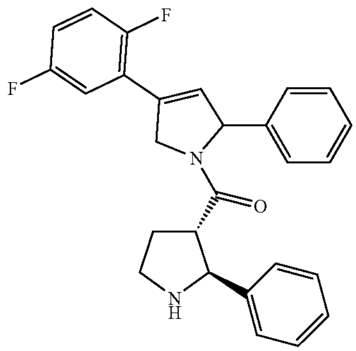 | 4-(2,5-difluorophenyl)-2-phenyl-1-{[(2S,3S)-2-phenylpyrrolidin-3-yl]carbonyl}-2,5-dihydro-1H-pyrrole | LRMS m/z (M + H) 431.2 found, 431.2 required |
| 15-41 | 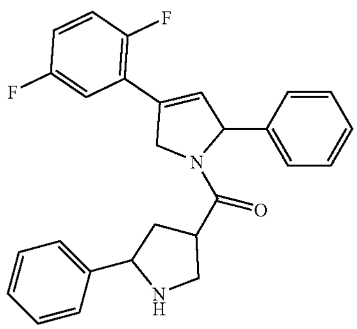 | 4-(2,5-difluorophenyl)-2-phenyl-1-[(5-phenylpyrrolidin-3-yl)carbonyl]-2,5-dihydro-1H-pyrrole | LRMS m/z (M + H) 431.2 found, 431.2 required |
| 15-42 | 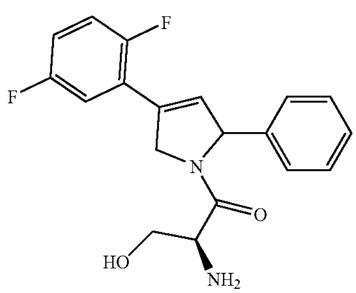 | (2S)-2-amino-3-[4-(2,5-difluorophenyl)-2-phenyl-2,5-dihydro-1H-pyrrol-1-yl]-3-oxopropan-1-ol | LRMS m/z (M + H) 345.1 found, 345.1 required |
| 15-43 | 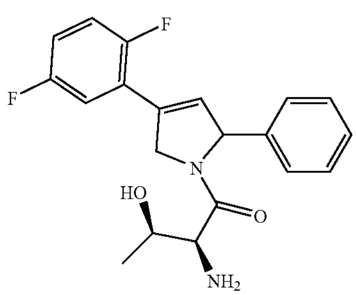 | (2R,3S)-3-amino-4-[4-(2,5-difluorophenyl)-2-phenyl-2,5-dihydro-1H-pyrrol-1-yl]-4-oxobutan-2-ol | LRMS m/z (M + H) 359.1 found, 359.2 required |
| 15-44 | 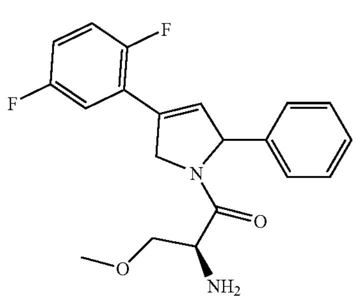 | (1S)-2-[4-(2,5-difluorophenyl)-2-phenyl-2,5-dihydro-1H-pyrrol-1-yl]-1-(methoxymethyl)-2-oxoethylamine | LRMS m/z (M + H) 359.1 found, 359.2 required |

-continued

| Cmpd | Structure | Name | LRMS m/z (M + H) |
|---|---|---|---|
| 15-45 | 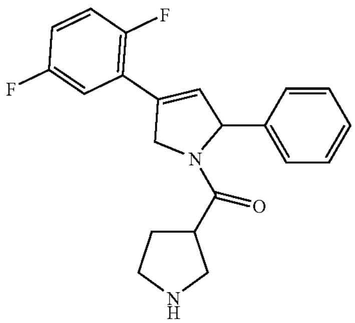 | 4-(2,5-difluorophenyl)-2-phenyl-1-(pyrrolidin-3-ylcarbonyl)-2,5-dihydro-1H-pyrrole | LRMS m/z (M + H) 355.1 found, 355.2 required |
| 15-46 | 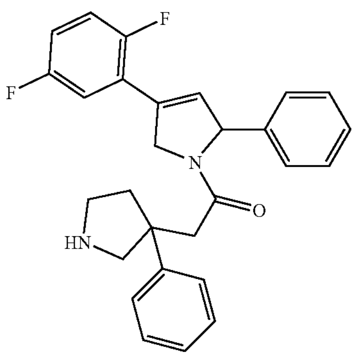 | 4-(2,5-difluorophenyl)-2-phenyl-1-[(3-phenylpyrrolidin-3-yl)acetyl]-2,5-dihydro-1H-pyrrole | LRMS m/z (M + H) 445.1 found, 445.2 required |
| 15-47 | 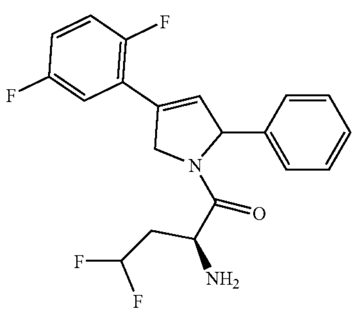 | (1S)-1-{[4-(2,5-difluorophenyl)-2-phenyl-2,5-dihydro-1H-pyrrol-1-yl]carbonyl}-3,3-difluoropropylamine | LRMS m/z (M + H) 379.1 found, 379.1 required |
| 15-48 | 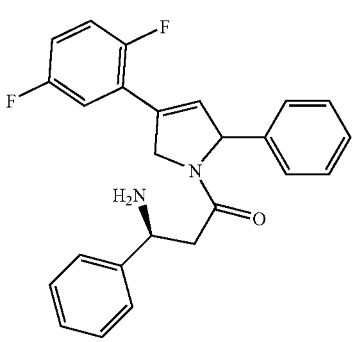 | (1S)-3-[4-(2,5-difluorophenyl)-2-phenyl-2,5-dihydro-1H-pyrrol-1-yl]-3-oxo-1-phenylpropan-1-amine | LRMS m/z (M + H) 405.2 found, 405.2 required |

| Cmpd | Structure | Name | LRMS m/z (M + H) |
|---|---|---|---|
| 15-49 | 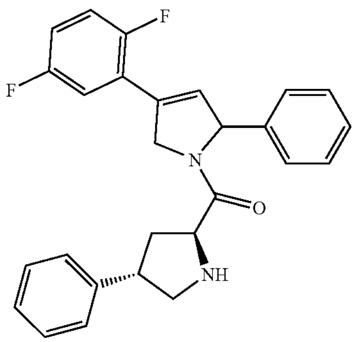 | 4-(2,5-difluorophenyl)-2-phenyl-1-[(4S)-4-phenyl-L-prolyl]-2,5-dihydro-1H-pyrrole | LRMS m/z (M + H) 431.3 found, 431.3 required |
| 15-50 | 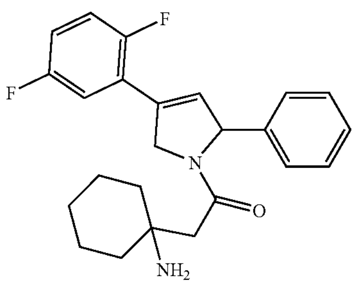 | 1-{2-[4-(2,5-difluorophenyl)-2-phenyl-2,5-dihydro-1H-pyrrol-1-yl]-2-oxoethyl}-cyclohexanamine | LRMS m/z (M + H) 397.0 found, 397.2 required |
| 15-51 | 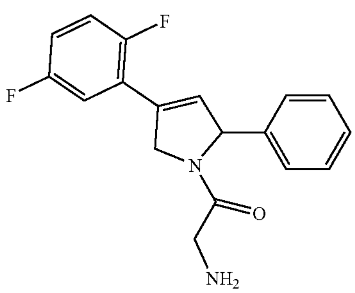 | 2-[4-(2,5-difluorophenyl)-2-phenyl-2,5-dihydro-1H-pyrrol-1-yl]-2-oxoethanamine | LRMS m/z (M + H) 315.0 found, 315.1 required |
| 15-52 | 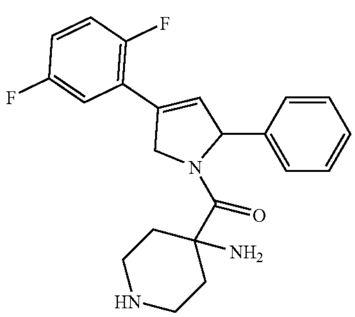 | 4-{[4-(2,5-difluorophenyl)-2-phenyl-2,5-dihydro-1H-pyrrol-1-yl]carbonyl}piperidin-4-amine | LRMS m/z (M + H) 384.1 found, 384.2 required |
| 15-53 | 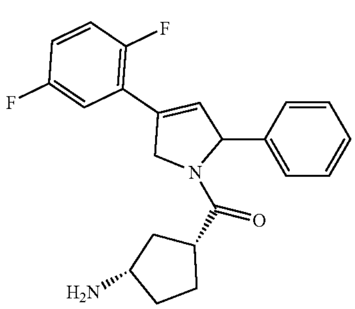 | (1S,3R)-3-{[4-(2,5-difluorophenyl)-2-phenyl-2,5-dihydro-1H-pyrrol-1-yl]carbonyl}cyclopentan-amine | LRMS m/z (M + H) 369.1 found, 369.2 required |

| Cmpd | Structure | Name | LRMS m/z (M + H) |
|---|---|---|---|
| 15-54 | 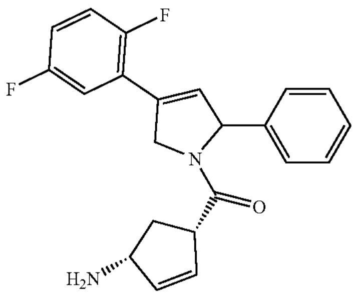 | (1R,4S)-4-{[4-(2,5-difluorophenyl)-2-phenyl-2,5-dihydro-1H-pyrrol-1-yl]carbonyl}cyclopent-2-en-1-amine | LRMS m/z (M + H) 367.1 found, 367.2 required |
| 15-55 | 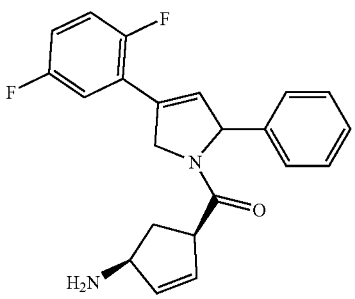 | (1S,4R)-4-{[4-(2,5-difluorophenyl)-2-phenyl-2,5-dihydro-1H-pyrrol-1-yl]carbonyl}cyclopent-2-en-1-amine | LRMS m/z (M + H) 367.1 found, 367.2 required |
| 15-56 | 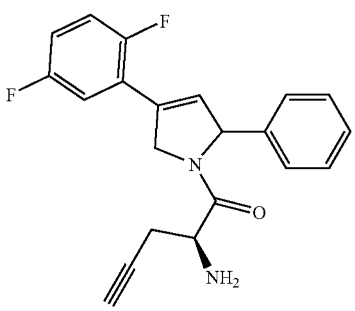 | (1S)-1-{[4-(2,5-difluorophenyl)-2-phenyl-2,5-dihydro-1H-pyrrol-1-yl]carbonyl)but-3-ynylamine | LRMS m/z (M + H) 353.1 found, 353.1 required |
| 15-57 | 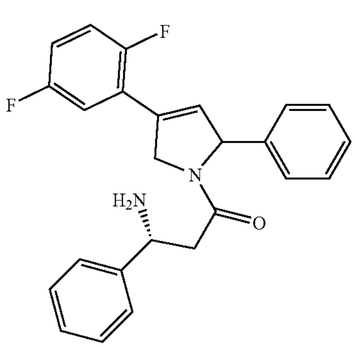 | (1R)-3-[4-(2,5-difluorophenyl)-2-phenyl-2,5-dihydro-1H-pyrrol-1-yl]-3-oxo-1-phenylpropan-1-amine | LRMS m/z (M + H) 405.1 found, 405.2 required |

-continued

| Cmpd | Structure | Name | LRMS m/z (M + H) |
|---|---|---|---|
| 15-58 | 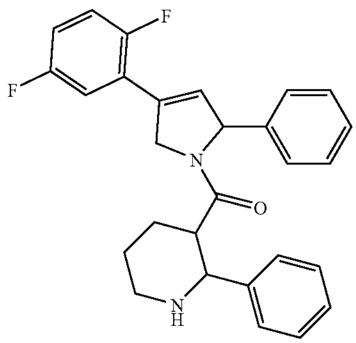 | 3-{[4-(2,5-difluorophenyl)-2-phenyl-2,5-dihydro-1H-pyrrol-1-yl]carbonyl}-2-phenylpiperidine | LRMS m/z (M + H) 445.1 found, 445.2 required |
| 15-59 | 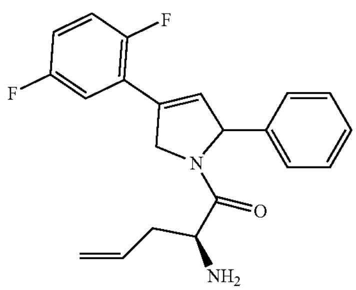 | (1S)-1-{[4-(2,5-difluorophenyl)-2-phenyl-2,5-dihydro-1H-pyrrol-1-yl]carbonyl}but-3-enylamine | LRMS m/z (M + H) 355.1 found, 355.2 required |
| 15-60 | 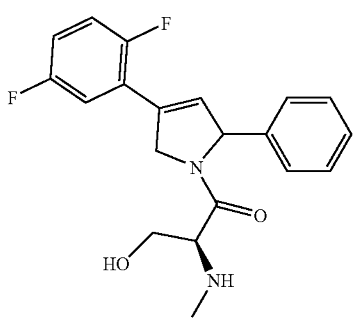 | (2S)-3-(4-(2,5-difluorophenyl)-2-phenyl-2,5-dihydro-1H-pyrrol-1-yl]-2-(methylamino)-3-oxopropan-1-ol | LRMS m/z (M + H) 359.1 found, 359.2 required |
| 15-61 | 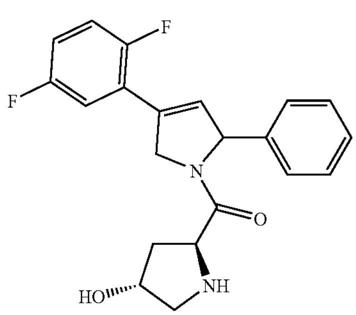 | (3R,5S)-5-{[4-(2,5-difluorophenyl)-2-phenyl-2,5-dihydro-1H-pyrrol-1-yl]carbonyl}pyrrolidin-3-ol | LRMS m/z (M + H) 371.1 found, 371.2 required |

| Cmpd | Structure | Name | LRMS m/z (M + H) |
|---|---|---|---|
| 15-62 | 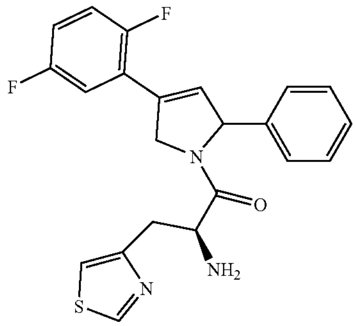 | (1S)-2-{4-(2,5-difluorophenyl)-2-phenyl-2,5-dihydro-1H-pyrrol-1-yl]-2-oxo-1-(1,3-thiazol-4-ylmethyl)ethylamine | LRMS m/z (M + H) 412.0 found, 412.1 required |
| 15-63 | 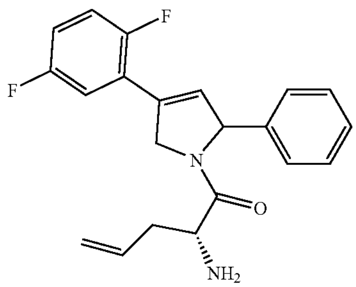 | (1R)-1-{[4-(2,5-difluorophenyl)-2-phenyl-2,5-dihydro-1H-pyrrol-1-yl]carbonyl}but-3-enylamine | LRMS m/z (M + H) 355.1 found, 355.2 required |
| 15-64 | 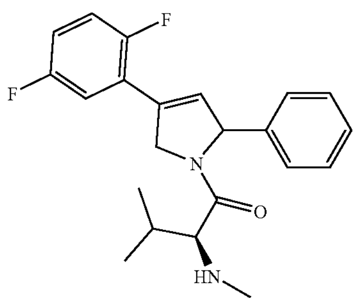 | (2S)-1-[4-(2,5-difluorophenyl)-2-phenyl-2,5-dihydro-1H-pyrrol-1-yl]-N,3-dimethyl-1-oxobutan-2-amine | LRMS m/z (M + H) 371.0 found, 371.2 required |
| 15-65 | 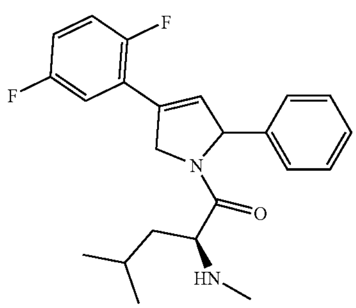 | (2S)-1-[4-(2,5-difluorophenyl)-2-phenyl-2,5-dihydro-1H-pyrrol-1-yl]-N,4-dimethyl-1-oxopentan-2-amine | LRMS m/z (M + H) 385.1 found, 385.2 required |
| 15-66 | 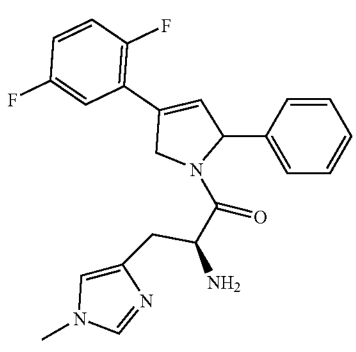 | (1S)-2-[4-(2,5-difluorophenyl)-2-phenyl-2,5-dihydro-1H-pyrrol-1-yl]-1-[(1-methyl-1H-imidazol-4-yl)methyl]-2-oxoethylamine | LRMS m/z (M + H) 409.2 found, 409.2 required |

-continued

| Cmpd | Structure | Name | LRMS m/z (M + H) |
|---|---|---|---|
| 15-67 | 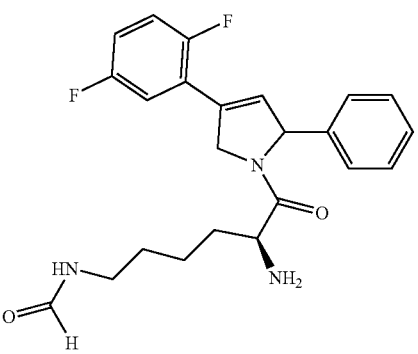 | 4-(2,5-difluorophenyl)-1-(N~6~-formyl-L-lysyl)-2-phenyl-2,5-dihydro-1H-pyrrole | LRMS m/z (M + H) 414.2 found, 414.2 required |
| 15-68 | 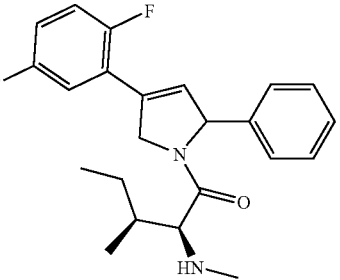 | (2S,3S)-1-[4-(2,5-difluorophenyl)-2-phenyl-2,5-dihydro-1H-pyrrol-1-yl]-N,3-dimethyl-1-oxopentan-2-amine | LRMS m/z (M + H) 385.2 found, 385.2 required |
| 15-69 | 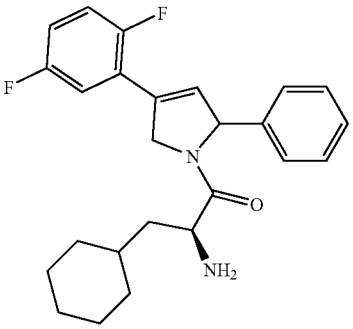 | (1S)-1-(cyclohexylmethyl)-2-[4-(2,5-difluorophenyl)-2-phenyl-2,5-dihydro-1H-pyrrol-1-yl]-2-oxoethylamine | LRMS m/z (M + H) 411.2 found, 411.2 required |
| 15-70 | 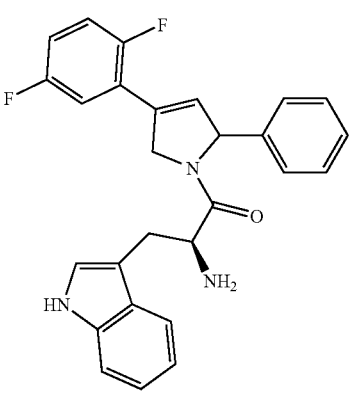 | (1S)-2-[4-(2,5-difluorophenyl)-2-phenyl-2,5-dihydro-1H-pyrrol-1-yl]-1-(1H-indol-3-ylmethyl)-2-oxoethylamine | LRMS m/z (M + H) 444.1 found, 444.2 required |

-continued

| Cmpd | Structure | Name | LRMS m/z (M + H) |
|---|---|---|---|
| 15-71 | 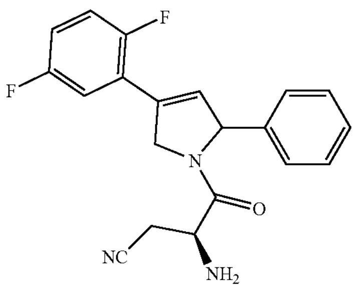 | (1S)-2-[4-(2,5-difluorophenyl)-2-phenyl-2,5-dihydro-1H-pyrrol-1-yl]-1-(isocyanomethyl)-2-oxoethylamine | LRMS m/z (M + H) 354.1 found, 354.1 required |
| 15-72 | 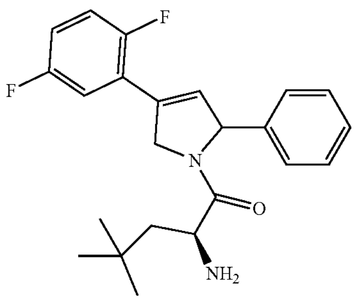 | (1S)-1-{[4-(2,5-difluorophenyl)-2-phenyl-2,5-dihydro-1H-pyrrol-1-yl]carbonyl}-3,3-dimethylbutylamine | LRMS m/z (M + H) 385.0 found, 385.2 required |
| 15-73 | 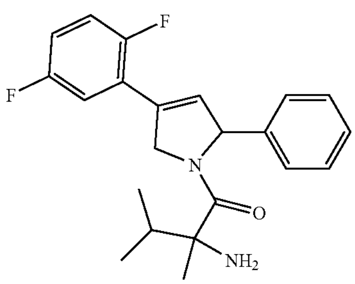 | 1-[4-(2,5-difluorophenyl)-2-phenyl-2,5-dihydro-1H-pyrrol-1-yl]-2,3-dimethyl-1-oxobutan-2-amine | LRMS m/z (M + H) 371.0 found, 371.2 required |
| 15-74 | 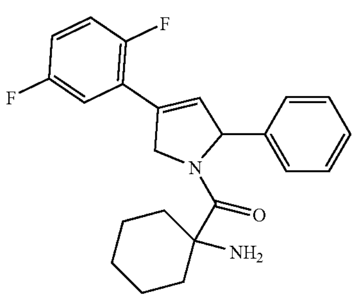 | 1-{[4-(2,5-difluorophenyl)-2-phenyl-2,5-dihydro-1H-pyrrol-1-yl]carbonyl}cyclohexanamine | LRMS m/z (M + H) 383.1 found, 383.2 required |
| 15-75 | 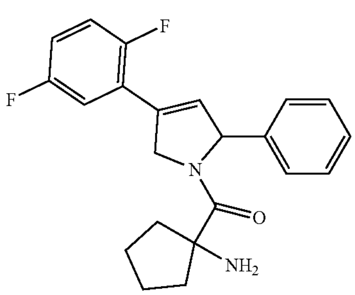 | 1-{[4-(2,5-difluorophenyl)-2-phenyl-2,5-dihydro-1H-pyrrol-1-yl]carbonyl}cyclopentanamine | LRMS m/z (M + H) 369.1 found, 369.2 required |

| Cmpd | Name | LRMS m/z (M + H) |
|---|---|---|
| 15-76 | (1S)-3-(benzyloxy)-1-{[4-(2,5-difluorophenyl)-2-phenyl-2,5-dihydro-1H-pyrrol-1-yl]carbonyl}propylamine | LRMS m/z (M + H) 449.1 found, 449.2 required |
| 15-77 | 1-{[4-(2,5-difluorophenyl)-2-phenyl-2,5-dihydro-1H-pyrrol-1-yl]carbonyl}cyclopent-3-en-1-amine | LRMS m/z (M + H) 367.0 found, 367.2 required |
| 15-78 | (1S)-1-cyclopentyl-2-[4-(2,5-difluorophenyl)-2-phenyl-2,5-dihydro-1H-pyrrol-1-yl]-2-oxoethanamine | LRMS m/z (M + H) 383.1 found, 383.2 required |
| 15-79 | 4-(2,5-difluorophenyl)-1-(2-methylprolyl)-2-phenyl-2,5-dihydro-1H-pyrrole | LRMS m/z (M + H) 369.1 found, 369.2 required |
| 15-80 | 1-[4-(5-chloro-2-fluorophenyl)-2-phenyl-2,5-dihydro-1H-pyrrol-1-yl]-2-methyl-1-oxopropan-2-amine; isolated as the free base | LRMS m/z (M + H) 359.0 found, 359.1 required |

-continued

| Cmpd | Structure | Name | LRMS m/z (M + H) |
|---|---|---|---|
| 15-81 | 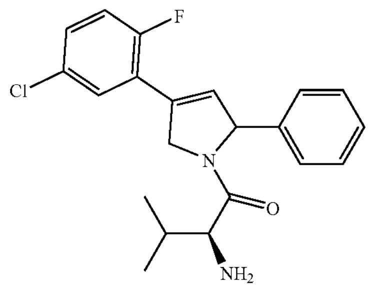 | (1S)-1-{[4-(5-chloro-2-fluorophenyl)-2-phenyl-2,5-dihydro-1H-pyrrol-1-yl]carbonyl}-2-methylpropylamine; isolated as the free base | LRMS m/z (M + H) 373.0 found, 373.1 required |
| 15-82 | 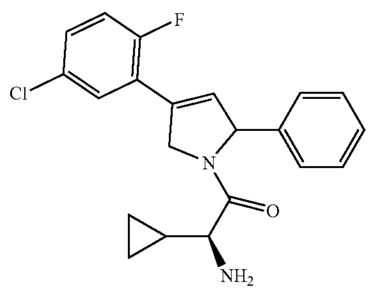 | (1S)-2-[4-(5-chloro-2-fluorophenyl)-2-phenyl-2,5-dihydro-1H-pyrrol-1-yl]-1-cyclopropyl-2-oxoethanamine | LRMS m/z (M + H) 371.1 found, 371.1 required |
| 15-83 | 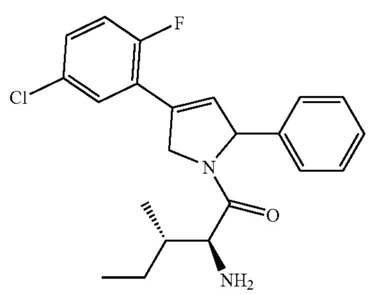 | (1S,2S)-1-{[4-(5-chloro-2-fluorophenyl)-2-phenyl-2,5-dihydro-1H-pyrrol-1-yl]carbonyl}-2-methylbutylamine | LRMS m/z (M + H) 387.0 found, 387.2 required |
| 15-84 | 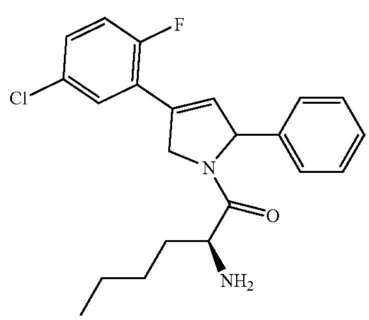 | (1S)-1-{[4-(5-chloro-2-fluorophenyl)-2-phenyl-2,5-dihydro-1H-pyrrol-1-yl]carbonyl}-pentylamine; isolated as the free base | LRMS m/z (M + H) 387.0 found, 387.2 required |
| 15-85 | 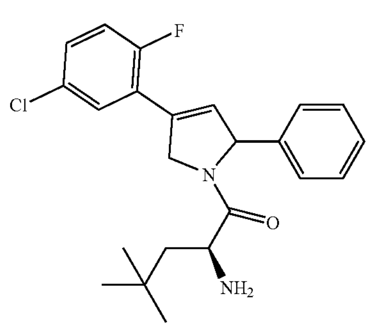 | (1S)-1-{[4-(5-chloro-2-fluorophenyl)-2-phenyl-2,5-dihydro-1H-pyrrol-1-yl]carbonyl}-3,3-dimethylbutylamine; isolated as the free base | LRMS m/z (M + H) 401.0 found, 401.2 required |

SCHEME 16

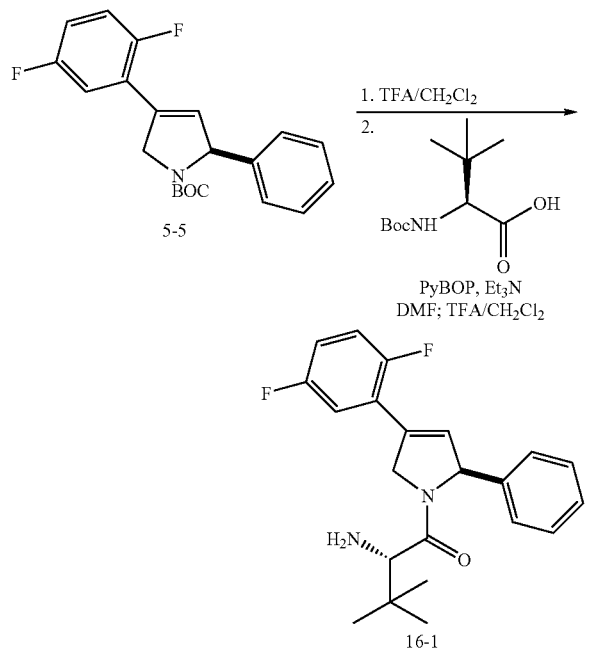

(1S)-1-{[(2S)-4-(2,5-difluorophenyl)-2-phenyl-2,5-dihydro-1H-pyrrol-1-yl]carbonyl}-2,2-dimethylpropylamine (16-1)

A solution of tert-butyl (2S)-4-(2,5-difluorophenyl)-2-phenyl-2,5-dihydro-1H-pyrrole-1-carboxylate (5-5, 400 mg, 1.12 mmol, 1 equiv) in a 4:1 mixture of dichloromethane and trifluoroacetic acid (20 mL) was stirred for 30 minutes, then concentrated. The residue was dried via toluene azeotrope (2×10 mL), then dissolved in DMF (5 mL). Triethylamine (0.780 mL, 5.60 mmol, 5.00 equiv), N-(tert-butoxycarbonyl)-3-methyl-L-valine (388 mg, 1.68 mmol, 1.50 equiv), and PYBOP (874 mg, 1.68 mmol, 1.50 equiv) were added, and the resulting mixture was stirred at 23° C. for 24 hours. The reaction mixture was partitioned between saturated aqueous sodium bicarbonate solution and ethyl acetate (2×50 mL). The combined organic layers were dried over sodium sulfate and concentrated. The residue was purified by flash column chromatography (hexanes initially, grading to 40% ethyl acetate in hexanes) to yield the desired coupled, N-Boc-protected intermediate, which was dissolved in a 2:1 mixture of dichloromethane and trifluoroacetic acid. The resulting solution was allowed to stand for 30 minutes, then concentrated. The residue was purified by reverse-phase LC ($H_2O/CH_3CN$ gradient w/0.1% TFA present). The desired fractions were partitioned between saturated aqueous sodium bicarbonate solution and ethyl acetate (2×50 mL), then the combined organic layers were dried over sodium sulfate and concentrated to provide (1S)-1-{[(2S)-4-(2,5-difluorophenyl)-2-phenyl-2,5-dihydro-1H-pyrrol-1-yl]carbonyl}-2,2-dimethylpropylamine (16-1) as a white solid. $^1$H NMR (500 MD, CDCl$_3$) major rotamer: δ 7.40 (t, 2H, J=7.6 Hz), 7.31 (m, 1H), 7.26 (d, 2H, J=7.8 Hz), 7.11-6.93 (m, 3H), 6.38 (s, 1H), 5.81 (m, 1H), 4.88 (m, 2H), 3.03 (s, 1H), 1.00 (s, 9H). LRMS m/z (M+H) 371.0 found, 371.2 required.

The following compounds were prepared by simple modifications of the above procedures. Unless noted otherwise, the compounds in the table were isolated as the free base.

| Cmpd | Structure | Name | LRMS m/z (M + H) |
|---|---|---|---|
| 16-2 | 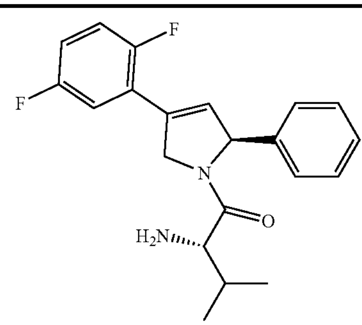 | (1S)-1-{[(2S)-4-(2,5-difluorophenyl)-2-phenyl-2,5-dihydro-1H-pyrrol-1-yl]carbonyl}-2-methylpropylamine | LRMS m/z (M + H) 357.1 found, 357.2 required. |
| 16-3 | 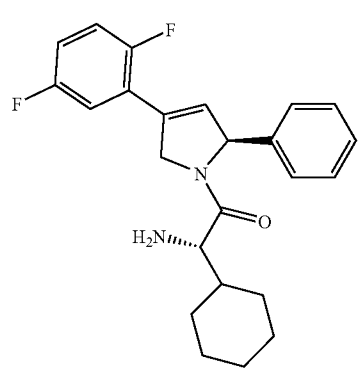 | (1S)-1-cyclohexyl-2-[(2S)-4-(2,5-difluorophenyl)-2-phenyl-2,5-dihydro-1H-pyrrol-1-yl]-2-oxoethanamine | LRMS m/z (M + H) 397.1 found, 397.2 required |

| Cmpd | Structure | Name | LRMS m/z (M + H) |
|---|---|---|---|
| 16-4 | 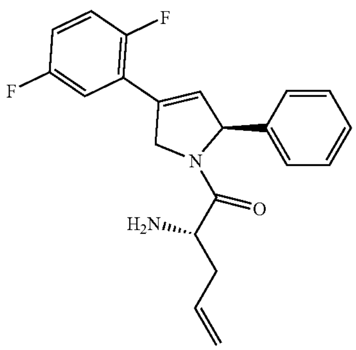 | (1S)-1-{[(2S)-4-(2,5-difluorophenyl)-2-phenyl-2,5-dihydro-1H-pyrrol-1-yl]carbonyl}but-3-enylamine; isolated as the TFA salt | LRMS m/z (M + H) 355.0 found, 355.2 required |
| 16-5 | 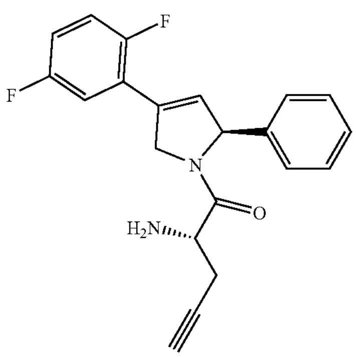 | (1S)-1-{[(2S)-4-(2,5-difluorophenyl)-2-phenyl-2,5-dihydro-1H-yl]carbonyl}but-3-ynylamine; isolated as the TFA salt | LRMS m/z (M + H) 353.0 found, 353.1 required |
| 16-6 | 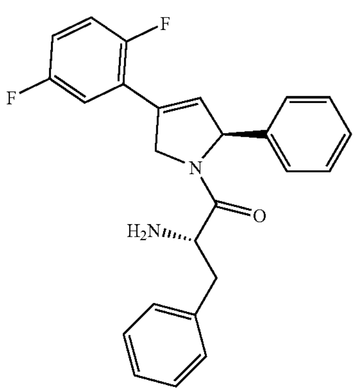 | (1S)-1-benzyl-2-[(2S)-4-(2,5-difluorophenyl)-2-phenyl-2,5-dihydro-1H-pyrrol-1-yl]-2-oxoethylamine | LRMS m/z (M + H) 405.0 found, 405.2 required |
| 16-7 | 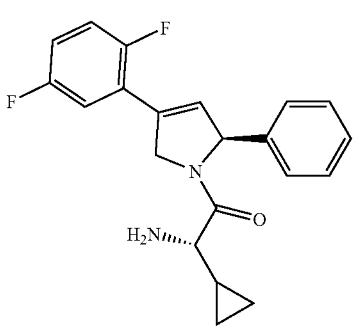 | (1S)-1-cyclopropyl-2-[(2S)-4-(2,5-difluorophenyl)-2-phenyl-2,5-dihydro-1H-pyrrol-1-yl]-2-oxoethanamine; isolated as the TFA salt | LRMS m/z (M + H) 355.0 found, 355.2 required |

-continued

| Cmpd | Structure | Name | LRMS m/z (M + H) |
|---|---|---|---|
| 16-8 | 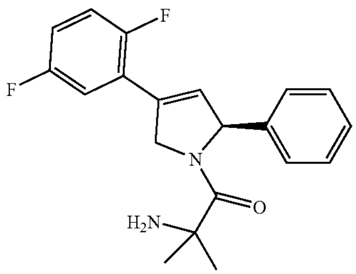 | 1-[(2S)-4-(2,5-difluorophenyl)-2-phenyl-2,5-dihydro-1H-pyrrol-1-yl]-2-methyl-1-oxopropan-2-amine | LRMS m/z (M + H) 343.0 found, 343.2 required |
| 16-9 | 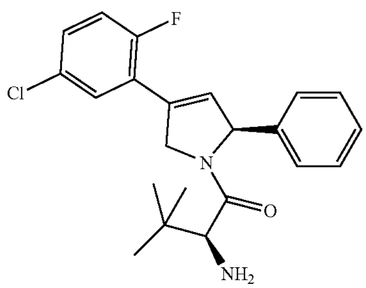 | (1S)-1-{[(2S)-4-(5-chloro-2-fluorophenyl)-2-phenyl-2,5-dihydro-1H-pyrrol-1-yl]carbonyl}-2,2-dimethylpropylamine | LRMS m/z (M + H) 387.0 found, 387.2 required |
| 16-10 | 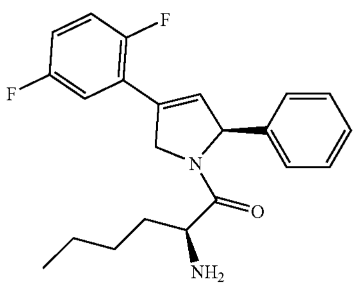 | (1S)-1-{[(2S)-4-(2,5-difluorophenyl)-2-phenyl-2,5-dihydro-1H-pyrrol-1-yl]carbonyl}-pentylamine | LRMS m/z (M + H) 371.1 found, 371.2 required |
| 16-11 | 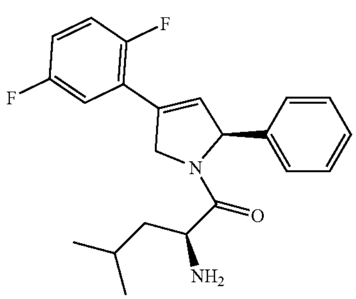 | (1S)-1-{[(2S)-4-(2,5-difluorophenyl)-2-phenyl-2,5-dihydro-1H-pyrrol-1-yl]carbonyl}-3-methylbutylamine | LRMS m/z (M + H) 371.1 found, 371.2 required |
| 16-12 | 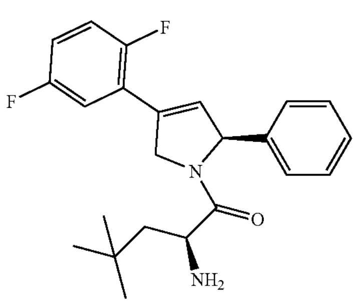 | (1S)-1-{[(2S)-4-(2,5-difluorophenyl)-2-phenyl-2,5-dihydro-1H-pyrrol-1-yl]carbonyl}-3,3-dimethylbutylamine | LRMS m/z (M + H) 385.1 found, 385.2 required |

| Cmpd | Structure | Name | LRMS m/z (M + H) |
|---|---|---|---|
| 16-13 | 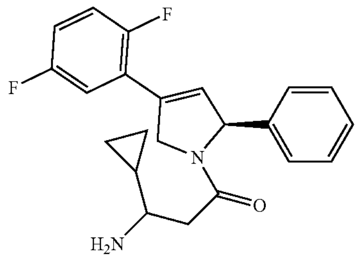 | 1-cyclopropyl-3-[(2S)-4-(2,5-difluorophenyl)-2-phenyl-2,5-dihydro-1H-pyrrol-1-yl]-3-oxopropan-1-amine; isolated as the TFA salt | LRMS m/z (M + H) 369.0 found, 369.2 required |
| 16-14 | 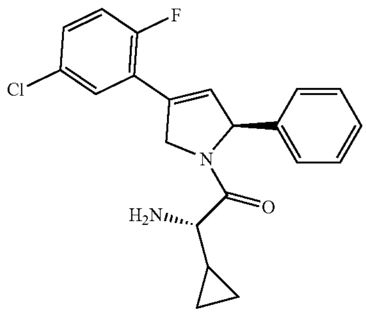 | (1S)-2-[(2S)-4-(5-chloro-2-fluorophenyl)-2-phenyl-2,5-dihydro-1H-pyrrol-1-yl]-1-cyclopropyl-2-oxoethanamine | LRMS m/z (M + H) 371.0 found, 371.1 required |
| 16-15 | 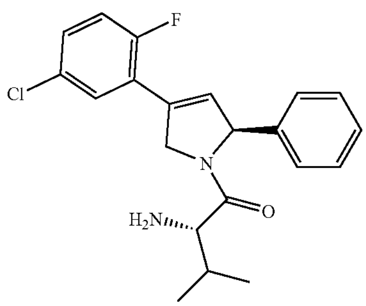 | (1S)-1-{[(2S)-4-(5-chloro-2-fluorophenyl)-2-phenyl-2,5-dihydro-1H-pyrrol-1-yl]carbonyl}-2-methylpropylamine | LRMS m/z (M + H) 372.9 found, 373.1 required |
| 16-16 | 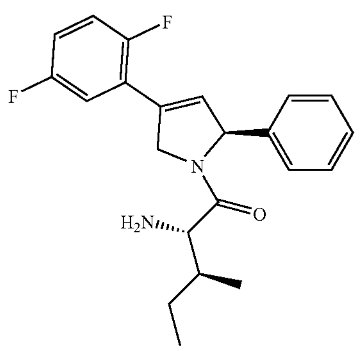 | (1S,2S)-1-{[(2S)-4-(2,5-difluorophenyl)-2-phenyl-2,5-dihydro-1H-pyrrol-1-yl]carbonyl}-2-methylbutylamine; isolated as the TFA salt | LRMS m/z (M + H) 371.1 found, 371.2 required |
| 16-17 | 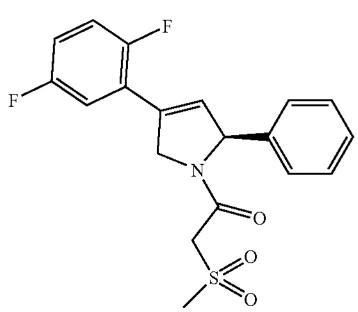 | (2S)-4-(2,5-difluorophenyl)-1-[(methylsulfonyl)acetyl]-2-phenyl-2,5-dihydro-1H-pyrrole | LRMS m/z (M + H) 378.3 found, 378.1 required. |

-continued
| Cmpd | Structure | Name | LRMS m/z (M + H) |
|---|---|---|---|
| 16-18 | 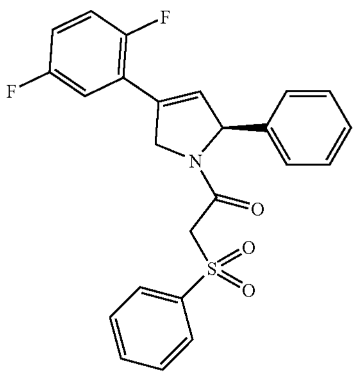 | (2S)-4-(2,5-difluorophenyl)-2-phenyl-1-[(phenylsulfonyl)acetyl]-2,5-dihydro-1H-pyrrole | LRMS m/z (M + H) 440.4 found, 440.1 required. |
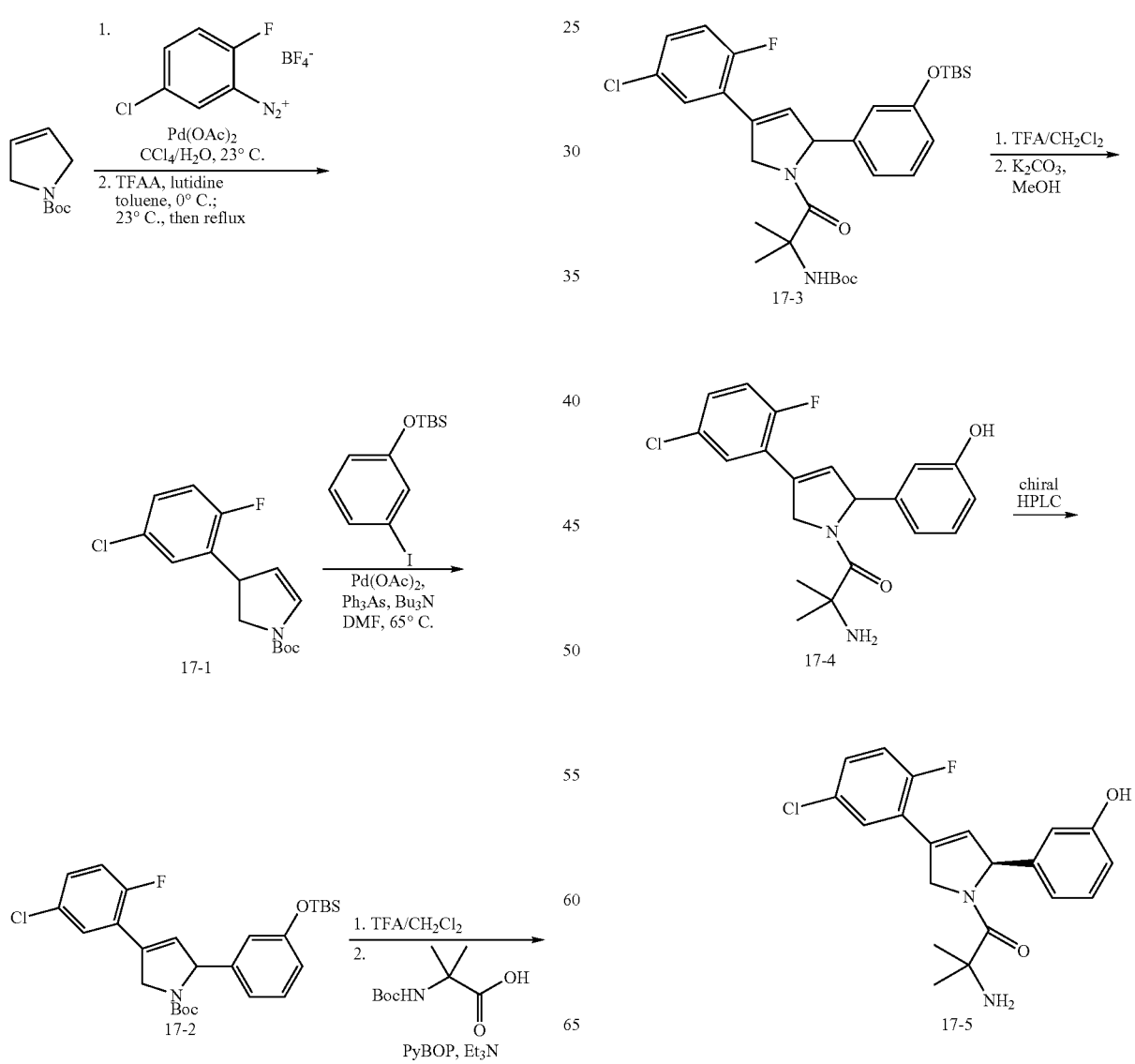

Step 1: tert-butyl 3-(5-chloro-2-fluorophenyl)-2,3-dihydro-1H-pyrrole-1-carboxylate (17-1)

Palladium(II) acetate (106 mg, 0.473 mmol, 0.020 equiv) was added to a vigorously stirred, deoxygenated mixture of tert-butyl 2,5-dihydro-1H-pyrrole-1-carboxylate (4.00 g, 23.6 mmol, 1 equiv) and 5-chloro-2-fluorobenzenediazonium tetrafluoroborate (10.4 g, 42.5 mmol, 1.80 equiv) in water and carbon tetrachloride (1:1, 150 mL) at 23° C., and the resulting mixture was stirred for 20 hours. The reaction mixture was partitioned between saturated aqueous sodium bicarbonate solution (200 ml) and dichloromethane (2×200 mL). The combined organic layers were dried over sodium sulfate and concentrated. The residue was dissolved in toluene (200 mL), and the resulting solution concentrated in vacuo to facilitate azeotropic removal of residual water. 2,6-Lutidine (5.51 mL, 47.3 mmol, 2.00 equiv) and trifluoroacetic anhydride (1.67 mL, 11.8 mmol, 0.500 equiv) were then sequentially added to a solution of the residue in toluene (150 mL) at −20° C. The resulting mixture was kept at −20° C. for 5 hours, then allowed to slowly warm to 23° C. After 16 hours at 23° C., the reaction mixture was heated at reflux for 30 minutes. The reaction mixture was allowed to cool to 23° C., then partitioned between ethyl acetate (100 mL) and saturated aqueous sodium bicarbonate solution (100 mL). The organic layer was dried over sodium sulfate and concentrated. The residue was purified by flash column chromatography (hexanes initially, grading to 30% EtOAc in hexanes) to give tert-butyl 3-(5-chloro-2-fluorophenyl)-2,3-dihydro-1H-pyrrole-1-carboxylate (17-1) as an orange oil. LRMS m/z (M+H CH$_3$) 283.0 found, 283.1 required.

Step 2: tert-butyl 2-(3-{[tert-butyl(dimethyl)silyl]oxy}phenyl)-4-(5-chloro-2-fluorophenyl)-2,5-dihydro-1H-pyrrole-1-carboxylate (17-2)

A deoxygenated mixture of tert-butyl 3-(5-chloro-2-fluorophenyl)-2,3-dihydro-1H-pyrrole-1-carboxylate (17-1, 1.100 g, 3.69 mmol, 1 equiv), tert-butyl(3-iodophenoxy)dimethylsilane (1.85 g, 5.54 mmol, 1.50 equiv), tributylamine (1.76 mL, 7.39 mmol, 2.00 equiv), triphenylarsine (0.453 g, 1.48 mmol, 0.400 equiv), and palladium acetate (0.166 g, 0.739 mmol, 0.200 equiv) in DMF (10 mL) was heated at 65° C. for 20 hours. The reaction mixture was partitioned between water (100 mL) and ethyl acetate (2×85 mL). The combined organic layers were dried over sodium sulfate and concentrated. The residue was purified by flash column chromatography (100% hexanes initially, grading to 50% ethyl acetate in hexanes) to provide tert-butyl 2-(3-{[tert-butyl(dimethyl)silyl]oxy}phenyl)-4-(5-chloro-2-fluorophenyl)-2,5-dihydro-1H-pyrrole-1-carboxylate (17-2) as an orange oil. $^1$H NMR (300 MHz, CDCl$_3$) major rotamer: δ 7.11-6.53 (m, 7H), 6.11 (s, 1M), 5.32 (m, 1H), 4.53 (m, 2H), 1.09 (s, 9H), 0.79 (s, 9H), 0.00 (s, 6H). LRMS m/z (M+H) 504.1 found, 504.2 required.

Step 3: tert-butyl 2-[2-(3 {[tert-butyl(dimethyl)silyl]oxy}phenyl)-4-(5-chloro-2-fluorophenyl)-2,5-dihydro-1H-pyrrol-1-yl]-1,1-dimethyl-2-oxoethylcarbamate (17-3)

A solution of tert-butyl 2-(3-{[tert-butyl(dimethyl)silyl]oxy}phenyl)-4-(5-chloro-2-fluorophenyl)-2,5-dihydro-1H-pyrrole-1-carboxylate (17-2, 276 mg, 0.683 mmol, 1 equiv), triethylamine (277 mg, 2.73 mmol, 4 equiv), PYBOP (711 mg, 1.37 mmol, 2 equiv) and 2-[(tert-butoxycarbonyl)amino]-2-methylpropanoic acid (278 mg, 1.37 mmol, 2 equiv) in in DMF (10 mL) was warmed at 60° C. for 18 hours. The solution was concentrated and the residue was partitioned between ethyl acetate and saturated aqueous sodium bicarbonate solution. The organic layer was washed with brine, dried over magnesium sulfate and concentrated. The residue was purified by flash column chromatography. Elution with 10% ethyl acetate/hexanes to 20% ethyl acetate/hexanes gave tert-butyl 2-[2-(3{[tert-butyl(dimethyl)silyl]oxy}phenyl)-4-(5-chloro-2-fluorophenyl)-2,5-dihydro-1H-pyrrol-1-yl]-1,1-dimethyl-2-oxoethylcarbamate (17-3) as a pale yellow gum. LRMS m/z (M+H) 588.9 found, 589.0 required.

Step 4: 4-(5-chloro-2-fluorophenyl)-2-(3-hydroxyphenyl)-1-(2-methylalanyl)-2,5-dihydro-1H-pyrrole (17-4)

A solution of tert-butyl 2-[2-(3 {[tert-butyl(dimethyl)silyl]oxy}phenyl)-4-(5-chloro-2-fluorophenyl)-2,5-dihydro-1H-pyrrol-1-yl]-1,1-dimethyl-2-oxoethylcarbamate (17-3, 247 mg, 0.419 mmol, 1 equiv) and trifluoroacetic acid (4 mL) in dichloromethane (10 mL) was stirred under ambient conditions for 1 hour. The reaction was concentrated at 23° C. and the residue was partitioned between ethyl acetate and saturated sodium bicarbonate solution. The organic layer was washed with brine, dried over magnesium sulfate and concentrated to yield a yellow gum. A solution of the gum in methanol (5 mL) was treated with potassium carbonate (290 mg, 2.10 mmol, 5.00 equiv) and water (1 mL). The reaction mixture was stirred under ambient conditions for 2 hours, then concentrated. The aqueous solution was acidified with aqueous 1 N HCl solution to pH 8 and the mixture was extracted with ethyl acetate. The organic layer was washed with brine, dried over magnesium sulfate and concentrated to provide 4-(5-chloro-2-fluorophenyl)-2-(3-hydroxyphenyl)-1-(2-methylalanyl)-2,5-dihydro-1H-pyrrole (174) as a cream-colored solid. $^1$H NMR (500 MHz, CDCl$_3$) δ 7.30 (dd, 1H, J=6.6, 2.7 Hz), 7.30 (m, 1H), 7.18 (t, 1H, J=7.8 Hz), 7.05 (t, 1H, J=9.2 Hz), 6.83 (br d, 1H, J=7.6 Hz), 6.78 (br s, 1H), 6.70 (dd, 1H, J=8.1, 1.8 Hz), 6.38 (s, 1H), 5.92 (br s, 1H), 5.30 (m, 1H), 5.08 (m, 1H), 1.46 (s, 6H). LRMS m/z (M+H) 375.0 found, 375.0 required.

Step 5: (2S)-4-(5-chloro-2-fluorophenyl)-2-(3-hydroxyphenyl)-1-(2-methylalanyl)-2,5-dihydro-1H-pyrrole (17-5)

Resolution of enantiomers of racemic 4-(5-chloro-2-fluorophenyl)-2-(3-hydroxyphenyl)-1-(2-methylalanyl)-2,5-dihydro-1H-pyrrole (174) by chiral normal-phase HPLC (Chiralcel OD column: 0.1% diethylamine in 10% ethanol in hexanes initially, grading to 30% ethanol in hexanes) provided (2S)-4-(5-chloro-2-fluorophenyl)-2-(3-hydroxyphenyl)-1-(2-methylalanyl)-2,5-dihydro-1H-pyrrole (17-5) as the first eluting, minus (−) enantiomer.

The following compounds were prepared by simple modifications of the above procedures. Unless otherwise indicated, the compounds in the table were isolated as the free base.

| Cmpd | Structure | Name | LRMS m/z (M + H) |
|---|---|---|---|
| 17-6 | 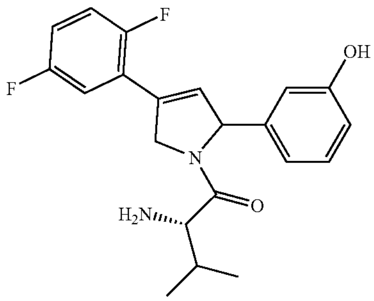 | 4-(2,5-difluorophenyl)-2-(3-hydroxyphenyl)-1-L-valyl-2,5-dihydro-1H-pyrrole; isolated as the TFA salt | LRMS m/z (M + H) 373.0 found, 373.2 required. |
| 17-7 | 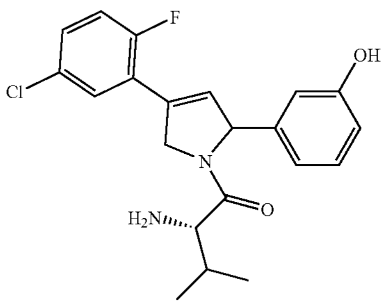 | 4-(5-chloro-2-fluorophenyl)-2-(3-hydroxyphenyl)-1-L-valyl-2,5-dihydro-1H-pyrrole | LRMS m/z (M + H) 389.0 found, 389.1 required |
| 17-8 | 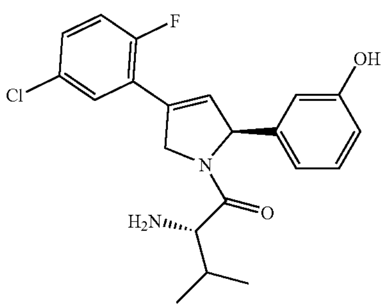 | (2S)-4-(5-chloro-2-fluorophenyl)-2-(3-hydroxyphenyl)-1-L-valyl-2,5-dihydro-1H-pyrrole | LRMS m/z (M + H) 389.0 found, 389.1 required |
| 17-9 | 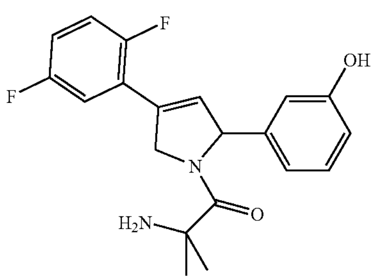 | 4-(2,5-difluorophenyl)-2-(3-hydroxyphenyl)-1-(2-methylalanyl)-2,5-dihydro-1H-pyrrole; isolated as the TFA salt | LRMS m/z (M + H) 359.0 found, 359.2 required |
| 17-10 | 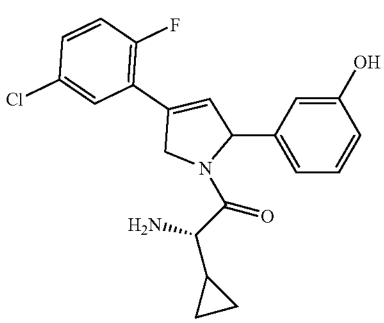 | 3-[1-[(2S)-2-amino-2-cyclopropylethanoyl]-4-(5-chloro-2-fluorophenyl)-2,5-dihydro-1H-pyrrol-2-yl]phenol; isolated as the TFA salt | LRMS m/z (M + H) 386.9 found, 387.1 required |

-continued

| Cmpd | Structure | Name | LRMS m/z (M + H) |
|---|---|---|---|
| 17-11 | 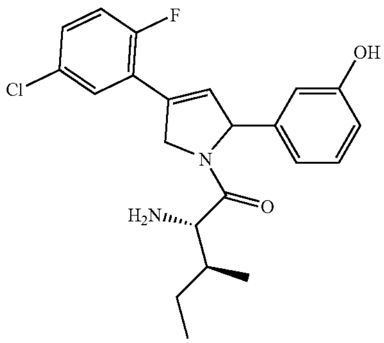 | 4-(5-chloro-2-fluorophenyl)-2-(3-hydroxyphenyl)-1-L-isoleucyl-2,5-dihydro-1H-pyrrole; isolated as the TFA salt | LRMS m/z (M + H) 403.0 found, 403.2 required |
| 17-12 | 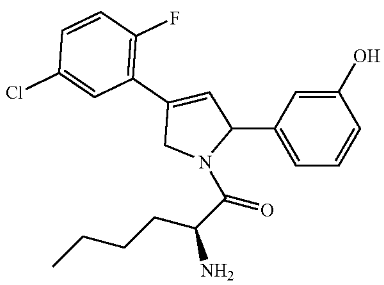 | 4-(5-chloro-2-fluorophenyl)-2-(3-hydroxyphenyl)-1-L-norleucyl-2,5-dihydro-1H-pyrrole | LRMS m/z (M + H) 403.0 found, 403.2 required |
| 17-13 | 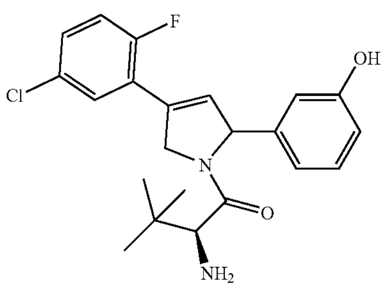 | (2S)-4-(5-chloro-2-fluorophenyl)-2-(3-hydroxyphenyl)-1-(3-methyl-L-valyl)-2,5-dihydro-1H-pyrrole | LRMS m/z (M + H) 403.0 found, 403.2 required |
| 17-14 | 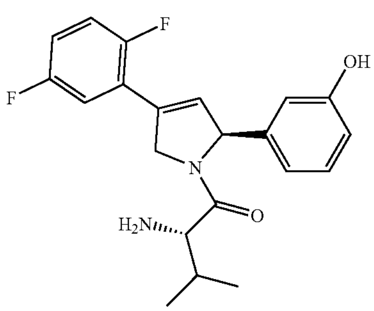 | (2S)-4-(2,5-difluorophenyl)-2-(3-hydroxyphenyl)-1-L-valyl-2,5-dihydro-1H-pyrrole | LRMS m/z (M + H) 373.0 found, 373.2 required |
| 17-15 | 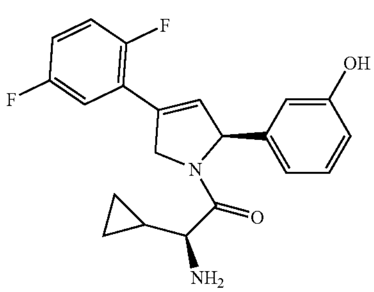 | 3-[(2S)-1-[(2S)-2-amino-2-cyclopropylethanoyl]-4-(2,5-difluorophenyl)-2,5-dihydro-1H-pyrrol-2-yl]phenol | LRMS m/z (M + H) 370.9 found, 371.2 required |

-continued

| Cmpd | Structure | Name | LRMS m/z (M + H) |
|---|---|---|---|
| 17-16 | 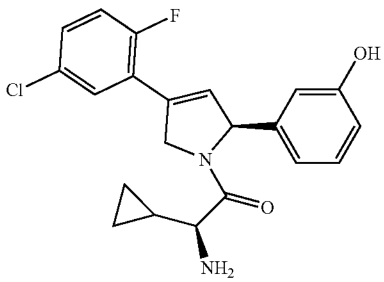 | 3-[(2S)-1-[(2S)-2-amino-2-cyclopropylethanoyl]-4-(5-chloro-2-fluorophenyl)-2,5-dihydro-1H-pyrrol-2-yl]phenol | LRMS m/z (M + H) 387.1 found, 387.1 required |
| 17-17 | 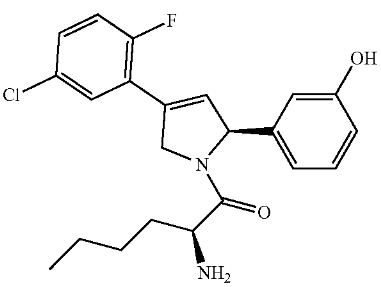 | (2S)-4-(5-chloro-2-fluorophenyl)-2-(3-hydroxyphenyl)-1-L-norleucyl-2,5-dihydro-1H-pyrrole | LRMS m/z (M + H) 403.3 found, 403.2 required |
| 17-18 | 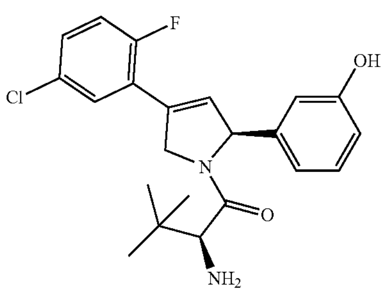 | (2S)-4-(5-chloro-2-fluorophenyl)-2-(3-hydroxyphenyl)-1-(3-methyl-L-valyl)-2,5-dihydro-1H-pyrrole | LRMS m/z (M + H) 413.4 found, 413.2 required |
| 17-19 | 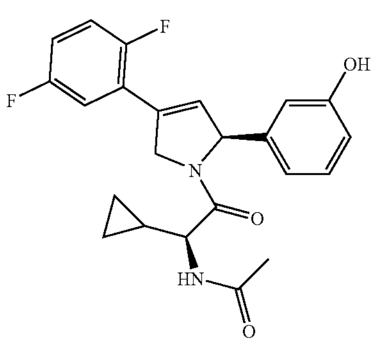 | N-{(1S)-1-cyclopropyl-2-[(2S)-4-(2,5-difluorophenyl)-2-(3-hydroxyphenyl)-2,5-dihydro-1H-pyrrol-1-yl]-2-oxoethyl}acetamide | LRMS m/z (M + H) 403.0 found, 403.2 required |

-continued
| Cmpd | Structure | Name | LRMS m/z (M + H) |
|---|---|---|---|
| 17-20 | 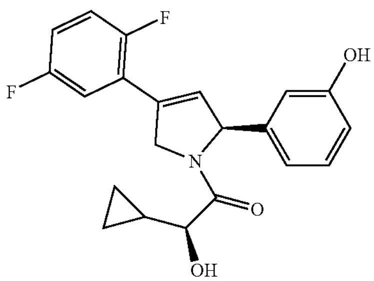 | 3-[(2S)-1-[(2S)-2-cyclopropyl-2-hydroxyethanoyl]-4-(2,5-difluorophenyl)-2,5-dihydro-1H-pyrrol-2-yl]phenol | LRMS m/z (M + H) 372.3 found, 372.4 required |
| 17-21 | 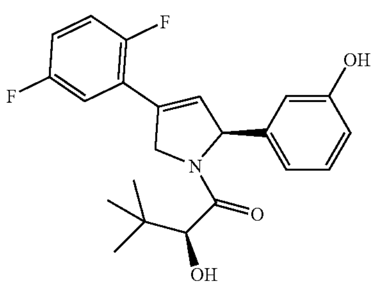 | 3-{(2S)-4-(2,5-difluorophenyl)-1-[(2S)-2-hydroxy-3,3-dimethylbutanoyl]-2,5-dihydro-1H-pyrrol-2-yl}phenol | LRMS m/z (M + H) 388.3 found, 388.4 required |
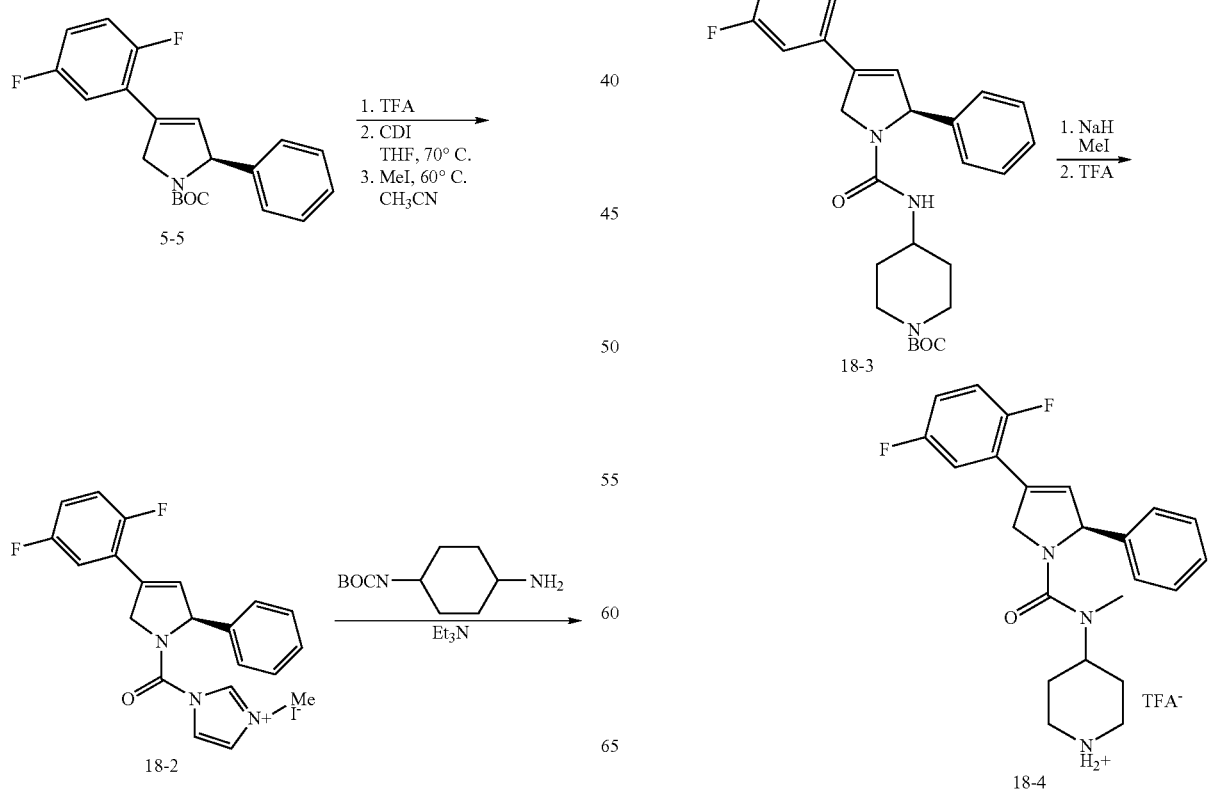
SCHEME 18

Step 1: 1-{[(2S)-4-(2,5-Difluorophenyl)-2-phenyl-2,5-dihydro-1H-pyrrol-1-yl]carbonyl}-3-methyl-1H-imidazol-3-ium (18-2)

To a flame-dried flask equipped with stir bar under nitrogen was charged 5-5 (0.63 g, 1.75 mmol) and anhydrous $CH_2CL_2$ (10 mL). The resulting solution was treated with trifluoroacetic acid (5 mL) and stirred 1.5 hours at 25° C. Upon completion, the reaction was concentrated, taken up in $CH_2Cl_2$ (50 mL) and washed with 5% $NaHCO_3$ (50 mL). The organic layer was dried ($MgSO_4$), filtered and concentrated under reduced pressure. The resulting free-amine was dissolved in anhydrous THF (10 mL) and treated with carbonyl diimidazole (0.31 g, 1.93 mmol). The resulting solution was refluxed for 4 hours until completion. The reaction was concentrated, taken up in EtOAc (50 mL) and washed with $H_2O$ and brine. The combined organic layers were dried ($MgSO_4$) and concentrated. The crude acyl imidazole was dissolved in anhydrous $CH_3CN$ and treated with MeI (2.2 mL, 36 mmol). The resulting solution was stirred at 25° C. overnight. Upon completion, the reaction was concentrated to give 18-2 as an orange colored solid: LRMS m/z (M+H) 365.9 found, 366.1 required.

Step 2: tert-Butyl 4-({[(2S)-4-(2,5-difluorophenyl)-2-phenyl-2,5-dihydro-1H-pyrrol-1-yl]carbonyl}amino)piperidine-1-carboxylate (18-3)

Crude 18-2 (115 mg, 0.24 mmol) was suspended in anhydrous $CH_2CL_2$ (3 mL) and treated successively with 4-amino-1-tert-butyloxycarbonyl-piperidine (235 mg, 1.17 mmol) and $Et_3N$ (0.1 mL, 0.7 mmol). The suspension was stirred for 6 hours and complete dissolution was observed. Upon completion, the reaction was diluted further with $CH_2Cl_2$ (20 mL) and washed with 1N HCl to remove all unbound amine and $Et_3N$. The organic layer was dried ($MgSO_4$), filtered and concentrated under reduced pressure to yield crude 18-3 as a yellow oil: LRMS m/z (N $C(CH_3)_3$+H) 427.9 found, 428.1 required.

Step 3: (2S)-4-(2,5-Difluorophenyl)-N-methyl-2-phenyl-N-piperidin-4-yl-2,5-dihydro-1H-pyrrole-1-carboxamide (18-4)

Crude 18-3 (100 mg, 0.2 mmol) was dissolved in anhydrous DMF (3 mL) and cooled to 0° C. under $N_2$. NaH (28 mg, 1.17 mmol) was added neat and the reaction was stirred 30 minutes at 0° C. Following cessation of $H_2$ evolution, MeI (0.15 mL, 2.4 mmol) was added and the reaction was stirred 12 hours at 25° C. Upon completion, the reaction was diluted with EtOAc (10 mL), and the organic layer was washed successively with 5% $NH_4Cl$ (1×10 mL), $H_2O$ (3×5 mL) and brine (1×10 mL). The organic layer was dried ($MgSO_4$), filtered and concentrated under reduced pressure. The crude oil was dissolved in anhydrous $CH_2Cl_2$ (10 mL). The resulting solution was treated with trifluoroacetic acid (5 mL) and stirred 1 hour at 25° C. Upon completion, the reaction was concentrated and directly subjected to reverse-phase column chromatography to provide 18-4: $^1$H NMR (300 MHz, $CD_3OD$) δ 7.33 (m, 4H), 7.25 (m, 2H), 7.17 (m, 1H), 7.08 (m, 1H), 6.41 (s, 1H), 6.00 (t, J=2.7 Hz, 1H), 5.07 (ddd, J=14.0, 5.6, 1.7 Hz, 1H), 4.55 (d, J=14.0 Hz, 1H), 3.82 (m, 1H), 3.40 (m, 2H), 3.03 (dt, J=12.5, 3.9 Hz, 1H), 2.88 (s, 3H), 2.81 (dt, J=13.1, 2.9 Hz, 1H), 1.90 (m, 4H); LRMS m/z (M+H) 398.0 found, 398.2 required.

SCHEME 18a

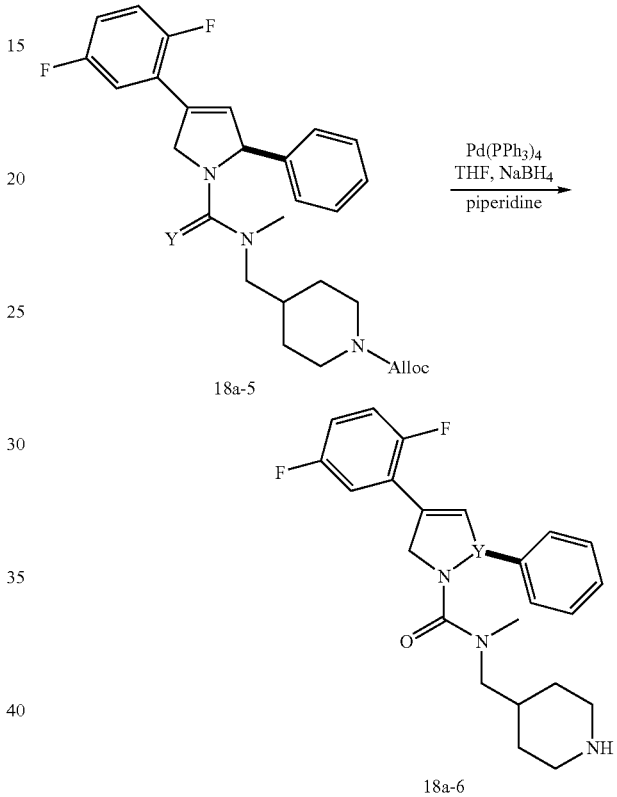

(2S)-4-(2,5-Difluorophenyl)-N-methyl-2-phenyl-N-(piperidin-4-ylmethyl)-2,5-dihydro-1H-pyrrole-1-carboxamide (18a-6)

To a flame-dried, $N_2$ purged flask equipped with stir bar was added 18a-5 (prepared in the same way as shown in Scheme 18 but utilizing N-methyl-N-(1-allyloxycarbonyl-4-piperidinylmethyl)-amine) (22 mg, 0.044 mmol) in anhydrous THF (1 mL). $Pd(PPh_3)_4$ (1 mg, 0.001 mmol) was added neat followed by $NaBH_4$ (3 mg, 0.088 mmol) and the reaction was stirred overnight at 25° C. Upon completion, piperidine (10 μL) was added and the reaction was diluted with EtOAc (10 mL), washed with 5% aq. $NaHCO_3$ (10 mL), brine (10 mL) and dried ($MgSO_4$). Following filtration and concentration under reduced pressure, the crude was subjected to reverse phase column chromatography to provide pure 18a-6 as the TFA salt: LRMS m/z (M+H) 412.0 found, 412.2 required.

SCHEME 18b

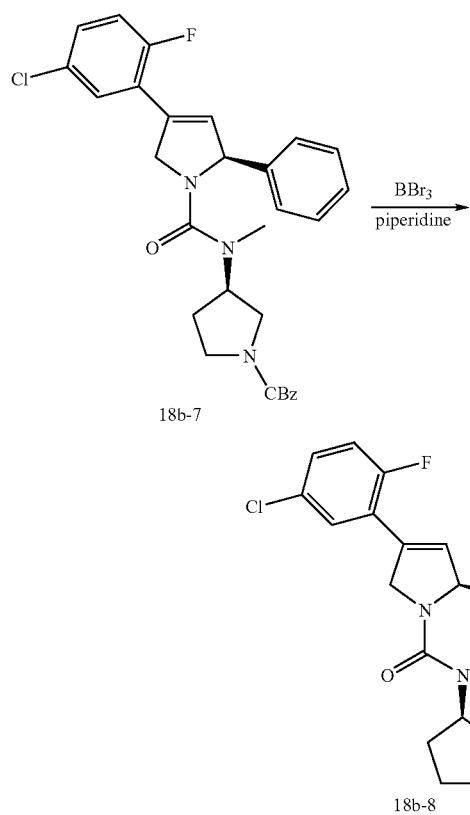

(2S)-4-(5-Chloro-2-fluorophenyl)-N-methyl-2-phenyl-N-[(3R)-pyrrolidin-3-yl]-2,5-dihydro-1H-pyrrole-1-carboxamide (18b-8)

To a flame-dried, $N_2$ purged flask equipped with stir bar was added 18b-7 (prepared in the same way as shown in Scheme 18 but utilizing N-methyl-N-(3-pyrolyl)-amine) (14 mg, 0.026 mmol) in $CH_2Cl_2$ (3 mL). Cooled to 0° C. prior to the addition of $BBr_3$ (0.10 mL, 0.10 mmol). The reaction stirred 1.5 hours at 0° C. Upon completion, piperidine (10 μL) was added and the reaction was diluted with $CH_2Cl_2$ (10 mL), and washed with 5% aq. $NaHCO_3$. The organic layer was dried ($MgSO_4$), filtered and concentrated under reduced pressure. Reverse phase chromatography provided 18b-8 as a white solid (isolated as the TFA salt): $^1$H NMR (300 MHz, $CDCl_3$) δ 11.86 (s, 1H), 8.06 (s, 1H), 7.30 (m, 7H), 7.08 (m, 1H), 6.37 (s, 1H), 5.88 (s, 1H), 4.94 (dd, J=5.4, 13.9 Hz, 1H), 4.48 (d, J=14.1, 1H), 3.79 (m, 1H), 3.49 (m, 1H), 3.36 (s, 2H), 3.00 (s, 31), 2.23 (m, 1H), 1.77 (m, 1H). LRMS m/z (M+H) 400.0 found, 400.1 required The following compounds were prepared by simple modifications of the above procedures. Unless otherwise indicated, the compounds in the table were isolated as the free base.

| Cmpd | Structure | Name | LRMS m/z (M + H) |
|---|---|---|---|
| 18-5 | 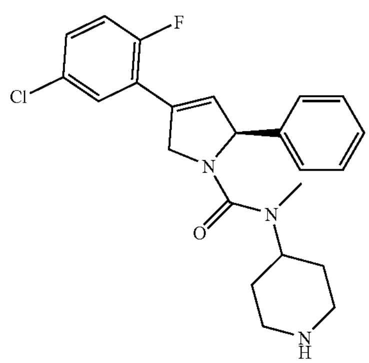 | (2S)-4-(5-chloro-2-fluorophenyl)-N-methyl-2-phenyl-N-piperidin-4-yl-2,5-dihydro-1H-pyrrole-1-carboxamide; isolated as the TFA salt | LRMS m/z (M + H) 414.0 found, 414.1 required. |
| 18-6 | 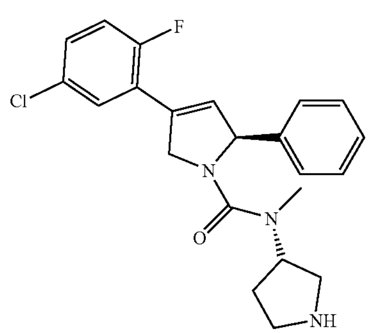 | (2S)-4-(5-chloro-2-fluorophenyl)-N-methyl-2-phenyl-N-[(3S)-pyrrolidin-3-yl]-2,5-dihydro-1H-pyrrole-1-carboxamide; isolated as the TFA salt | LRMS m/z (M + H) 400.0 found, 400.1 required |

| Cmpd | Structure | Name | LRMS m/z (M + H) |
|---|---|---|---|
| 18-7 | 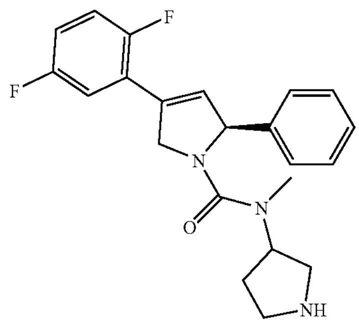 | (2S)-4-(2,5-difluorophenyl)-N-methyl-2-phenyl-N-pyrrolidin-3-yl-2,5-dihydro-1H-pyrrole-1-carboxamide; isolated as the TFA salt | LRMS m/z (M + H) 384.0 found, 384.2 required. |
| 18-8 | 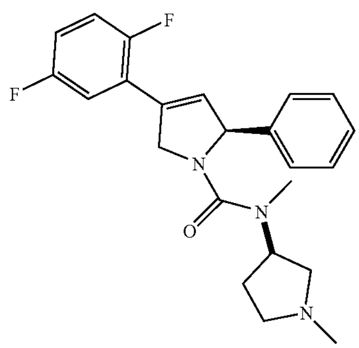 | (2S)-4-(2,5-difluorophenyl)-N-methyl-N-[(3S)-1-methylpyrrolidin-3-yl]-2-phenyl-2,5-dihydro-1H-pyrrole-1-carboxamide | LRMS m/z (M + H) 398.1 found, 398.2 required. |
| 18-9 | 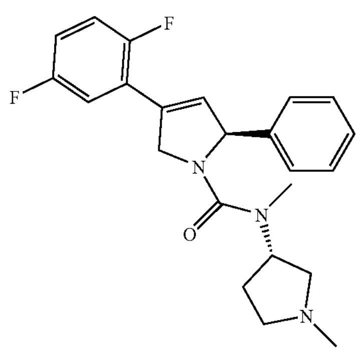 | (2S)-4-(2,5-difluorophenyl)-N-methyl-N-[(3R)-1-methylpyrrolidin-3-yl]-2-phenyl-2,5-dihydro-1H-pyrrole-1-carboxamide | LRMS m/z (M + H) 398.1 found, 398.2 required. |
| 18-10 | 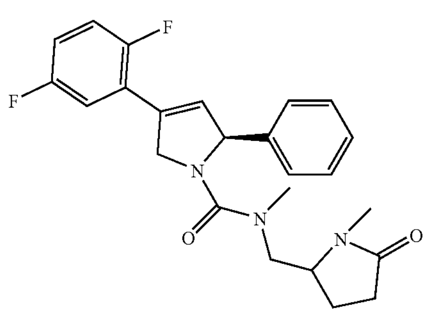 | (2S)-4-(2,5-difluorophenyl)-N-methyl-N-[(1-methyl-5-oxopyrrolidin-2-yl)methyl]-2-phenyl-2,5-dihydro-1H-pyrrole-1-carboxamide | LRMS m/z (M + H) 426.1 found, 426.2 required. |

-continued

| Cmpd | Structure | Name | LRMS m/z (M + H) |
|---|---|---|---|
| 18-11 | 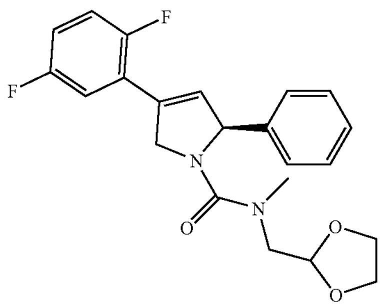 | (2S)-4-(2,5-difluorophenyl)-N-(1,3-dioxolan-2-ylmethyl)-N-methyl-2-phenyl-2,5-dihydro-1H-pyrrole-1-carboxamide | LRMS m/z (M + H) 401.0 found, 401.2 required. |
| 18-12 | 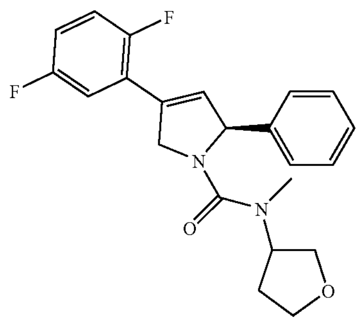 | (2S)-4-(2,5-difluorophenyl)-N-methyl-2-phenyl-N-tetrahydrofuran-3-yl-2,5-dihydro-1H-pyrrole-1-carboxamide | LRMS m/z (M + H) 385.0 found, 385.2 required. |
| 18-13 | 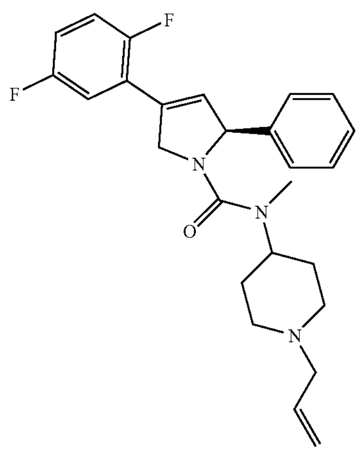 | (2S)-N-(1-allylpiperidin-4-yl)-4-(2,5-difluorophenyl)-N-methyl-2-phenyl-2,5-dihydro-1H-pyrrole-1-carboxamide; isolated as the TFA salt | LRMS m/z (M + H) 438.1 found, 438.2 required. |
| 18-14 | 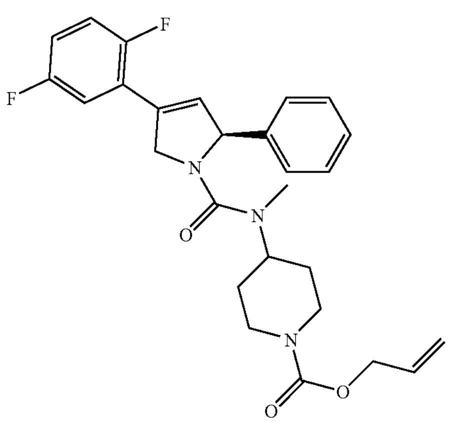 | allyl 4-[{[(2S)-4-(2,5-difluorophenyl)-2-phenyl-2,5-dihydro-1H-pyrrol-1-yl]carbonyl}(methyl)amino]piperidine-1-carboxylate | LRMS m/z (M + H) 482.0 found, 482.2 required. |

| Cmpd | Structure | Name | LRMS m/z (M + H) |
|---|---|---|---|
| 18-15 | 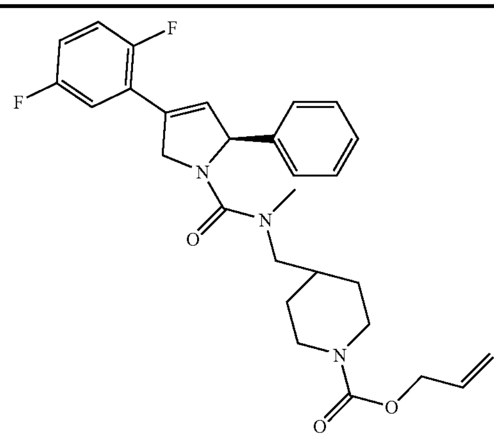 | allyl 4-{[{[(2S)-4-(2,5-difluorophenyl)-2-phenyl-2,5-dihydro-1H-pyrrol-1-yl]carbonyl}(methyl)amino]methyl}piperidine-1-carboxylate | LRMS m/z (M + H) 496.1 found, 496.2 required. |
| 18-16 | 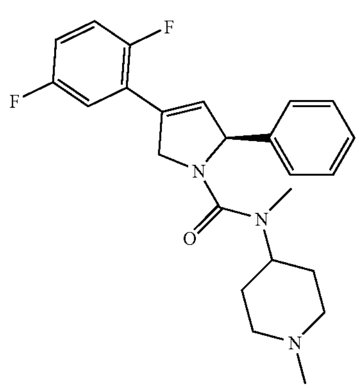 | (2S)-4-(2,5-difluorophenyl)-N-methyl-N-(1-methylpiperidin-4-yl)-2-phenyl-2,5-dihydro-1H-pyrrole-1-carboxamide | LRMS m/z (M + H) 412.4 found, 412.5 required. |
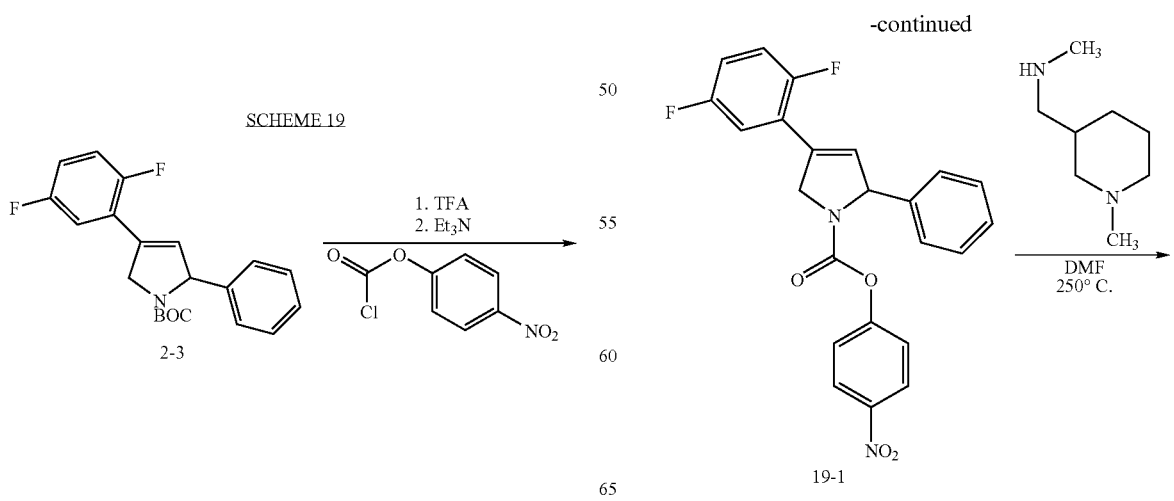

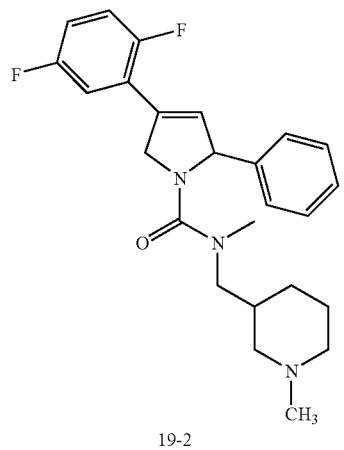

19-2

Step 1: 4-Nitrophenyl 4-(2,5-difluorophenyl)-2-phenyl-2,5-dihydro-1H-pyrrole-1-carboxylate (19-1)

To a flame-dried flask equipped with stir bar under nitrogen was charged 2-3 (0.71 g, 1.98 mmol) and anhydrous $CH_2Cl_2$ (50 mL). The resulting solution was treated with trifluoroacetic acid (10 mL) and stirred 1 hour at 25° C. Upon completion, the reaction was concentrated, taken up in $CH_2Cl_2$ (50 mL) and washed with 5% $NaHCO_3$ (50 mL). The organic layer was dried ($MgSO_4$), filtered and concentrated under reduced pressure. The resulting free-amine was dissolved in anhydrous $CH_2Cl_2$ (50 mL) and treated with p-nitrophenyl chloroformate (0.44 g, 2.17 mmol). The resulting solution was stirred 4 hours at 25° C. until completion. The reaction was concentrated to give 19-1 as a yellow oil: $^1H$ NMR (300 MD, $CDCl_3$) δ 8.22 (d, J=9.4 Hz, 1H), (d, J=9.1 Hz, 1H), 7.38 (m, 5H), 7.02 (m, 5H), 6.43 (m, 1H), 5.85 (m, 1H), 4.90 (m, 2H); LRMS m/z (M+H) 422.9 found, 423.1 required.

Step 2: 4-(2,5-Difluorophenyl)-N-methyl-N-[(1-methylpiperidin-3-yl)methyl]-2-phenyl-2,5-dihydro-1H-pyrrole-1-carboxamide (19-2)

19-1 (20 mg, 0.05 mmol) was dissolved in anhydrous DMP (1.0 mL) in a microwave reaction tube. The resulting solution was treated with 4-aminomethyl-N,N'-dimethyl-piperidine (13 mg, 0.09 mmol). The solution was stirred for 6 minutes at 250° C. under microwave irradiation. The dark brown reaction was directly purified by reverse phase column chromatography to yield 4-(2,5-difluorophenyl)-N-methyl-N-[(1-methylpiperidin-3-yl)methyl]-2-phenyl-2,5-dihydro-1H-pyrrole-1-carboxamide 19-2 (mix of four diastereomers) (isloated as the TFA salt): LRMS m/z (M+H) 426.2 found, 426.2 required.

The following compounds were prepared by simple modifications of the above procedures. Unless otherwise indicated, the compounds in the table were isolated as the free base.

| Cmpd | Structure | Name | LRMS m/z (M + H) |
|---|---|---|---|
| 19-3 | 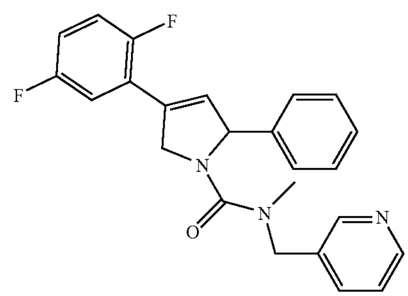 | 4-(2,5-difluorophenyl)-N-methyl-2-phenyl-N-(pyridin-3-ylmethyl)-2,5-dihydro-1H-pyrrole-1-carboxamide; isolated as the TFA salt | LRMS m/z (M + H) 406.1 found, 406.2 required. |
| 19-4 | 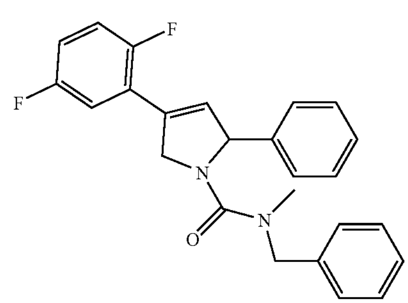 | N-benzyl-4-(2,5-difluorophenyl)-N-methyl-2-phenyl-2,5-dihydro-1H-pyrrole-1-carboxamide | LRMS m/z (M + H) 405.2 found, 405.2 required. |

-continued

| Cmpd | Structure | Name | LRMS m/z (M + H) |
|---|---|---|---|
| 19-5 | 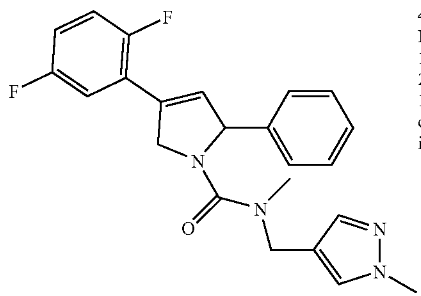 | 4-(2,5-difluorophenyl)-N-methyl-N-[(1-methyl-1H-pyrazol-4-yl)methyl]-2-phenyl-2,5-dihydro-1H-pyrrole-1-carboxamide; isolated as the TFA salt | LRMS m/z (M + H) 409.2 found, 409.2 required. |
| 19-6 | 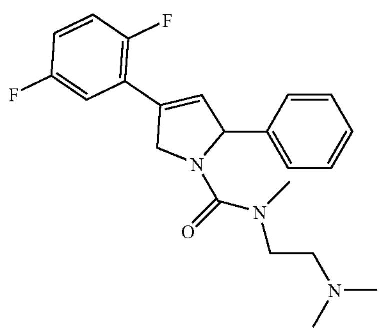 | 4-(2,5-difluorophenyl)-N-[2-(dimethylamino)ethyl]-N-methyl-2-phenyl-2,5-dihydro-1H-pyrrole-1-carboxamide; isolated as the TFA salt | LRMS m/z (M + H) 386.2 found, 386.2 required. |
| 19-7 | 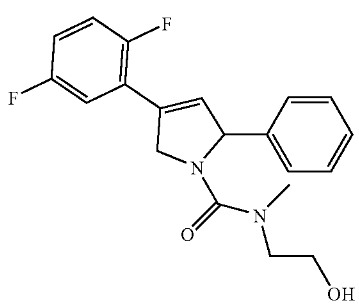 | 4-(2,5-difluorophenyl)-N-(2-hydroxyethyl)-N-methyl-2-phenyl-2,5-dihydro-1H-pyrrole-1-carboxamide | LRMS m/z (M + H) 359.1 found, 359.0 required. |
| 19-8 | 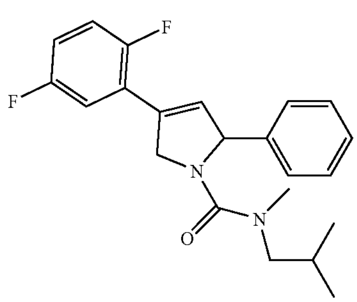 | 4-(2,5-difluorophenyl)-N-isobutyl-N-methyl-2-phenyl-2,5-dihydro-1H-pyrrole-1-carboxamide | LRMS m/z (M + H) 371.2 found, 371.2 required. |

-continued

| Cmpd | Structure | Name | LRMS m/z (M + H) |
|---|---|---|---|
| 19-9 | 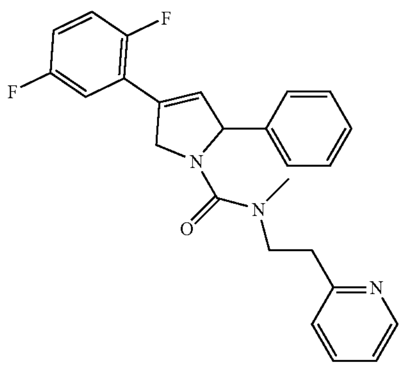 | 4-(2,5-difluorophenyl)-N-methyl-2-phenyl-N-(2-pyridin-2-ylethyl)-2,5-dihydro-1H-pyrrole-1-carboxamide; isolated as the TFA salt | LRMS m/z (M + H) 420.2 found, 420.2 required. |
| 19-10 | 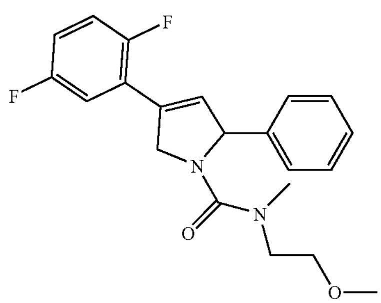 | 4-(2,5-difluorophenyl)-N-(2-methoxyethyl)-N-methyl-2-phenyl-2,5-dihydro-1H-pyrrole-1-carboxamide | LRMS m/z (M + H) 373.1 found, 373.2 required. |
| 19-11 | 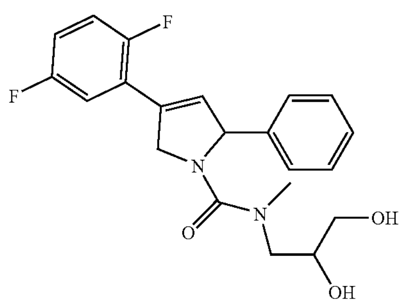 | 4-(2,5-difluorophenyl)-N-(2,3-dihydroxypropyl)-N-methyl-2-phenyl-2,5-dihydro-1H-pyrrole-1-carboxamide | LRMS m/z (M + H) 389.1 found, 389.2 required. |
| 19-12 | 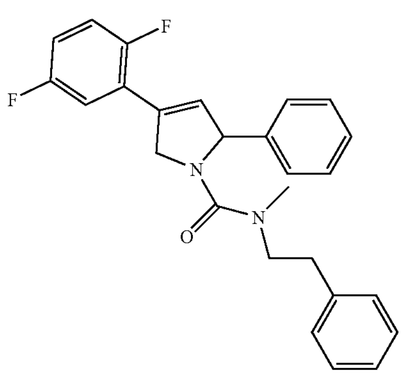 | 4-(2,5-difluorophenyl)-N-methyl-2-phenyl-N-(2-phenylethyl)-2,5-dihydro-1H-pyrrole-1-carboxamide | LRMS m/z (M + H) 419.1 found, 419.2 required. |

-continued

| Cmpd | Structure | Name | LRMS m/z (M + H) |
|---|---|---|---|
| 19-13 | 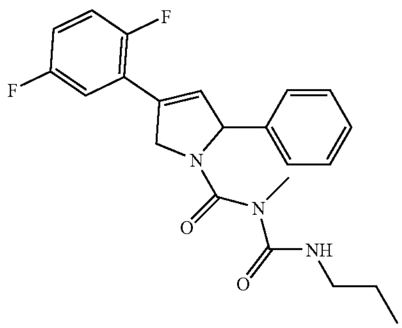 | 4-(2,5-difluorophenyl)-2-phenyl-N-propyl-2,5-dihydro-1H-pyrrole-1-carboxamide | LRMS m/z (M + H) 343.1 found, 343.1 required. |
| 19-14 | 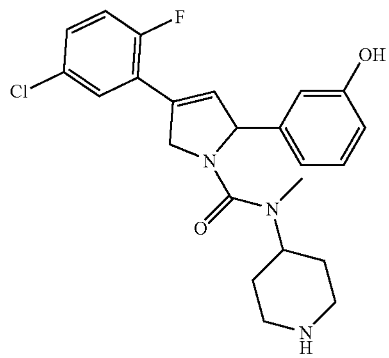 | 4-(5-chloro-2-fluorophenyl)-2-(3-hydroxyphenyl)-N-methyl-N-piperidin-4-yl-2,5-dihydro-1H-pyrrole-1-carboxamide; isolated as the TFA salt | LRMS m/z (M + H) 430.0 found, 429.2 required. |
| 19-15 | 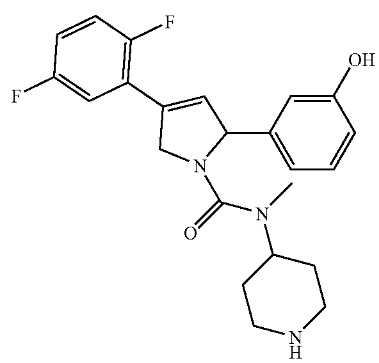 | 4-(2,5-difluorophenyl)-2-(3-hydroxyphenyl)-N-methyl-N-piperidin-4-yl-2,5-dihydro-1H-pyrrole-1-carboxamide; isolated as the TFA salt | LRMS m/z (M + H) 414.0 found, 413.2 required. |

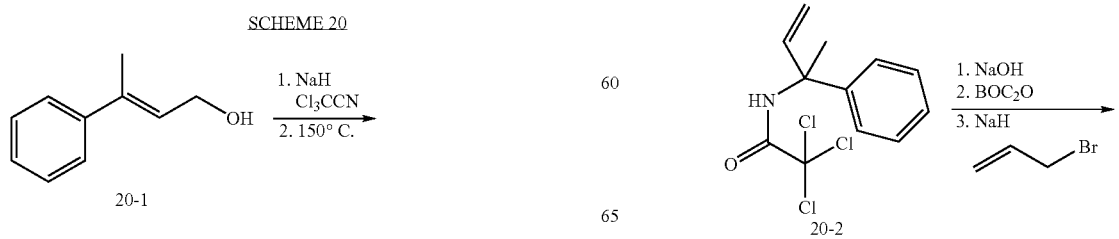

SCHEME 20

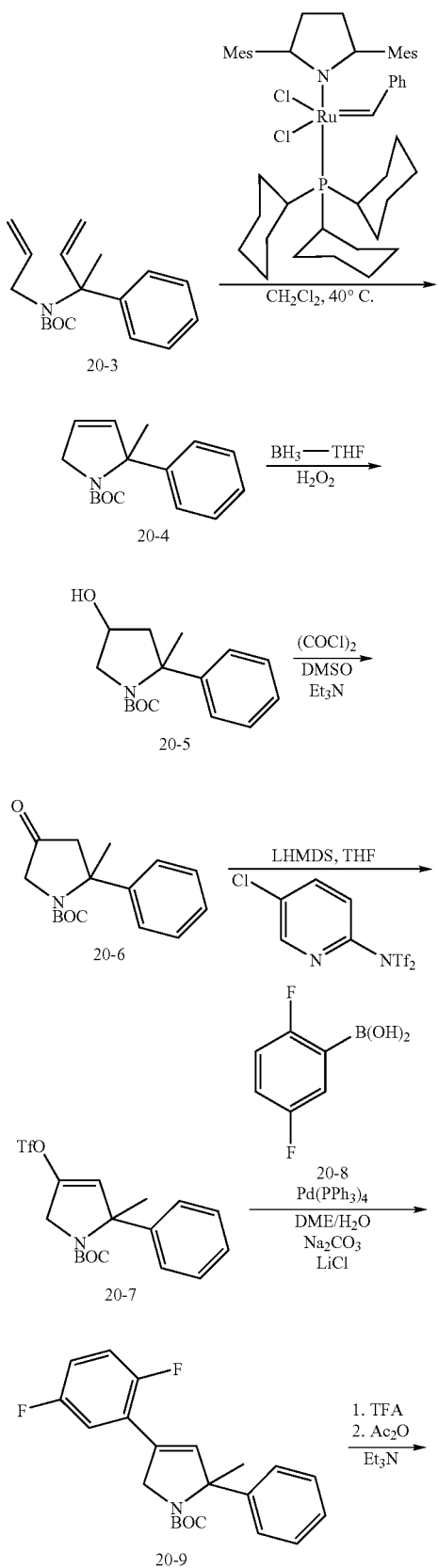

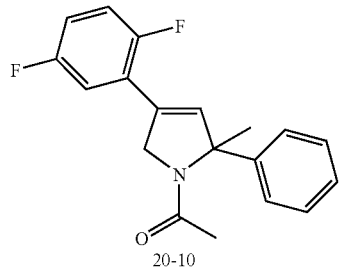

20-10

Step 1: 2,2,2-Trichloro-N-(1-methyl-1-phenylprop-2-enyl)-N-(2-methylprop-2-enyl)acetamide (20-2)

To a flame-dried flask equipped with stir bar under nitrogen was charged Z-3-phenyl-buten-1-ol (3.1 g, 21.0 mmol) and anhydrous $Et_2O$ (100 mL). The resulting solution was treated with NaH (0.05 g, 2.1 mmol) and stirred 30 minutes at 0° C. Trichloroactonitrile (4.12 mL, 41.1 mmol) was added to the cooled solution and stirred an additional 2 hours. The reaction mixture was concentrated under reduced pressure then pentane (100 mL), containing 0.1 equivalent of methanol was added to the residue and stirred vigorously for 1 hour. The resulting solution was concentrated and washed with pentane (3×20 mL). The filtrate was concentrated under reduced pressure to give 2-(E)-3-phenylbul-2-enyl 2,2,2-trichloroethanimidoate. Xylene (80 mL) was added to the crude residue and the solution was heated 3 hours at 150° C. The warm solution was concentrated under reduced pressure and purified by flash column chromotography ($SiO_2$, 0-20% EtOAc/Hexanes gradient) to give 2,2,2-trichloro-N-(1-methyl-1-phenylprop-2-enyl)-N-(2-methylprop-2-enyl)acetamide, 20-2. $^1$H NMR (300 MHz, $CDCl_3$) δ 7.39 (m, 5H), 6.98 (s, 1H), 6.29 (dd, J=17.4, 10.6 Hz, 1H), 5.30 (d, J=10.6 Hz, 1H), 5.26 (d, J=17.4 Hz, 1H) 1.89 (s, 3H); LRMS m/z (M+H) 294.2 found, 294.6 required.

Step 2: tert-Butyl allyl(1-methyl-1-phenylprop-2-enyl)carbamate (20-3)

Trichloroacetamide (20-2) (0.98 g, 3.9 mmol) was stirred 72 h. in a 1:1 solution of 6M NaOH/EtOH (100 mL). The solution was concentrated under reduced pressure and purified by flash column chromatography ($SiO_2$, 0-20% EtOAc/Hexanes gradient). The purified amine was combined with $BOC_2O$ (3.81 g, 17.4 mmol) and $Et_3N$ (1.76 g, 17.4 mmol) in $CH_2Cl_2$ (100 mL). The solution was then heated at 35° C. for 24 hours. Partitioned between 5% aq. $NaHCO_3$ (150 mL) and EtOAc (3×75 mL). The combined organic layers were dried over $Na_2SO_4$, filtered, and concentrated under reduced pressure. The residue was purified by flash column chromotography ($SiO_2$, 0-20% EtOAc/Hexanes gradient) to give tert-butyl-1-methyl-1-phenylprop-2-enylcarbamate. The BOC-protected amine was dissolved in anhydrous DMF (100 mL) under $N_2$ at 0° C. NaH (0.19 g, 7.9 mmol) was added and the solution was stirred at 0° C. for 30 minutes. Allyl bromide (1.37 mL, 15.8 mmol) was added neat, and the reaction stirred 24 hours. at 25° C. The reaction mixture was partitioned between 5% aq. NaHCO$_3$ (150 mL) and Et$_2$O (3×75 mL). The combined organic layers were then dried over Na$_2$SO$_4$, filtered, and concentrated under reduced pressure. The residue was purified by flash column chromotography (SiO$_2$, 0-20% EtOAc/Hexanes gradient) to give tert-butyl allyl(1-methyl-1-phenylprop-2-enyl)carbamate, 20-3. $^1$H NMR (300 MHz, CDCl$_3$) δ 7.20 (m, 5H), 6.34 (dd, J=10.6, 17.4 Hz, 1H), 6.00 (ddt, J=5.8, 11.3, 21.7 Hz, 1H), 5.18 (m, 2H), 5.09 (d, J=20.7 Hz, 1H), 5.01 (d, J=16.8 Hz, 1H), 4.07 (d, J=5.5 Hz, 2H), 1.76 (s, 3H), 1.19 (s, 9H); LRMS m/z (M+H C(CH$_3$)$_3$) 232.1 found, 232.2 required.

Step 3: tert-Butyl 2-methyl-2-phenyl-2,5-dihydro-1H-pyrrole-1-carboxylate (20-4)

A solution of 20-3 (0.78 g, 2.7 mmol) and tricyclohexylphosphine[1,3-bis(2,4,6-trinmethylphenyl)-4,5-dihydroimidazol-2-ylidene][benylidine]ruthenium (IV)dichloroide (0.04 g, 0.05 mmol) in CH$_2$Cl$_2$ (500 mL) was stirred 1 hour. at 40° C. under N$_2$. The reaction mixture was concentrated under reduced pressure and purified by flash column chromatography (SiO$_2$, O-30% EtOAc/Hexanes gradient) to give tert-butyl 2-methyl-2-phenyl-2,5-dihydro-1H-pyrrole-1-carboxylate, 20-4. $^1$H NMR (300 MHz, CDCl$_3$) δ 7.25 (m, 5H), 5.79 (m, 1H), 5.58 (m, 1H), 4.32 (m, 1H), 4.43 (m, 1H), 1.8 (s, 3H), 1.5 (s, 9H); LRMS m/z (M+H) 260.1 found, 260.2 required.

Step 4: tert-Butyl 4-hydroxy-2-methyl-2-phenylpyrrolidine-1-carboxylate (20-5)

A solution of 20-4 (0.50 g, 1.9 mmol) in anhydrous THF (80 mL) at 0° C. was treated with BH3:THF (1.93 mL, 1.9 mmol) then stirred for 1 hour. at 25° C. Water (0.35 mL, 19.2 mmol) was added, followed by 3 N NaOH (0.23 mL, 5.8 mmol). The resulting solution was cooled to 0° C. prior to the addition of 30% H$_2$O$_2$ (0.22 mL, 1.9 mmol). The reaction was partitioned between sat. aq. NaHCO$_3$ (100 mL) and EtOAc (2×100 mL). The combined organic layers were dried over Na$_2$SO$_4$, filtered, and concentrated under reduced pressure. The residue was purified by flash column (SiO$_2$, O-100% EtOAc/Hexanes gradient) to yield tert-butyl 4-hydroxy-2-methyl-2-phenylpyrrolidine-1-carboxylate, 20-5: LRMS m/z (M+H) 278.2 found, 278.1 required.

Step 5: tert-Butyl 2-methyl-4-oxo-2-phenylpyrrolidine-1-carboxylate (20-6)

To a flame-dried flask equipped with stir bar under nitrogen was charged anhydrous CH$_2$Cl$_2$ (5 mL). The flask was immersed in a cooling bath at −78° C. Oxalyl chloride (0.24 mL, 2.7 mmol) was added neat followed by DMSO (0.29 mL, 4.1 mmol) dropwise. The reaction was stirred 10 minutes at −78° C. prior to the addition of alcohol 20-5 (0.19 g, 0.7 mmol) in minimal CH$_2$Cl$_2$. The resulting solution was stirred an additional 1 hour at −78° C. prior to the addition of Et$_3$N (0.76 mL, 5.4 mmol) neat and dropwise. The reaction warmed to 0° C. over 2 hour. Upon completion, the reaction solution was washed with 5% aq. NaHCO$_3$, dried (MgSO$_4$), filtered and concentrated. The residue was carried crude into the vinyl triflate formation: LRMS m/z (M-C(CH$_3$)$_3$+H) 220.1 found, 220.2 required.

Step 6: tert-Butyl 2-methyl-2-phenyl-4-{[(trifluoromethyl)sulfonyl]oxy}-2,5-dihydro-1H-pyrrole-1-carboxylate (20-7)

To a solution of ketone 20-6 (70 mg, 25 µmoL) in anhydrous THF (2 mL) at −78° C. was added LHMDS (254 mL, 25 µmoL), and the resulting yellow-tinted solution was stirred for 1 hours. Comins reagent (110 mg, 28 µmoL) was added neat and the reaction was allowed to warm to 0° C. over 1 hour. The reaction mixture was poured into a separatory funnel containing 5% NH$_4$Cl, and was then extracted with CH$_2$CL (2×10 mL). The combined organic layers were dried (Na$_2$SO$_4$), filtered and concentrated to provide the crude triflate 20-7, which was carried on directly to the Suzuki coupling: LRMS m/z (M-CH$_3$+H) 393.0 found, 393.2 required.

Step 7: tert-Butyl 4-(2,5-difluorophenyl)-2-methyl-2-phenyl-2,5-dihydro-1H-pyrrole-1-carboxylate (20-9)

Crude intermediate 20-7 (100 mg, 25 µmoL) in degassed 4:1 DME/H$_2$O (2 mL) was treated with 2,5-difluorophenyl boronic acid (20-8, 100 mg, 61 µmoL), sodium carbonate (78 mg, 74 µmoL), LiCl (31 mg, 74 µmoL) and Pd(PPh$_3$)$_4$ (13 mg, 12 µmoL). The reaction was kept under N$_2$ and heated to 90° C. for 1 hour. Upon completion, the reaction was diluted with CH$_2$Cl$_2$ (10 mL), washed with sat. aq. NaHCO$_3$ (10 mL), and brine (10 mL). The organic layer was dried (MgSO$_4$), filtered and concentrated under reduced pressure. The residue was purified by flash column chromatography (SiO$_2$, 0-30% EtOAc/hexanes gradient) to provide pure 20-9 as a clear oil: LRMS m/z (M+H) 408.0 found, 408.2 required.

Step 9: 1-Acetyl-4-(2,5-difluorophenyl)-2-methyl-2-phenyl-2,5-dihydro-1H-pyrrole (20-10)

To a flame-dried flask equipped with stir bar under nitrogen was charged 20-9 (14 mg, 38 µmol) and anhydrous CH$_2$CL$_2$ (1 mL). The resulting solution was treated with trifluoroacetic acid (0.2 mL) and stirred 1 hour at 25° C. Upon completion, the reaction was concentrated, diluted with toluene (5 mL) and again concentrated. The TFA salt was then suspended in CH$_2$CL$_2$ at 25° C., and treated successively with Et$_3$N (50 µL, 380 µmol) and acetic anhydride (25 µL, 20 µmol). After 1 hour, the reaction was complete. The reaction was concentrated and flash column chromatography (SiO$_2$, 0-50% EtOAc/hex gradient) provided 20-10 as a clear oil: $^1$H NMR (300 MHz, CDCl$_3$) δ 7.36 (m, 5H), 7.03 (m, 3H), 6.22 (m, 1H), 4.82 (m, 2H), 2.15 and 2.05 (s, 3H, rotamers), 1.98 and 1.74 (s, 3H, rotamers); LRMS m/z (M+H) 314.0 found, 314.2 required.

The following compound was prepared by simple modifications of the above procedures and isolated as the TFA salt.

| Cmp | Structure | Name | LRMS m/z (M + H) |
|---|---|---|---|
| 20-11 | 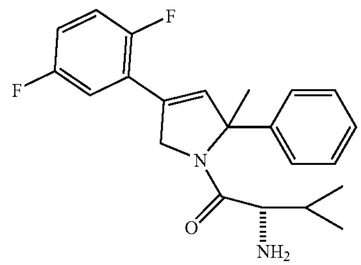 | (2S)-1-[4-(2,5-difluorophenyl)-2-methyl-2-phenyl-2,5-dihydro-1H-pyrrol-1-yl]-3-methyl-1-oxobutan-2-amine | LRMS m/z (M + H) 371.1 found, 371.2 required. |

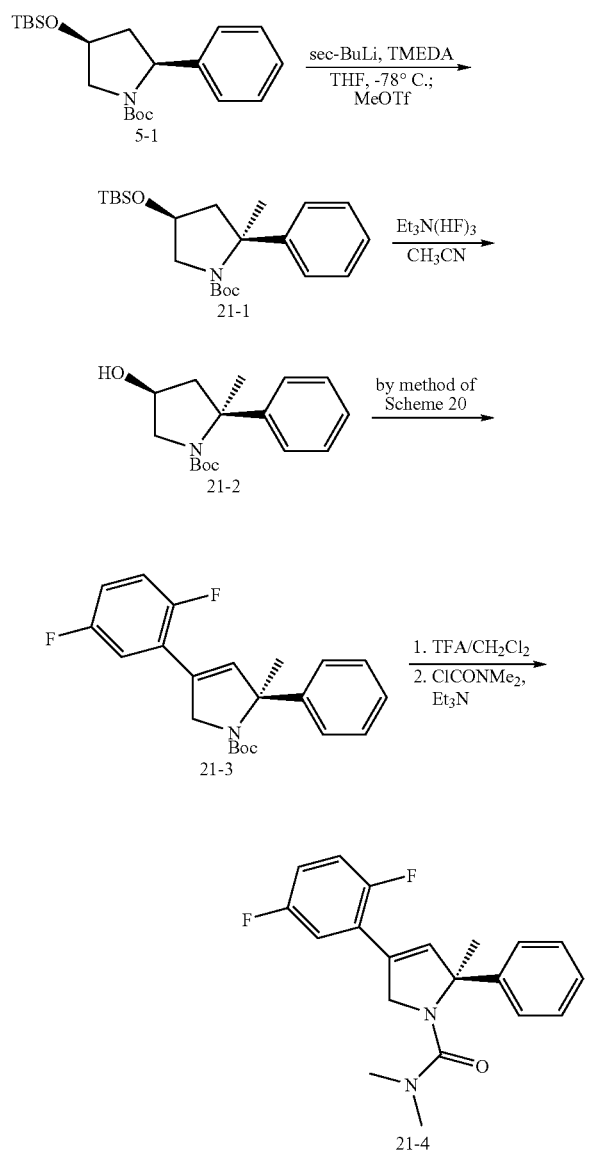

SCHEME 21

Step 1: tert-butyl(2S,4S)-4-{[tert-butyl(dimethyl)silyl]oxy}-2-methyl-2-phenylpyrrolidine-1-carboxylate (21-1)

A solution of sec-BuLi in cyclohexane (1.4 M, 2.65 mL, 3.71 mmol, 1.40 equiv) was added to a solution of tertramethylethylenediamine (0.880 mL, 5.83 mmol, 2.20 equiv) and tert-butyl(2S,4S)-4-{[tert-butyl(dimethyl)silyl]oxy}-2-phenylpyrrolidine-1-carboxylate (5-1, 1.00 g, 2.65 mmol, 1 equiv) in THF (150 mL) at −78° C. The resulting bright yellow mixture was stirred for 1 hour, then methyl trifluoromethanesulfonate (1.20 mL, 10.6 mmol, 4.00 equiv) was added. The mixture was warmed to 0° C. and stirred for 30 minutes, then partitioned between saturated sodium chloride solution (100 mL) and ethyl acetate (2×75 mL). The combined organic layers were dried over sodium sulfate and concentrated. The residue was purified by flash column chromatography (hexanes, grading to 50% ethyl acetate in hexanes) to provide tert-butyl(2S,4S)-4-{[tert-butyl(dimethyl)silyl]oxy}-2-methyl-2-phenylpyrrolidine-1-carboxylate (21-1) as a colorless oil. $^1$H NMR (500 MHz, CDCl$_3$) δ 7.38-7.18 (m, 5H), 4.39 (m, 1), 3.92 (dd, 1H, J=10.8, 5.1 Hz), 3.65 (br d, 1H, J=10.8 Hz), 2.28 (dd, 1H, J=13.0, 4.5 Hz), 2.13 (br d, 1H, J=12.8 Hz), 1.92 (s, 3H), 1.12 (s, 9H), 0.91 (s, 9H), 0.03 (s, 3H), 0.02 (s, 3H). LRMS m/z (M+H-Boc) 292.2 found, 292.2 required.

Step 2: tert-butyl (2S,4S)-4-hydroxy-2-methyl-2-phenylpyrrolidine-1-carboxylate (21-2)

A solution of (2S,4S)-4-{[tert-butyl(dimethyl)silyl]oxy}-2-methyl-2-phenylpyrrolidine-1-carboxylate (21-1, 250 mg, 0.638 mmol, 1 equiv) and triethylamine trihydrofluoride (0.310 mL, 1.91 mmol, 3.00 equiv) in acetonitrile (10 mL) was stirred at 23° C. for 16 hours. The reaction mixture was partitioned between aqueous saturated sodium bicarbonate solution (100 mL) and ethyl acetate (2×50 mL). The combined organic layers were dried over sodium sulfate and concentrated. The residue was purified by flash column chromatography (hexanes initially, grading to 50% ethyl acetate in hexanes) to provide tert-butyl(2S,4S)-4-hydroxy-2-methyl-2-phenylpyrrolidine-1-carboxylate (21-2) as a colorless oil. LRMS m/z (M+H-Boc) 278.2 found, 278.2 required.

Step 3: (2S)-4-(2,5-difluorophenyl)-N,N,2-trimethyl-2-phenyl-2,5-dihydro-1H-pyrrole-1-carboxamide (21-4)

A solution of tert-butyl(2S)-4-(2,5-difluorophenyl)-2-methyl-2-phenyl-2,5-dihydro-1H-pyrrole-1-carboxylate (21-3, prepared from tert-butyl(2S,4S)-4-hydroxy-2-methyl-2-phenylpyrrolidine-1-carboxylate (21-2) by the procedures of Scheme 20, 24 mg, 0.065 mmol, 1 equiv) in a 1:1 mixture of trifluoroacetic acid and dichloromethane (10 mL) was stirred for 30 minutes, then concentrated. The residue was dried via toluene azeotrope (2×10 mL), then dissolved in dichloromethane (10 mL). Triethylamine (0.090 mL, 0.65 mmol, 10 equiv) and dimethylcarbamoyl chloride (0.030 mL, 0.33 mmol, 5.0 equiv) were added, and the resulting mixture was stirred at 40° C. for 6 hours, then 23° C. for 2 days. The reaction mixture was partitioned between aqueous saturated sodium bicarbonate solution (30 mL) and ethyl acetate (2×25 mL). The combined organic layers were dried over sodium sulfate and concentrated. The residue was purified by flash column chromatography (hexanes initially, grading to 40% ethyl acetate in hexanes) to provide (2S)-4-(2,5-difluorophenyl)-N,N,2-trimethyl-2-phenyl-2,5-dihydro-1H-pyrrole-1-carboxamide (21-4) as an off-white solid. $^1$H NMR (500 MD, CDCl$_3$) δ 7.40 (br d, 2H, J=7.7 Hz), 7.32 (br t, 2H, J=7.8 Hz), 7.22 (t, 1H, J=7.5 Hz), 7.08-6.91 (m, 3H), 6.24 (m, 1H), 4.82 (dd, 1H, J=13.9, 1.5 Hz), 4.77 (dd, 1H, J=13.9, 1.5 Hz), 2.77 (s, 6H), 2.02 (s, 3H). LRMS m/z (M+H) 343.0 found, 343.2 required.

The following compounds were prepared by simple modifications of the above procedures.

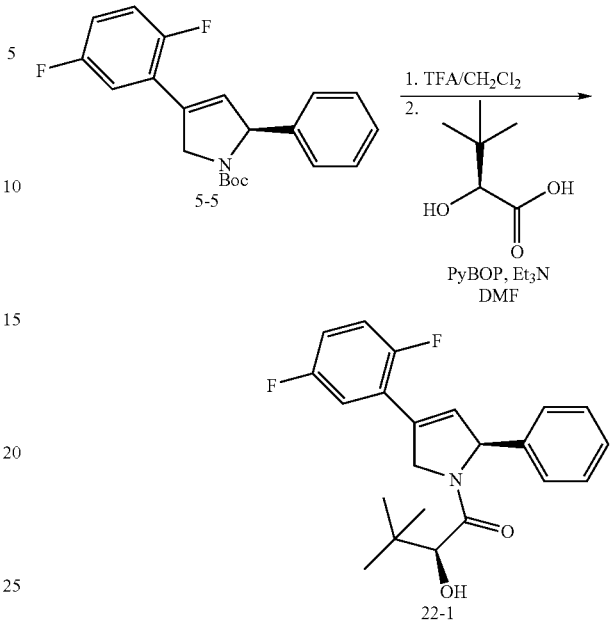

| Cmpd | Structure | Name | LRMS m/z (M + H) |
|------|-----------|------|------------------|
| 21-5 | 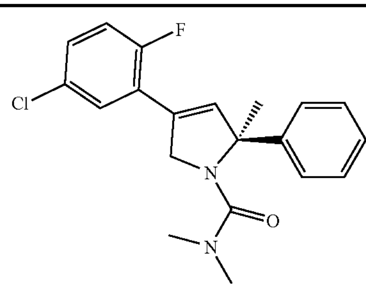 | (2S)-4-(5-chloro-2-fluorophenyl)-N,N,2-trimethyl-2-phenyl-2,5-dihydro-1H-pyrrole-1-carboxamide | LRMS m/z (M + H) 359.0 found, 359.1 required. |
| 21-6 | 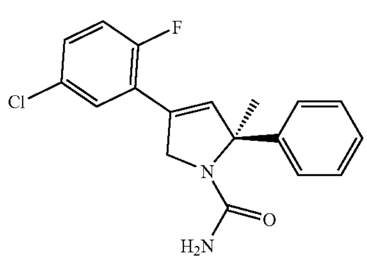 | (2S)-4-(5-chloro-2-fluorophenyl)-2-methyl-2-phenyl-2,5-dihydro-1H-pyrrole-1-carboxamide | LRMS m/z (M + H) 331.0 found, 331.1 required |
| 21-7 | 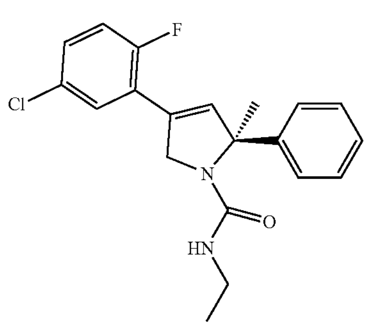 | (2S)-4-(5-chloro-2-fluorophenyl)-N-ethyl-2-methyl-2-phenyl-2,5-dihydro-1H-pyrrole-1-carboxamide | LRMs m/z (M + H) 359.0 found, 359.1 required |

(2S)-1-[(2S)-4-(2,5-difluorophenyl)-2-phenyl-2,5-dihydro-1H-pyrrol-1-yl]-3,3-dimethyl-1-oxobutan-2-ol (22-1)

A solution of tert-butyl(2S)-4-(2,5-difluorophenyl)-2-phenyl-2,5-dihydro-1H-pyrrole-1-carboxylate (5-5, 113 mg, 0.316 mmol, 1 equiv) in a 1:1 mixture of dichloromethane and trifluoroacetic acid (20 mL) was stirred for 30 minutes, then concentrated. The residue was dried via toluene azeotrope (1×10 mL), then dissolved in DMF (4 mL). Triethylamine (0.176 mL, 1.27 mmol, 4.00 equiv), (2S)-2-hydroxy-3,3-dimethylbutanoic acid (84 mg, 0.632 mmol, 2.00 equiv), and PYBOP (329 mg, 0.632 mmol, 2.00 equiv) were added, and the resulting mixture was stirred at 23° C. for 24 hours. Additional triethylamine (0.176 mL, 1.27 mmol, 4.00 equiv), (2S)-2-hydroxy-3,3-dimethylbutanoic acid (84 mg, 0.632 mmol, 2.00 equiv), and PYBOP (329 mg, 0.632 mmol, 2.00 equiv) were added, and the resulting mixture was stirred at 23° C. for 20 hours. The reaction mixture was partitioned between water (70 mL) and ethyl acetate (2×55 mL). The combined organic layers were dried over sodium sulfate and concentrated. The residue was purified by reverse-phase LC ($H_2O$/$CH_3CN$ gradient w/0.1% TFA present) to provide (2S)-1-[(2S)-4-(2,5-difluorophenyl)-2-phenyl-2,5-dihydro-1H-pyrrol-1-yl]-3,3-dimethyl-1-oxobutan-2-ol (22-1) as a white solid. $^1$H NMR (500 MHz, $CDCl_3$) rotamers: δ 7.43-7.02 (m, 8H), 6.42 (m, 1H), 5.93 (m, 1H), 5.01-4.82 (m, 2H), 4.16 (major rotamer, s, 1H), 3.85 (minor rotamer, s, 1H), 1.00 (minor, s, 9H), 0.92 (major, s, 9H). LRMS m/z (M+H) 372.0 found, 372.2 required.

The following compounds were prepared by simple modifications of the above procedures.

| Cmpd | Structure | Name | LRMS m/z (M + H) |
|---|---|---|---|
| 22-2 | 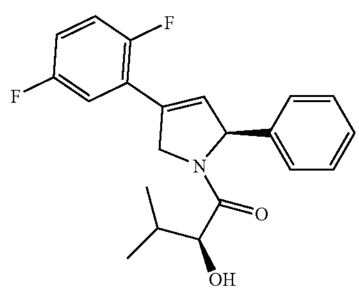 | (2S)-1-[(2S)-4-(2,5-difluorophenyl)-2-phenyl-2,5-dihydro-1H-pyrrol-1-yl]-3-methyl-1-oxobutan-2-ol | LRMS m/z (M + H) 358.0 found, 358.2 required. |
| 22-3 | 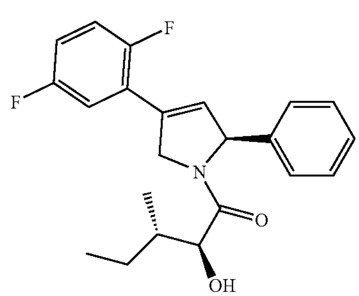 | (2S,3S)-1-[(2S)-4-(2,5-difluorophenyl)-2-phenyl-2,5-dihydro-1H-pyrrol-1-yl]-3-methyl-1-oxopentan-2-ol | LRMS m/z (M + H) 372.0 found, 372.2 required |
| 22-4 | 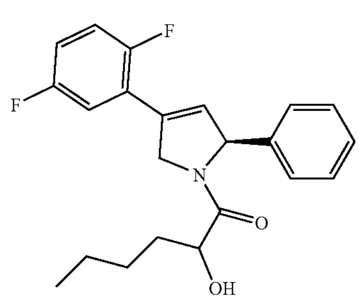 | 1-[(2S)-4-(2,5-difluorophenyl)-2-phenyl-2,5-dihydro-1H-pyrrol-1-yl]-1-oxohexan-2-ol | LRMS m/z (M + H) 372.0 found, 372.2 required |

| Cmpd | Structure | Name | LRMS m/z (M + H) |
|---|---|---|---|
| 22-5 | 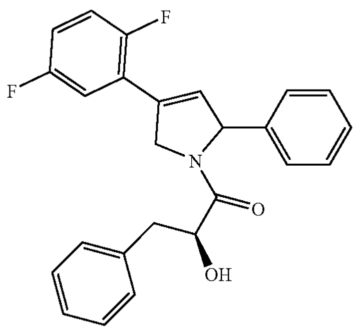 | (2S)-1-[4-(2,5-difluorophenyl)-2-phenyl-2,5-dihydro-1H-pyrrol-1-yl]-1-oxo-3-phenylpropan-2-ol | LRMS m/z (M + H) 406.1 found, 406.2 required |
| 22-6 | 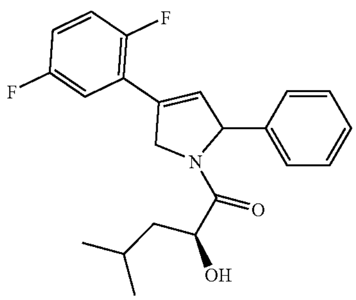 | (2S)-1-[4-(2,5-difluorophenyl)-2-phenyl-2,5-dihydro-1H-pyrrol-1-yl]-4-methyl-1-oxopentan-2-ol | LRMS m/z (M + H) 372.0 found, 372.2 required |
| 22-7 | 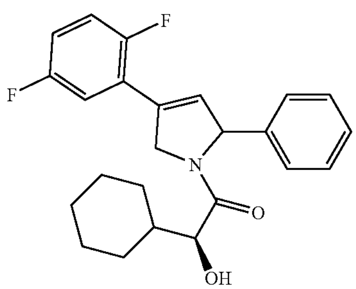 | (1S)-1-cyclohexyl-2-{4-(2,5-difluorophenyl)-2-phenyl-2,5-dihydro-1H-pyrrol-1-yl]-2-oxoethanol | LRMS m/z (M + H) 398.1 found, 398.2 required |
| 22-8 | 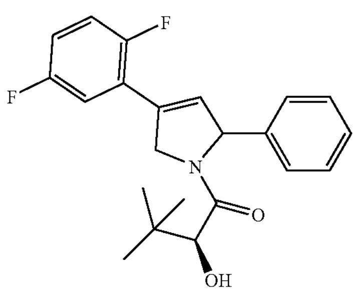 | (2S)-1-[4-(2,5-difluorophenyl)-2-phenyl-2,5-dihydro-1H-pyrrol-1-yl]-3,3-dimethyl-1-oxobutan-2-ol | LRMS m/z (M + H) 372.0 found, 372.2 required |
| 22-9 | 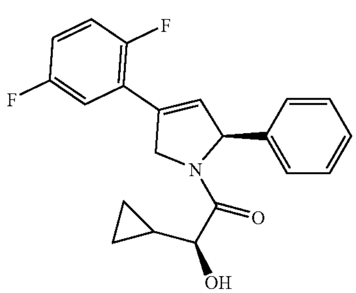 | (1S)-1-cyclopropyl-2-(2S)-4-(2,5-difluorophenyl)-2-phenyl-2,5-dihydro-1H-pyrrol-1-yl]-2-oxoethanol | LRMS m/z (M + H) 356.3 found, 356.1 required |

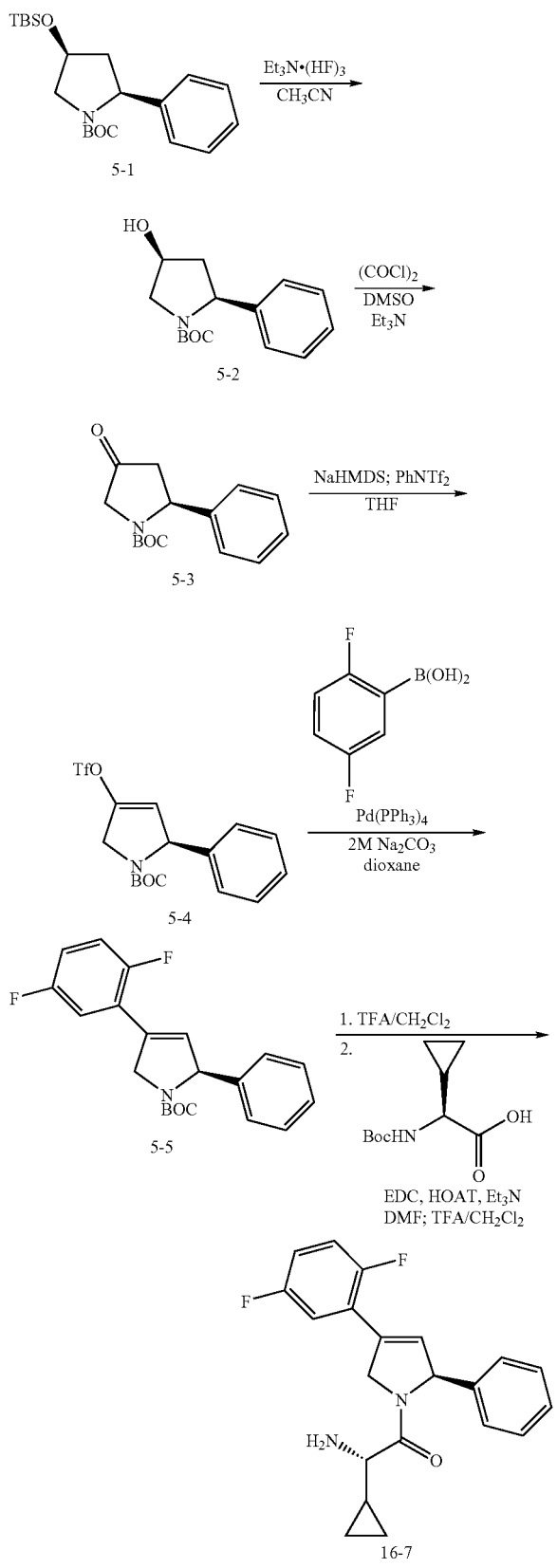

SCHEME 23

Step 1: tert-butyl (2S,4S)-4-hydroxy-2-phenylpyrrolidine-1-carboxylate (5-2)

To a flame dried flask equipped with stir bar was added tert-butyl (2S,4S)-4-{[tert-butyl(dimethyl)silyl]oxy}-2-phenylpyrrolidine-1-carboxylate (5-1, prepared from (S)-(−)-4-chloro-3-hydroxybutyronitrile by the method of Maeda, et al *Synlett* 2001, 1808-1810, 7.8 g, 20.7 mmol) and anhydrous acetonitrile (20.0 mL). The resulting solution was treated with triethylamine trihydrofluoride (10.1 mL, 62.0 mmol) while stirring under $N_2$. The reaction stirred 12 hours at 40° C. The reaction was then diluted with EtOAc (100 mL) and poured into 5% aq. $NaHCO_3$. Following cessation of gas evolution, the organic layer was washed three addition times with 5% aq. $NaHCO_3$. The organic layer was dried over magnesium sulfate, filtered and concentrated to provide crude product. Recrystallization was effected from EtOAc/hexanes to provide tert-butyl(2S,4S)-4-hydroxy-2-phenylpyrrolidine-1-carboxylate (5-2) as a white crystalline solid. $^1H$ NMR (300 MHz, $CDCl_3$) rotamers δ 7.38-7.18 (m, 5H), 4.90 (m, 1H), 4.42 (m, 1H), 3.88 (m, 1H), 3.56 (dd, J=11.5, 4.0 Hz, 1H), 2.60 (m, 1H), 2.03 (m, 1H), 1.50 and 1.20 (br s, 9H); MS 208.0 found, 208.1 (M-C($CH_3$)$_3$) required.

Step 2: tert-butyl (2S)-4-oxo-2-phenylpyrrolidine-1-carboxylate (5-3)

To a flame dried flask equipped with stir bar was added 150 mL anhydrous dichloromethane which was cooled to −78° C. Oxalyl chloride (3.8 mL, 44 mmol) and DMSO (4.8 mL, 61 mmol) were added sequentially and the reaction stirred for 10 min. tert-butyl(2S,4S)-4-hydroxy-2-phenylpyrrolidine-1-carboxylate (5-2, 2.28 g, 8.73 mmol) in 10 mL anhydrous dichloromethane was added dropwise and stirred 1 hour at −78° C. Triethylamine (12 mL, 87 mmol) was added and the reaction was warmed to 0° C. over 1 hour. Upon completion, the reaction was washed with 5% $NaHCO_3$, brine and dried over $MgSO_4$. The organic layer was concentrated to provide crude tert-butyl(2S)-4-oxo-2-phenylpyrrolidine-1-carboxylate (5-3).

Recrystallization was effected with EtOAc/hexanes. $^1H$ NMR (300 MHz, $CDCl_3$) δ 7.35 (m, 3H), 7.17 (m, 2H), 5.38 (m, 1H), 4.08 (d, J=19.5 Hz, 1H), 3.90 (d, J=19.3 Hz, 1H), 3.13 (dd, J=18.8, 9.8 Hz, 1H), 2.58 (dd, J=18.6, 2.4 Hz, 1H), 1.40 (br s, 9H); MS 206.0 found, 206.1 (M-C($CH_3$)$_3$) required.

Step 3: tert-butyl (2S)-2-phenyl-4-{[(trifluoromethyl)sulfonyl]oxy}-2,5-dihydro-1H-pyrrole-1-carboxylate (5-4)

To a flame dried flask equipped with stir bar was added ketone tert-butyl (2S)-4-oxo-2-phenylpyrrolidine-1-carboxylate (5-3, 2.00 g, 7.65 mmol) and anhydrous THF (100 mL). The resulting solution was cooled to −78° C., and treated dropwise with sodium hexamethyldisilylamide (NaHMDS, 8.42 mL, 1M in THF, 8.42 mmoL). The reaction was stirred 1 hour at −78° C., and a solution of 1,1,1-trifluoro-N-phenyl-N-[(trifluoromethyl)sulfonyl]methanesulfonamide (3.01 g, 8.42 mmol) in THF (30 mL) was added via cannula. The reaction mixture was warmed to 0° C. and stirred 30 minutes. The reaction mixture was then partitioned between brine (200 mL) and a 1:1 mixture of ethyl acetate and hexane (200 mL). The organic layer was dried over sodium sulfate and concentrated to provide crude tert-butyl(2S)-2-phenyl-4-{[(trifluoromethyl)sulfonyl]

oxy}-2,5-dihydro-1H-pyrrole-1-carboxylate (5-4) as an orange oil. ¹H NMR (300 MHz, CDCl₃) major rotamer: δ 7.30 (m, 5H), 5.72 (m, 1H), 5.48 (m, 1H), 4.42 (m, 2H), 1.18 (s, 9H); MS 379.0 found 379.1 (M-CH₃) required.

Step 4: tert-butyl (2S)-4-(2,5-difluorophenyl)-2-phenyl-2,5-dihydro-1H-pyrrole-1-carboxylate (5-5)

A deoxygenated mixture of crude tert-butyl(2S)-2-phenyl-4-{[(trifluoromethyl)sulfonyl]oxy}-2,5-dihydro-1H-pyrrole-1-carboxylate (5-4, 7.65 mmol), 2,5-difluorophenyl boronic acid (1.81 g, 11.5 mmol), aqueous Na₂CO₃ solution (2 M, 11.5 mL, 23.0 mmol), and Pd(PPh₃)₄ (0.442 g, 0.383 mmol) in dioxane (100 mL) was heated at 90° C. for 45 minutes. The reaction mixture was cooled, then partitioned between brine (200 mL) and a 1:1 mixture of ethyl acetate and hexane (200 mL). The organic layer was dried over sodium sulfate and concentrated. The residue was purified by flash column chromatography (SiO₂, 0-50% EtOAc/hexanes gradient) to provide tert-butyl(2S)-4-(2,5-difluorophenyl)-2-phenyl-2,5-dihydro-1H-pyrrole-1-carboxylate (5-5) as a white solid. LRMS m/z (M+H CH₃) 358.0 found, 358.2 required.

Step 5: (1S)-1-cyclopropyl-2-[(2S)-4-(2,5-difluorophenyl)-2-phenyl-2,5-dihydro-1H-pyrrol-1-yl]-2-oxoethanamine (16-7)

A solution of tert-butyl(2S)-4-(2,5-difluorophenyl)-2-phenyl-2,5-dihydro-1H-pyrrole-1-carboxylate (5-5, 1.00 g, 2.80 mmol, 1 equiv) in a 4:1 mixture of dichloromethane and trifluoroacetic acid (20 mL) was stirred for 30 minutes, then concentrated. The residue was dried via benzene azeotrope (1×50 mL), then dissolved in DMP (30 mL). (2S)-[(tert-butoxycarbonyl)amino](cyclopropyl)ethanoic acid (0.903 g, 4.20 mmol, 1.50 equiv), 1-(3-dimethylaminopropyl)-3-ethylcarbodiimide hydrochloride (EDC, 0.805 g, 4.20 mmol, 1.50 equiv), 1-hydroxy-7-azabenzotriazole (0.571, 4.20 mmol, 1.50 equiv) and triethylamine (1.95 mL, 14.0 mmol, 5.00 equiv) were added, and the resulting mixture was stirred at 23° C. for 5 days. The reaction mixture was partitioned between saturated aqueous sodium bicarbonate solution and ethyl acetate (2×100 mL). The combined organic layers were dried over sodium sulfate and concentrated. The residue was dissolved in a 4:1 mixture of dichloromethane and trifluoroacetic acid. The resulting solution was allowed to stand for 25 minutes, then concentrated. The residue was purified by reverse-phase LC (H₂O/CH₃CN gradient w/0.1% TFA present). The desired fractions were partitioned between saturated aqueous sodium bicarbonate solution and ethyl acetate (2×50 mL), and the combined organic layers were washed with aqueous sodium bicarbonate solution (2×100 mL), then brine (100 mL), and dried over sodium sulfate and concentrated to provide (1S)-1-cyclopropyl-2-[(2S)-4-(2,5-difluorophenyl)-2-phenyl-2,5-dihydro-1H-pyrrol-1-yl]-2-oxoethanamine (16-7) as a white solid. ¹H NMR (500 MHz, CD₃OD) major rotamer: δ 7.41 (t, 2H, J=7.6 Hz), 7.33 (m, 3H), 7.26 (m, 1H), 7.18 (m, 1H), 7.09 (m, 1H), 6.46 (s, 1H), 5.91 (m, 1H), 5.02 (d, 2H, J=13.9 Hz), 4.96 (ddd, 1H, J=13.9, 4.4, 1.7 Hz), 3.08 (d, 1H, J=7.6 Hz), 1.04 (m, 1H), 0.52 (m, 3H), 0.37 (m, 1H). LRMS m/z (M+H) 355.0 found, 355.2 required.

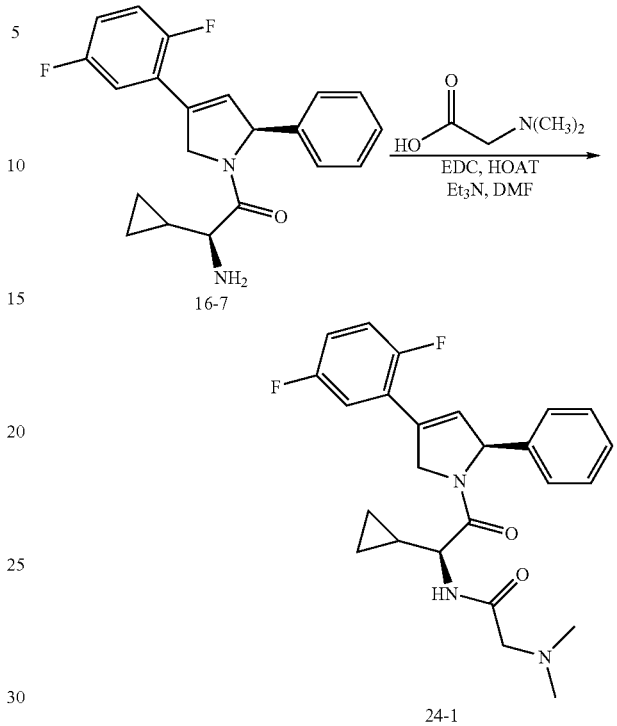

N-1-{(1S)-1-cyclopropyl-2-[(2S)-4-(2,5-difluorophenyl)-2-phenyl-2,5-dihydro-1H-pyrrol-1-yl]-2-oxoethyl}-N-2,N-2-dimethylglycinamide (24-1)

A solution of (1S)-1-cyclopropyl-2-[(2S)-4-(2,5-difluorophenyl)-2-phenyl-2,5-dihydro-1H-pyrrol-1-yl]-2-oxoethanamine (16-7, 30 mg, 0.085 mmol, 1 equiv), (N,N-dimethylglycine (17 mg, 0.17 mmol, 2.0 equiv), 1-(3-dimethylaminopropyl)-3-ethylcarbodiimide hydrochloride (EDC, 32 mg, 0.17 mmol, 2.0 equiv), 1-hydroxy-7-azabenzotriazole (23 mg, 0.17 mmol, 2.0 equiv) and triethylamine (35 µL, 0.25 mmol, 3.0 equiv) in DMF (1 mL) was stirred at 23° C. for 20 hours. The reaction mixture was partitioned between saturated aqueous sodium bicarbonate solution and ethyl acetate (2×20 mL). The combined organic layers were dried over sodium sulfate and concentrated. The residue was purified by reverse-phase LC (H₂O/CH₃CN gradient w/0.1% TFA present) to provide N-1-{(1S)-1-cyclopropyl-2-[(2S)-4-(2,5-difluorophenyl)-2-phenyl-2,5-dihydro-1H-pyrrol-1-yl]-2-oxoethyl}-N-2,N-2-dimethylglycinamide (24-1) as a colorless gum (TFA salt). ¹H NMR (500 MHz, CD₃OD) major rotamer: δ 7.33 (m, 4H), 7.26 (m, 2H), 7.26 (m, 1H), 7.19 (m, 1H), 7.10 (m, 1H), 6.46 (s, 1H), 5.91 (m, 1H), 5.23 (d, 2H, J=13.9 Hz), 5.02 (ddd, 1H, J=13.9, 4.4, 1.7 Hz), 4.19 (d, 1H, J=9.0 Hz), 4.01 (d, 1H, J=15.6 Hz), 3.94 (d, 1H, J=15.4 Hz), 2.92 (s, 6H), 1.14 (m, 1H), 0.62 (m, 3H), 0.40 (m, 1H). LRMS m/z (M+H) 440.5 found, 440.2 required.

The following compounds were prepared by simple modifications of the above procedure. For many of the examples below, Boc-protected amino acids were utilized. In these cases the coupling products required a deprotection step (TPA/dichloromethane) to afford the depicted final products. Unless otherwise noted, the compounds were isolated as the free base. Additionally, the amine n-oxides below were prepared by treating the corresponding amines with hydrogen peroxide in isopropanol at 23° C.

| Cmpd | Structure | Name | LRMS m/z (M + H) |
|---|---|---|---|
| 24-2 | 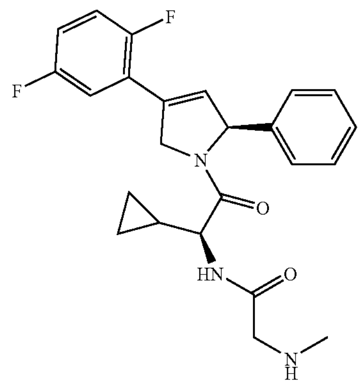 | N-1-{(1S)-1-cyclopropyl-2-[(2S)-4-(2,5-difluorophenyl)-2-phenyl-2,5-dihydro-1H-pyrrol-1-yl]-2-oxoethyl}-N-2-methylglycinamide; isolated as the TFA salt | m/z (M + H) 426.4 found, 426.2 required. |
| 24-3 | 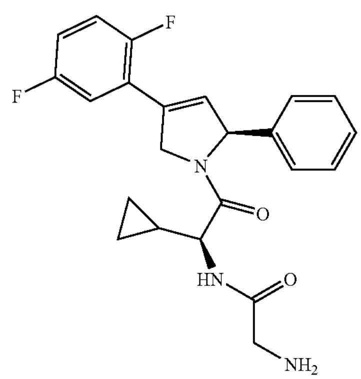 | N-1-{(1S)-1-cyclopropyl-2-[(2S)-4-(2,5-difluorophenyl)-2-phenyl-2,5-dihydro-1H-pyrrol-1-yl]-2-oxoethyl}glycinamide; isolated as the TFA salt | m/z (M + H) 412.4 found, 412.2 required |
| 24-4 | 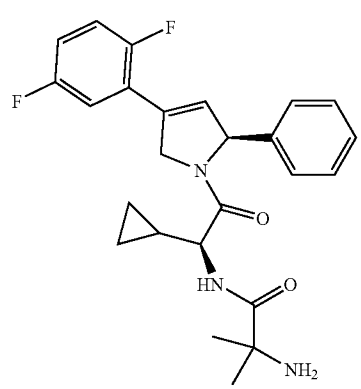 | N-1-{(1S)-1-cyclopropyl-2-[(2S)-4-(2,5-difluorophenyl)-2-phenyl-2,5-dihydro-1H-pyrrol-1-yl]-2-oxoethyl}-2-methylalaninamide; isolated as the TFA salt | m/z (M + H) 440.4 found, 440.2 required |

| Cmpd | Structure | Name | LRMS m/z (M + H) |
|---|---|---|---|
| 24-5 | 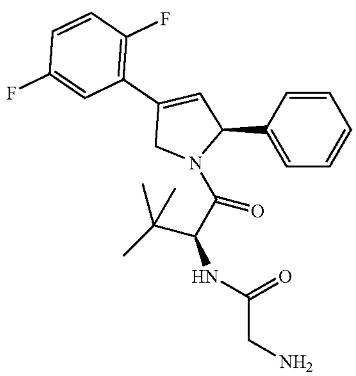 | N-1-{(1S)-1-tert-butyl-2-[(2S)-4-(2,5-difluorophenyl)-2-phenyl-2,5-dihydro-1H-pyrrol-1-yl]-2-oxoethyl}glycinamide | m/z (M + H) 428.5 found, 428.2 required |
| 24-6 | 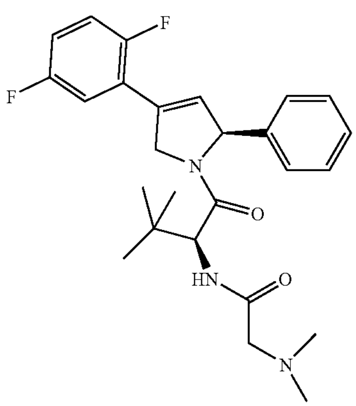 | N-1-{(1S)-1-tert-butyl-2-[(2S)-4-(2,5-difluorophenyl)-2-phenyl-2,5-dihydro-1H-pyrrol-1-yl]-2-oxoethyl}-N-2,N-2-dimethylglycinamide | m/z (M + H) 456.6 found, 456.2 required |
| 24-7 | 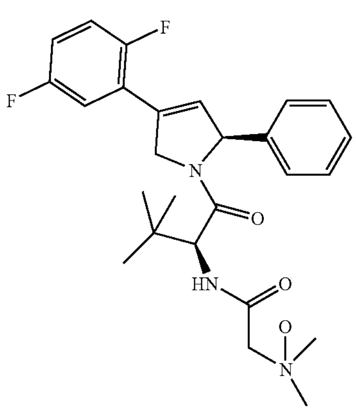 | N-1-{(1S)-1-tert-butyl-2-[(2S)-4-(2,5-difluorophenyl)-2-phenyl-2,5-dihydro-1H-pyrrol-1-yl]-2-oxoethyl}-N-2,N-2-dimethylglycinamide, N-oxide | m/z (M + H) 472.5 found, 472.2 required |
| 24-8 | 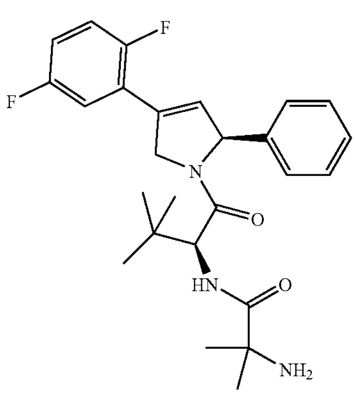 | N-1-{(1S)-1-tert-butyl-2-[(2S)-4-(2,5-difluorophenyl)-2-phenyl-2,5-dihydro-1H-pyrrol-1-yl]-2-oxoethyl}-2-methylalaninamide | m/z (M + H) 456.5 found, 456.2 required |

-continued

| Cmpd | Structure | Name | LRMS m/z (M + H) |
|---|---|---|---|
| 24-9 | 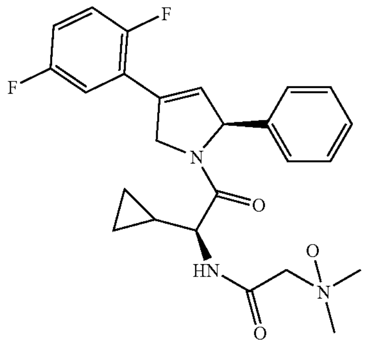 | N-1-{(1S)-1-cyclopropyl-2-[(2S)-4-(2,5-difluorophenyl)-2-phenyl-2,5-dihydro-1H-pyrrol-1-yl]-2-oxoethyl}-N-2-,N-2-dimethylglycinamide n-oxide | LRMS m/z (M + H) 456.5 found, 456.2 required |

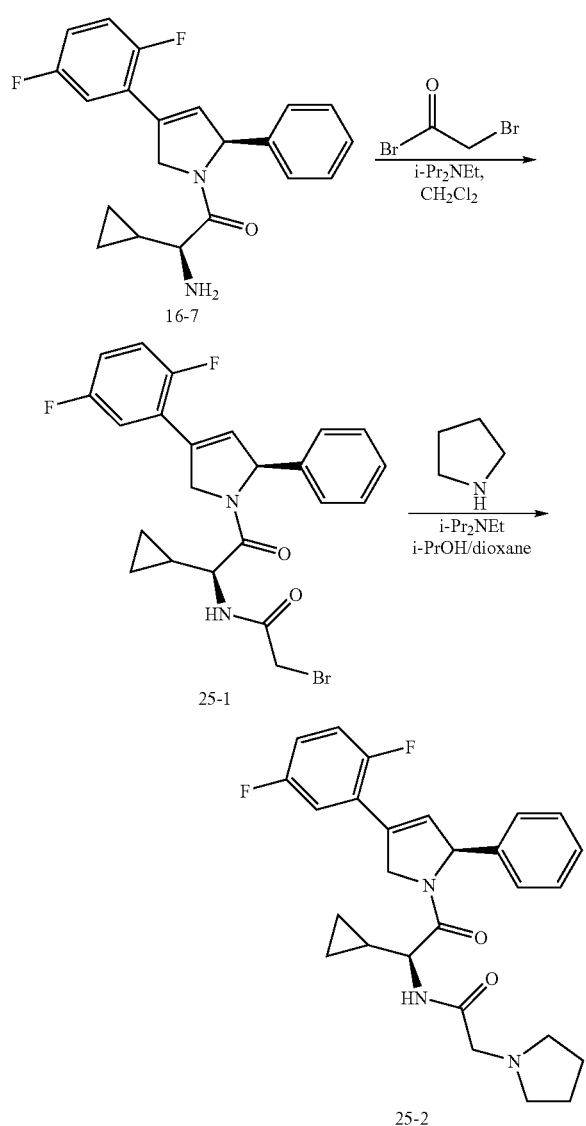

SCHEME 25

Step 1: 2-bromo-N-{(1S)-1-cyclopropyl-2-[(2S)-4-(2,5-difluorophenyl)-2-phenyl-2,5-dihydro-1H-pyrrol-1-yl]-2-oxoethyl}acetamide (25-1)

Bromoacetyl bromide (49 µL, 0.56 mmol, 1.1 equiv) was added to a solution of (1S)-1-cyclopropyl-2-[(2S)-4-(2,5-difluorophenyl)-2-phenyl-2,5-dihydro-1H-pyrrol-1-yl]-2-oxoethanamine (16-7, 181 mg, 0.511 mmol, 1 equiv) and N,N-diisopropylethylamine (107 µL, 0.613 mmol, 1.20 equiv) in dichloromethane (10 mL) at 23° C., and the resulting mixture was allowed to stir for 30 minutes. The reaction mixture was partitioned between water (70 mL) and dichloromethane (2×60 mL). The combined organic layers were dried over sodium sulfate and concentrated to give 2-bromo-N-{(1S)-1-cyclopropyl-2-[(2S) (2,5-difluorophenyl)-2-phenyl-2,5-dihydro-1H-pyrrol-1-yl]-2-oxoethyl}acetamide (25-1) as a pink foam. LRMS m/z (M+H) 477.3 found, 477.1 required.

Step 2: N-{(1S)-1-cyclopropyl-2-[(2S)-4-(2,5-difluorophenyl)-2-phenyl-2,5-dihydro-1H-pyrrol-1-yl]-2-oxoethyl}-2-pyrrolidin-1-ylacetamide (25-2)

A solution of 2-bromo-N-{(1S)-1-cyclopropyl-2-[(2S)-4-(2,5-difluorophenyl)-2-phenyl-2,5-dihydro-1H-pyrrol-1-yl]-2-oxoethyl}acetamide (25-1, 40 mg, 0.084 mmol, 1 equiv), N,N-diisopropylethylamine (19 µL, 0.11 mmol, 1.30 equiv), and pyrrolidine (8 µL, 0.093 mmol, 1.1 equiv) in a 1:1 mixture of dioxane and isopropanol (4 mL) was stirred at 23° C. for 20 hours. The reaction mixture was partitioned between water (50 mL) and ethyl acetate (50 mL). The organic layer was dried over sodium sulfate and concentrated. The residue was purified by reverse-phase LC (H₂O/CH₃CN gradient w/0.1% TFA present) to provide N-{(1S)-1-cyclopropyl-2-[(2S)-4-(2,5-difluorophenyl)-2-phenyl-2,5-dihydro-1H-pyrrol-1-yl]-2-oxoethyl}-2-pyrrolidin-1-ylacetamide (25-2) as a colorless oil (TFA salt). LRMS m/z (M+H) 466.2 found, 466.2 required.

The following compounds were prepared by simple modifications of the above procedure. Unless otherwise noted, the compounds were isolated as the free base.

| Cmpd | Structure | Name | LRMS m/z (M + H) |
|---|---|---|---|
| 25-3 | 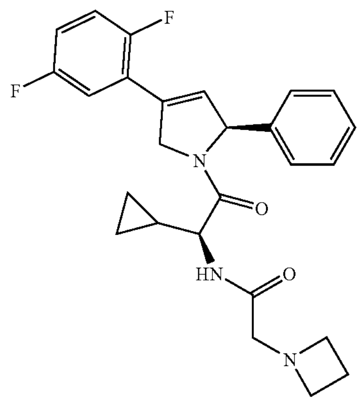 | 2-azetidin-1-yl-N-{(1S)-1-cyclopropyl-2-[(2S)-4-(2,5-difluorophenyl)-2-phenyl-2,5-dihydro-1H-pyrrol-1-yl]-2-oxoethyl}acetamide; isolated as the TFA salt | m/z (M + H) 452.2 found, 452.2 required |
| 25-4 | 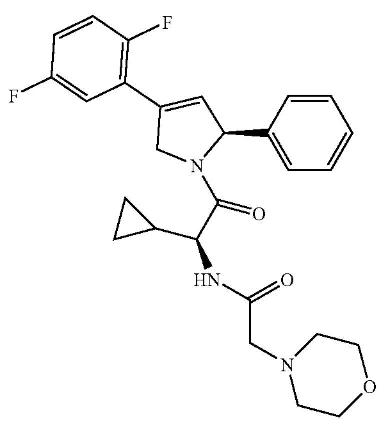 | N-{(1S)-1-cyclopropyl-2-[(2S)-4-(2,5-difluorophenyl)-2-phenyl-2,5-dihydro-1H-pyrrol-1-yl]-2-oxoethyl}-2-morpholin-4-ylacetamide; isolated as the TFA salt | m/z (M + H) 482.2 found, 482.2 required |
| 25-5 | 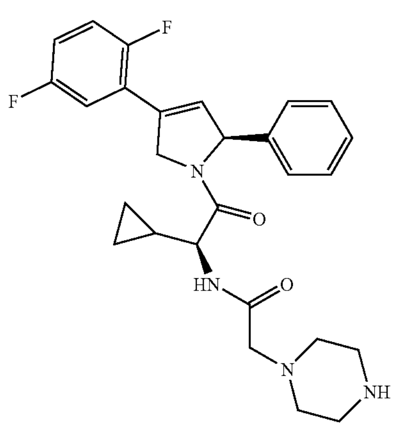 | N-{(1S)-1-cyclopropyl-2-[(2S)-4-(2,5-difluorophenyl)-2-phenyl-2,5-dihydro-1H-pyrrol-1-yl]-2-oxoethyl}-2-piperazin-1-ylacetamide; isolated as the TFA salt | m/z (M + H) 481.2 found, 481.2 required |

-continued

| Cmpd | Structure | Name | LRMS m/z (M + H) |
|---|---|---|---|
| 25-6 | 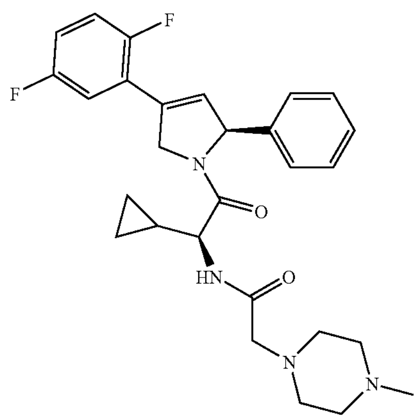 | N-{(1S)-1-cyclopropyl-2-[(2S)-4-(2,5-difluorophenyl)-2-phenyl-2,5-dihydro-1H-pyrrol-1-yl]-2-oxoethyl}-2-(4-methylpiperazin-1-yl)acetamide; isolated as the TFA salt | m/z (M + H) 495.2 found, 495.2 required |
| 25-7 | 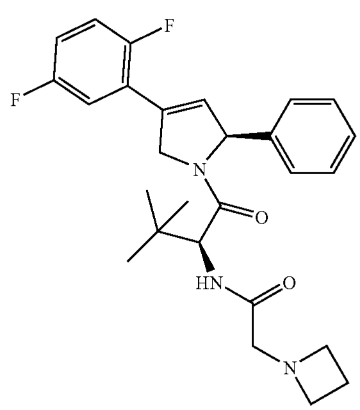 | 2-azetidin-1-yl-N-{(1S)-1-tert-butyl-2-[(2S)-4-(2,5-difluorophenyl)-2-phenyl-2,5-dihydro-1H-pyrrol-1-yl]-2-oxoethyl}acetamide | m/z (M + H) 468.6 found, 468.2 required |
| 25-8 | 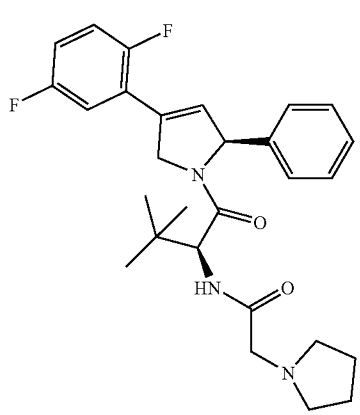 | N-{(1S)-1-tert-butyl-2-[(2S)-4-(2,5-difluorophenyl)-2-phenyl-2,5-dihydro-1H-pyrrol-1-yl]-2-oxoethyl}-2-pyrrolidin-1-ylacetamide | m/z (M + H) 482.6 found, 482.3 required |

-continued

| Cmpd | Structure | Name | LRMS m/z (M + H) |
|---|---|---|---|
| 25-9 | 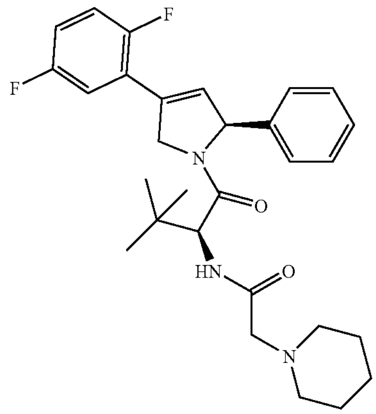 | N-{(1S)-1-tert-butyl-2-[(2S)-4-(2,5-difluorophenyl)-2-phenyl-2,5-dihydro-1H-pyrrol-1-yl]-2-oxoethyl}-2-piperidin-1-ylacetamide | m/z (M + H) 496.6 found, 496.3 required |
| 25-10 | 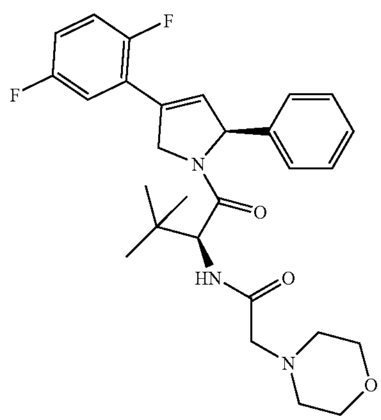 | N-{(1S)-1-tert-butyl-2-[(2S)-4-(2,5-difluorophenyl)-2-phenyl-2,5-dihydro-1H-pyrrol-1-yl]-2-oxoethyl}-2-morpholin-4-ylacetamide | m/z (M + H) 498.5 found, 498.3 required |
| 25-11 | 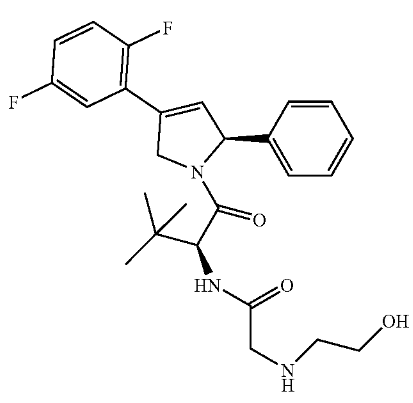 | N-1-{(1S)-1-tert-butyl-2-[(2S)-4-(2,5-difluorophenyl)-2-phenyl-2,5-dihydro-1H-pyrrol-1-yl]-2-oxoethyl}-N-2-(2-hydroxyethyl)glycinamide | m/z (M + H) 472.6 found, 472.2 required |

-continued

| Cmpd | Structure | Name | LRMS m/z (M + H) |
|---|---|---|---|
| 25-12 | 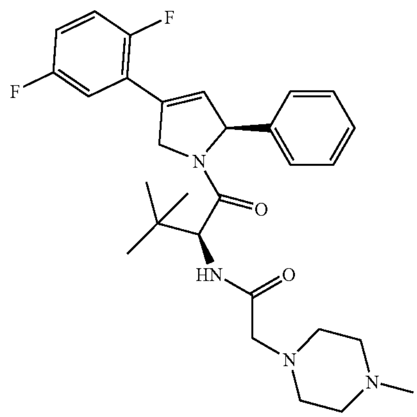 | N-{(1S)-1-tert-butyl-2-[(2S)-4-(2,5-difluorophenyl)-2-phenyl-2,5-dihydro-1H-pyrrol-1-yl]-2-oxoethyl}-2-(4-methylpiperazin-1-yl)acetamide | m/z (M + H) 511.7 found, 511.3 required |
| 25-13 | 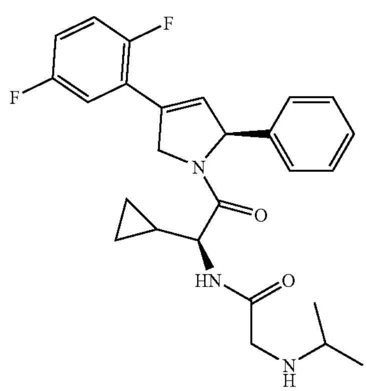 | N-1-{(1S)-1-cyclopropyl-2-[(2S)-4-(2,5-difluorophenyl)-2-phenyl-2,5-dihydro-1H-pyrrol-1-yl]-2-oxoethyl}-N-2-isopropylglycinamide; isolated as the TFA salt | m/z (M + H) 454.2 found, 454.2 required |
| 25-14 | 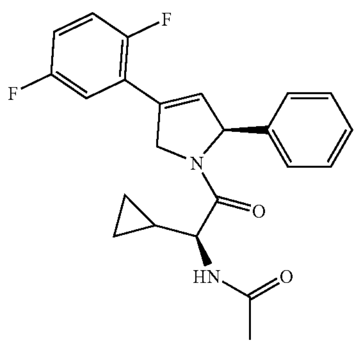 | N-{(1S)-1-cyclopropyl-2-[(2S)-4-(2,5-difluorophenyl)-2-phenyl-2,5-dihydro-1H-pyrrol-1-yl]-2-oxoethyl}acetamide | m/z (M + H) 397.3 found, 397.2 required |

-continued

| Cmpd | Structure | Name | LRMS m/z (M + H) |
|---|---|---|---|
| 25-15 | 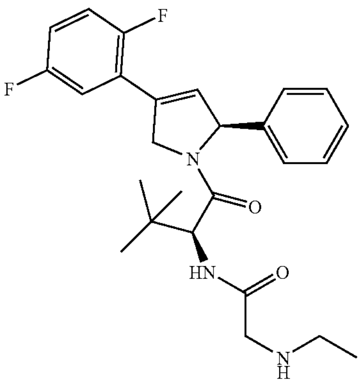 | N-1-{(1S)-1-tert-butyl-2-[(2S)-4-(2,5-difluorophenyl)-2-phenyl-2,5-dihydro-1H-pyrrol-1-yl]-2-oxoethyl}-N-2-ethylglycinamide | m/z (M + H) 456.6 found, 456.2 required |
| 25-16 | 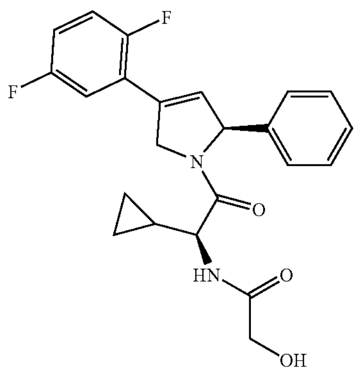 | N-{(1S)-1-cyclopropyl-2-[(2S)-4-(2,5-difluorophenyl)-2-phenyl-2,5-dihydro-1H-pyrrol-1-yl]-2-oxoethyl}-2-hydroxyacetamide | m/z (M + H) 413.4 found, 413.2 required |

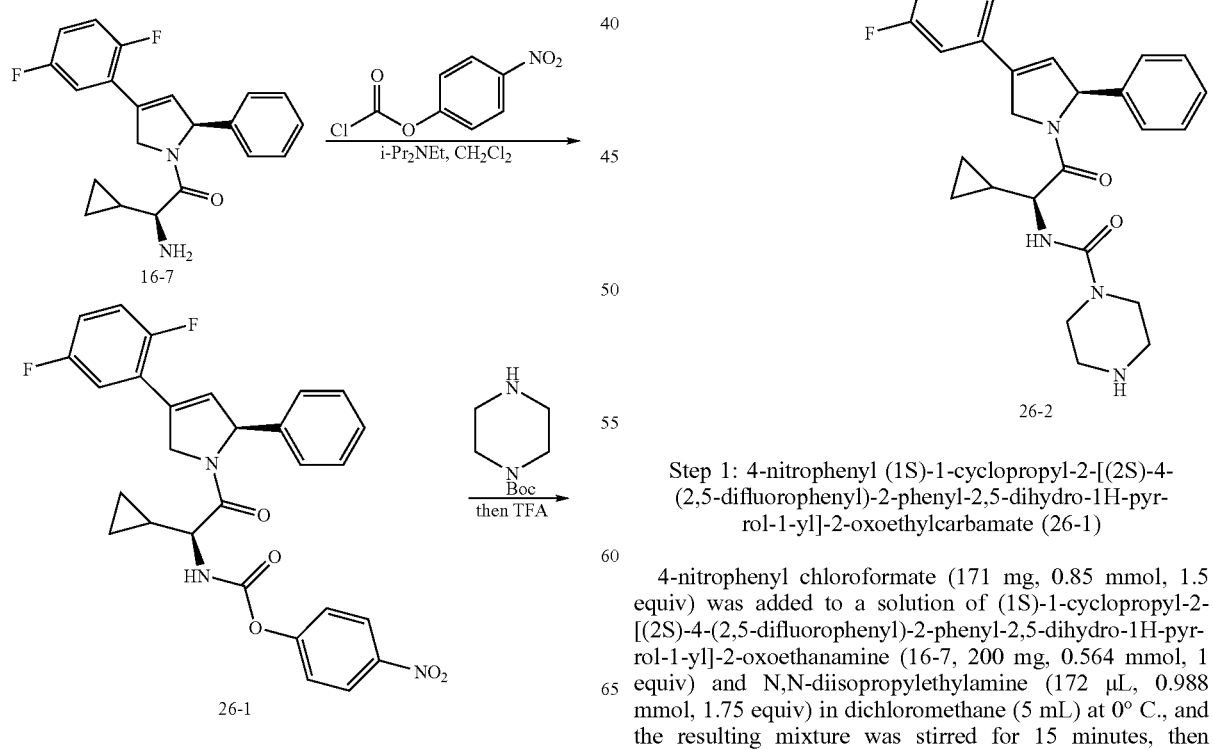

Step 1: 4-nitrophenyl (1S)-1-cyclopropyl-2-[(2S)-4-(2,5-difluorophenyl)-2-phenyl-2,5-dihydro-1H-pyrrol-1-yl]-2-oxoethylcarbamate (26-1)

4-nitrophenyl chloroformate (171 mg, 0.85 mmol, 1.5 equiv) was added to a solution of (1S)-1-cyclopropyl-2-[(2S)-4-(2,5-difluorophenyl)-2-phenyl-2,5-dihydro-1H-pyrrol-1-yl]-2-oxoethanamine (16-7, 200 mg, 0.564 mmol, 1 equiv) and N,N-diisopropylethylamine (172 μL, 0.988 mmol, 1.75 equiv) in dichloromethane (5 mL) at 0° C., and the resulting mixture was stirred for 15 minutes, then warmed to 23° C. and stirred for an additional 30 minutes. Additional 4-nitrophenyl chloroformate (1.0 equiv) and N,N-diisopropylethylamine (1.0 equiv) were added and the mixture was stirred for 2.5 hours, then partitioned between water (55 mL) and dichloromethane (2×45 mL). The combined organic layers were dried over sodium sulfate and concentrated. The residue was purified by reverse-phase LC (H$_2$O/CH$_3$CN gradient w/0.1% TFA present) to provide 4-nitrophenyl(1S)-1-cyclopropyl-2-[(2S)-4-(2,5-difluorophenyl)-2-phenyl-2,5-dihydro-1H-pyrrol-1-yl]-2-oxoethylcarbamate (26-1) as a light yellow oil. LRMS m/z (M+H) 520.4 found, 520.2 required.

Step 2: N-{(1S)-1-cyclopropyl-2-[(2S)-4-(2,5-difluorophenyl)-2-phenyl-2,5-dihydro-1H-pyrrol-1-yl]-2-oxoethyl}piperazine-1-carboxamide (26-2)

A solution of 4-nitrophenyl(1S)-1-cyclopropyl-2-[(2S)-4-(2,5-difluorophenyl)-2-phenyl-2,5-dihydro-1H-pyrrol-1-yl]-2-oxoethylcarbamate (26-1, 40 mg, 0.077 mmol, 1 equiv), N,N-diisopropylethylamine (27 μL, 0.15 mmol, 2.0 equiv), and tert-butyl piperazine-1-carboxylate (22 mg, 0.11 mmol, 1.5 equiv) in dioxane (5 mL) was heated at 70° C. for 3 hours. The reaction mixture was partitioned between half-saturated aqueous sodium chloride solution (75 mL) and ethyl acetate (55 mL). The organic layer was dried over sodium sulfate and concentrated. A solution of the residue in a 1:1 mixture of TFA and dichloromethane (3 mL) was stirred for 1 hour, then concentrated. The residue was purified by reverse-phase LC (H$_2$O/CH$_3$CN gradient w/0.1% TFA present) to provide N-{(1S)-1-cyclopropyl-2-[(2S)-4-(2,5-difluorophenyl)-2-phenyl-2,5-dihydro-1H-pyrrol-1-yl]-2-oxoethyl}piperazine-1-carboxamide (26-2) as a colorless oil (TFA salt). LRMS m/z (M+H) 467.4 found, 467.2 required.

The following compounds were prepared by simple modifications of the above procedure. All of the compounds in the table below were isolated as the TFA salt.

| Cmpd | Structure | Name | LRMS m/z (M + H) |
|---|---|---|---|
| 26-3 | 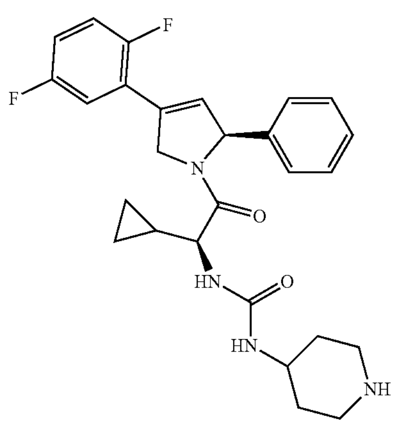 | N-{(1S)-1-cyclopropyl-2-[(2S)-4-(2,5-difluorophenyl)-2-phenyl-2,5-dihydro-1H-pyrrol-1-yl]-2-oxoethyl)-N'-piperidin-4-ylurea | m/z (M + H) 481.4 found, 481.2 required |
| 26-4 | 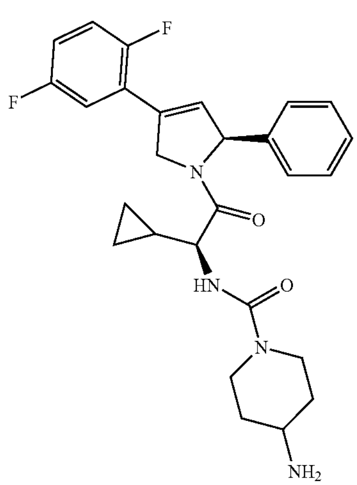 | 4-amino-N-{(1S)-1-cyclopropyl-2-[(2S)-4-(2,5-difluorophenyl)-2-phenyl-2,5-dihydro-1H-pyrrol-1-yl]-2-oxoethyl}piperidine-1-carboxamide | m/z (M + H) 481.4 found, 481.2 required |

-continued

| Cmpd | Structure | Name | LRMS m/z (M + H) |
|---|---|---|---|
| 26-5 | 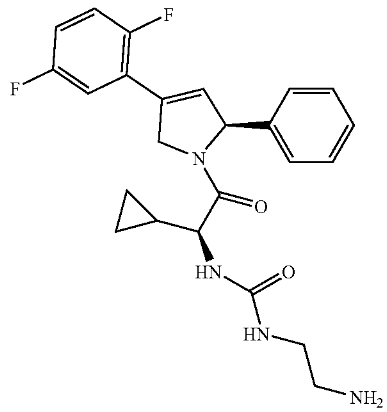 | N-(2-aminoethyl)-N'-{(1S)-1-cyclopropyl-2-[(2S)-4-(2,5-difluorophenyl)-2-phenyl-2,5-dihydro-1H-pyrrol-1-yl]-2-oxoethyl}urea | m/z (M + H) 441.4 found, 441.2 required |
| 26-6 | 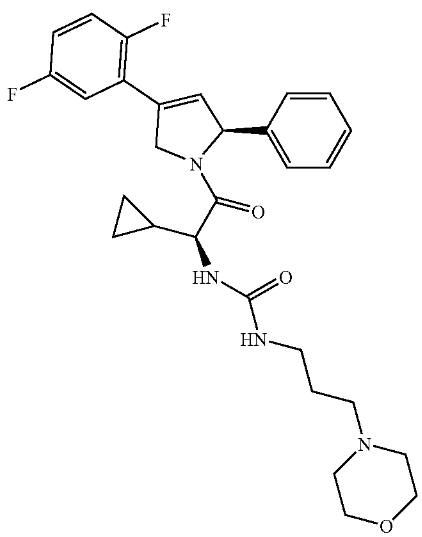 | N-{(1S)-1-cyclopropyl-2-[(2S)-4-(2,5-difluorophenyl)-2-phenyl-2,5-dihydro-1H-pyrrol-1-yl]-2-oxoethyl}-N'-(3-morpholin-4-ylpropyl)urea | m/z (M + H) 525.4 found, 525.3 required |
| 26-7 | 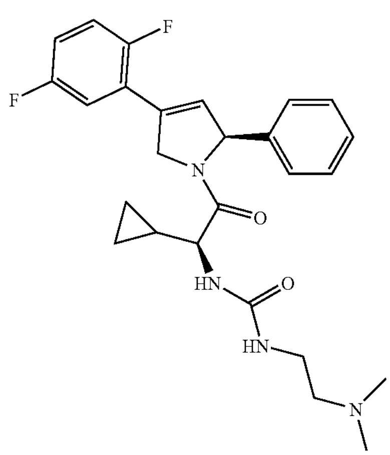 | N-{(1S)-1-cyclopropyl-2-[(2S)-4-(2,5-difluorophenyl)-2-phenyl-2,5-dihydro-1H-pyrrol-1-yl]-2-oxoethyl}-N'-[2-(dimethylamino)ethyl]urea | m/z (M + H) 469.4 found, 469.2 required |

SCHEME 27

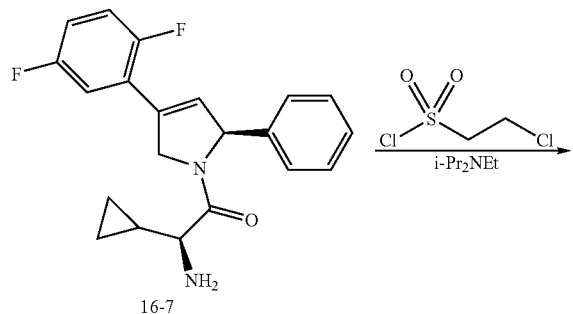

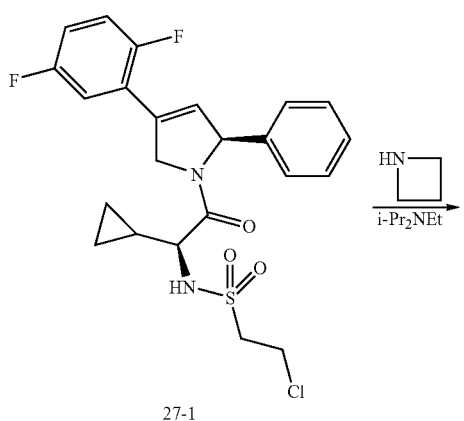

Step 1: 2-chloro-N-{(1S)-1-cyclopropyl-2-[(2S)-4-(2,5-difluorophenyl)-2-phenyl-2,5-dihydro-1H-pyrrol-1-yl]-2-oxoethyl}ethanesulfonamide (27-1)

2-chloroethanesulfonyl chloride (81 µL, 0.78 mmol, 1.1 equiv) was added to a solution of (1S)-1-cyclopropyl-2-[(2S)-4-(2,5-difluorophenyl)-2-phenyl-2,5-dihydro-1H-pyrrol-1-yl]-2-oxoethanamine (16-7, 250 mg, 0.705 mmol, 1 equiv) and N,N-diisopropylethylamine (160 µL, 0.917 mmol, 1.30 equiv) in dichloromethane (5 mL) at 0° C., and the resulting mixture was stirred for 15 minutes, then warmed to 23° C. and stirred for an additional 15 minutes. Additional 2-chloroethanesulfonyl chloride (1.2 equiv) and N,N-diisopropylethylamine (1.3 equiv) were added and the mixture was stirred for 30 minutes, then partitioned between water (75 mL) and dichloromethane (2×60 mL). The combined organic layers were dried over sodium sulfate and concentrated to give 2-chloro-N-{(1S)-1-cyclopropyl-2-[(2S)-4-(2,5-difluorophenyl)-2-phenyl-2,5-dihydro-1H-pyrrol-1-yl]-2-oxoethyl}ethanesulfonamide (27-1) as a colorless oil. LRMS m/z (M+H—Cl) 445.4 found, 445.1 required.

Step 2: 2-azetidin-1-yl-N-{(1S)-1-cyclopropyl-2-[(2S)-4-(2,5-difluorophenyl)-2-phenyl-2,5-dihydro-1H-pyrrol-1-yl]-2-oxoethyl}ethanesulfonamide (27-2)

A solution of 2-chloro-N-{(1S)-1-cyclopropyl-2-[(2S)-4-(2,5-difluorophenyl)-2-phenyl-2,5-dihydro-1H-pyrrol-1-yl]-2-oxoethyl}ethanesulfonamide (27-1, 55 mg, 0.11 mmol, 1 equiv), N,N-diisopropylethylamine (80 µL, 0.46 mmol, 4.0 equiv), and azetidine (15 uL, 0.23 mmol, 2.0 equiv) in dioxane (2 mL) was heated at 60° C. for 20 hours. The reaction mixture was partitioned between water (40 mL) and ethyl acetate (40 mL). The organic layer was dried over sodium sulfate and concentrated. The residue was purified by reverse-phase LC (H₂O/CH₃CN gradient w/0.1% TFA present) to provide 2-azetidin-1-yl-N-{(1S)-1-cyclopropyl-2-[(2S)-4-(2,5-difluorophenyl)-2-phenyl-2,5-dihydro-1H-pyrrol-1-yl]-2-oxoethyl}ethanesulfonamide (27-2) as a light yellow oil (TFA salt). LRMS m/z (M+H) 502.4 found, 502.2 required.

The following compounds were prepared by simple modifications of the above procedure. All of the compounds in the table below were isolated as the TFA salt.

| Cmpd | Structure | Name | LRMS m/z (M + H) |
|---|---|---|---|
| 27-3 | 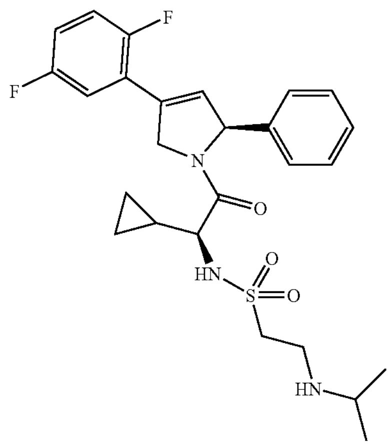 | N-{(1S)-1-cyclopropyl-2-[(2S)-4-(2,5-difluorophenyl)-2-phenyl-2,5-dihydro-1H-pyrrol-1-yl]-2-oxoethyl}-2-(isopropylamino)ethane-sulfonamide | m/z (M + H) 504.4 found, 504.2 required. |
| 27-4 | 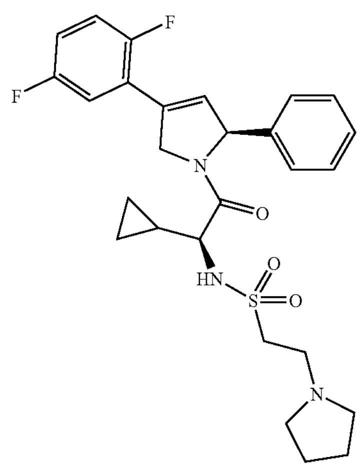 | N-((1S)-1-cyclopropyl-2-[(2S)-4-(2,5-difluorophenyl)-2-phenyl-2,5-dihydro-1H-pyrrol-1-yl]-2-oxoethyl}-2-pyrrolidin-1-ylethanesulfonamide | LRMS m/z (M + H) 516.4 found, 516.2 required |
| 27-5 | 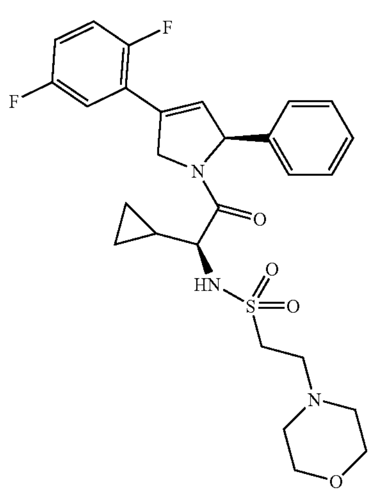 | N-{(1S)-1-cyclopropyl-2-[(2S)-4-(2,5-difluorophenyl)-2-phenyl-2,5-dihydro-1H-pyrrol-1-yl]-2-oxoethyl}-2-morpholin-4-ylethanesulfonamide | m/z (M + H) 532.3 found, 532.2 required |

-continued
| Cmpd | Structure | Name | LRMS m/z (M + H) |
|---|---|---|---|
| 27-6 | 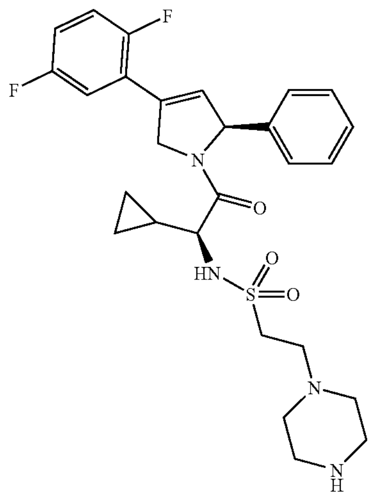 | N-{(1S)-1-cyclopropyl-2-[(2S)-4-(2,5-difluorophenyl)-2-phenyl-2,5-dihydro-1H-pyrrol-1-yl]-2-oxoethyl}-2-piperazin-1-ylethanesulfonamide | m/z (M + H) 531.4 found, 531.2 required |
| 27-7 | 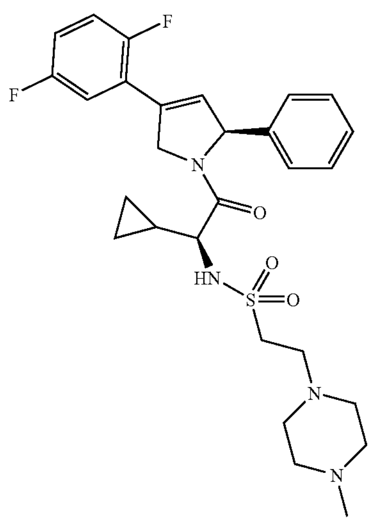 | N-{(1S)-1-cyclopropyl-2-[(2S)-4-(2,5-difluorophenyl)-2-phenyl-2,5-dihydro-1H-pyrrol-1-yl]-2-oxoethyl}-2-(4-methylpiperazin-1-yl)ethanesulfonamide | m/z (M + H) 545.4 found, 545.2 required |
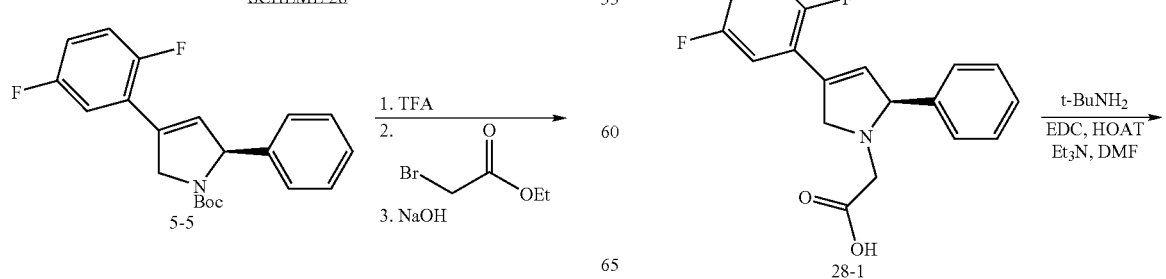

-continued

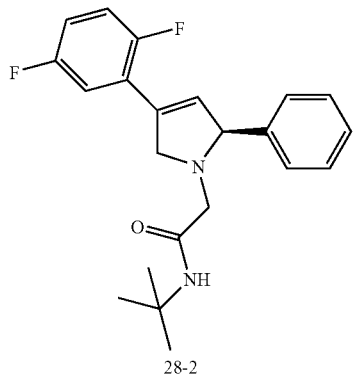

28-2

Step 1: [(2S)-4-(2,5-difluorophenyl)-2-phenyl-2,5-dihydro-1H-pyrrol-1-yl]acetic acid (28-1)

A solution of tert-butyl(2S)-4-(2,5-difluorophenyl)-2-phenyl-2,5-dihydro-1H-pyrrole-1-carboxylate (5-5, 50 mg, 0.14 mmol, 1 equiv) in a 1:1 mixture of dichloromethane and trifluoroacetic acid (10 mL) was stirred for 30 minutes, then concentrated. The residue was partitioned between aqueous saturated sodium bicarbonate solution (60 mL) and ethyl acetate (50 mL). The organic layer was dried over sodium sulfate and concentrated. A solution of the residue, ethyl bromoacetate (16 µL, 0.14 mmol, 1.0 equiv) and N,N-diisopropylethylamine (29 µL, 0.17 mmol, 1.2 equiv) in DMP (5 mL) was heated at 70° C. for 3 hours. The reaction mixture was partitioned between water (125 mL) and ethyl acetate (2×100 mL). The combined organic layers were dried over sodium sulfate and concentrated. A solution of the residue and sodium hydroxide (1N, 280 µL, 0.28 mmol, 2.0 equiv) in tert-butanol (10 mL) was heated at 45° C. for 20 hours. The reaction mixture was then partitioned between water and ethyl ether. The aqueous layer was acidified to pH 4 with aqueous HCl solution, then extracted with ethyl acetate (2×40 mL). The combined organic layers were dried over sodium sulfate and concentrated to provide [(2S)-4-(2,5-difluorophenyl)-2-phenyl-2,5-dihydro-1H-pyrrol-1-yl] acetic acid (28-1) as a colorless oil. LRMS m/z (M+H) 316.3 found, 316.1 required.

Step 2: N-(tert-butyl)-2-[(2S)-4-(2,5-difluorophenyl)-2-phenyl-2,5-dihydro-1H-pyrrol-1-yl]acetamide (28-2)

A solution of [(2S)-4-(2,5-difluorophenyl)-2-phenyl-2,5-dihydro-1H-pyrrol-1-yl]acetic acid (28-1, 16 mg, 0.051 mmol, 1 equiv), tert-butylamine (6 µL, 0.06 mmol, 1.2 equiv), 1-(3-dimethylaminopropyl)-3-ethylcarbodiimide hydrochloride (EDC, 12 mg, 0.061 mmol, 1.2 equiv), 1-hydroxy-7-azabenzotriazole (8 mg, 0.06 mmol, 1.2 equiv) and triethylamine (18 µL, 0.13 mmol, 2.5 equiv) in DMF (2 mL) was stirred at 23° C. for 20 hours. The reaction mixture was partitioned between saturated aqueous sodium bicarbonate solution (50 mL) and ethyl acetate (50 mL). The organic layer was dried over sodium sulfate and concentrated. The residue was purified by reverse-phase LC (H$_2$O/CH$_3$CN gradient w/0.1% TFA present) to provide N-(tert-butyl)-2-[(2S)-4-(2,5-difluorophenyl)-2-phenyl-2,5-dihydro-1H-pyrrol-1-yl]acetamide (28-2) as a colorless oil (TFA salt). LRMS m/z (M+1H) 371.4 found, 371.2 required.

The following compounds were prepared by simple modifications of the above procedure. All of the compounds in the table below were isolated as the TFA salt.

| Cmpd | Structure | Name | LRMS m/z (M + H) |
|---|---|---|---|
| 28-3 | 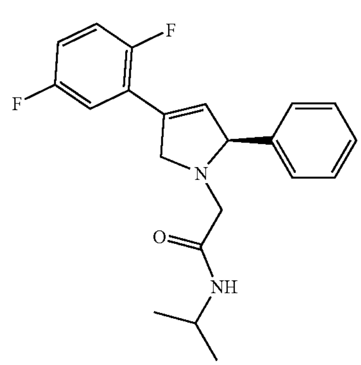 | 2-[(2S)-4-(2,5-difluorophenyl)-2-phenyl-2,5-dihydro-1H-pyrrol-1-yl]-N-isopropylacetamide | m/z (M + H) 357.2 found, 357.2 required |

-continued

| Cmpd | Structure | Name | LRMS m/z (M + H) |
|---|---|---|---|
| 28-4 | 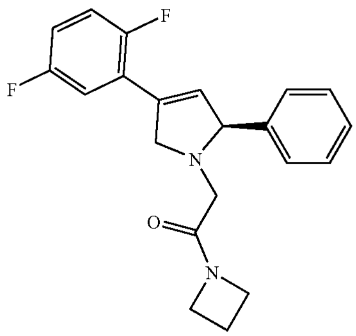 | (2S)-1-(2-azetidin-1-yl-2-oxoethyl)-4-(2,5-difluorophenyl)-2-phenyl-2,5-dihydro-1H-pyrrole | m/z (M + H) 355.1 found, 355.2 required |
| 28-5 | 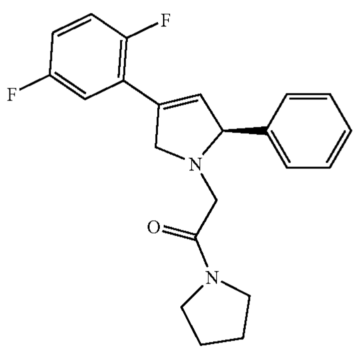 | (2S)-4-(2,5-difluorophenyl)-1-(2-oxo-2-pyrrolidin-1-ylethyl)-2-phenyl-2,5-dihydro-1H-pyrrole | m/z (M + H) 369.1 found, 369.2 required |
| 28-6 | 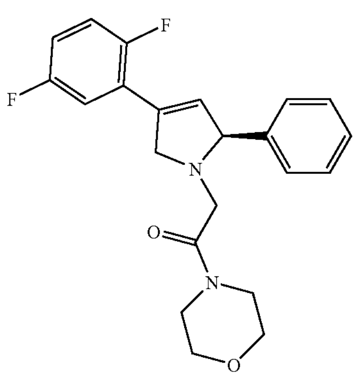 | 4-{[(2S)-4-(2,5-difluorophenyl)-2-phenyl-2,5-dihydro-1H-pyrrol-1-yl]acetyl}morpholine | m/z (M + H) 385.1 found, 385.2 required |
| 28-7 | 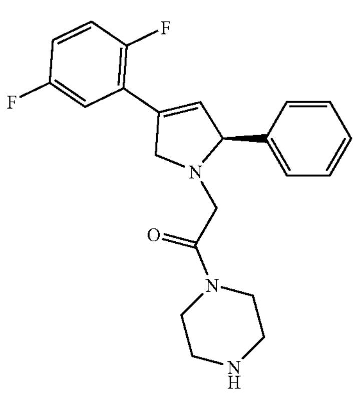 | 1-{[(2S)-4-(2,5-difluorophenyl)-2-phenyl-2,5-dihydro-1H-pyrrol-1-yl]acetyl}piperazine | m/z (M + H) 384.2 found, 384.2 required |

| Cmpd | Structure | Name | LRMS m/z (M + H) |
|---|---|---|---|
| 28-8 | 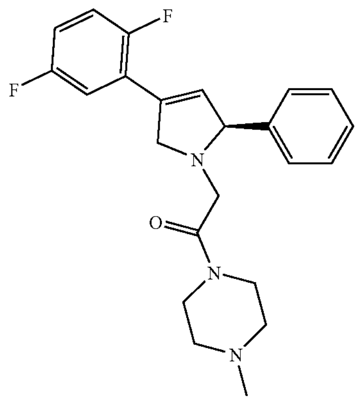 | 1-{[(2S)-4-(2,5-difluorophenyl)-2-phenyl-2,5-dihydro-1H-pyrrol-1-yl]acetyl}-4-methylpiperazine | m/z (M + H) 398.2 found, 398.2 required |
| 28-9 | 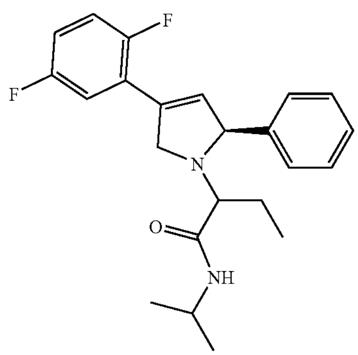 | 2-[(2S)-4-(2,5-difluorophenyl)-2-phenyl-2,5-dihydro-1H-pyrrol-1-yl]-N-isopropylbutanamide | m/z (M + H) 385.3 found, 385.2 required |
| 28-10 | 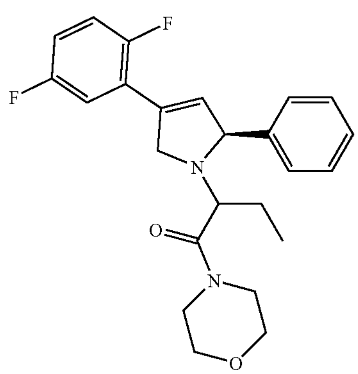 | 4-{2-[(2S)-4-(2,5-difluorophenyl)-2-phenyl-2,5-dihydro-1H-pyrrol-1-yl]butanoyl}morpholine | m/z (M + H) 413.4 found, 413.2 required |
| 28-11 | 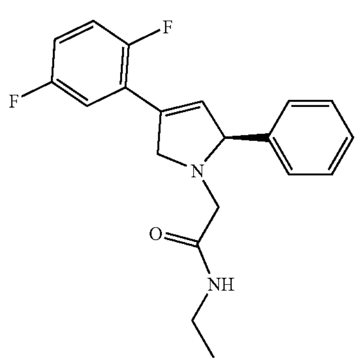 | 2-[(2S)-4-(2,5-difluorophenyl)-2-phenyl-2,5-dihydro-1H-pyrrol-1-yl]-N-ethylacetamide | m/z (M + H) 343.3 found, 343.2 required |

-continued

| Cmpd | Structure | Name | LRMS m/z (M + H) |
|---|---|---|---|
| 28-12 | 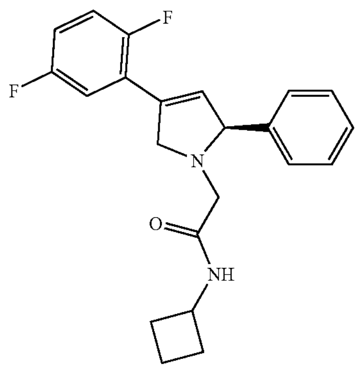 | N-cyclobutyl-2-[(2S)-4-(2,5-difluorophenyl)-2-phenyl-2,5-dihydro-1H-pyrrol-1-yl]acetamide | m/z (M + H) 369.3 found, 369.2 required |
| 28-13 | 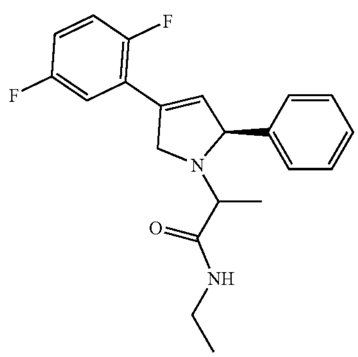 | 2-[(2S)-4-(2,5-difluorophenyl)-2-phenyl-2,5-dihydro-1H-pyrrol-1-yl]-N-ethylpropanamide | m/z (M + H) 357.3 found, 357.2 required |
| 28-14 | 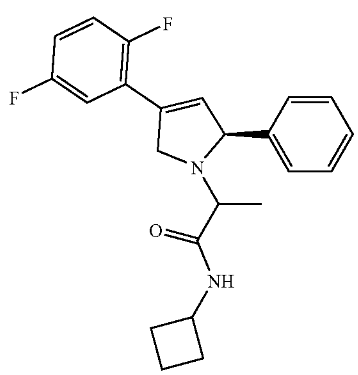 | N-cyclobutyl-2-[(2S)-4-(2,5-difluorophenyl)-2-phenyl-2,5-dihydro-1H-pyrrol-1-yl]propanamide | m/z (M + H) 383.4 found, 383.2 required |
| 28-15 | 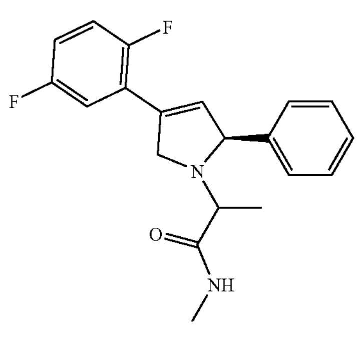 | 2-[(2S)-4-(2,5-difluorophenyl)-2-phenyl-2,5-dihydro-1H-pyrrol-1-yl]-N-methylpropanamide | m/z (M + H) 343.2 found, 343.2 required |

-continued
| Cmpd | Structure | Name | LRMS m/z (M + H) |
| --- | --- | --- | --- |
| 28-16 | 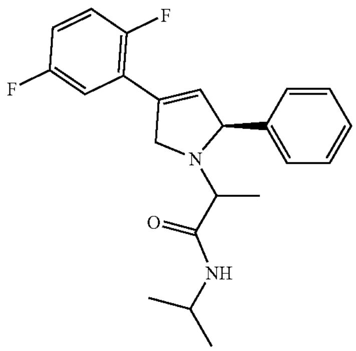 | 2-[(2S)-4-(2,5-difluorophenyl)-2-phenyl-2,5-dihydro-1H-pyrrol-1-yl]-N-isopropylpropanamide | m/z (M + H) 371.4 found, 371.2 required |
| 28-17 | 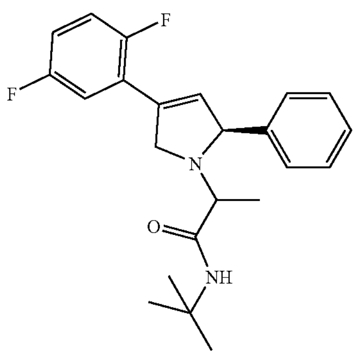 | N-(tert-butyl)-2-[(2S)-4-(2,5-difluorophenyl)-2-phenyl-2,5-dihydro-1H-pyrrol-1-yl]propanamide | m/z (M + H) 385.3 found, 385.2 required |
| 28-18 | 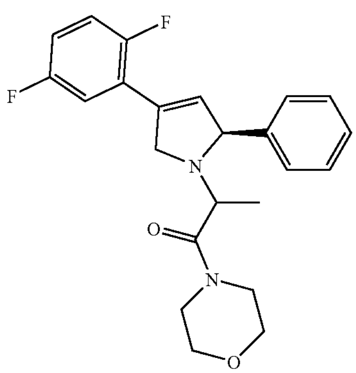 | 4-{2-[(2S)-4-(2,5-difluorophenyl)-2-phenyl-2,5-dihydro-1H-pyrrol-1-yl]propanoyl}morpholine | m/z (M + H) 399.3 found, 399.2 required |
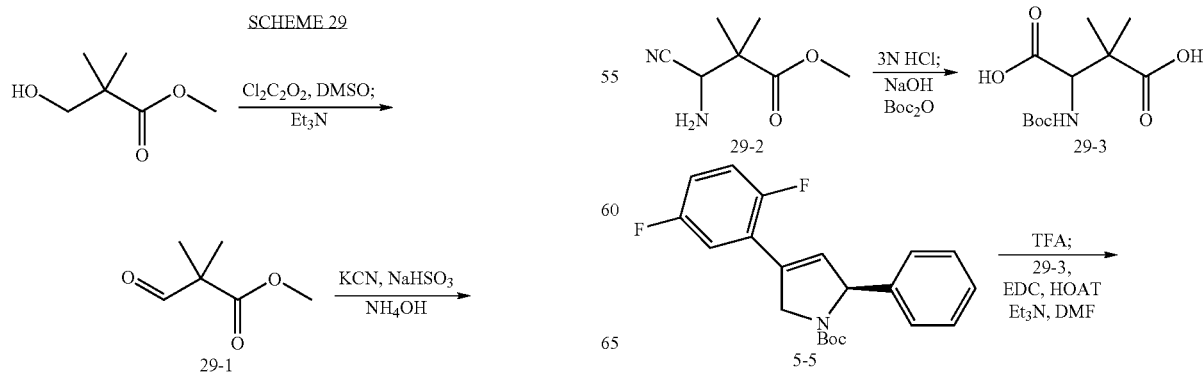
SCHEME 29

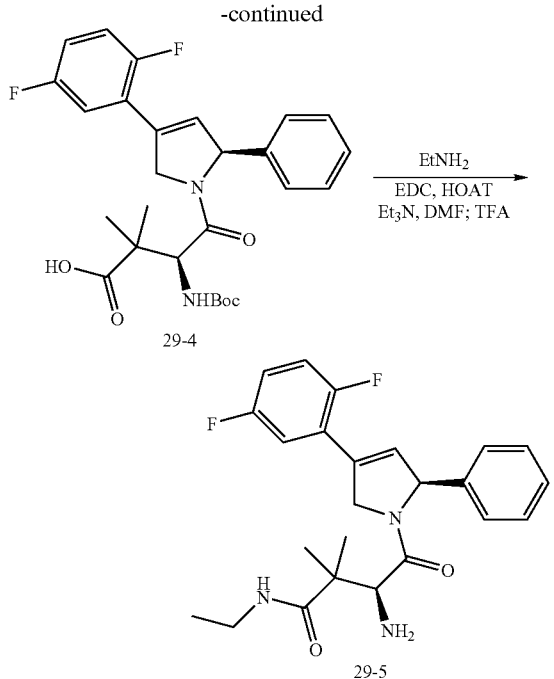

Step 1: methyl 2,2-dimethyl-3-oxopropanoate (29-1)

DMSO (22.0 mL, 303 mmol, 4.00 equiv) was added to a pre-cooled solution of oxalyl chloride (13.7 mL, 151 mmol, 2.00 equiv) in dichloromethane (40 mL) at −78° C., and the resulting mixture was stirred for 15 minutes before a solution of methyl 3-hydroxy-2,2-dimethylpropanoate (10.0 g, 75.7 mmol, 1 equiv) in dichloromethane (100 mL) was added. The reaction mixture was stirred for 1 hour, then triethylamine (52.7 mL, 378 mmol, 5.00 equiv) was added. The mixture was warmed to 0° C. and held for 30 minutes, then concentrated to a volume of ca 50 mL. The residue was partitioned between aqueous saturated sodium bicarbonate solution (200 mL) and ethyl acetate (200 mL). The organic layer was dried over sodium sulfate and concentrated on a rotorary evaporator without using heat (product is volatile) to provide methyl 2,2-dimethyl-3-oxopropanoate (29-1) as a colorless oil. $^1$H NMR (300 MHz, CDCl$_3$) δ 9.66 (s, 1H), 3.76 (s, 3M), 1.36 (s, 6H).

Step 2: methyl 3-amino-3-cyano-2,2-dimethylpropanoate (29-2)

A solution of methyl 2,2-dimethyl-3-oxopropanoate (29-1, 6.50 g, 49.9 mmol, 1 equiv), sodium bisulfite (10.4 g, 99.9 mmol, 2.00 equiv), and concentrated ammonium hydroxide (15 M, 33.3 mL, 499 mmol, 10.0 equiv) in water (200 mL) was stirred at 23° C. for 20 minutes, then potassium cyanide (6.51 g, 99.9 mmol, 2.00 equiv) was added. The resulting mixture was stirred at 23° C. for 20 hours, then extracted with ethyl ether (3×100 mL). The combined organic layers were washed with brine, then dried over sodium sulfate and concentrated to provide methyl 3-amino-3-cyano-2,2-dimethylpropanoate (29-2) as a colorless oil. $^1$H NMR (300 MHz, CDCl$_3$) δ 3.93 (br m, 1H), 3.93 (s, 3H), 1.76 (br s, 2H), 1.36 (s, 3H), 1.35 (s, 3H).

Step 3: N-(tert-butoxycarbonyl)-3,3-dimethylaspartic acid (29-3)

A solution of methyl 3-amino-3-cyano-2,2-dimethylpropanoate (29-2, 6.5 g, 41.6 mmol, 1 equiv) in aqueous 3 N HCl solution (100 mL) was heated at reflux for 6 h, then concentrated. Di-tert-butyl dicarbonate (13.6 g, 62.4 mmol, 1.50 equiv) was added to a solution of the residue in a mixture of aqueous 1 N NaOH solution (125 mL, 125 mmol, 3.00 equiv) and dioxane (125 mL) at 23° C. The resulting mixture was stirred for 5 hours, then extracted with ethyl ether (2×100 mL, discarded). The aqueous layer was acidified to pH 3 with aqueous HCl, then extracted with ethyl ether (3×150 mL). The combined organic layers were dried over sodium sulfate and concentrated to provide N-(tert-butoxycarbonyl)-3,3-dimethylaspartic acid (29-3) as a colorless oil. $^1$H NMR (300 MHz, CDCl$_3$) δ 5.43 (d, 1H, J=9.8 Hz), 4.57 (d, 1H, J=10.1 Hz), 1.76 (br s, 2H), 1.46 (s, 9H), 1.42 (s, 3H), 1.26 (s, 3H).

Step 4: (3S)-3-[(tert-butoxycarbonyl)amino]-4-[(2S)-4-(2,5-difluorophenyl)-2-phenyl-2,5-dihydro-1H-pyrrol-1-yl]-2,2-dimethyl-4-oxobutanoic acid (29-4)

A solution of tert-butyl(2S)-4-(2,5-difluorophenyl)-2-phenyl-2,5-dihydro-1H-pyrrole-1-carboxylate (5-5, 1.00 g, 2.80 mmol, 1 equiv) in a 4:1 mixture of dichloromethane and trifluoroacetic acid (20 mL) was stirred for 30 minutes, then concentrated. The residue was dried via benzene azeotrope (1×50 mL), then dissolved in DMF (30 mL). N-(tert-butoxycarbonyl)-3,3-dimethylaspartic acid (29-3, 1.08 g, 4.20 mmol, 1.50 equiv), 1-(3-dimethylaminopropyl)-3-ethylcarbodiimide hydrochloride (EDC, 0.805 g, 4.20 mmol, 1.50 equiv), 1-hydroxy-7-azabenzotriazole (0.571 g, 4.20 mmol, 1.50 equiv) and triethylamine (2.73 mL, 19.6 mmol, 7.00 equiv) were added, and the resulting mixture was stirred at 23° C. for 20 hours. The reaction mixture was partitioned between water, acidified to pH 2, and ethyl acetate (2×100 mL). The combined organic layers were dried over sodium sulfate and concentrated. The residue was purified by flash column chromatography through silica gel (hexane initially, grading to 100% EtOAc) followed by reverse-phase LC (H$_2$O/CH$_3$CN gradient w/0.1% TFA present) to provide (3S)-3-[(tert-butoxycarbonyl)amino]4-[(2S)-4-(2,5-difluorophenyl)-2-phenyl-2,5-dihydro-1H-pyrrol-1-yl]-2,2-dimethyl-4-oxobutanoic acid (29-4) as a white foam. $^1$H NMR (500 M CDCl$_3$) major rotamer: δ 7.28 (m, 5H), 7.05 (m, 3H), 6.40 (s, 1H), 5.89 (br s, 1H), 5.74 (d, 1H, J=10.2 Hz), 5.17 (d, 1H, J=14.2 Hz), 4.93 (ddd, 1H, J=13.9, 4.4, 1.7 Hz), 4.62 (d, 1H, J=10.2 Hz), 1.45 (s, 9H), 1.30 (s, 3H), 1.05 (s, 3H). LRMS m/z (M+H) 501.5 found, 501.2 required.

Step 5: (3S)-3-amino-4-[(2S)-4-(2,5-difluorophenyl)-2-phenyl-2,5-dihydro-1H-pyrrol-1-yl]-N-ethyl-2,2-dimethyl-4-oxobutanamide (29-5)

A solution of (3S)-3-[(tert-butoxycarbonyl)amino]4-[(2S)-4-(2,5-difluorophenyl)-2-phenyl-2,5-dihydro-1H-pyrrol-1-yl]-2,2-dimethyl-4-oxobutanoic acid (29-4, 50 mg, 0.10 mmol, 1.0 equiv), ethylamine hydrochloride (81 mg, 1.0 mmol, 10 equiv), 1-(3-dimethylaminopropyl)-3-ethylcarbodiimide hydrochloride (EDC, 29 mg, 0.15 mmol, 1.5 equiv), 1-hydroxy-7-azabenzotriazole (20 mg, 0.15 mmol, 1.5 equiv) and triethylamine (209 μL, 1.5 mmol, 15 equiv) in DMP (4 mL) was stirred at 23° C. for 20 hours. The reaction mixture was partitioned between aqueous saturated sodium bicarbonate solution (50 mL) and ethyl acetate (2×50 mL). The combined organic layers were dried over sodium sulfate and concentrated. There residue was purified by flash column chromatography (hexanes initially, grading to 100% EtOAc). A solution of the product was stirred in a 1:1 mixture of TFA and dichloromethane (2 mL) for 1 hour, then concentrated to provide (3S)-3-amino-4-[(2S)-4-(2,5-difluorophenyl)-2-phenyl-2,5-dihydro-1H-pyrrol-1-yl]-N-ethyl-2,2-dimethyl-4-oxobutanamide (29-5) as a white foam (TFA salt). LRMS m/z (M+H) 428.5 found, 428.2 required.

The following compounds were prepared by simple modifications of the above procedure. All of the compounds in the table below were isolated as the TFA salt.

| Cmpd | Structure | Name | LRMS m/z (M + H) |
|---|---|---|---|
| 29-6 | 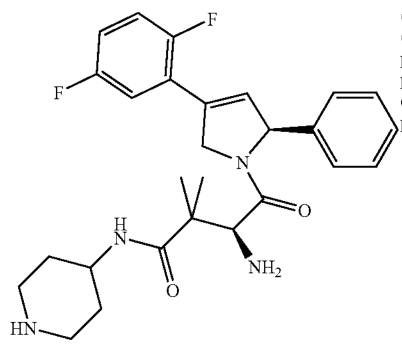 | (3S)-3-amino-4-[(2S)-4-(2,5-difluorophenyl)-2-phenyl-2,5-dihydro-1H-pyrrol-1-yl]-2,2-dimethyl-4-oxo-N-piperidin-4-ylbutanamide | m/z (M + H) 483.6 found, 483.3 required |
| 29-7 | 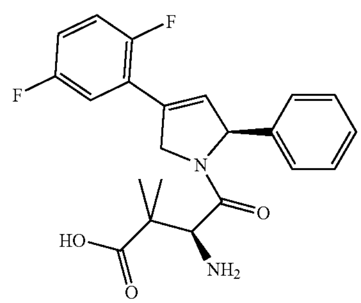 | (3S)-3-amino-4-[(2S)-4-(2,5-difluorophenyl)-2-phenyl-2,5-dihydro-1H-pyrrol-1-yl]-2,2-dimethyl-4-oxobutanoic acid | m/z (M + H) 401.4 found, 401.2 required |
| 29-8 | 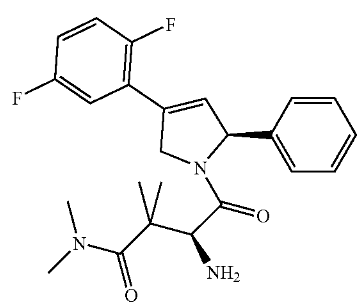 | (3S)-3-amino-4-[(2S)-4-(2,5-difluorophenyl)-2-phenyl-2,5-dihydro-1H-pyrrol-1-yl]-N,N,2,2-tetramethyl-4-oxobutanamide | m/z (M + H) 428.5 found, 428.2 required |
| 29-9 | 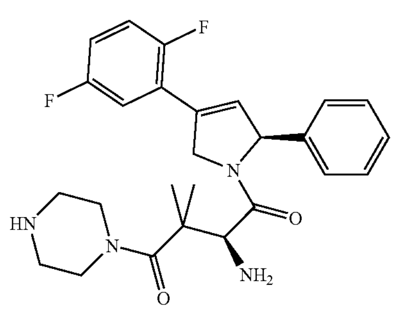 | (1S)-1-{[(2S)-4-(2,5-difluorophenyl)-2-phenyl-2,5-dihydro-1H-pyrrol-1-yl]carbonyl}-2,2-dimethyl-3-oxo-3-piperazin-1-ylpropylamine | LRMS m/z (M + H) 469.5 found, 469.2 required |

-continued

| Cmpd | Structure | Name | LRMS m/z (M + H) |
|---|---|---|---|
| 29-10 | 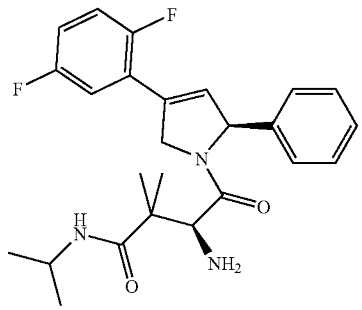 | (3S)-3-amino-4-[(2S)-4-(2,5-difluorophenyl)-2-phenyl-2,5-dihydro-1H-pyrrol-1-yl]-N-isopropyl-2,2-dimethyl-4-oxobutanamide | m/z (M + H) 442.4 found, 442.2 required |
| 29-11 | 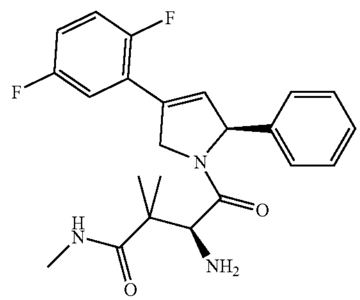 | (3S)-3-amino-4-[(2S)-4-(2,5-difluorophenyl)-2-phenyl-2,5-dihydro-1H-pyrrol-1-yl]-N,2,2-trimethyl-4-oxobutanamide | m/z (M + H) 414.5 found, 414.2 required |
| 29-12 | 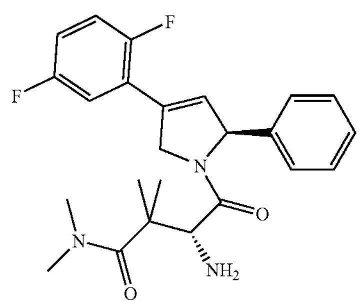 | (3R)-3-amino-4-[(2S)-4-(2,5-difluorophenyl)-2-phenyl-2,5-dihydro-1H-pyrrol-1-yl]-N,N,2,2-tetramethyl-4-oxobutanamide | m/z (M + H) 428.5 found, 428.2 required |
| 29-13 | 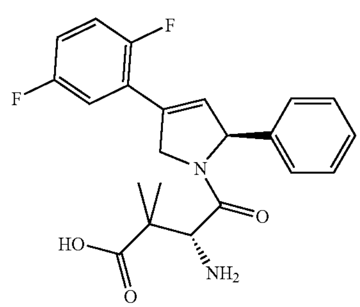 | (3R)-3-amino-4-[(2S)-4-(2,5-difluorophenyl)-2-phenyl-2,5-dihydro-1H-pyrrol-1-yl]-2,2-dimethyl-4-oxobutanoic acid | m/z (M + H) 401.4 found, 401.2 required |
| 29-14 | 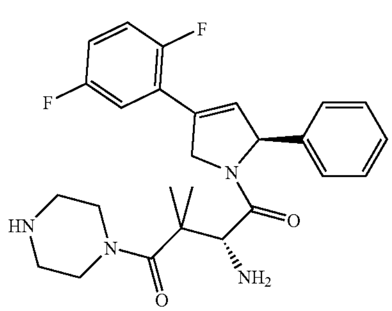 | (1R)-1-{[(2S)-4-(2,5-difluorophenyl)-2-phenyl-2,5-dihydro-1H-pyrrol-1-yl]carbonyl}-2,2-dimethyl-3-oxo-3-piperazin-1-ylpropylamine | m/z (M + H) 469.5 found, 469.2 required |

SCHEME 30

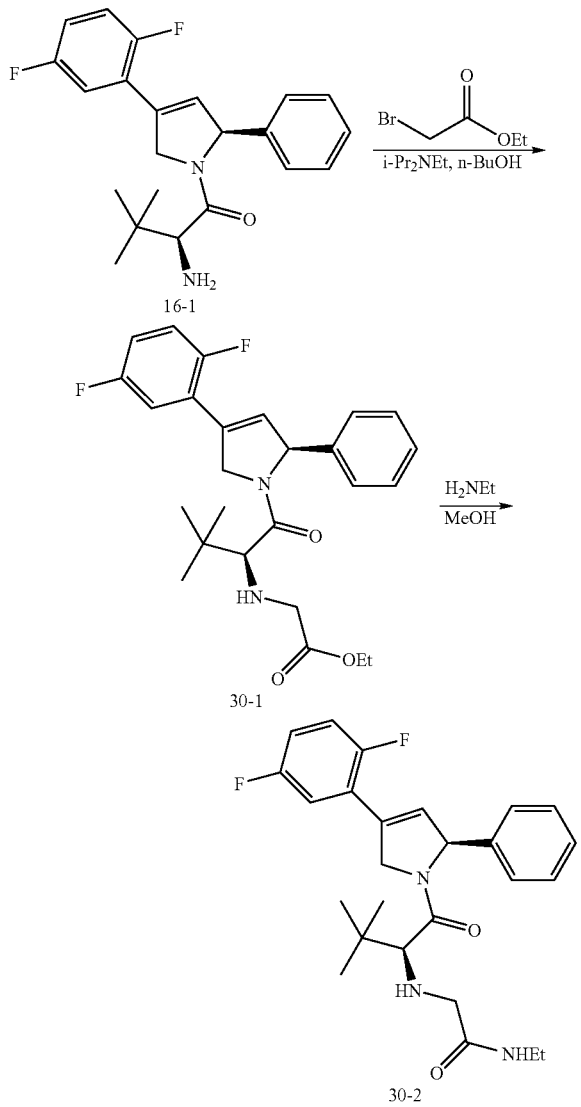

Step 1: ethyl ({(1S)-1-tert-butyl-2-[(2S)-4-(2,5-difluorophenyl)-2-phenyl-2,5-dihydro-1H-pyrrol-1-yl]-2-oxoethyl}amino)acetate (30-1)

A solution of (1S)-1-{[(2S)-4-(2,5-difluorophenyl)-2-phenyl-2,5-dihydro-1H-pyrrol-1-yl]carbonyl}-2,2-dimethylpropylamine (16-1, 325 mg, 0.877 mmol, 1 equiv), ethyl bromoacetate (0.195 mL, 1.76 mmol, 2.00 equiv), and N,N-diisopropylethylamine (0.613 mL, 3.51 mmol, 4.00 equiv) in n-BuOH (4.0 mL) was heated under microwave irradiation at 150° C. for 15 minutes. The reaction mixture was concentrated and the residue was partitioned between a ethyl acetate (100 mL) and a 1:1 mixture of saturated aqueous potassium bisulfate solution and brine (100 mL). The organic layer was then washed with saturated aqueous sodium bicarbonate solution (100 mL) followed by brine (100 mL), then dried over magnesium sulfate and concentrated to give ethyl({(1S)-1-tert-butyl-2-[(2S)-4-(2,5-difluorophenyl)-2-phenyl-2,5-dihydro-1H-pyrrol-1-yl]-2-oxoethyl}amino)acetate (30-1) as an off-white solid. LRMS m/z (M+H) 457.5 found, 457.2 required.

Step 2: 2-({(1S)-1-tert-butyl-2-[(2S)-4-(2,5-difluorophenyl)-2-phenyl-2,5-dihydro-1H-pyrrol-1-yl]-2-oxoethyl}amino)-N-ethylacetamide (30-2)

A solution of ethyl({(1S)-1-tert-butyl-2-[(2S)-4-(2,5-difluorophenyl)-2-phenyl-2,5-dihydro-1H-pyrrol-1-yl]-2-oxoethyl}amino)acetate (30-1, 50 mg, 0.11 mmol) in a solution of ethylamine in THF (2 M, 2 mL) was heated in a sealable tube at 100° C. for 16 hours. The reaction mixture was concentrated and the residue purified by flash column chromatography (EtOAc) to give 2-({(1S)-1-tert-butyl-2-[(2S)-4-(2,5-difluorophenyl)-2-phenyl-2,5-dihydro-1H-pyrrol-1-yl]-2-oxoethyl}amino)-N-ethylacetamide (30-2) as a white solid. $^1$H NMR (500 MHz, CDCl$_3$) showed a 1:1 mixture of rotamers; one rotamer: δ 7.43-7.22 (m, 5H), 7.11-6.96 (m, 3H), 6.89 (br m, 1H), 6.38 (br s, 1H), 5.94 (m, 1H), 4.92 (ddd, 1H, J=14.9, 4.4, 1.7 Hz), 4.87 (br d, 1H, J=15.3 Hz), 3.42 (d, 1H, J=16.8 Hz), 3.35 (m, 2H), 3.03 (s, 1H), 2.88 (d, 1H, J=16.8 Hz), 2.34 (br s, 1H), 1.18 (t, 3H, J=7.3 Hz), 1.06 (s, 9H). LRMS m/z (M+H) 456.5 found, 456.2 required.

The following compounds were prepared by simple modifications of the above procedure.

| Cmpd | Structure | Name | LRMS m/z (M + H) |
|---|---|---|---|
| 30-3 | ![structure] | 2-({(1S)-1-tert-butyl-2-[(2S)-4-(2,5-difluorophenyl)-2-phenyl-2,5-dihydro-1H-pyrrol-1-yl]-2-oxoethyl}amino)-N-methylacetamide | LRMS m/z (M + H) 442.5 found, 442.2 required. |

-continued

| Cmpd | Structure | Name | LRMS m/z (M + H) |
|---|---|---|---|
| 30-4 | 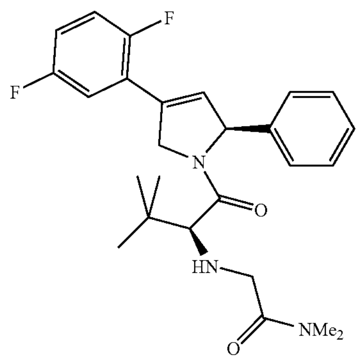 | 2-({(1S)-1-tert-butyl-2-[(2S)-4-(2,5-difluorophenyl)-2-phenyl-2,5-dihydro-1H-pyrrol-1-yl]-2-oxoethyl}amino)-N,N-dimethylacetamide | LRMS m/z (M + H) 456.5 found, 456.2 required |
| 30-5 | 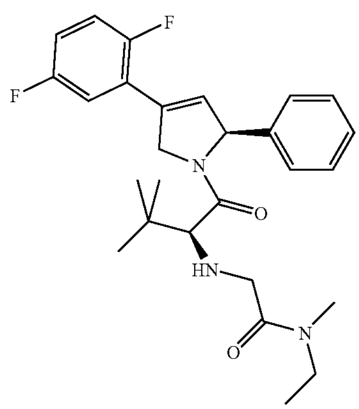 | 2-({(1S)-1-tert-butyl-2-[(2S)-4-(2,5-difluorophenyl)-2-phenyl-2,5-dihydro-1H-pyrrol-1-yl]-2-oxoethyl}amino)-N-methyl-N ethylacetamide | LRMS m/z (M + H) 470.5 found, 470.2 required |
| 30-6 | 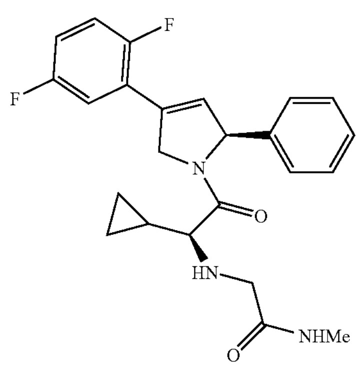 | 2-({(1S)-1-cyclopropyl-2-[(2S)-4-(2,5-difluorophenyl)-2-phenyl-2,5-dihydro-1H-pyrrol-1-yl]-2-oxoethyl}amino)-N-methylacetamide | LRMS m/z (M + H) 426.4 found, 426.2 required |
| 30-7 | 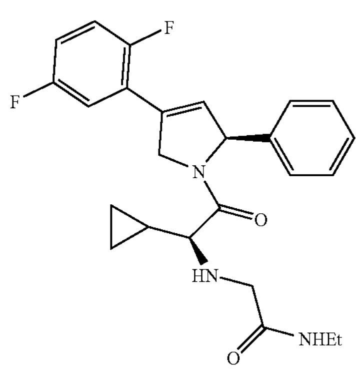 | 2-({(1S)-1-cyclopropyl-2-[(2S)-4-(2,5-difluorophenyl)-2-phenyl-2,5-dihydro-1H-pyrrol-1-yl]-2-oxoethyl}amino)-N-ethylacetamide | LRMS m/z (M + H) 440.4 found, 440.2 required |

| Cmpd | Structure | Name | LRMS m/z (M + H) |
|---|---|---|---|
| 30-8 | 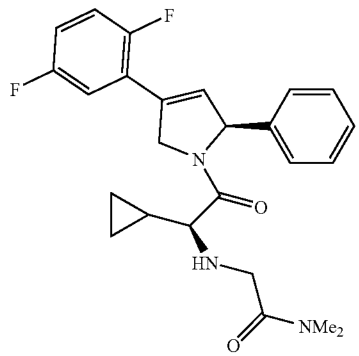 | 2-({(1S)-1-cyclopropyl-2-[(2S)-4-(2,5-difluorophenyl)-2-phenyl-2,5-dihydro-1H-pyrrol-1-yl]-2-oxoethyl}amino)-N,N-dimethylacetamide | LRMS m/z (M + H) 440.5 found, 440.2 required |
| 30-9 | 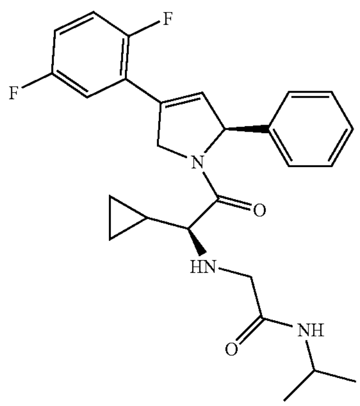 | 2-({(1S)-1-cyclopropyl-2-[(2S)-4-(2,5-difluorophenyl)-2-phenyl-2,5-dihydro-1H-pyrrol-1-yl]-2-oxoethyl}amino)-N-isopropylacetamide | LRMS m/z (M + H) 454.5 found, 454.2 required |
| 30-10 | 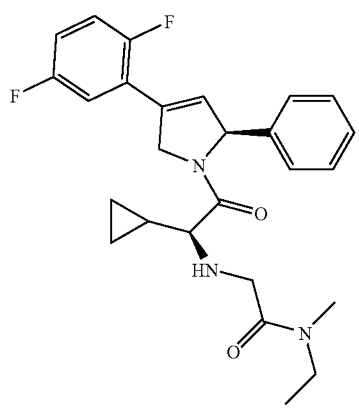 | 2-({(1S)-1-cyclopropyl-2-[(2S)-4-(2,5-difluorophenyl)-2-phenyl-2,5-dihydro-1H-pyrrol-1-yl]-2-oxoethyl}amino)-N-ethyl-N-methylacetamide | LRMS m/z (M + H) 454.4 found, 454.2 required |
| 30-11 | 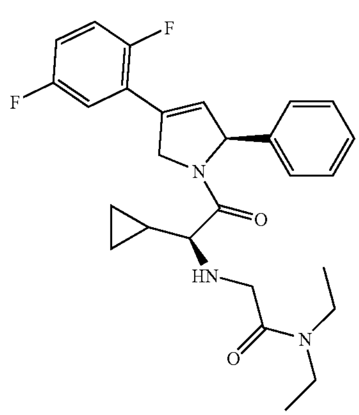 | 2-({(1S)-1-cyclopropyl-2-{(2S)-4-(2,5-difluorophenyl)-2-phenyl-2,5-dihydro-1H-pyrrol-1-yl]-2-oxoethyl}amino)-N,N-diethylacetamide | LRMS m/z (M + H) 468.5 found, 468.2 required |

-continued

| Cmpd | Structure | Name | LRMS m/z (M + H) |
|---|---|---|---|
| 30-12 | 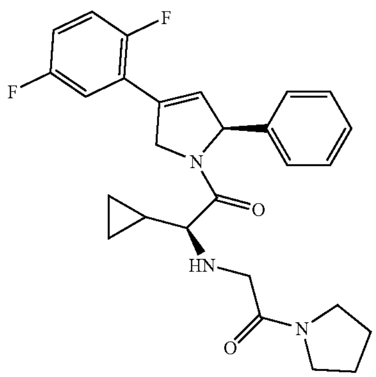 | (1S)-1-cyclopropyl-2-[(2S)-4-(2,5-difluorophenyl)-2-phenyl-2,5-dihydro-1H-pyrrol-1-yl]-2-oxo-N-(2-oxo-2-pyrrolidin-1-ylethyl)ethanamine | LRMS m/z (M + H) 466.5 found, 466.2 required |
| 30-13 | 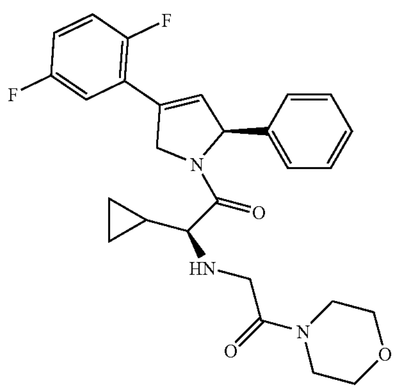 | (1S)-1-cyclopropyl-2-[(2S)-4-(2,5-difluorophenyl)-2-phenyl-2,5-dihydro-1H-pyrrol-1-yl]-N-(2-morpholin-4-yl-2-oxoethyl)-2-oxoethanamine | LRMS m/z (M + H) 482.4 found, 482.2 required |
| 30-14 | 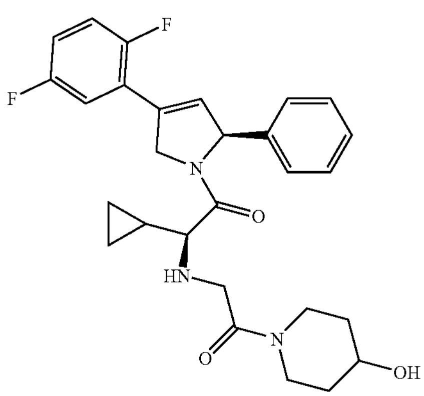 | 1-[({(1S)-1-cyclopropyl-2-[(2S)-4-(2,5-difluorophenyl)-2-phenyl-2,5-dihydro-1H-pyrrol-1-yl]-2-oxoethyl}amino)acetyl]piperidin-4-ol | LRMS m/z (M + H) 496.6 found, 496.2 required |
| 30-15 | 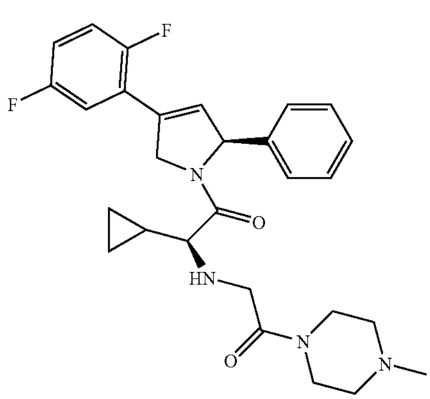 | (1S)-1-cyclopropyl-2-[(2S)-4-(2,5-difluorophenyl)-2-phenyl-2,5-dihydro-1H-pyrrol-1-yl]-N-[2-(4-methylpiperazin-1-yl)-2-oxoethyl]-2-oxoethanamine | LRMS m/z (M + H) 495.5 found, 495.2 required |

-continued

| Cmpd | Structure | Name | LRMS m/z (M + H) |
|---|---|---|---|
| 30-16 | 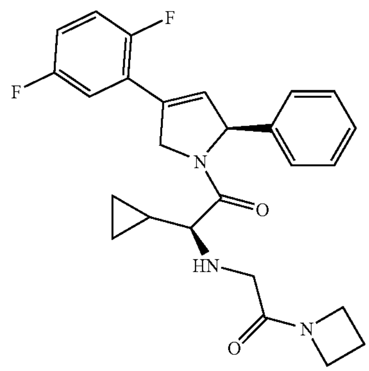 | (1S)-N-(2-azetidin-1-yl-2-oxoethyl)-1-cyclopropyl-2-[(2S)-4-(2,5-difluorophenyl)-2-phenyl-2,5-dihydro-1H-pyrrol-1-yl]-2-oxoethanamine | LRMS m/z (M + H) 452.5 found, 452.2 required |
| 30-17 | 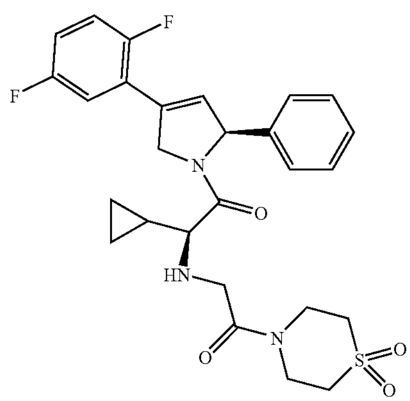 | (1S)-1-cyclopropyl-2-[(2S)-4-(2,5-difluorophenyl)-2-phenyl-2,5-dihydro-1H-pyrrol-1-yl]-N-[2-(1,1-dioxidothiomorpholin-4-yl)-2-oxoethyl]-2-oxoethanamine | LRMS m/z (M + H) 530.5 found, 530.2 required |
| 30-18 | 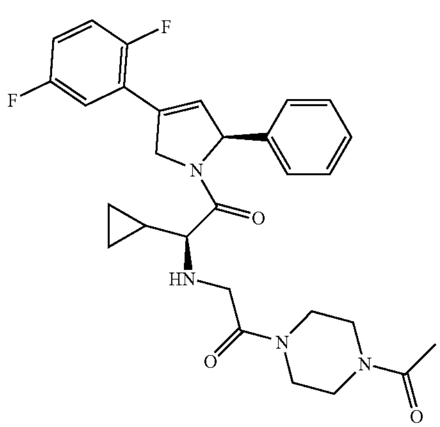 | (1S)-N-[2-(4-acetylpiperazin-1-yl)-2-oxoethyl]-1-cyclopropyl-2-[(2S)-4-(2,5-difluorophenyl)-2-phenyl-2,5-dihydro-1H-pyrrol-1-yl]-2-oxoethanamine | LRMS m/z (M + H) 423.6 found, 523.2 required |

| Cmpd | Structure | Name | LRMS m/z (M + H) |
|---|---|---|---|
| 30-19 | 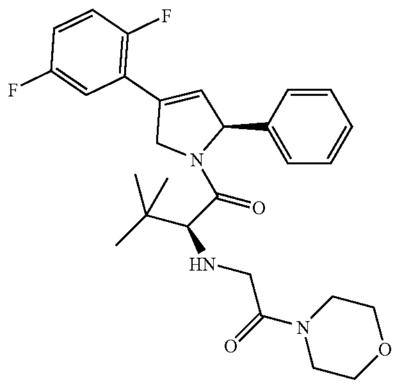 | (1S)-1-tert-butyl-2-[(2S)-4-(2,5-difluorophenyl)-2-phenyl-2,5-dihydro-1H-pyrrol-1-yl]-N-(2-morpholin-4-yl-2-oxoethyl)-2-oxoethanamine | LRMS m/z (M + H) 498.6 found, 498.2 required |
| 30-20 | 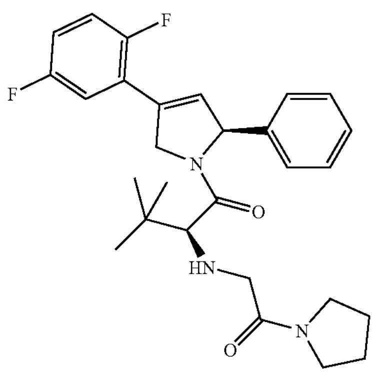 | (1S)-1-tert-butyl-2-[(2S)-4-(2,5-difluorophenyl)-2-phenyl-2,5-dihydro-1H-pyrrol-1-yl]-2-oxo-N-(2-oxo-2-pyrrolidin-1-ylethyl)ethanamine | LRMS m/z (M + H) 482.6 found, 482.2 required |
| 30-21 | 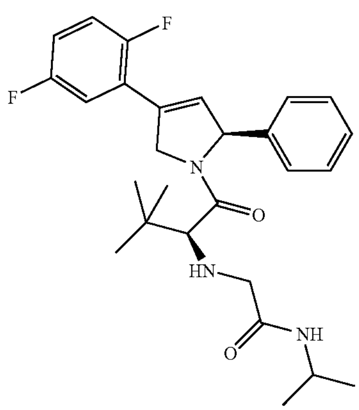 | 2-({(1S)-1-tert-butyl-2-[(2S)-4-(2,5-difluorophenyl)-2-phenyl-2,5-dihydro-1H-pyrrol-1-yl]-2-oxoethyl}amino)-N-isopropylacetamide | LRMS m/z (M + H) 470.5 found, 470.2 required |

SCHEME 31

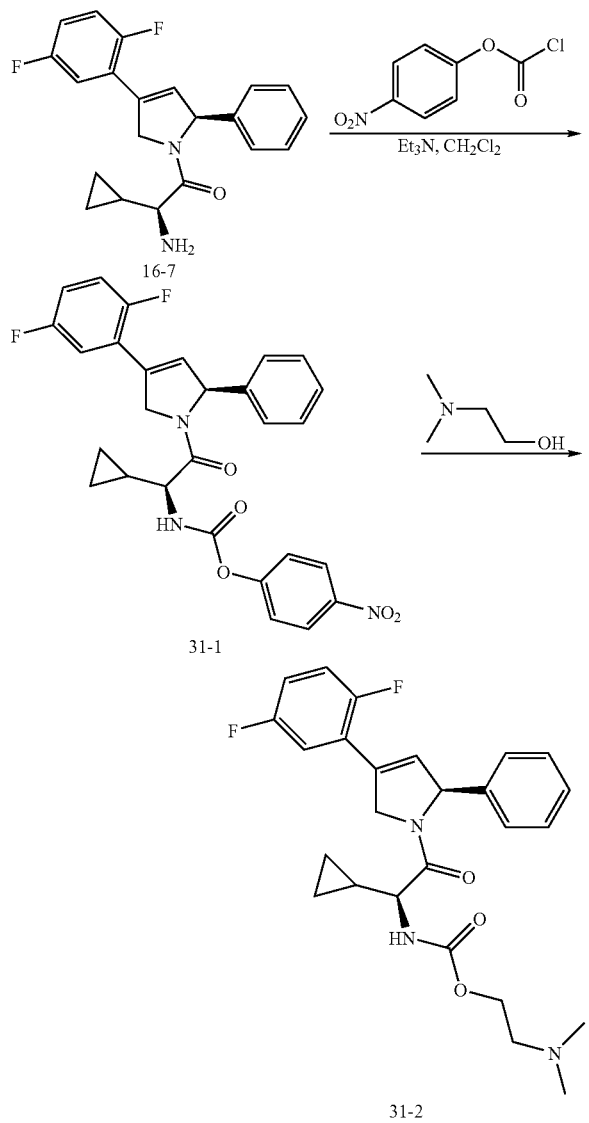

Step 1: 4-nitrophenyl (1S)-1-cyclopropyl-2-[(2S)-4-(2,5-difluorophenyl)-2-phenyl-2,5-dihydro-1H-pyrrol-1-yl]-2-oxoethylcarbamate (31-1)

A solution of 4-nitrophenyl chloroformate (188 mg, 0.931 mmol, 1.10 equiv) in dichloromethane (5 mL) was added dropewise to a solution of (1S)-1-cyclopropyl-2-[(2S)-4-(2,5-difluorophenyl)-2-phenyl-2,5-dihydro-1H-pyrrol-1-yl]-2-oxoethanamine (16-7, 300 mg, 0.847 mmol, 1 equiv) and triethylamine (0.354 mL, 2.54 mmol, 3.00 equiv) in dichloromethane (10 mL) at 0° C. The reaction mixture was warmed to 23° C. and stirred for 20 hours. The reaction mixture was then partitioned between saturated aqueous sodium bicarbonate solution (50 mL) and ethyl acetate (75 mL). The organic layer was washed with brine, then dried over magnesium sulfate and concentrated to provide 4-nitrophenyl(1S)-1-cyclopropyl-2-[(2S)-4-(2,5-difluorophenyl)-2-phenyl-2,5-dihydro-1H-pyrrol-1-yl]-2-oxoethylcarbamate (31-1) as a pale yellow solid. LRMS m/z (M+H) 520.5 found, 520.2 required.

Step 2: 2-(dimethylamino)ethyl (1S)-1-cyclopropyl-2-[(2S)-4-(2,5-difluorophenyl)-2-phenyl-2,5-dihydro-1H-pyrrol-1-yl]-2-oxoethylcarbamate (31-2)

A solution of (1S)-1-cyclopropyl-2-[(2S)-4-(2,5-difluorophenyl)-2-phenyl-2,5-dihydro-1H-pyrrol-1-yl]-2-oxoethylcarbamate (31-1, 50 mg, 0.096 mmol) in 2-(dimethylamino)ethanol (1 mL) was heated at 100° C. for 1 hour. The reaction mixture was cooled, then partitioned between ethyl acetate (40 mL) and brine (3×40 mL). The organic layer was dried over magnesium sulfate and concentrated. The residue was purified by flash column chromatography (EtOAc initially, grading to 10% saturated NH$_3$/ethanol in EtOAc) to give 2-(dimethylamino)ethyl(1S)-1-cyclopropyl-2-[(2S)-4-(2,5-difluorophenyl)-2-phenyl-2,5-dihydro-1H-pyrrol-1-yl]-2-oxoethylcarbamate (31-2) as a pale yellow solid. $^1$H NMR (500 MHz, CDCl$_3$) showed a 2:1 mixture of rotamers; major rotamer: δ 7.42-7.24 (m, 5H), 7.11-6.95 (m, 3H), 6.41 (br s, 1H), 5.93 (m, 1H), 5.58 (d, 1H, J=7.6 Hz), 5.04 (br d, 1H, J=13.9 Hz), 4.91 (ddd, 1H, J=14.7, 4.4, 1.7 Hz), 4.30 (t, 1H, J=7.8 Hz), 4.15 (m, 2H), 2.54 (m, 2H), 2.27 (s, 6H), 1.14 (m, 1H), 0.57-0.33 (m, 4H). LRMS m/z (M+H) 470.5 found, 470.2 required.

The following compound was prepared by simple modifications of the above procedure.

| Cmpd | Structure | Name | LRMS m/z (M + H) |
|---|---|---|---|
| 31-3 | (structure shown) | 1-methylpiperidin-4-yl (1S)-1-ccyclopropyl-2-[(2S)-4-(2,5-difluorophenyl)-2-phenyl-2,5-dihydro-1H-pyrrol-1-yl]-2-oxoethylcarbamate | LRMS m/z (M + H) 496.6 found, 496.2 required. |

SCHEME 32

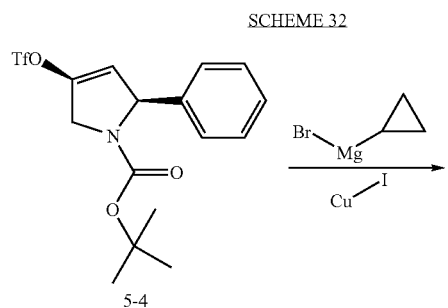

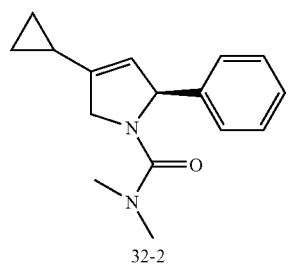

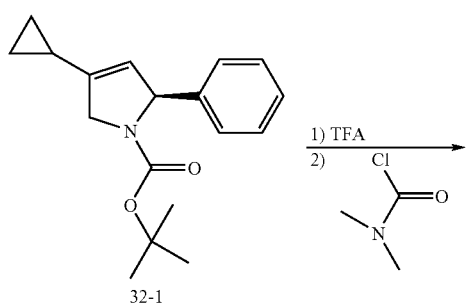

Tert-butyl (2S)-2-phenyl-4-{[(trifluoromethyl)sulfonyl]oxy}-2,5-dihydro-1H-pyrrole-1-carboxylate (5-4, 100 mg, 0.254 mmol, 1 equiv) was added to a solution of dry THF (5 ml) containing copper iodide (5 mg, 0.025 mmol, 0.2 equiv) at −10° C. Cyclopropyl magnesium bromide (0.508 mL, 0.508 mmol, 2 equiv) was added drop wise and the resulting solution was stirred at −10° C. for 15 minutes. The reaction mixture was partitioned between aqueous ammonium chloride solution (15 mL) and ethyl acetate (3×10 mL). The combined organic layers were then dried over sodium sulfate, filtered, and concentrated to give tert-butyl (2S)-4-cyclopropyl-2-phenyl-2,5-dihydro-1H-pyrrole-1-carboxylate (32-1), which is converted to (2S)-4-cyclopropyl-N,N-dimethyl-2-phenyl-2,5-dihydro-1H-pyrrole-1-carboxamide (32-2) in the experimental mentioned above. $^1$H NMR (300 MHz, CDCl$_3$) δ 7.22 (m, 5H), 5.82 (m, 1H), 5.35 (m, 1H), 4.43 (dd, J=14.5, 5.5 Hz, 1H), 4.00 (d, J=14.5 Hz, 1H), 2.82 (s, 6H), 1.40 (m, 1H), 0.76 (m, 2H), 0.54 (m, 2H). LRMS m/z (M+H) 257.2 found, 257.3 required.

The following compound was prepared by simple modifications of the above procedure.

| cmpd | Structure | Name | LRMS m/z (M + H) |
|---|---|---|---|
| 32-3 | 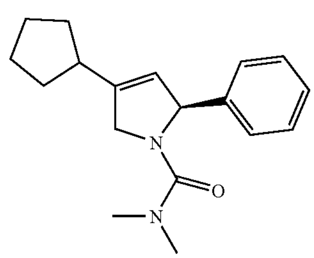 | (2S)-4-cyclopentyl-N,N-dimethyl-2-phenyl-2,5-dihydro-1H-pyrrole-1-carboxamide | LRMS m/z (M + H) 285.3 found, 285.4 required. |

SCHEME 33

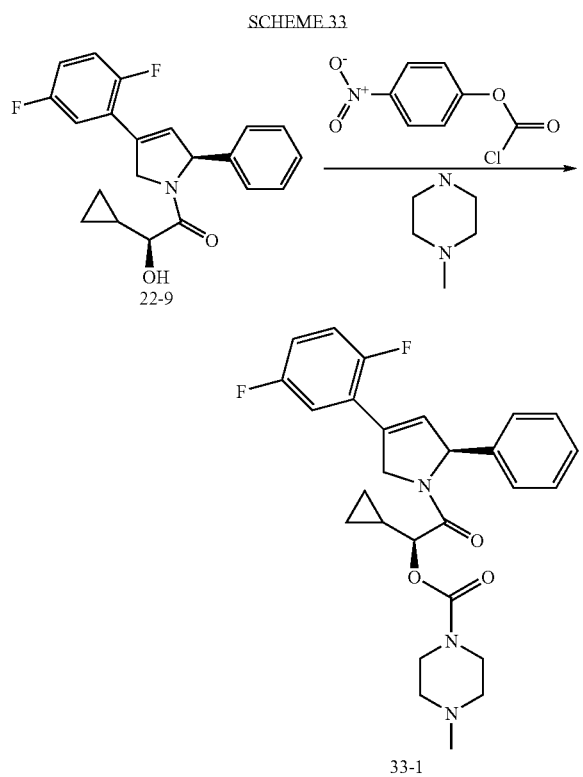

To a solution of 1-cyclopropyl-2-[(2S)-4-(2,5-difluorophenyl)-2-phenyl-2,5-dihydro-1H-pyrrol-1-yl]-2-oxoethanol (22-9) in dichloromethane at 0° C. was added DMAP (1.0 mg. 0.006 mmol, 0.1 equiv), triethylamine (16 μL, 0.113 mmol, 2 equiv), and para-nitrophenyl chloroformate (23 mg, 0.113 mmol, 2 equiv). The resulting mixture was warmed to 23° C. and stirred for 2 h. N-methyl piperazine (23 mg, 0.225 mmol, 4.0 equiv) was added, and the resulting solution stirred another hour at 23° C. Upon reaction completion, the reaction mixture was concentrated and purified by reverse phase liquid chromatography to yield (1S)-1-cyclopropyl-2-[(2S)-4-(2,5-difluorophenyl)-2-phenyl-2,5-dihydro-1H-pyrrol-1-yl]-2-oxoethyl 4-methylpiperazine-1-carboxylate (33-1) as the TFA salt. $^1$H NMR (300 MHz, CDCl$_3$): δ 7.35 (m, 5H), 7.05 (m, 3H), 6.40 (s, 1H), 5.98 (s, 1H), 5.17 (d, J=13.4 Hz, 1H), 4.85 (m, 1H,), 4.62 (m, 1H), 4.28 (m, 2H), 3.50 (m, 4H), 3.04 (m, 1H), 2.83 (s, 3H), 2.82 (m, 1H), 1.21 (m, 1H), 0.60 (m, 4H)

The following compounds were prepared by simple modifications of the above procedure. Unless otherwise indicated, the trifluoroacetate salt of the compound was isolated,

| Cmpd | Structure | Name | LRMS m/z (M + H) |
|---|---|---|---|
| 33-2 | 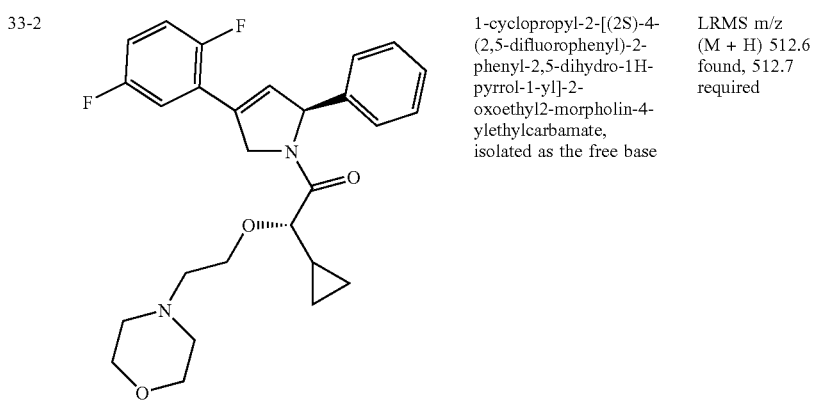 | 1-cyclopropyl-2-[(2S)-4-(2,5-difluorophenyl)-2-phenyl-2,5-dihydro-1H-pyrrol-1-yl]-2-oxoethyl2-morpholin-4-ylethylcarbamate, isolated as the free base | LRMS m/z (M + H) 512.6 found, 512.7 required |

-continued

| Cmpd | Structure | Name | LRMS m/z (M + H) |
|------|-----------|------|------------------|
| 33-3 | 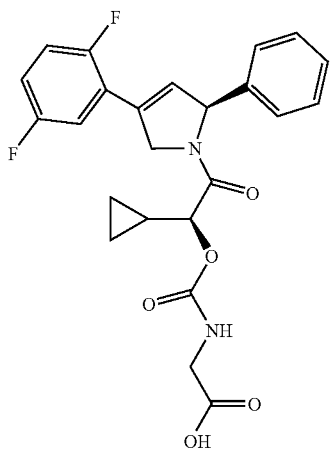 | N-[({(1S)-1-cyclopropyl-2-[(2S)-4-(2,5-difluorophenyl)-2-phenyl-2,5-dihydro-1H-pyrrol-1-yl]-2-oxoethyl}oxy)-carbonyl]glycine, isolated as the free base | LRMS m/z (M + H) 457.4 found, 457.4 required |
| 33-4 | 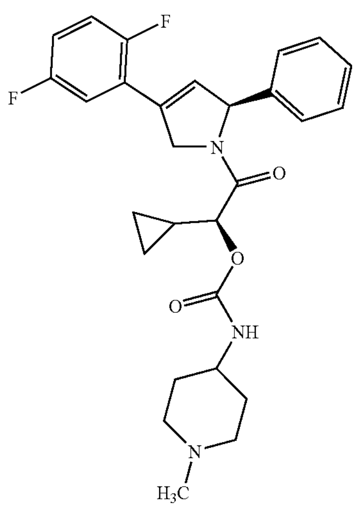 | (1S)-1-cyclopropyl-2-[(2S)-4-(2,5-difluorophenyl)-2-phenyl-2,5-dihydro-1H-pyrrol-1-yl]-2-oxoethyl 1-methylpiperidin-4-ylcarbamate | LRMS m/z (M + H) 496.5 found, 496.6 required |
| 33-5 | 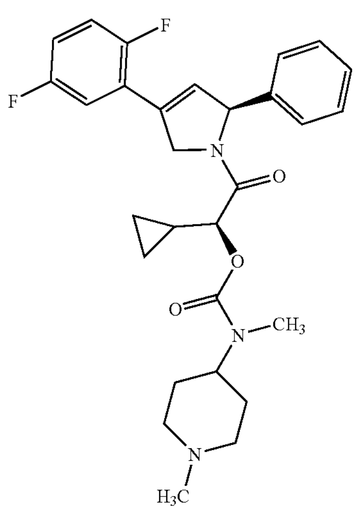 | (1S)-1-cyclopropyl-2-[(2S)-4-(2,5-difluorophenyl)-2-phenyl-2,5-dihydro-1H-pyrrol-1-yl]-2-oxoethylmethyl(1-methylpiperidin-4-yl)carbamate | LRMS m/z (M + H) 510.5 found, 510.6 required |

-continued

| Cmpd | Structure | Name | LRMS m/z (M + H) |
|---|---|---|---|
| 33-6 | 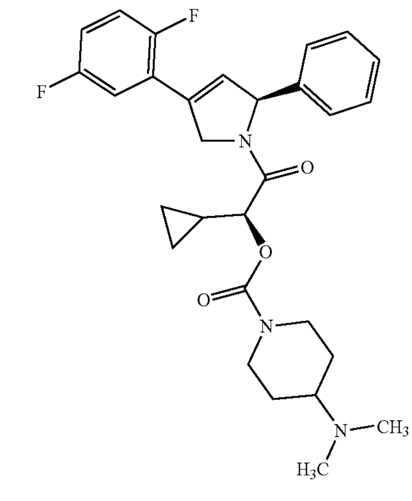 | (1S)-1-cyclopropyl-2-[(2S)-4-(2,5-difluorophenyl)-2-phenyl-2,5-dihydro-1H-pyrrol-1-yl]-2-oxoethyl 4-dimethylamino)piperidine-1-carboxylate | MRNS m/z (M + H) 510.6 found, 510.6 required |

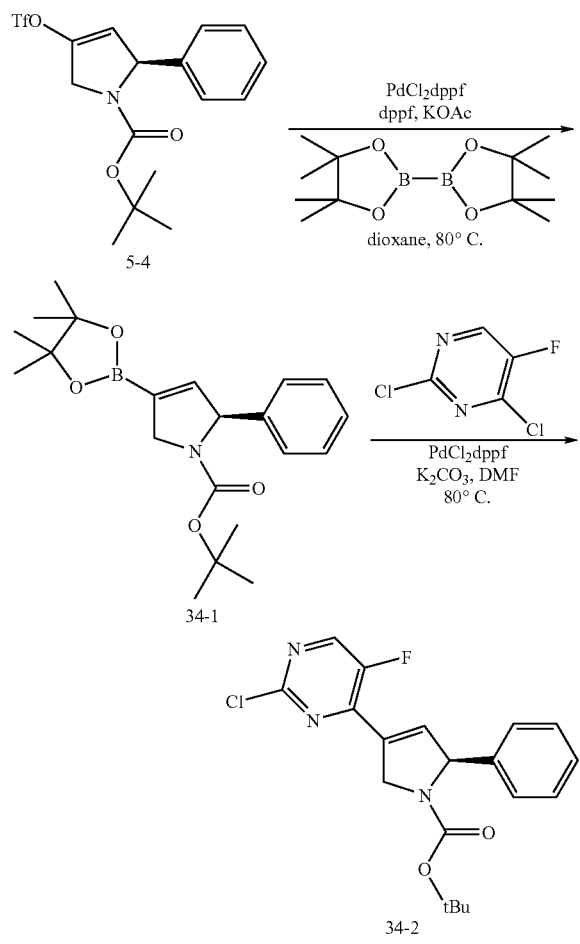

SCHEME 34

Tert-butyl (2S)-2-phenyl-4-{[(trifluoromethyl)sulfonyl]oxy}-2,5-dihydro-1H-pyrrole-1-carboxylate (5-4, 1.6 g, 4.05 mmol) was dissolved in anhydrous dioxane (5 mL) and added to a degassed and $N_2$ purged solution of pinnacol diborane (1.13 g, 4.46 mmol), potassium acetate (1.19 g, 12.2 mmol), bisdiphenylphosiphne ferrocene (0.11 g, 0.2 mmol) and Pd(Cl)2(dppf) (0.15 g, 0.2 mmol) in dioxane (50 mL). The resulting mixture was heated under $N_2$ at 80° C. for 12 h. The reaction mixture was partitioned between water (100 mL) and ethyl acetate (3×100 mL). The combined organic layers were then washed with sat. aqueous NaCl, dried over sodium sulfate, filtered, and concentrated to give tert-butyl (2S)-2-phenyl-4-(4,4,5,5-tetramethyl-1,3,2-dioxaborolan-2-yl)-2,5-dihydro-1H-pyrrole-1-carboxylate (34-1) which is used crude in the subsequent Suzuki coupling.

Crude 34-1 (0.364 g, 0.98 mmol) was dissolved in anhydrous DMF (10 mL), degassed and filled with an $N_2$ atomsphere. 2,4-dichloro-5-fluoropyrimidine (0.25 g, 1.47 mmol), potassium carbonate (0.40 g, 2.94 mmol) and $PdCl_2$(dppf) (36 mg, 0.05 mmol) were added to the solution and the mixture was stirred at 80° C. for 2.5 h. The reaction mixture was partitioned between water (3×100 mL) and ethyl acetate (100 mL). The organic layer was then washed with sat. aqueous NaCl, dried over sodium sulfate, filtered, and concentrated. The crude oil was purified using reverse phase HPLC ($CH_3CN/H_2O$/TFA 0-90% gradient) to provide tert-butyl (2S)-4-(2-chloro-5-fluoropyrimidinyl)-2-phenyl-2,5-dihydro-1H-pyrrole-1-carboxylate (34-2). $^1$H NMR (300 MHz, $CDCl_3$) δ 8.47 (d, J=2.4 Hz, 1H), 7.35 (m, 5H), 6.96 (m, 1H), 5.82 and 5.66 (m, 1H), 4.82 (m, 2H), 1.50 and 1.22 (s, 9H). LRMS: m/z (M-$CH_3$) 361.3 found, 361.3 required.

The following compounds were prepared by simple modifications of the above procedure. Unless otherwise indicated, the compounds were isolated as the free base.

| cmpd | Structure | Name | LRMS m/z (M + H) |
|---|---|---|---|
| 34-3 | 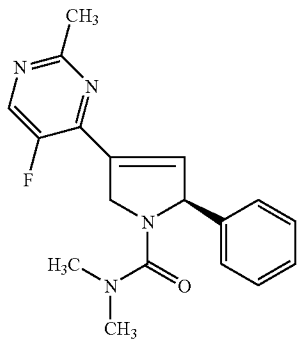 | (2S)-4-(5-fluoro-2-methylpyrimidin-4-yl)-N,N-dimethyl-2-phenyl-2,5-dihydro-1H-pyrrole-1-carboxamide | LRMS m/z (M + H) 327.3 found, 327.4 required. |
| 34-4 | 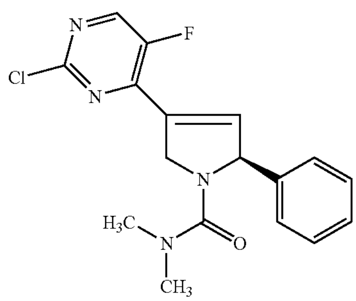 | (2S)-4-(2-chloro-5-fluoropyrimidin-4-yl)-N,N-dimethyl-2-phenyl-2,5-dihydro-1H-pyrrole-1-carboxamide | LRMS m/z (M + H) 347.7 found, 347.8 required. |
| 34-5 | 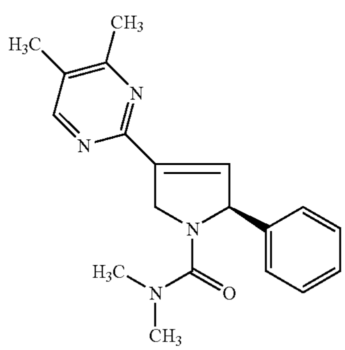 | (2S)-4-(4-chloro-5-methylpyrimidn-2-yl)-N,N-dimethyl-2-phhenyl-2,5-dihydro-1H-pyrrole-1-carboxamide | LRMS m/z (M + H) 343.7 found, 343.8 required. |
| 34-6 | 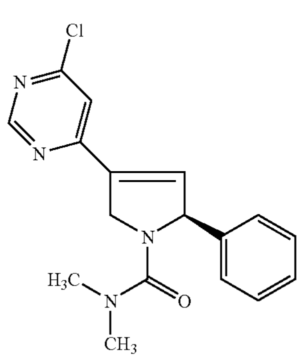 | (2S)-4-(6-chloropyrimidin-4-yl)-N,N-dimethyl-2-phenyl-2,5-dihydro-1H-pyrrole-1-carboxamide | LRMS m/z (M + H) 329.7 found, 329.8 required. |

| cmpd | Structure | Name | LRMS m/z (M + H) |
|---|---|---|---|
| 34-7 | 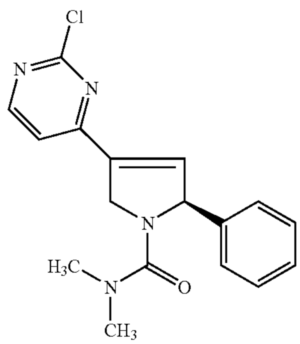 | (2S)-4-(2-chloropyrimidin-4-yl)-N,N-dimethyl-2-phenyl-2,5-dihydro-1H-pyrrole-1-carboxamide | LRMS m/z (M + H) 329.7 found, 329.8 required. |
| 34-8 | 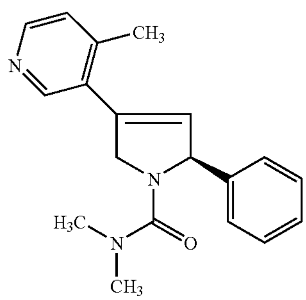 | (2S)-N,N-dimethyl-4-(4-methylpyridin-3-yl)-2-phenyl-2,5-dihydro-1H-pyrrole-1-carboxamide, issolated as the TFA salt | LRMS m/z (M + H) 308.3 found, 308.4 required. |
| 34-9 | 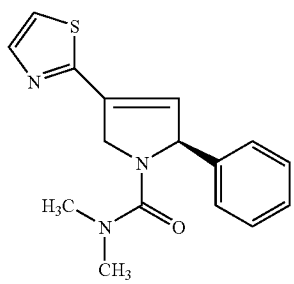 | (2S)-N,N-dimethyl-2-phenyl-4-(1,3-thiazol-2-yl)-2,5-dihydro-1H-pyrrole-1-carboxamide | LRMS m/z (M + H) 300.3 found, 300.4 required. |
| 34-10 | 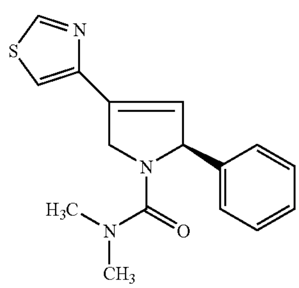 | (2S)-N,N-dimethyl-2-phenyl-4-(1,3-thiazol-4-yl)-2,5-dihydro-1H-pyrrole-1-carboxamide | LRMS m/z (M + H) 300.3 found, 300.4 required. |
| 34-11 | 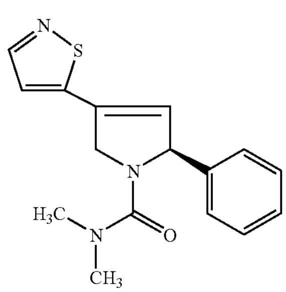 | (2S)-N,N-dimethyl-2-phenyl-4-(1,2-thiazol-5-yl)-2,5-dihydro-1H-pyrrole-1-carboxamide | LRMS m/z (M + H) 300.3 found, 300.4 required. |

SCHEME 35

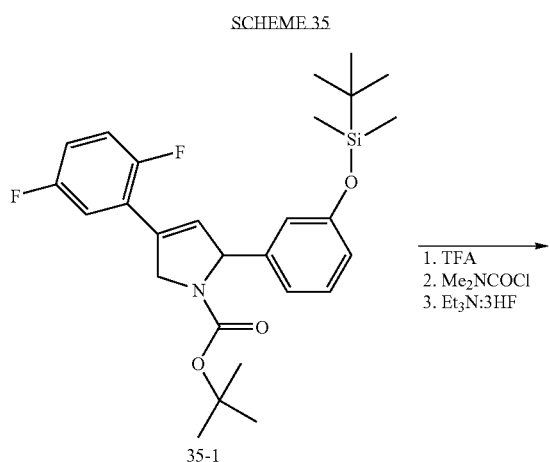

35-1

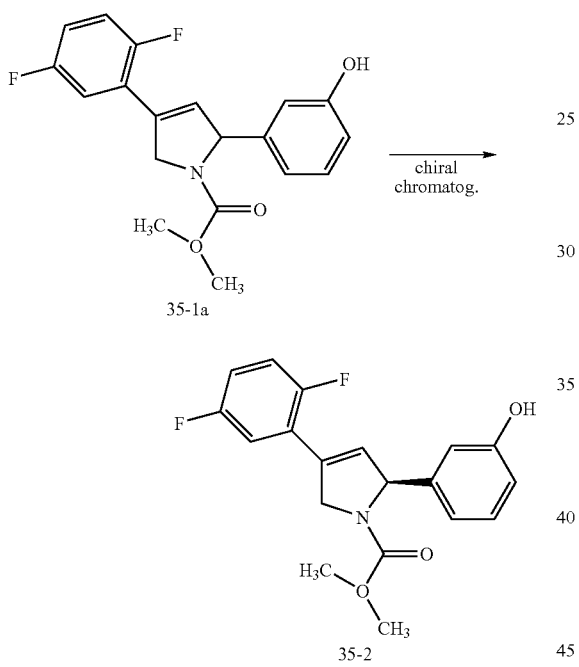

and the combined organic layers were concentrated. The desired compound crystallized from $CH_2Cl_2$ and as filtered to provide 4-(2,5-difluorophenyl)-2-(3-hydroxyphenyl)-N,N-dimethyl-2,5-dihydro-1H-pyrrole-1-carboxamide 35-1a as a white solid. $^1$H NMR (300 MHz, $CDCl_3$) δ 7.18 (t, J=7.8 Hz, 2H), 7.00 (m, 3H), 6.90 (s, 1H), 6.84 (d, J=7.7 Hz, 1H), 6.74 (dd, J=7.9, 2.4 Hz, 1H), 4.90 (dd, J=13.4, 3.7 Hz, 1H), 4.50 (d, J=13.4 Hz, 1H), 2.91 (s, 6H). LRMS: m/z (M-$CH_3$) 345.3 found, 345.4 required.

Racemic 35-1a was subjected to chiral column chromatography (ChiralPak AD column, 4.6 mm×265 mm, 10 micron, 85% hexanes/10% MeOH/5% EtOH, 60 mL/min) to resolve the enantiomers and yield (2S)-4-(2,5-difluorophenyl)-2-(3-hydroxyphenyl)-N,N-dimethyl-2,5-dihydro-1H-pyrrole-1-carboxamide 35-2.

SCHEME 35A

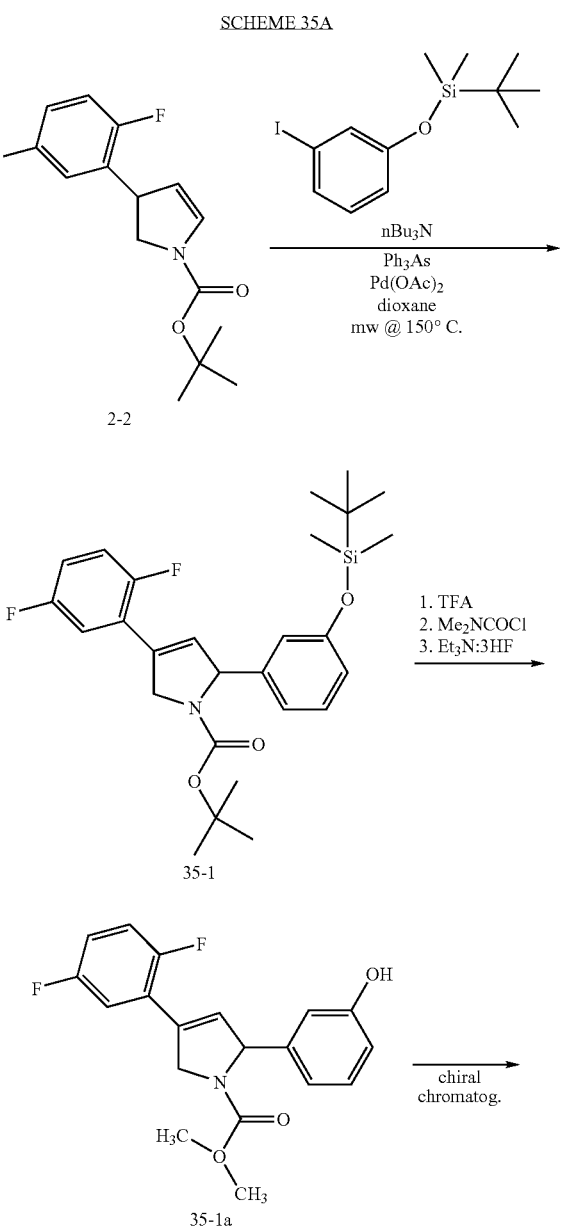

tert-Butyl 2-(3-{[tert-butyl(dimethyl)silyl]oxy}phenyl)-4-phenyl-2,5-dihydro-1H-pyrrole-1-carboxylate (35-1 [an intermediate in the preparation of compound 17-6], 1.48 g, 3.82 mmol) was dissolved in anhydrous $CH_2Cl_2$ (25 mL) and treated with TFA (5 mL) for 1 hour. The reaction mixture was partitioned between sat. aq. $NaHCO_3$ (100 mL) and ethyl acetate (3×20 mL). The combined organic layers were then washed with sat. aqueous NaCl, dried over sodium sulfate, filtered, and concentrated. The crude amine was then dissolved in $CH_2Cl_2$, and treated successively with $Et_3N$ (1.6 mL, 11.5 mmol) and dimethylcarbamoyl chloride (0.37 mL, 4.01 mmol), and the resulting solution was stirred 3.5 h at 25° C. Upon completion as judged by mass spectrometry, the reaction was concentrated, redissolved in $CH_2Cl_2$ (30 mL) and triethylamine trihydrofluroide complex (0.6 mL, 3.82 mmol) was added and the reaction stirred an additional 12 h at 25° C. Upon completion, the reaction was partitioned between $NH_4Cl$ (10 mL) and $CH_2Cl_2$ (3×10 mL), -continued

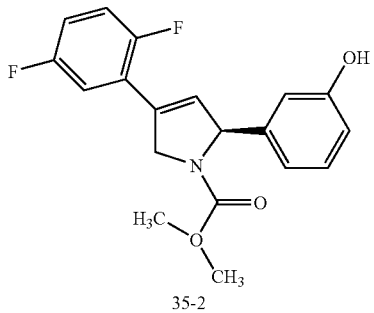
35-2

2-2 (0.5 g, 1.78 mmol) was added to a microwave vessel and combined with tert-butyldimethylsilyl-3-iodophenol (1.78 g, 5.33 mmol, 3.0 equiv), tributylamine (1.0 g, 5.33 mmol, 3.0 equiv), triphenylarsine (0.22 g, 0.71 mmol, 0.4 equiv), and palladium (II) acetate (0.08 g, 0.35 mmol, 0.2 equiv). The vessel was sealed, evacuated and charged with $N_2$. Anhydrous 1,4-dioxane (1.5 mL) was added and the heterogenous mixture was again degassed and charged with $N_2$. The vessel was placed in a Personal Chemistry microwave and heated at 150° C. for 15 minutes. Following completion, the reaction was diluted with EtOAc (50 mL) and washed sequentially with sat. aq. $NH_4Cl$ (50 mL), water (50 mL) and brine (50 mL). The combined organic extracts were dried with $MgSO_4$, concentrated and subjected to flash column chromatography ($SiO_2$, 100 g, 0-15% EtOAc/hexanes graident) to provide tert-Butyl 2-(3-{[tert-butyl(dimethyl)silyl]oxy}phenyl)-4-phenyl-2,5-dihydro-1H-pyrrole-1-carboxylate 35-1 as a clear oil: $^1$H NMR (300 MHz, $CDCl_3$) major rotamer δ 7.17 (t, J=7.6 Hz, 1H), 6.95 (m, 3H), 6.83 (d, J=7.6 Hz, 1H), 6.73 (m, 2H), 6.31 (s, 1H), 5.50 (s, 1), 4.66 (d, 2H), 1.27 (s, 9H), 0.97 (s, 9H), 0.18 (s, 6H). LRMS: m/z (M+H+) 488.5 found, 488.7 required.

tert-Butyl 2-(3-{[tert-butyl(dimethyl)silyl]oxy}phenyl)-4-phenyl-2,5-dihydro-1H-pyrrole-1-carboxylate 35-1 (1.48 g, 3.82 mmol) was reacted as described in Scheme 35 to provide the racemic 35-1a, which was subjected to chiral column chromatography (ChiralPak AD column, 4.6 mm×265 mm, 10 micron, 85% hexanes/10% MeOH/5% EtOH, 60 mL/min) to resolve the enantiomers and yield (2S)-4-(2,5-difluorophenyl)-2-(3-hydroxyphenyl)-N,N-dimethyl-2,5-dihydro-1H-pyrrole-1-carboxamide 35-2.

The following compounds were prepared by simple modifications of the above procedure or those earlier listed. Unless otherwise indicated, the compounds in the table were isolated as the free base.

| Cmpd | Structure | Name | LRMS m/z (M + H) |
|---|---|---|---|
| 35-3 | 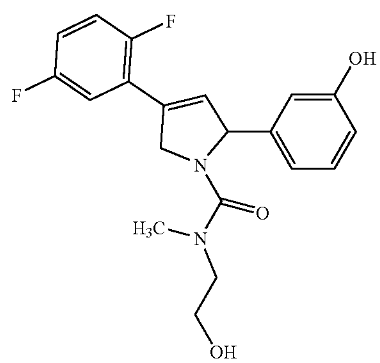 | (2S)-4-(2,5-difluorophenyl)-N-(2-hydroxyethyl)-N-methyl-2-phenyl-2,5-dihydro-1H-pyrrole-1-carboxamide | LRMS m/z (M + H) 359.3 found, 359.4 required. |
| 35-4 | 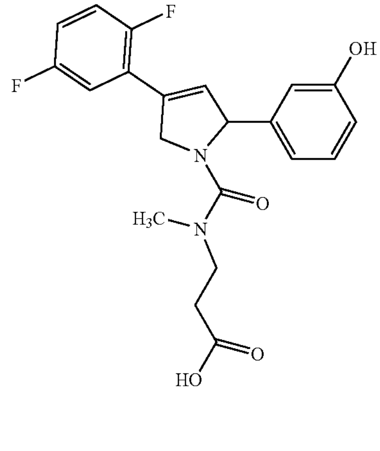 | N-{[4-(2,5-difluorophenyl)-2-(3-hydroxyphhenyl)-2,5-dihydro-1H-pyrrol-1-yl]carbonyl}-N-methyl-beta-alanine | LRMS m/z (M + H) 403.3 found, 403.4 required. |

-continued

| Cmpd | Structure | Name | LRMS m/z (M + H) |
|---|---|---|---|
| 35-5 | 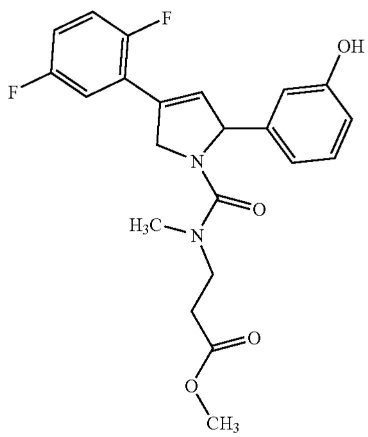 | methyl N-{[4-(2,5-difluorophenyl)-2-(3-hydroxyphenyl)-2,5-dihydro-1H-pyrrol-1-yl]carbonyl}-N-methyl-beta-alaninate | LRMS m/z (M + H) 417.3 found, 417.4 required. |
| 35-6 | 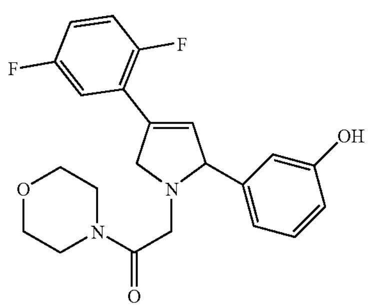 | 4-{[4-(2,5-difluorophenyl)-2-(3-hydroxyphenyl)-2,5-dihydro-1H-pyrrol-1-yl]acetyl}-morpholin-4-ium; isolated as the trifluoroacetate salt | LRMS m/z (M + H) 401.3 found, 401.4 required. |
| 35-7 | 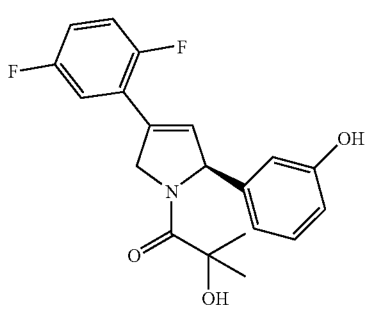 | 2-[(2S)-4-(2,5-difluorophenyl)-1-(2-hydroxy-2-methylpropanoyl)-2,5-dihydro-1H-pyrrol-2-yl]phenol | LRMS m/z (M + H) 360.3 found, 360.4 required. |
| 35-8 | 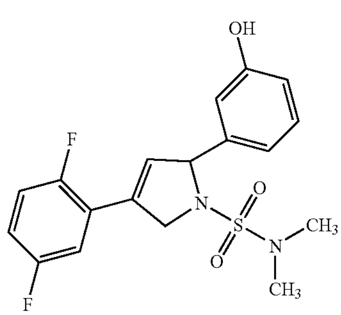 | 4-(2,5-difluorophenyl)-2-(3-hydroxyphenyl)-N,N-dimethyl-2,5-dihydro-1H-pyrrole-1-sulfonamide | LRMS m/z (M + H) 381.3 found, 381.4 required. |

-continued

| Cmpd | Structure | Name | LRMS m/z (M + H) |
|---|---|---|---|
| 35-9 | 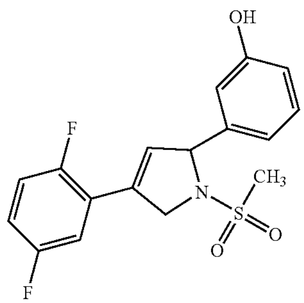 | 3-[4-(2,5-difluorophenyl)-1-(methylsulfonyl)-2,5-dihydro-1H-pyrrol-2-yl]phenol | LRMS m/z (M + H) 352.3 found, 352.4 required. |
| 35-10 | 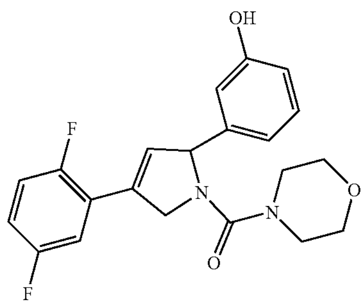 | 3-[4-(2,5-difluorophenyl)-1-(morpholin-4-ylcarbonyl)-2,5-dihydro-1H-pyrrol-2-yl]phenol | LRMS m/z (M + H) 387.3 found, 387.4 required. |
| 35-11 | 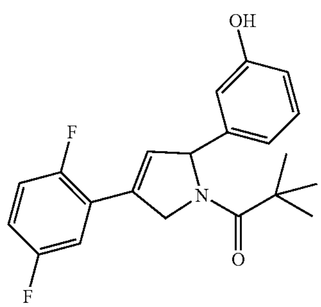 | 3-[4-(2,5-difluorophenyl)-1-(2,2-dimethylpropanoyl)-2,5-dihydro-1H-pyrrol-2-yl]phenol | LRMS m/z (M + H) 358.3 found, 358.4 required. |
| 35-12 | 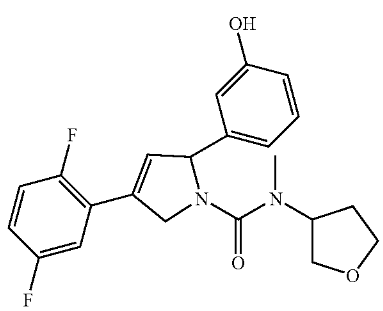 | (2S)-4-(2,5-difluorophenyl)-2-(3-hydroxyphenyl)-N-methyl-N-tetrahydrofuran-3-yl-2,5-dihydro-1H-pyrrole-1-carboxamide | LRMS m/z (M + H) 401.5 found, 401.4 required. |
| 35-13 | 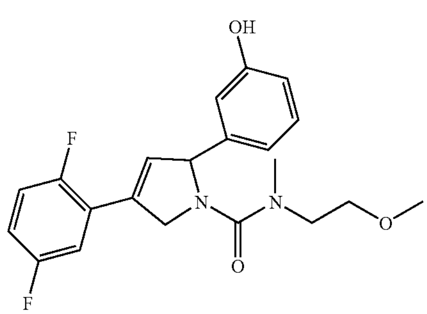 | (2S)-4-(2,5-difluorophenyl)-2-(3-hydroxyphenyl)-N-(2-methoxyethyl)-N-methyl-2,5-dihydro-1H-pyrrole-1-carboxamide | LRMS m/z (M + H) 389.4 found, 389.4 required. |

| Cmpd | Structure | Name | LRMS m/z (M + H) |
|------|-----------|------|------------------|
| 35-14 | 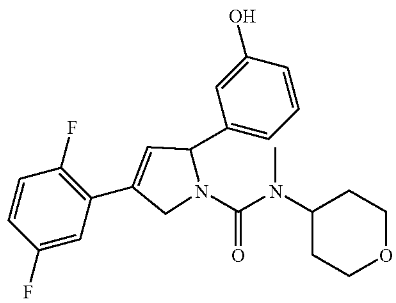 | (2S)-4-(2,5-difluorophhenyl)-2-(3-hydroxyphenyl)-N-methyl-N-tetrahydro-2H-pyran-4-yl-2,5-dihydro-1H-pyrrole-1-carboxamide | LRMS m/z (M + H) 415.4 found, 415.5 required. |
| 35-15 | 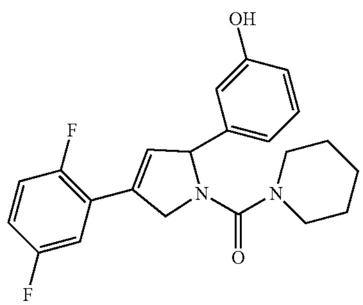 | 3-[(2S)-4-(2,5-difluorophenyl)-1-(piperidin-1-ylcarbonyl)-2,5-dihydro-1H-pyrrol-2-yl]phenol | LRMS m/z (M + H) 385.3 found, 385.4 required. |
| 35-16 | 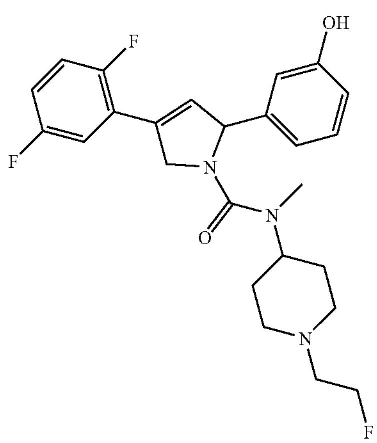 | 4-(2,5-difluoro-phenyl)-N-[1-(2-fluoroethyl)piperidin-4-yl]-2-(3-hydroxyphenyl)-N-methyl-2,5-dihydro-1H-pyrrole-1-carboxamide | LRMS m/z (M + H) 460.4 found, 460.6 required. |
| 35-17 | 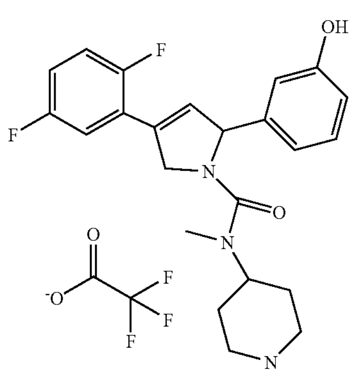 | 4-(2,5-difluoro-phenyl)-2-(3-hydroxyphenyl)-N-methyl-N-piperidin-4-yl-2,5-dihydro-1H-pyrrole-1-carboxamide | LRMS m/z (M + H) 415.2 found, 415.5 required. |

-continued

| Cmpd | Structure | Name | LRMS m/z (M + H) |
|---|---|---|---|
| 35-18 | 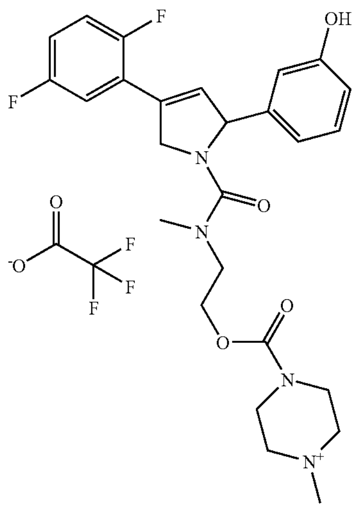 | 2-[{[4-(2,5-difluorophenyl)-2-(3-hydroxyphenyl)-2,5-dihydro-1H-pyrrol-1-yl]carbonyl}(methyl)amino]ethyl-4-methylpiperazine-1-carboxylate | LRMS m/z (M + H) 501.5 found, 510.6 required. |
| 35-19 | 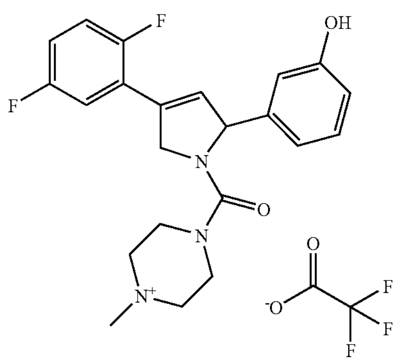 | 3-{4-(2,5-difluorophenyl)-1-[(4-methylpiperazin-1-yl)carbonyl]-2,5-dihydro-1H-pyrrol-2-yl}phenol | LRMS m/z (M + H) 400.4 found, 400.4 required. |
| 35-20 | 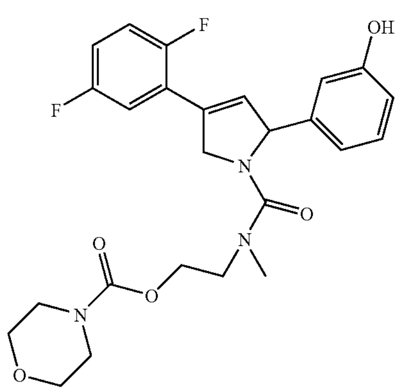 | 2-[{[4-(2,5-difluorophenyl)-2-(3-hydroxyphenyl)-2,5-dihydro-1H-pyrrol-1-yl]carbonyl}(methyl)amino]ethyl morpholine-4-carboxylate | LRMS m/z (M + H) 488.5 found, 488.5 required. |

| Cmpd | Structure | Name | LRMS m/z (M + H) |
|---|---|---|---|
| 35-21 | 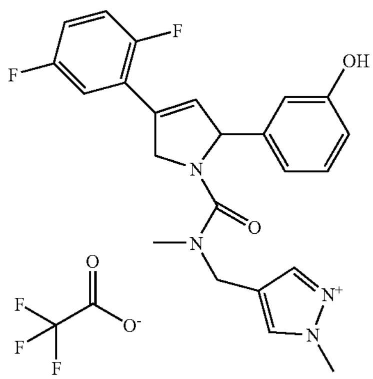 | 4-(2,5-difluorophenyl)-2-(3-hydroxyphenyl)-N-methyl-N-[(1-methyl-1H-pyrazol-4-yl)methyl]-2,5-dihydro-1H-pyrrole-1-carboxamide | LRMS m/z (M + H) 425.5 found, 425.4 required. |
| 35-22 | 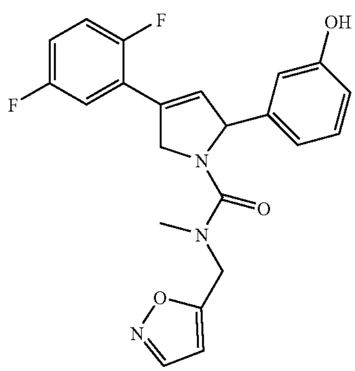 | 4-(2,5-difluorophenyl)-2-(3-hydroxyphenyl)-N-(isoxazol-5-ylmethyl)-N-methyl-2,5-dihydro-1H-pyrrole-1-carboxamide | LRMS m/z (M + H) 412.4 found, 412.4 required. |
| 35-23 | 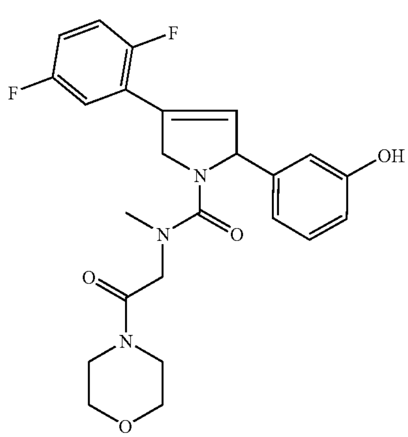 | 4-(2,5-difluoro-phenyl)-2,5-dihydro-2-(3-hydroxy-phenyl)-N-methyl-N-[2-(4-morpholinyl)-2-oxoethyl]-H-pyrrole-1-carboxamide | LRMS m/z (M + H) 458.5 found, 458.5 required. |

-continued

| Cmpd | Structure | Name | LRMS m/z (M + H) |
|---|---|---|---|
| 35-24 | 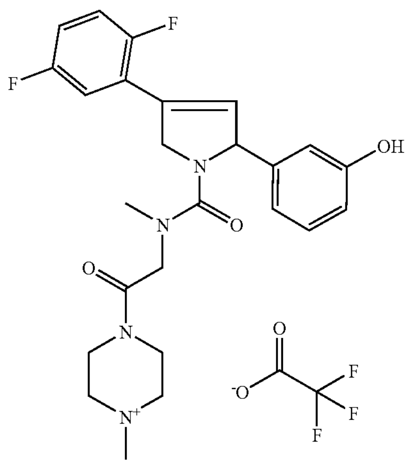 | 4-(2,5-difluoro-phenyl)-2,5-dihydro-2-(3-hydroxy-phenyl)-N-methyl-N-[2-(4-methyl-1-piperazinyl)-2-oxoethyl]-H-pyrrole-1-carboxamide | LRMS m/z (M + H) 471.6 found, 471.5 required. |
| 35-25 | 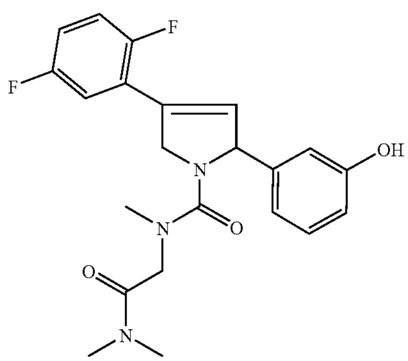 | 2-[{[4-(2,5-difluoro-phenyl)-2-(3-hydroxyphenyl)-2,5-dihydro-1H-pyrrol-1-yl]carbonyl}-(methyl)amino]ethyl dimethylamino-carboxylate | LRMS m/z (M + H) 416.4 found, 416.4 required. |
| 35-26 | 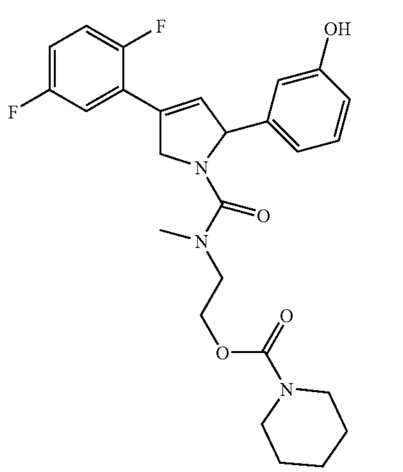 | 2-[{[4-(2,5-difluorophenyl)-2-(3-hydroxyphenyl)-2,5-dihydro-1H-pyrrol-1-yl]carbonyl}(methyl)amino]ethyl piperidin-1-carboxylate | LRMS m/z (M + H) 486.6 found, 486.5 required. |

-continued

| Cmpd | Structure | Name | LRMS m/z (M + H) |
|---|---|---|---|
| 35-27 | 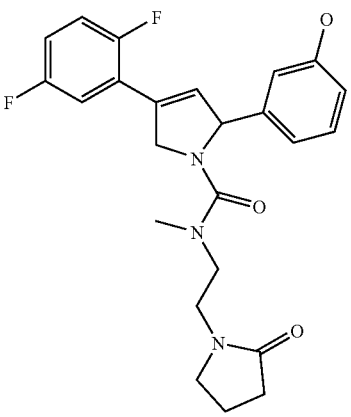 | 4-(2,5-difluorophenyl)-2-(3-hydroxyphenyl)-N-methyl-N-[2-(2-oxopyrrolidin-1-yl)ethyl]-2,5-dihydro-1H-pyrrole-1-carboxamide | LRMS m/z (MN + H) 442.5 found, 442.5 required. |
| 35-28 | 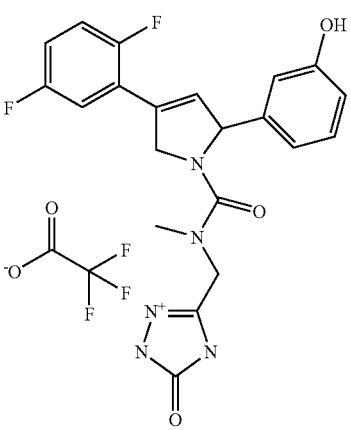 | 4-(2,5-difluorophenyl)-2-(3-hydroxyphenyl)-N-methyl-N-[(5-oxo-4,5-dihydro-1H-1,2,4-triazol-3-yl)methyl]-2,5-dihydro-1H-pyrrole-1-carboxamide | LRMS m/z (M + H) 428.4 found, 428.4 required. |
| 35-29 | 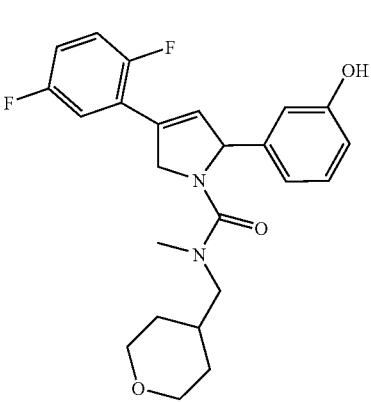 | 4-(2,5-difluorophenyl)-2-(3-hydroxyphenyl)-N-methyl-N-(tetrahydro-2H-pyran-4-ylmethyl)-2,5-dihydro-1H-pyrrole-1-carboxamide | LRMS m/z (M + H) 429.5 found, 429.5 required. |

-continued

| Cmpd | Structure | Name | LRMS m/z (M + H) |
|---|---|---|---|
| 35-30 | 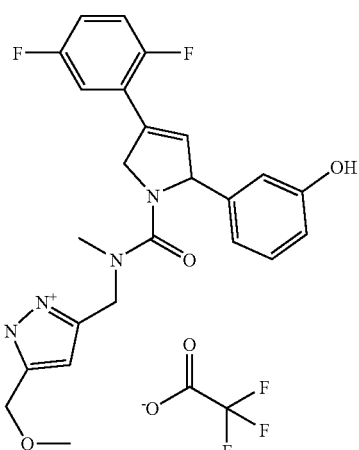 | 4-(2,5-difluorophenyl)-2-(3-hydroxyphenyl)-N-{[5-(methoxymethyl)-1H-pyrazol-3-yl]methyl}-N-methyl-2,5-dihydro-1H-pyrrole-1-carboxamide | LRMS m/z (M + H) 455.5 found, 455.5 required. |
| 35-31 | 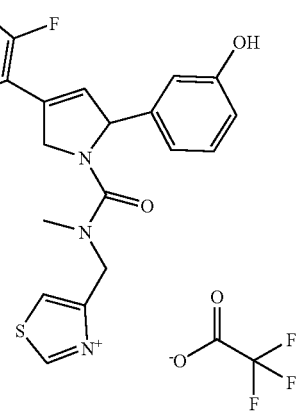 | 4-(2,5-difluorophenyl)-2-(3-hydroxyphenyl)-N-methyl-N-(1,3-thiazol-4-ylmethyl)-2,5-dihydro-1H-pyrrole-1-carboxamide | LRMS m/z (M + H) 428.4 found, 428.5 required. |
| 35-32 | 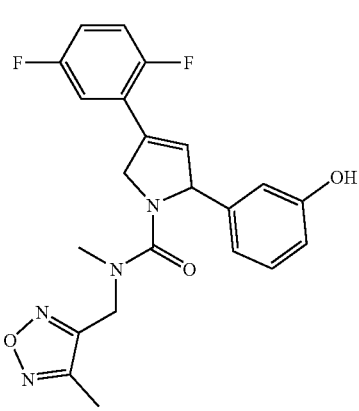 | 4-(2,5-difluorophenyl)-2-(3-hydroxyphenyl)-N-methyl-N-[(4-methyl-1,2,5-oxadiazol-3-yl)methyl]-2,5-dihydro-1H-pyrrole-1-carboxamide | LRMS m/z (M + H) 427.4 found, 427.4 required. |

-continued

| Cmpd | Structure | Name | LRMS m/z (M + H) |
|---|---|---|---|
| 35-33 | 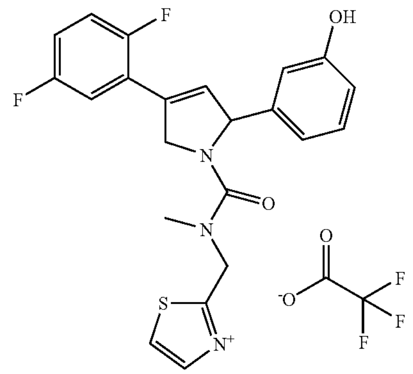 | 4-(2,5-difluorophenyl)-2-(3-hydroxyphenyl)-N-methyl-N-(1,3-thiazol-2-ylmethyl)-2,5-dihydro-1H-pyrrole-1-carboxamide | LRMS m/z (M + H) 428.4 found, 428.5 required. |
| 35-34 | 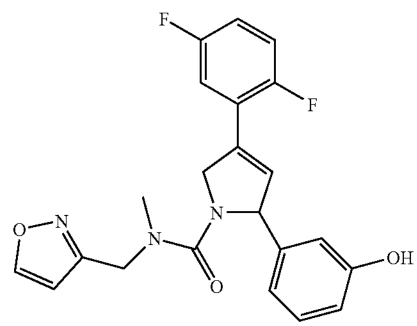 | 4-(2,5-difluorophenyl)-2-(3-hydroxyphenyl)-N-(isoxazol-3-ylmethyl)-N-methyl-2,5-dihydro-1H-pyrrole-1-carboxamide | LRMS m/z (M + H) 412.4 found, 412.4 required. |
| 35-35 | 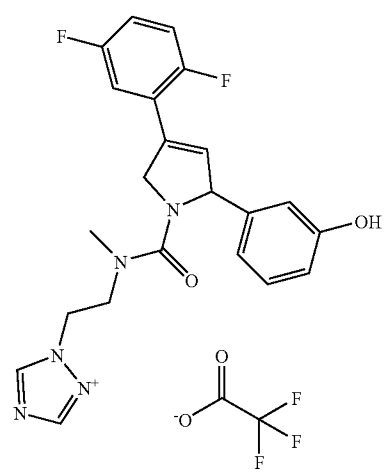 | 4-(2,5-difluorophenyl)-2-(3-hydroxyphenyl)-N-methyl-N-[2-(1H-1,2,4-triazol-1-yl)ethyl]-2,5-dihydro-1H-pyrrole-1-carboxamide | LRMS m/z (M + H) 426.4 found, 426.4 required. |
| 35-36 | 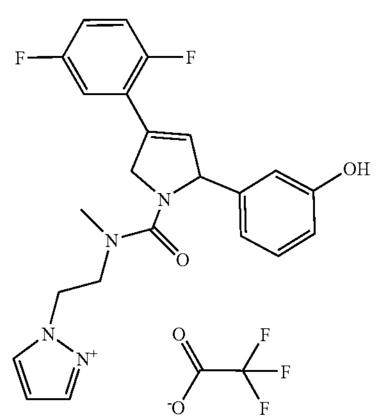 | 4-(2,5-difluorophenyl)-2-(3-hydroxyphenyl)-N-methyl-N-[2-(1H-pyrazol-1-yl)ethyl]-2,5-dihydro-1H-pyrrole-1-carboxamide | LRMS m/z (M + H) 425.4 found, 425.5 required. |

| Cmpd | Structure | Name | LRMS m/z (M + H) |
|---|---|---|---|
| 35-37 | 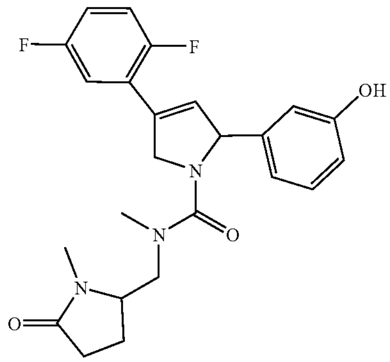 | 4-(2,5-difluorophenyl)-2-(3-hydroxyphenyl)-N-methyl-N-[(1-methyl-5-oxopyrrolidin-2-yl)methyl]-2,5-dihydro-1H-pyrrole-1-carboxamide | LRMS m/z (M + H) 442.4 found, 442.5 required. |
| 35-38 | 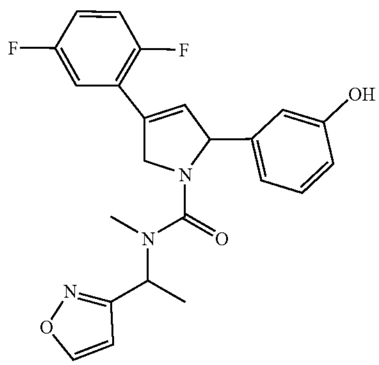 | 4-(2,5-difluorophenyl)-2-(3-hydroxyphenyl)-N-(1-isoxazol-3-ylethyl)-N-methyl-2,5-dihydro-1H-pyrrole-1-carboxamide | LRMS m/z (M + H) 426.4 found, 426.4 required. |
| 35-39 | 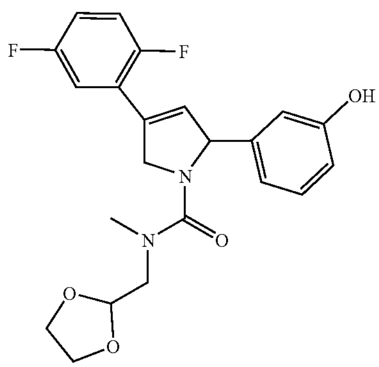 | 4-(2,5-difluorophenyl)-N-(1,3-dioxolan-2-ylmethyl)-2-(3-hydroxyphenyl)-N-methyl-2,5-dihydro-1H-pyrrole-1-carboxamide | LRMS m/z (M + H) 417.4 found, 417.4 required. |
| 35-40 | 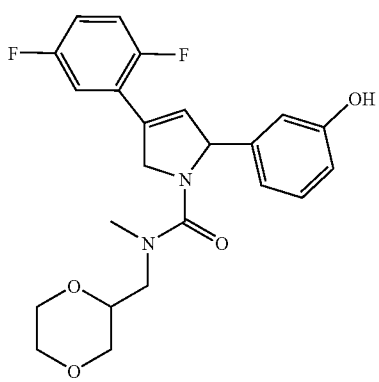 | 4-(2,5-difluorophenyl)-N-(1,4-dioxan-2-ylmethyl)-2-(3-hydroxyphenyl)-N-methyl-2,5-dihydro-1H-pyrrole-1-carboxamide | LRMS m/z (M + H) 431.5 found, 431.5 required. |

| Cmpd | Structure | Name | LRMS m/z (M + H) |
|---|---|---|---|
| 35-41 | 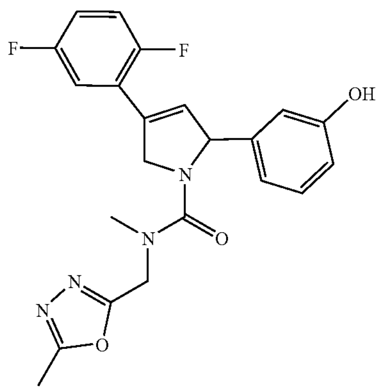 | 4-(2,5-difluorophenyl)-2-(3-hydroxyphenyl)-N-methyl-N-[(5-methyl-1,3,4-oxadiazol-2-yl)methyl]-2,5-dihydro-1H-pyrrole-1-carboxamide | LRMS m/z (M + H) 427.4 found, 427.4 required. |
| 35-42 | 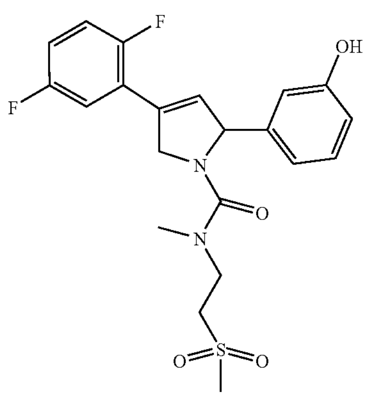 | 4-(2,5-difluorophenyl)-2-(3-hydroxyphenyl)-N-methyl-N-[2-(methylsulfonyl)-ethyl]2,5-dihydro-1H-pyrrole-1-carboxamide | LRMS m/z (M + H) 437.4 found, 437.5 required. |
| 35-43 | 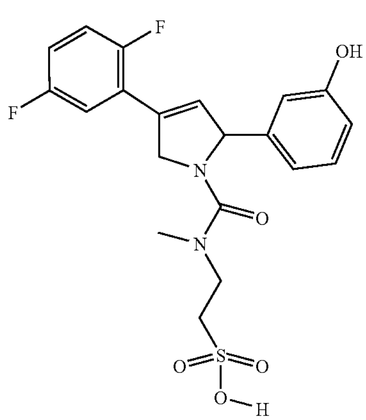 | 2-[{[4-(2,5-difluoro-phenyl)-2-(3-hydroxyphenyl)-2,5-dihydro-1H-pyrrol-1-yl]-carbonyl}-(methyl)amino]-ethane sulfonic acid | LRMS m/z (M + H) 439.4 found, 4395 required. |

SCHEME 36

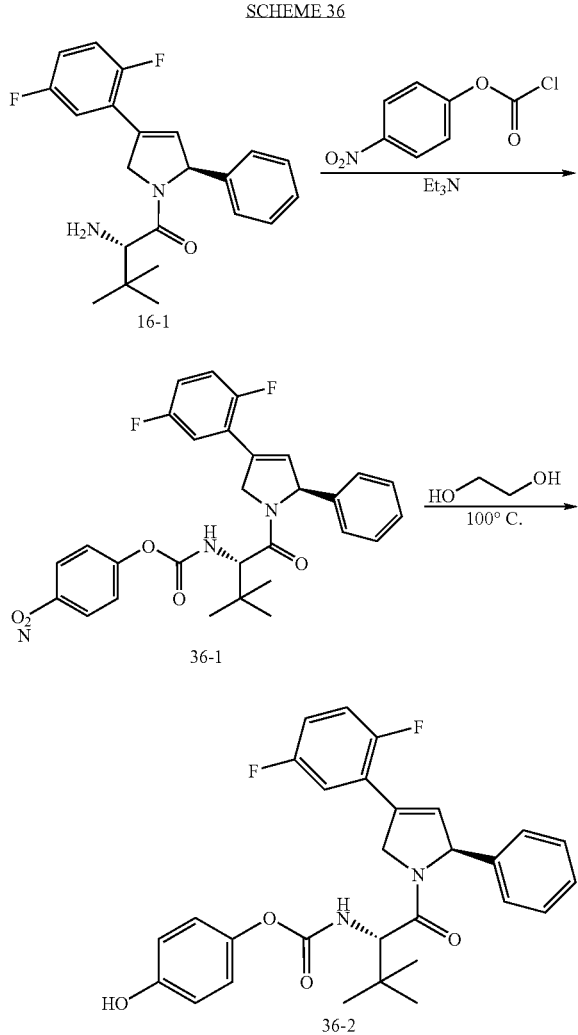

Step 1: 4-nitrophenyl (1S)-1-{[(2S)-4-(2,5-difluorophenyl)-2-phenyl-2,5-dihydro-1H-pyrrol-1-yl]carbonyl}-2,2-dimethylpropylcarbamate (36-1)

A solution of 4-nitrophenyl chloroformate (300 mg, 1.49 mmol, 1.2 equiv) in THF (10 mL) was added drop wise to a stirred solution of (1S)-1-{[(2S)-4-(2,5-difluorophenyl)-2-phenyl-2,5-dihydro-1H-pyrrol-1-yl]-carbonyl}-2,2-dimethylpropylamine (16-1, 460 mg, 1.24 mmol, 1.0 equiv) and triethylamine (151 mg, 1.49 mmol, 1.2 equiv) in THF (10 mL) at 23° C. After 1 hr the reaction was filtered and the filtrate concentrated to a pale yellow gum which was purified by flash chromatography on silica gel. Elution with dichloromethane to 3% ethyl acetate/dichloromethane provided 2-hydroxyethyl (1S)-1-{[(2S)-4-(2,5-difluorophenyl)-2-phenyl-2,5-dihydro-1H-pyrrol-1-yl]carbonyl}-2,2-dimethylpropylcarbamate (36-1) as a colorless foam. LRMS m/z (M+H) 536.5 found, 535.2 required.

Step 2: 2-hydroxyethyl (1S)-1-{[(2S)-4-(2,5-difluorophenyl)-2-phenyl-2,5-dihydro-1H-pyrrol-1-yl]carbonyl}-2,2-dimethylpropylcarbamate (36-2)

A mixture of 4-nitrophenyl (1S)-1-{[(2S)-4-(2,5-difluorophenyl)-2-phenyl-2,5-dihydro-1H-pyrrol-1-yl]carbonyl}-2,2-dimethylpropylcarbamate (36-1, 500 mg, 0.93 mmol, 1.0 equiv) and ethylene glycol (3 mL, excess) was heated at 100° C. for 1 h. The reaction mixture was cooled and partitioned between ethyl acetate and water. The organic layer was washed with brine, dried over magnesium sulfate and concentrated. The residue was purified by flash chromatography on silica gel. Elution with 20% ethyl acetate/dichloromethane to 50% ethyl acetate/dichloromethane gave 2-hydroxyethyl (1S)-1-{[(2S)-4-(2,5-difluorophenyl)-2-phenyl-2,5-dihydro-1H-pyrrol-1-yl]carbonyl}-2,2-dimethylpropylcarbamate (36-2) as a colorless foam. $^1$H NMR (500 MD, CDCl$_3$) major rotamer: δ 7.38-7.21 (m, 5H), 7.11-6.94 (m, 3H), 6.40 (s, 1H), 5.92 (m, 1H), 5.51 (m, 1H), 5.07 (d, 1H, J=13 Hz), 4.91 (m, 1H), 4.37 (d, 1H, J=10 Hz), 4.20 (m, 2H), 3.81 (t, 2H, J=4.5 Hz), 3.64 (t, 1H, J=4 Hz),) 0.91 (s, 9H). LRMS m/z (M+H) 459.3 found, 459.2 required.

The following compounds were prepared by simple modifications of the above procedures.

| Cmpd | Structure | Name | LRMS m/z (M + H) |
|---|---|---|---|
| 36-3 | 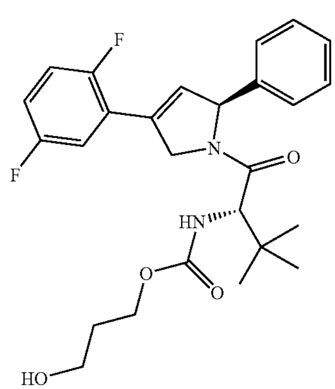 | 3-hydroxypropyl (1S)-1-{[(2S)-4-(2,5-difluorophenyl)-2-phhenyl-2,5-dihydro-1H-pyrrol-1-yl]carbonyl}-2,2-dimethylpropylcarbamate | LRMS m/z (M + H) 473.5 found, 472.2 required. |

-continued

| Cmpd | Structure | Name | LRMS m/z (M + H) |
|---|---|---|---|
| 36-4 | 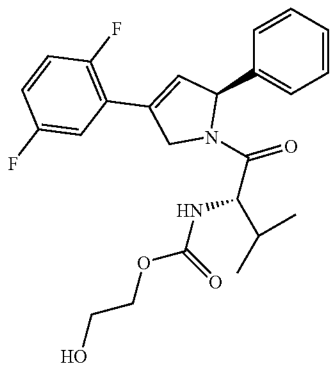 | 2-hydroxyethyl {(1S)-1-isopropyl-2-[(2S)-4-(2,5-difluorophenyl)-2-phenyl-2,5-dihydro-1H-pyrrol-1-yl]-2-oxoethyl}carbamate | LRMS m/z (M + H) 445.4 found, 445.2 required |
| 36-5 | 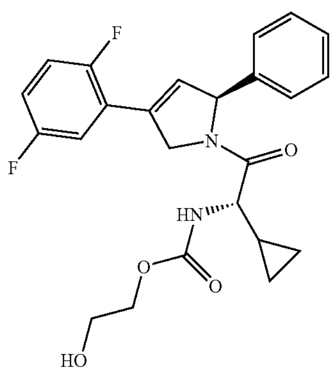 | 2-hydroxyethyl {(1S)-1-cyclopropyl-2-[(2S)-4-(2,5-difluorophenyl)-2-phenyl-2,5-dihydro-1H-pyrrol-1-yl]-2-oxoethyl}carbamate | LRMS m/z (M + H) 443.4 found, 443.2 required |
| 36-6 | 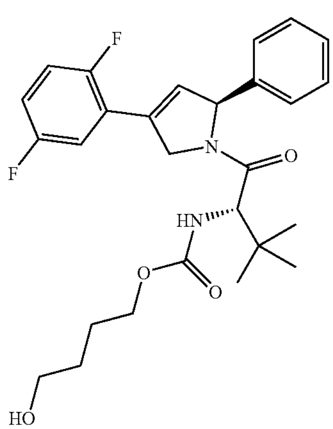 | 4-hydroxybutyl (1S)-1-{[(2S)-4-(2,5-difluorophenyl)-2-phenyl-2,5-dihydro-1H-pyrrol-1-yl]carbonyl}-2,2-dimethylpropylcarbamte | LRMS m/z (M + H) 487.4 found, 486.2 required |

SCHEME 37

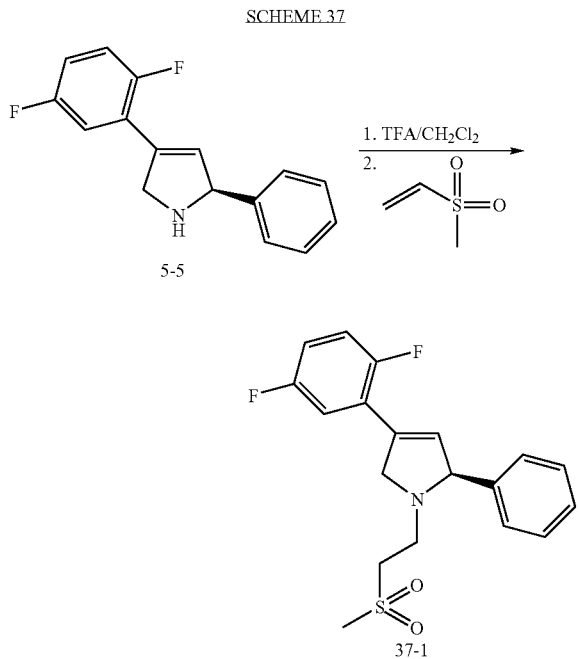

(2S)-4-(2,5-difluorophenyl)-1-[2-(methylsulfonyl)ethyl]-2-phenyl-2,5-dihydro-1H-pyrrole (37-1)

A solution of tert-butyl (2S)-4-(2,5-difluorophenyl)-2-phenyl-2,5-dihydro-1H-pyrrole-1-carboxylate (5-5, 100 mg, 0.280 mmol, 1 equiv) in a 4:1 mixture of dichloromethane and trifluoroacetic acid (20 mL) was stirred for 30 min, then concentrated. The residue was partitioned between saturated aqueous sodium bicarbonate solution and ethyl acetate (2×50 mL). The combined organic layers were dried over sodium sulfate and were concentrated. A solution of the residue and methyl vinyl sulfone (0.025 mL, 0.28 mmol, 1.0 equiv) in a 1:1 mixture of dioxane and ethanol (5 mL) was stirred at 23° C. for 16 h. Additional methyl vinyl sulfone (0.025 mL, 0.28 mmol, 1.0 equiv) was added and stirring was continued for 4 h. The reaction mixture was concentrated and the residue was purified by flash column chromatography (hexanes initially, grading to 50% EtOAc in hexanes) to give (2S)-4-(2,5-difluorophenyl)-1-[2-(methylsulfonyl)ethyl]-2-phenyl-2,5-dihydro-1H-pyrrole (37-1) as a white solid. $^1$H NMR (300 MHz, CDCl$_3$) δ 7.38-7.28 (m, 5H), 7.09-6.89 (m, 3H), 6.28 (br s, 1H), 4.69 (td, 1H, J=4.9, 1.8 Hz), 4.34 (dd, 1H, J=12.5, 4.9 Hz), 3.84 (ddd, 1H, J=13.0, 4.8, 1.7 Hz), 3.36-3.02 (m, 4H), 2.79 (s, 3H). LRMS m/z (M+H) 364.3 found, 364.1 required.

The following compounds were prepared by simple modifications of the above procedure. Compounds 37-4 and 37-5 were isolated as TFA salts following purification by reverse-phase LC (H$_2$O/CH$_3$CN gradient w/0.1% TFA present).

| Cmpd | Structure | Name | LRMS m/z (M + H) |
|---|---|---|---|
| 37-2 | 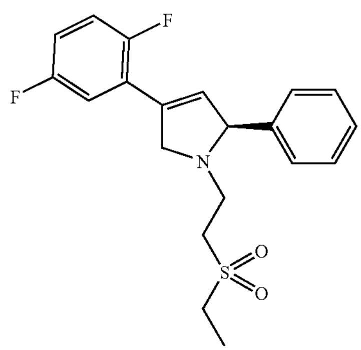 | (2S)-4-(2,5-difluorophhenyl)-1-[2-(ethylsulfonyl)ethyl]-2-phenyl-2,5-dihydro-1H-pyrrole | LRMS m/z (M + H) 378.2 found, 378.1 required. |
| 37-3 | 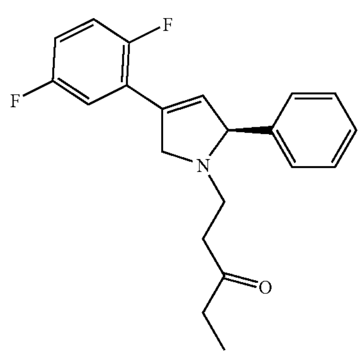 | 1-[(2S)-4-(2,5-difluorophenyl)-2-phenyl-2,5-dihydro-1H-pyrrol-1-yl]pentan-3-one | LRMS m/z (M + H) 342.4 found, 342.2 required. |

-continued

| Cmpd | Structure | Name | LRMS m/z (M + H) |
|---|---|---|---|
| 37-4 | 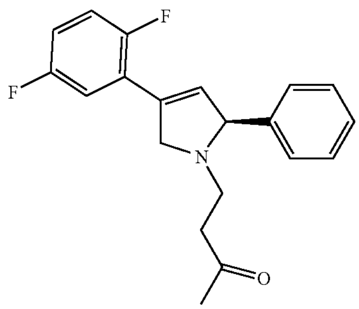 | 4-[(2S)-4-(2,5-difluorophenyl)-2-phenyl-2,5-dihydro-1H-pyrrol-1-yl]butan-2-one | LRMS m/z (M + H) 328.2 found, 328.1 required. |
| 37-5 | 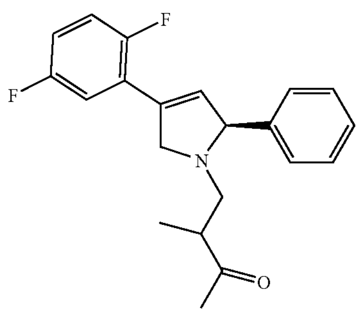 | 4-[(2S)-4-(2,5-difluorophenyl)-2-phenyl-2,5-dihydro-1H-pyrrol-1-yl]-3-methylbutan-2-one | LRMS m/z (M + H) 342.3 found, 342.2 required. |
| 37-6 | 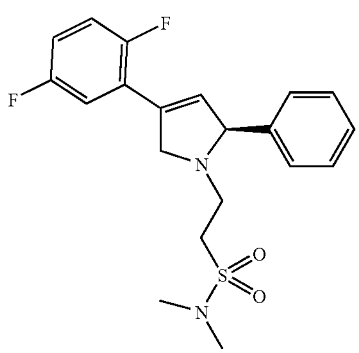 | 2-[(2S)-4-(2,5-difluorophenyl)-2-phenyl-2,5-dihydro-1H-pyrrol-1-yl]-N,N-dimethylethanesulfonamide | LRMS m/z (M + H) 393.3 found, 393.1 required. |
| 37-7 | 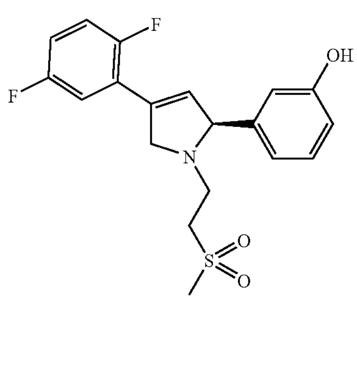 | 3-{(2S)-4-(2,5-difluorophenyl)-1-[2-(methylsulfonyl)ethyl]-2,5-dihydro-1H-pyrrol-2-yl}phenol | LRMS m/z (M + H) 380.2 found, 380.4 required. |

| Cmpd | Structure | Name | LRMS m/z (M + H) |
|---|---|---|---|
| 37-8 | 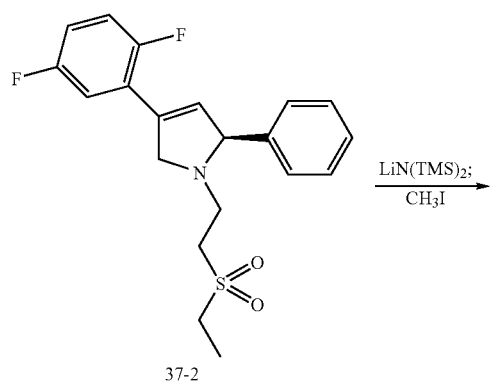 | methyl 3-[(2S)-4-(2,5-difluorophenyl)-2-phenyl-2,5-dihydro-1H-pyrrol-1-yl]propanoate | LRMS m/z (M + H) 344.3 found, 344.1 required. |

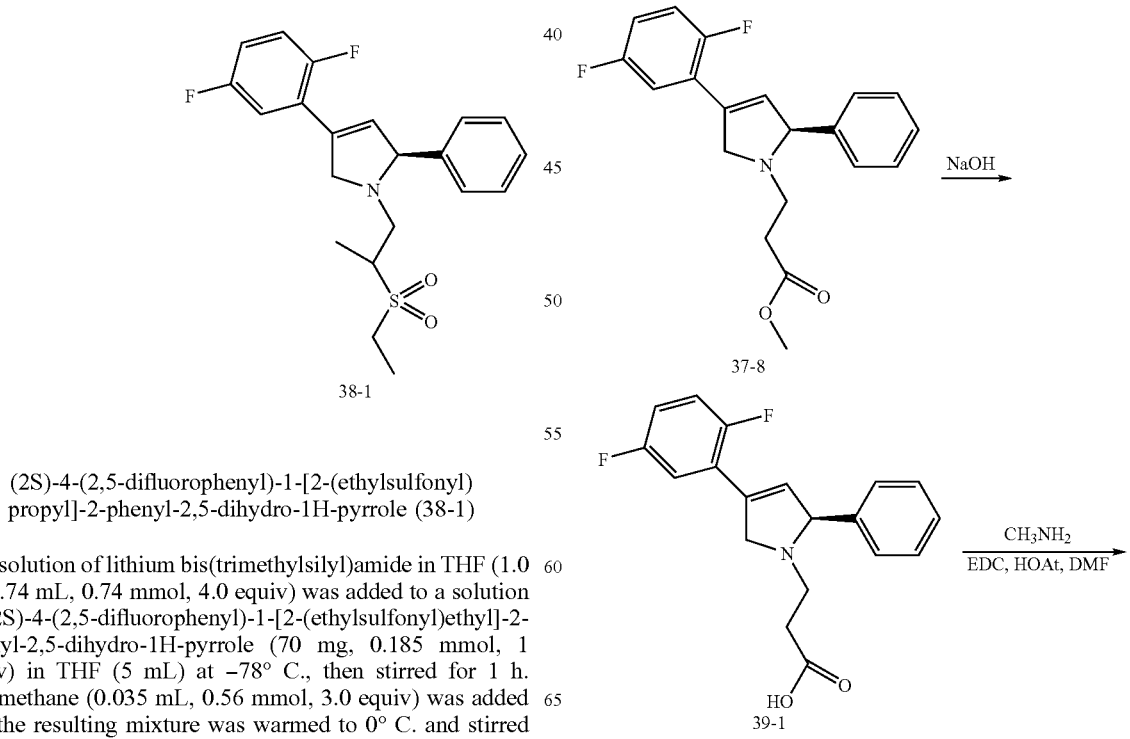

(2S)-4-(2,5-difluorophenyl)-1-[2-(ethylsulfonyl)propyl]-2-phenyl-2,5-dihydro-1H-pyrrole (38-1)

A solution of lithium bis(trimethylsilyl)amide in THF (1.0 M, 0.74 mL, 0.74 mmol, 4.0 equiv) was added to a solution of (2S)-4-(2,5-difluorophenyl)-1-[2-(ethylsulfonyl)ethyl]-2-phenyl-2,5-dihydro-1H-pyrrole (70 mg, 0.185 mmol, 1 equiv) in THF (5 mL) at −78° C., then stirred for 1 h. Iodomethane (0.035 mL, 0.56 mmol, 3.0 equiv) was added and the resulting mixture was warmed to 0° C. and stirred for 30 minutes. The mixture was then partitioned between saturated potassium bisulfate solution and ethyl acetate (2×40 mL). The combined organic layers were dried over magnesium sulfate and were concentrated. The residue was purified by flash column chromatography ($CH_2Cl_2$ initially, grading to 4% EtOAc in $CH_2Cl_2$) to give $(2S)_4$ (2,5-difluorophenyl)-1-[2-(ethylsulfonyl)propyl]-2-phenyl-2,5-dihydro-1H-pyrrole (38-1) as a single diastereomer (colorless oil). $^1H$ NMR (500 M, $CDCl_3$) δ 7.38-7.28 (m, 5H), 7.08-6.92 (m, 3H), 6.29 (br s, 1H), 4.66 (br s), 4.37 (dd, 1H, J=12.5, 4.9 Hz), 3.84 (br d, 1H, J=13.0 Hz), 3.36 (dd, 1H, J=13.7, 7.1 Hz), 2.99 (m, 1H), 2.84 (m, 2H), 2.77 (dd, 1H, J=13.9, 7.3 Hz), 1.31 (d, 3H, J=7.1 Hz), 1.19 (t, 3H, J=7.6 Hz). LRMS m/z (M+H) 392.4 found, 392.1 required.

-continued

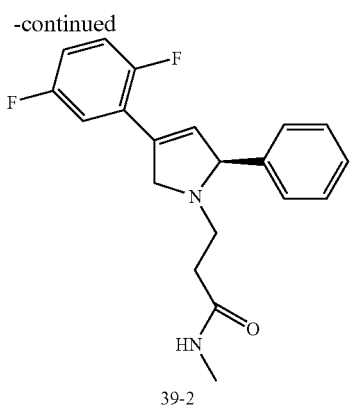

39-2

Step 1: 3-[(2S)-4-(2,5-difluorophenyl)-2-phenyl-2,5-dihydro-1H-pyrrol-1-yl]propanoic acid (39-1)

A solution of methyl 3-[(2S)-4-(2,5-difluorophenyl)-2-phenyl-2,5-dihydro-1H-pyrrol-1-yl]propanoate (37-8, 200 mg, 0.582 mmol, 1 equiv) and sodium hydroxide (1N, 1.16 mL, 1.16 mmol, 2.00 equiv) in t-BuOH (5 mL) was heated at 50° C. for 2 h. The reaction mixture was concentrated and the residue was partitioned between brine made acidic with aqueous 1 N HCL solution (1.2 mL) and ethyl acetate (2×40 mL). The combined organic layers were dried over sodium sulfate and concentrated to give 3-[(2S)-4-(2,5-difluorophenyl)-2-phenyl-2,5-dihydro-1H-pyrrol-1-yl]propanoic acid (39-1) as a white foam. LRMS m/z (M+H) 330.1 found, 330.3 required.

Step 2: 3-[(2S)-4-(2,5-difluorophenyl)-2-phenyl-2,5-dihydro-1H-pyrrol-1-yl]-N-methylpropanamide (39-2)

A solution of 3-[(2S)-4-(2,5-difluorophenyl)-2-phenyl-2,5-dihydro-1H-pyrrol-1-yl]propanoic acid (39-1, 50 mg, 0.15 mmol, 1 equiv), methylamine (2M, 1.0 mL, 2.0 mmol, 13 equiv), 1-(3-dimethylaminopropyl)-3-ethylcarbodiimide hydrochloride EDC, 90 mg, 0.47 mmol, 3.0 equiv), 1-hydroxy-7-azabenzotriazole (62 mg, 0.47 mmol, 3.0 equiv) and triethylamine (0.32 mL, 2.3 mmol, 15 equiv) in DMF (3 mL) was heated in a sealable tube at 60° C. for 20 h. The reaction mixture was partitioned between saturated aqueous sodium bicarbonate solution (50 mL) and ethyl acetate (2×50 mL). The organic layer was dried over sodium sulfate and concentrated. The residue was purified by reverse-phase LC ($H_2O/CH_3CN$ gradient w/0.1% TPA present) to provide 3-[(2S)-4-(2,5-difluorophenyl)-2-phenyl-2,5-dihydro-1H-pyrrol-1-yl]-N-methylpropanamide (39-2) as a colorless oil (TFA salt). $^1$H NMR (300 MHz, $CD_3OD$) δ 7.58-7.52 (m, 5H), 7.44-7.18 (m, 3H), 6.60 (br s, 1H), 5.72 (br s, 1H), 4.86 (br m, 1H), 4.64 (br m), 3.70 (br m, 2H), 2.72 (m, 2H), 2.68 (s, 3H). LRMS m/z (M+H) 343.3 found, 343.2 required.

The following compounds were prepared by simple modifications of the above procedure. All compounds were isolated as TFA salts.

| Cmpd | Structure | Name | LRMS m/z (M + H) |
|---|---|---|---|
| 39-3 | 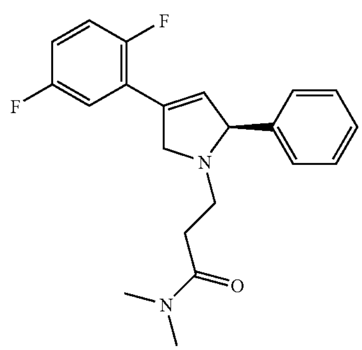 | 3-[(2S)-4-(2,5-difluorophenyl)-2-phenyl-2,5-dihydro-1H-pyrrol-1-yl]-N,N-dimethylpropanamide | LRMS m/z (M + H) 357.4 found, 357.2 required. |
| 39-4 | 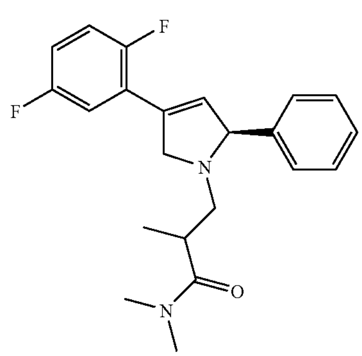 | 3-[(2S)4-(2,5-difluorophenyl)-2-phenyl-2,5-dihydro-1H-pyrrol-1-yl]-N,N,2-trimethylpropanamide | LRMS m/z (M + H) 371.4 found, 371.2 required. |

-continued

| Cmpd | Structure | Name | LRMS m/z (M + H) |
|---|---|---|---|
| 39-5 | 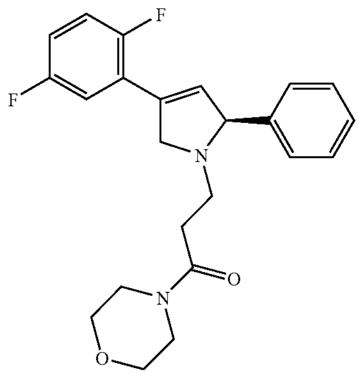 | 4-{3-[(2S)-4-(2,5-difluorophenyl)-2-phenyl-2,5-dihydro-1H-pyrrol-1-yl]propanoyl}morpholine | LRMS m/z (M + H) 399.3 found, 399.2 required. |
| 39-6 | 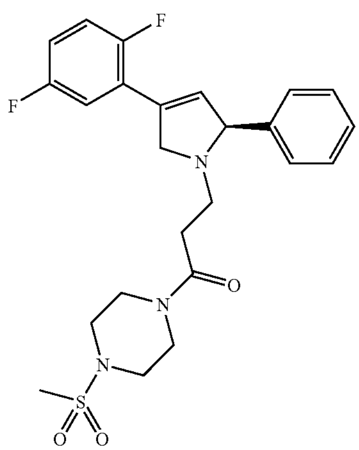 | 1-{3-[(2S)-4-(2,5-difluorophenyl)-2-phenyl-2,5-dihydro-1H-pyrrol-1-yl]propanoyl}-4-(methylsufonyl)piperazine | LRMS m/z (M + H) 476.5 found, 476.2 required. |
| 39-7 | 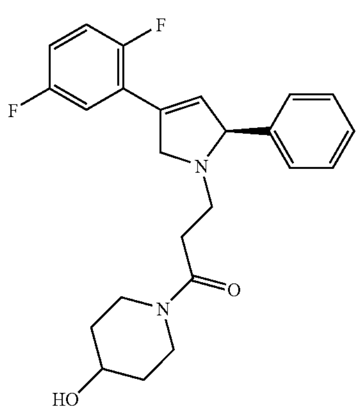 | 1-{3-[(2S)-4-(2,5-difluorophenyl)-2-phenyl-2,5-dihydro-1H-pyrrol-1-yl]propanoyl}piperidin-4-ol | LRMS m/z (M + H) 413.5 found, 413.2 required. |

-continued

| Cmpd | Structure | Name | LRMS m/z (M + H) |
|---|---|---|---|
| 39-8 | 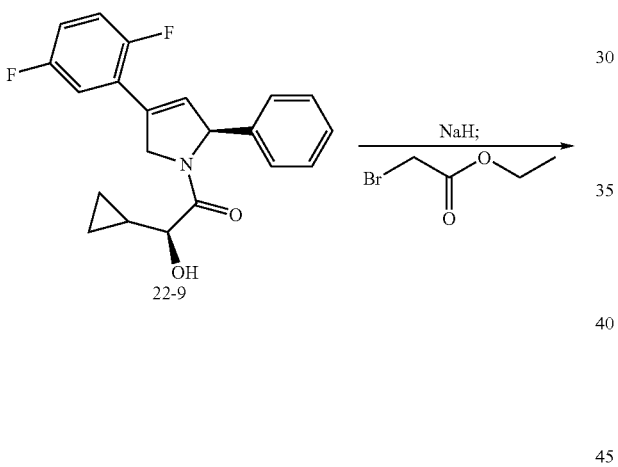 | methyl 3-[(2S)-4-(2,5-difluorophenyl)-2-phenyl-2,5-dihydro-1H-pyrrol-1-yl]propanoate | LRMS m/z (M + H) 439.6 found, 439.2 required. |

SCHEME 40

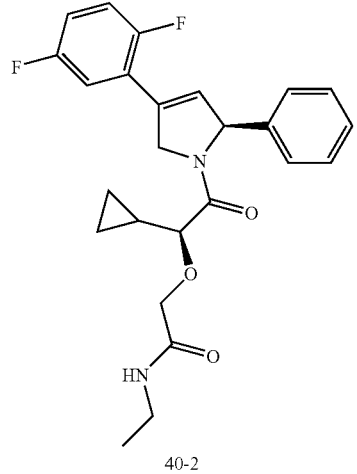

-continued

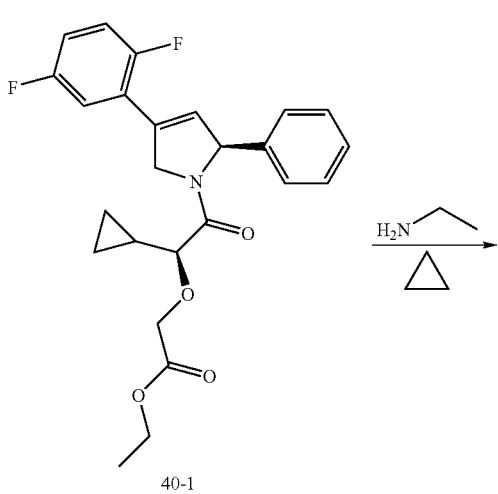

Step 1: ethyl ({(1S)-1-cyclopropyl-2-[(2S)-4-(2,5-difluorophenyl)-2-phenyl-2,5-dihydro-1H-pyrrol-1-yl]-2-oxoethyl}oxy)acetate (40-1)

A solution of (1S)-1-cyclopropyl-2-[(2S)-4-(2,5-difluorophenyl)-2-phenyl-2,5-dihydro-1H-pyrrol-1-yl]-2-oxoethanol (22-9, 150 mg, 0.422 mmol, 1 equiv) in DMP (1 mL) was cooled to 0° C. and treated with a solution of NaH (12 mg, 0.506 mmol, 1.2 eq) in DMF (0.5 ml), then stirred for 10 min. Ethyl bromoacetate (0.078 mL, 0.46 mmol, 1.1 eq) was added to the maroon-colored reaction mixture and the resulting mixture was stirred at 0° C. for 5 min, then warmed to 23° C. and stirred for 30 min. The yellow reaction mixture was partitioned between and water (65 mL) and EtOAc (2×60 mL) and the combined organic layers were dried over sodium sulfate and concentrated. The residue was purified by reverse-phase liquid chromatography (acetonitrile/H$_2$O with 0.1% TEA present) to afford ethyl ({(1S)-1-cyclopropyl-2-[(2S)-4-(2,5-difluorophenyl)-2-phenyl-2,5-dihydro- 1H-pyrrol-1-yl]-2-oxoethyl}oxy)acetate (40-1) as a light yellow oil. ¹H NMR (300, CDCl₃) major rotamer: δ 7.22-7.39 (m, 5H), 6.93-7.12 (m, 3H), 6.42 (br s), 5.87 (d, 1H, J=2.4 Hz), 4.93 (br s, 2H), 4.29 (m, 2H), 3.92 (d, 1H, J=7.6 Hz), 3.66 (d, 1H, J=8.8 Hz), 3.41 (d, 1H, J=8.8 Hz), 1.18 (t, 3H, J=7.3 Hz), 0.61 (m, 4H). LRMS m/z (M+H) 442.4 found, 442.5 required.

Step 2: 2-({(1S)-1-cyclopropyl-2-[(2S)-4-(2,5-difluorophenyl)-2-phenyl-2,5-dihydro-1H-pyrrol-1-yl]-2-oxoethyl}oxy)-N-ethylacetamide (40-2)

A solution of ethyl ({(1S)-1-cyclopropyl-2-[(2S)-4-(2,5-difluorophenyl)-2-phenyl-2,5-dihydro-1H-pyrrol-1-yl]-2-oxoethyl}oxy)acetate (40-1, 16 mg, 0.036 mmol) and ethylamine (10 equiv) in methanol (1 mL) was heated in a sealable tube at 75 deg C. for 20 h. The reaction mixture was concentrated, then purified by reverse-phase liquid chromatography (acetonitrile/H₂O with 0.1% TFA present) to provide 2-({(1S)-1-cyclopropyl-2-[(2S)-4-(2,5-difluorophenyl)-2-phenyl-2,5-dihydro-1H-pyrrol-1-yl]-2-oxoethyl}oxy)-N-ethylacetamide (40-2) as a light yellow oil. LRMS m/z (M+H) 441.5 found, 441.5 required.

The following compounds were prepared by simple modifications of the above procedure. All compounds were isolated as TFA salts.

| Cmpd | Structure | Name | LRMS m/z (M + H) |
|---|---|---|---|
| 40-3 | 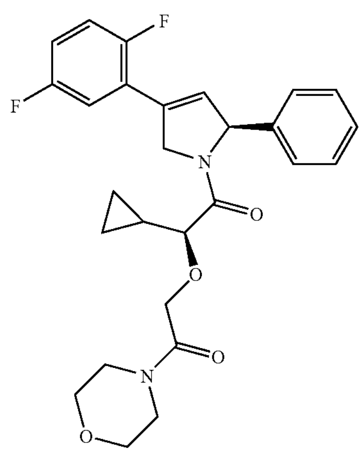 | 4-({(1S)-1-cyclopropyl-2-[(2S)-4-(2,5-difluorophenyl)-2-phenyl-2,5-dihydro-1H-pyrrol-1-yl]-2-oxoethoxy}acetyl)morpholine | LRMS m/z (M + H) 483.5 found, 483.2 required. |
| 40-4 | 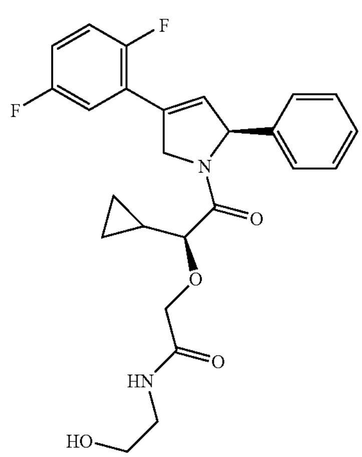 | 2-{(1S)-1-cyclopropyl-2-[(2S)-4-(2,5-difluorophenyl)-2-phenyl-2,5-dihydro-1H-pyrrol-1-yl[-2-oxoethoxyl-N-(2-hydroxyethyl)acetamide | LRMS m/z (M + H) 457.4 found, 457.2 required. |

-continued

| Cmpd | Structure | Name | LRMS m/z (M + H) |
|---|---|---|---|
| 40-5 | 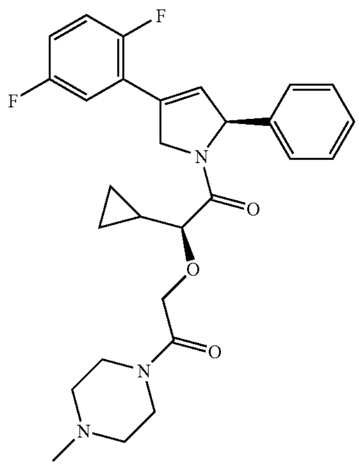 | 1-({(1S)-1-cyclopropyl-2-[(2S)-4-(2,5-difluorophenyl)-2-phenyl-2,5-dihydro-1H-pyrrol-1-yl]-2-oxoethoxy}acetyl)-4-methylpiperazine | LRMS m/z (M + H) 496.6 found, 496.2 required. |
| 40-6 | 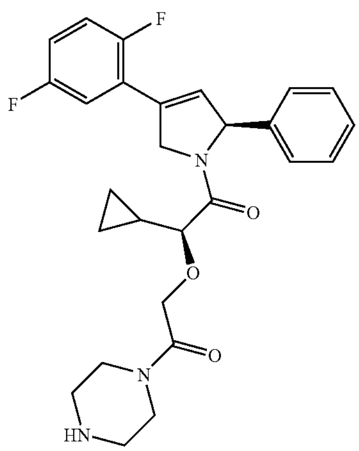 | 1-({(1S)-1-cyclopropyl-2-[(2S)-4-(2,5-difluorophenyl)-2-phenyl-2,5-dihydro-1H-pyrrol-1-yl]-2-oxoethoxy}-acetyl)piperazine | LRMS m/z (M + H) 482.6 found, 482.2 required. |
| 40-7 | 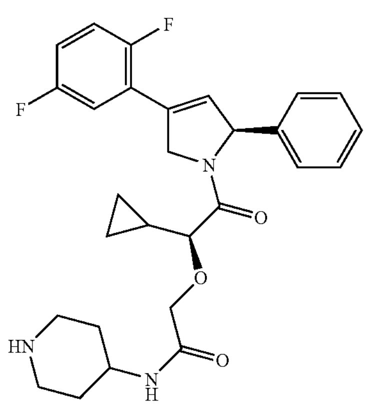 | 2-{(1S)-1-cyclopropyl-2-[(2S)-4-(2,5-difluorophenyl)-2-phenyl-2,5-dihydro-1H-pyrrol-1-yl]-2-oxoethoxy}-N-piperidin-4-ylacetamide | LRMS m/z (M + H) 496.6 found, 496.2 required. |

| Cmpd | Structure | Name | LRMS m/z (M + H) |
|---|---|---|---|
| 40-8 | 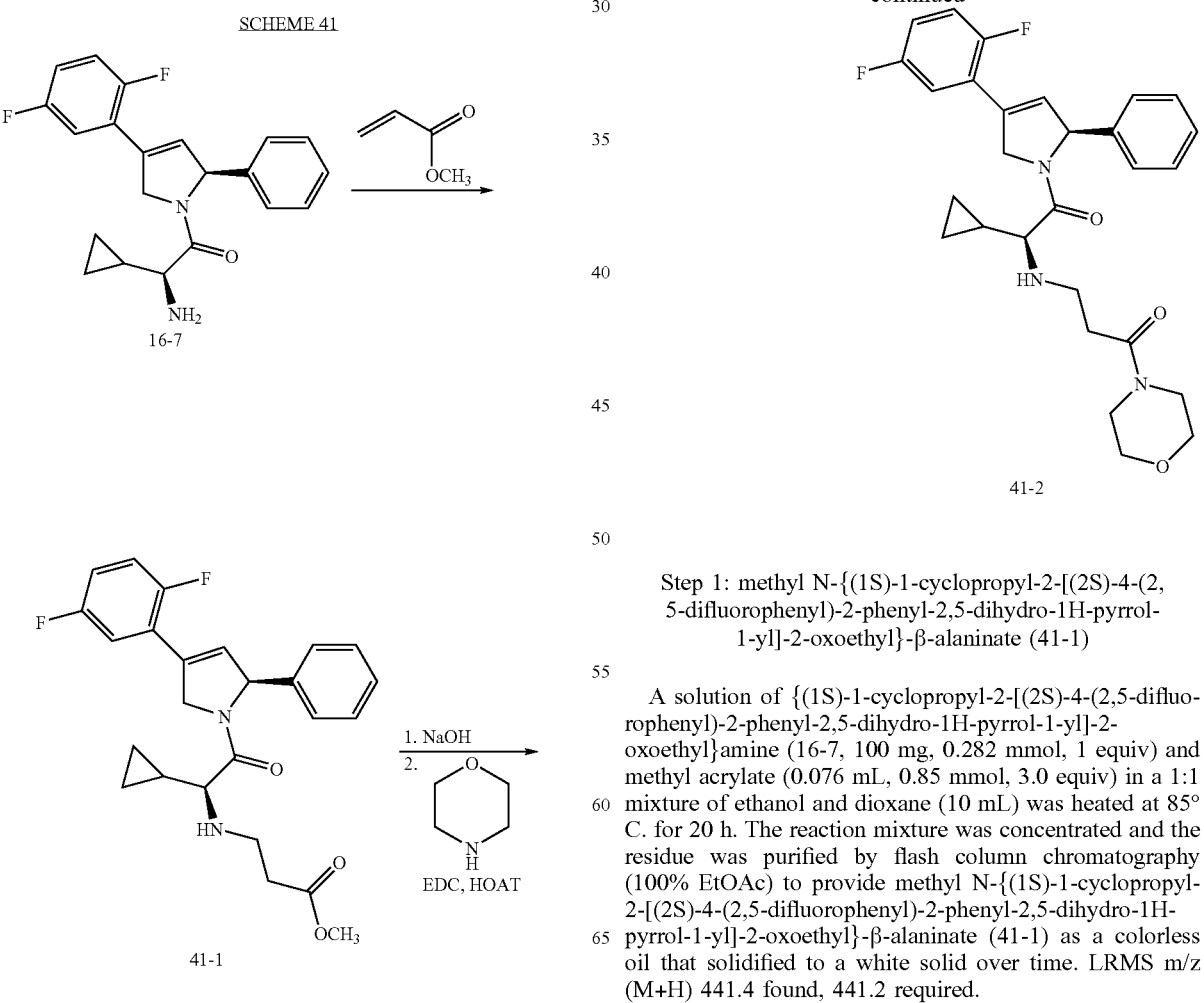 | 1-({(1S)-1-cyclopropyl-2-[(2S)-4-(2,5-difluorophenyl)-2-phenyl-2,5-dihydro-1H-pyrrol-1-yl]-2-oxoethoxy}acetyl)piperidin-4-amine | LRMS m/z (M + H) 496.6 found, 496.2 required. |

Step 1: methyl N-{(1S)-1-cyclopropyl-2-[(2S)-4-(2,5-difluorophenyl)-2-phenyl-2,5-dihydro-1H-pyrrol-1-yl]-2-oxoethyl}-β-alaninate (41-1)

A solution of {(1S)-1-cyclopropyl-2-[(2S)-4-(2,5-difluorophenyl)-2-phenyl-2,5-dihydro-1H-pyrrol-1-yl]-2-oxoethyl}amine (16-7, 100 mg, 0.282 mmol, 1 equiv) and methyl acrylate (0.076 mL, 0.85 mmol, 3.0 equiv) in a 1:1 mixture of ethanol and dioxane (10 mL) was heated at 85° C. for 20 h. The reaction mixture was concentrated and the residue was purified by flash column chromatography (100% EtOAc) to provide methyl N-{(1S)-1-cyclopropyl-2-[(2S)-4-(2,5-difluorophenyl)-2-phenyl-2,5-dihydro-1H-pyrrol-1-yl]-2-oxoethyl}-β-alaninate (41-1) as a colorless oil that solidified to a white solid over time. LRMS m/z (M+H) 441.4 found, 441.2 required.

Step 2: N-{(1S)-1-cyclopropyl-2-[(2S)-4-(2,5-difluorophenyl)-2-phenyl-2,5-dihydro-1H-pyrrol-1-yl]-2-oxoethyl}-3-morpholin-4-yl-3-oxopropan-1-amine (41-2)

A solution of methyl N-{(1S)-1-cyclopropyl-2-[(2S)-4-(2,5-difluorophenyl)-2-phenyl-2,5-dihydro-1H-pyrrol-1-yl]-2-oxoethyl}-β-alaninate (40-1, 84 mg, 0.19 mmol, 1 equiv) and sodium hydroxide (1N, 0.57 mL, 0.57 mmol, 3.00 equiv) in t-BuOH (4 mL) was stirred at 23 deg C. for 4 h. The reaction mixture was concentrated and the residue was partitioned between brine adjusted to pH 4 with aqueous 1 N HCL solution and ethyl acetate (2×40 mL). The combined organic layers were dried over sodium sulfate and concentrated. A solution of the residue, morpholine (0.083 mL, 0.95 mmol, 5.0 equiv), 1-(3-dimethylaminopropyl)-3-ethylcarbodiimide hydrochloride (EDC, 73 mg, 0.38 mmol, 2.0 equiv), and 1-hydroxy-7-azabenzotriazole (52 mg, 0.38 mmol, 2.0 equiv) in DMF (2 mL) was heated at 50° C. for 20 h. The reaction mixture was partitioned between aqueous saturated sodium bicarbonate solution and ethyl acetate (2×30 mL). The combined organic layers were dried over sodium sulfate and were concentrated. The residue was purified by reverse-phase LC ($H_2O$/$CH_3CN$ gradient w/0.1% TFA present) and the desired fractions partitioned between saturated sodium bicarbonate solution and ethyl acetate. The organic layer was dried over sodium sulfate and concentrated to provide N-{(1S)-1-cyclopropyl-2-[(2S)-4-(2,5-difluorophenyl)-2-phenyl-2,5-dihydro-1H-pyrrol-1-yl]-2-oxoethyl}-3-morpholin-4-yl-3-oxopropan-1-amine (41-2) as a white foam. LRMS m/z M+H) 496.5 found, 496.2 required.

The following compound was prepared by simple modification of the above procedure.

| Cmpd | Structure | Name | LRMS m/z (M + H) |
|---|---|---|---|
| 41-3 | 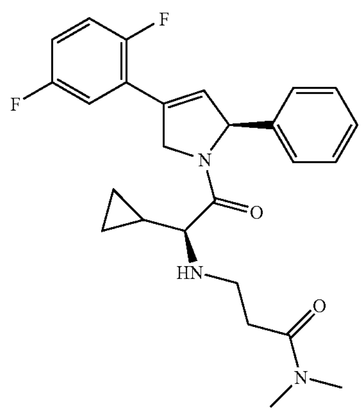 | $N^3$-{(1S)-1-cyclopropyl-2-[(2S)-4-(2,5-difluorophenyl)-2-phenyl-2,5-dihydro-1H-pyrrol-1-yl]-2-oxoethyl}-$N^1$,$N^1$-dimethyl-β-alaninamide | LRMS m/z (M + H) 454.5 found, 454.2 required. |
| 41-4 | 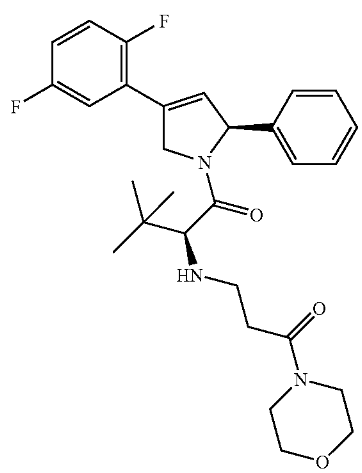 | ((1S)-1-{[(2S)-4-(2,5-difluorophenyl)-2-phenyl-2,5-dihydro-1H-pyrrol-1-yl]carbonyl}-2,2-dimethylpropyl)(3-morpholin-4-yl-3-oxopropyl)amine | LRMS m/z (M + H) 512.5 found, 512.3 required. |

What is claimed is:

1. A compound of Formula I:

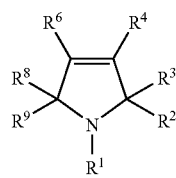

I or a pharmaceutically acceptable salt or stereoisomer thereof, wherein
- a is 0 or 1;
- b is 0 or 1;
- m is 0, 1, or 2;
- n is 0 or 1;
- r is 0 or 1;
- s is 0 or 1;
- $R^1$ is:
  1) $(C_1-C_6\text{-alkylene})_n(C=X)NR^cR^{c'}$,
  said alkylene is optionally substituted with one or more substituents selected from $R^{10}$;
- $R^2$ and $R^6$ are independently selected from:
  1) phenyl,
  said phenyl is optionally substituted with one or more substituents selected from $R^{10}$;
- $R^3$, $R^4$, $R^8$, and $R^9$ are independently selected from:
  1) H, and
  2) $C_1-C_{10}$ alkyl;
- $R^{10}$ is independently selected from:
  1) $C_1-C_{10}$ alkyl,
  7) halo,
  8) CN, and
  9) OH,
  said alkyl is optionally substituted with one or more halo;
- $R^{11}$ is selected from:
  1) $(C=O)_rO_s(C_1-C_{10})$alkyl,
  2) $O_r(C_1-C_3)$perfluoroalkyl,
  3) $(C_0-C_6)$alkylene-$S(O)_mR^a$,
  4) oxo,
  5) OH,
  6) halo,
  7) CN,
  8) $(C=O)_rO_s(C_2-C_{10})$alkenyl,
  9) $(C=O)_rO_s(C_2-C_{10})$alkynyl,
  10) $(C=O)_rO_s(C_3-C_6)$cycloalkyl,
  11) $(C=O)_rO_s(C_0-C_6)$alkylene-aryl,
  12) $(C=O)_rO_s(C_0-C_6)$alkylene-heterocyclyl,
  13) $(C=O)_rO_s(C_0-C_6)$alkylene-$N(R^b)_2$,
  14) $C(O)R^a$,
  15) $(C_0-C_6)$alkylene-$CO_2R^a$,
  16) C(O)H,
  17) $(C_0-C_6)$alkylene-$CO_2H$,
  18) $C(O)N(R^b)_2$,
  19) $S(O)_mR^a$, and
  20) $S(O)_2N(R^b)_2$
  said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
- $R^{12}$ and $R^{13}$ are independently selected from:
  1) H,
  2) $(C=O)O_bC_1-C_{10}$ alkyl,
  3) $(C=O)O_bC_3-C_8$ cycloalkyl,
  4) $(C=O)O_b$ aryl,
  5) $(C=O)O_b$ heterocyclyl,
  6) $C_1-C_{10}$ alkyl,
  7) aryl,
  8) $C_2-C_{10}$ alkenyl,
  9) $C_2-C_{10}$ alkynyl,
  10) heterocyclyl,
  11) $C_3-C_8$ cycloalkyl,
  12) $SO_2R^a$, and
  13) $(C=O)NR^b_2$,
  said alkyl, cycloalkyl, aryl, heterocylyl, alkenyl, and alkynyl is optionally substituted with one or more substituents selected from $R^{11}$, or
- $R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{11}$;
- $R^{14}$ is independently selected from:
  1) $(C=O)_aO_bC_1-C_{10}$ alkyl,
  2) $(C=O)_aO_b$ aryl,
  3) $C_2-C_{10}$ alkenyl, 4) $C_2$-$C_{10}$ alkynyl,
5) $(C=O)_aO_b$ heterocyclyl,
6) $CO_2H$,
7) halo,
8) CN,
9) OH,
10) $O_bC_1$-$C_6$ perfluoroalkyl,
11) $O_a(C=O)_bNR^{12}R^{13}$,
12) $S(O)_mR^a$,
13) $S(O)_2NR^{12}R^{13}$,
14) oxo,
15) CHO,
16) $(N=O)R^{12}R^{13}$, or
17) $(C=O)_aO_bC_3$-$C_8$ cycloalkyl,
said alkyl, aryl, alkenyl, alkynyl, heterocyclyl, and cycloalkyl optionally substituted with one or more substituents selected from $R^{11}$;
$R^a$ is $(C_1$-$C_6)$alkyl, $(C_3$-$C_6)$cycloalkyl, aryl, or heterocyclyl, optionally substituted with one to three substituents selected from $R^{14}$;
$R^b$ is H, $(C_1$-$C_6)$alkyl, aryl, heterocyclyl, $(C_3$-$C_6)$cycloalkyl, $(C=O)OC_1$-$C_6$ alkyl, $(C=O)C_1$-$C_6$ alkyl or $S(O)_2R^a$, optionally substituted with one to three substituents selected from $R^{14}$;
$R^c$ and $R^{c'}$ are independently selected from: H, morpholine, piperazine, pyrrolidine, phenyl, pyridine, oxazole, pyrazole, oxadiazole, thiazole, triazole, oxopyridine, piperidine, tetrahydrofuran, dioxane, and $(C_3$-$C_6)$cycloalkyl, optionally substituted with one, two or three substituents selected from $C_1$-$C_{10}$ alkyl, $C_2$-$C_{10}$ alkenyl, $C_2$-$C_{10}$ alkynyl, $NR^{12}R^{13}$ or $S(O)_mR^a$ wherein said alkyl is optionally substituted with OH, —$CO_2H$, alkoxy, (C=O)morpholine (which is optionally substituted with alkyl), O(C=O)piperazine, O(C=O)piperidine, O(C=O)morpholine, phenyl, pyridine, oxazole, pyrazole, oxadiazole, thiazole, triazole, oxopyridine, piperidine, piperazine, tetrahydrofuran, dioxane or pyrrolidinyl,
or
$R^c$ and $R^{c'}$ can be taken together with the nitrogen to which they are attached to form morpholine, azetidine or pyrrolidine;
X is O.

2. The compound according to claim 1 of the Formula I:

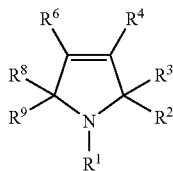

or a pharmaceutically acceptable salt or stereoisomer thereof, wherein
a is 0 or 1;
b is 0 or 1;
m is 0, 1, or 2;
n is 0 or 1;
r is 0 or 1;
s is 0 or 1;
$R^1$ is;
1) $(C_1$-$C_6$-alkylene$)_n(C=X)NR^cR^{c'}$,
said alkylene is optionally substituted with one or more substituents selected from $R^{10}$;

$R^2$ and $R^6$ are independently selected from:
1) phenyl,
said phenyl, is optionally substituted with one or more substituents selected from $R^{10}$;
$R^3$, $R^4$, $R^8$, and $R^9$ are independently selected from:
1) H, and
2) $C_1$-$C_{10}$ alkyl;
$R^{10}$ is independently selected from:
1) $C_1$-$C_{10}$ alkyl,
7) halo,
8) CN, and
9) OH,
said alkyl is optionally substituted with one or more halo;
$R^{11}$ is selected from:
1) $(C=O)_rO_s(C_1$-$C_{10})$alkyl,
2) $O_r(C_1$-$C_3)$perfluoroalkyl,
3) $(C_0$-$C_6)$alkylene-$S(O)_mR^a$,
4) oxo,
5) OH,
6) halo,
7) CN,
8) $(C=O)_rO_s(C_2$-$C_{10})$alkenyl,
9) $(C=O)_rO_s(C_2$-$C_{10})$alkynyl,
10) $(C=O)_rO_s(C_3$-$C_6)$cycloalkyl,
11) $(C=O)_rO_s(C_0$-$C_6)$alkylene-aryl,
12) $(C=O)_rO_s(C_0$-$C_6)$alkylene-heterocyclyl,
13) $(C=O)_rO_s(C_0$-$C_6)$alkylene-$N(R^b)_2$,
14) $C(O)R^a$,
15) $(C_0$-$C_6)$alkylene-$CO_2R^a$,
16) $C(O)H$,
17) $(C_0$-$C_6)$alkylene-$CO_2H$,
18) $C(O)N(R^b)_2$,
19) $S(O)_mR^a$, and
20) $S(O)_2N(R^b)_2$
said alkyl, alkenyl, alkynyl, cycloalkyl, aryl, alkylene and heterocyclyl is optionally substituted with up to three substituents selected from $R^b$, OH, $(C_1$-$C_6)$alkoxy, halogen, $CO_2H$, CN, $O(C=O)C_1$-$C_6$ alkyl, oxo, and $N(R^b)_2$;
$R^{12}$ and $R^{13}$ are independently selected from:
1) H,
2) $(C=O)O_bC_1$-$C_{10}$ alkyl,
3) $(C=O)O_bC_3$-$C_8$ cycloalkyl,
4) $(C=O)O_b$ aryl,
5) $(C=O)O_b$ heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) $(C=O)NR^b{}_2$,
said alkyl, cycloalkyl, aryl, heterocylyl, alkenyl, and alkynyl is optionally substituted with one or more substituents selected from $R^{11}$, or
$R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{11}$;
$R^a$ is $(C_1$-$C_6)$alkyl, $(C_3$-$C_6)$cycloalkyl, aryl, or heterocyclyl;

$R^b$ is H, $(C_1\text{-}C_6)$alkyl, aryl, heterocyclyl, $(C_3\text{-}C_6)$cycloalkyl, $(C{=}O)OC_1\text{-}C_6$ alkyl, $(C{=}O)C_1\text{-}C_6$ alkyl or $S(O)_2R^a$;

$R^c$ and $R^{c'}$ are independently selected from: H, morpholine, piperazine, pyrrolidine, phenyl, pyridine, oxazole, pyrazole, oxadiazole, thiazole, triazole, oxopyridine, piperidine, tetrahydrofuran, dioxane, and $(C_3\text{-}C_6)$cycloalkyl, optionally substituted with one, two or three substituents selected from, $C_1\text{-}C_{10}$ alkyl, $C_2\text{-}C_{10}$ alkenyl, $C_2\text{-}C_{10}$ alkynyl, $NR^{12}R^{13}$ or $S(O)_mR^a$, wherein said alkyl is optionally substituted with OH, —$CO_2H$, alkoxy, $(C{=}O)$morpholine (which is optionally substituted with alkyl), $O(C{=}O)$piperazine, $O(C{=}O)$piperidine, $O(C{=}O)$morpholine, phenyl, pyridine, oxazole, pyrazole, oxadiazole, thiazole, triazole, oxopyridine, piperidine, piperazine, tetrahydrofuran, dioxane or pyrrolidinyl, or $R^c$ and $R^{c'}$ can be taken together with the nitrogen to which they are attached to form morpholine, azetidine or pyrrolidine;

and

X is O.

3. The compound according to claim 2 of Formula I:

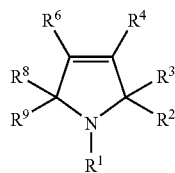

I or a pharmaceutically acceptable salt or stereoisomer thereof, wherein a is 0 or 1;
b is 0 or 1;
m is 0, 1, or 2;
n is 0 or 1;
r is 0 or 1;
s is 0 or 1;

$R^1$ is;
  1) $(C_1\text{-}C_6\text{-alkylene})_n(C{=}X)NR^cR^{c'}$,
said alkylene is optionally substituted with one or more substituents selected from $R^{10}$;

$R^2$ and $R^6$ are independently selected from:
  1) phenyl,
said phenyl, is optionally substituted with one or more substituents selected from $R^{10}$;

$R^3$, $R^4$, $R^8$, and $R^9$ are independently selected from:
  1) H, and
  2) $C_1\text{-}C_{10}$ alkyl;

$R^{10}$ is independently selected from:
  1) $C_1\text{-}C_{10}$ alkyl,
  7) halo,
  8) CN, and
  9) OH,
said alkyl is optionally substituted with one or more halo;

$R^{11}$ is selected from:
  1) $(C{=}O)_rO_s(C_1\text{-}C_{10})$alkyl,
  2) $O_r(C_1\text{-}C_3)$perfluoroalkyl,
  3) $(C_0\text{-}C_6)$alkylene-$S(O)_mR^a$,
  4) oxo,
  5) OH,
  6) halo,
  7) CN,
  8) $(C{=}O)_rO_s(C_2\text{-}C_{10})$alkenyl,
  9) $(C{=}O)_rO_s(C_2\text{-}C_{10})$alkynyl,
  10) $(C{=}O)_rO_s(C_3\text{-}C_6)$cycloalkyl,
  11) $(C{=}O)_rO_s(C_0\text{-}C_6)$alkylene-aryl,
  12) $(C{=}O)_rO_s(C_0\text{-}C_6)$alkylene-heterocyclyl,
  13) $(C{=}O)_rO_s(C_0\text{-}C_6)$alkylene-$N(R^b)_2$,
  14) $C(O)R^a$,
  15) $(C_0\text{-}C_6)$alkylene-$CO_2R^a$,
  16) $C(O)H$,
  17) $(C_0\text{-}C_6)$alkylene-$CO_2H$,
  18) $C(O)N(R^b)_2$,
  19) $S(O)_mR^a$, and
  20) $S(O)_2N(R^b)_2$ said alkyl, alkenyl, alkynyl, cycloalkyl, aryl, alkylene and heterocyclyl is optionally substituted with up to three substituents selected from $R^b$, OH, $(C_1\text{-}C_6)$alkoxy, halogen, $CO_2H$, CN, $O(C{=}O)C_1\text{-}C_6$ alkyl, oxo, and $N(R^b)_2$;

$R^{12}$ and $R^{13}$ are independently selected from:
  1) H,
  2) $(C{=}O)O_bC_1\text{-}C_{10}$ alkyl,
  3) $(C{=}O)O_bC_3\text{-}C_8$ cycloalkyl,
  4) $(C{=}O)O_b$ aryl,
  5) $(C{=}O)O_b$ heterocyclyl,
  6) $C_1\text{-}C_{10}$ alkyl,
  7) aryl,
  8) $C_2\text{-}C_{10}$ alkenyl,
  9) $C_2\text{-}C_{10}$ alkynyl,
  10) heterocyclyl,
  11) $C_3\text{-}C_8$ cycloalkyl,
  12) $SO_2R^a$, and
  13) $(C{=}O)NR^b_2$, said alkyl, cycloalkyl, aryl, heterocylyl, alkenyl, and alkynyl is optionally substituted with one or more substituents selected from $R^{11}$, or $R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{11}$;

$R^a$ is $(C_1\text{-}C_6)$alkyl, $(C_3\text{-}C_6)$cycloalkyl, aryl, or heterocyclyl;

$R^b$ is H, $(C_1\text{-}C_6)$alkyl, aryl, heterocyclyl, $(C_3\text{-}C_6)$cycloalkyl, $(C{=}O)OC_1\text{-}C_6$ alkyl, $(C{=}O)C_1\text{-}C_6$ alkyl or $S(O)_2R^a$;

$R^c$ and $R^{c'}$ are independently selected from: H, morpholine, piperazine, pyrrolidine, phenyl, pyridine, oxazole, pyrazole, oxadiazole, thiazole, triazole, oxopyridine, piperidine, tetrahydrofuran, dioxane, and $(C_3\text{-}C_6)$cycloalkyl, or $R^c$ and $R^{c'}$ can be taken together with the nitrogen to which they are attached to form morpholine, azetidine or pyrrolidine;

and

X is O.

4. The compound according to claim 2 of the Formula II,

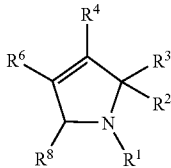

II or a pharmaceutically acceptable salt or stereoisomer thereof, wherein
a is 0 or 1;
b is 0 or 1;
m is 0, 1, or 2;
r is 0 or 1;
s is 0 or 1;
$R^1$ is;
1) $(C_1-C_6\text{-alkylene})_n(C=X)NR^cR^{c'}$,
said alkylene is optionally substituted with one or more substituents selected from $R^{10}$;
$R^2$ and $R^6$ are independently selected from:
1) phenyl,
said phenyl, is optionally substituted with one or more substituents selected from $R^{10}$;
$R^3$, $R^4$, $R^8$, and $R^9$ are independently selected from:
1) H, and
2) $C_1-C_{10}$ alkyl;
$R^{10}$ is independently selected from:
1) $C_1-C_{10}$ alkyl,
7) halo,
8) CN, and
9) OH,
said alkyl is optionally substituted with halo;
$R^{11}$ is selected from:
1) $(C=O)_rO_s(C_1-C_{10})$alkyl,
2) $O_r(C_1-C_3)$perfluoroalkyl,
3) $(C_0-C_6)$alkylene-$S(O)_mR^a$,
4) oxo,
5) OH,
6) halo,
7) CN,
8) $(C=O)_rO_s(C_2-C_{10})$alkenyl,
9) $(C=O)_rO_s(C_2-C_{10})$alkynyl,
10) $(C=O)_rO_s(C_3-C_6)$cycloalkyl,
11) $(C=O)_rO_s(C_0-C_6)$alkylene-aryl,
12) $(C=O)_rO_s(C_0-C_6)$alkylene-heterocyclyl,
13) $(C=O)_rO_s(C_0-C_6)$alkylene-$N(R^b)_2$,
14) $C(O)R^a$,
15) $(C_0-C_6)$alkylene-$CO_2R^a$,
16) $C(O)H$,
17) $(C_0-C_6)$alkylene-$CO_2H$,
18) $C(O)N(R^b)_2$,
19) $S(O)_mR^a$, and
20) $S(O)_2N(R^b)_2$
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^{12}$ and $R^{13}$ are independently selected from:
1) H,
2) $(C=O)O_bC_1-C_{10}$ alkyl,
3) $(C=O)O_bC_3-C_8$ cycloalkyl,
4) $(C=O)O_b$ aryl,
5) $(C=O)O_b$ heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl,
12) $SO_2R^a$, and
13) $(C=O)NR^b_2$,
said alkyl, cycloalkyl, aryl, heterocylyl, alkenyl, and alkynyl is optionally substituted with one, two or three substituents selected from $R^{11}$, or
$R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{11}$;
$R^a$ is $(C_1-C_6)$alkyl, $(C_3-C_6)$cycloalkyl, aryl; or heterocyclyl;
$R^b$ is H, $(C_1-C_6)$alkyl, aryl, heterocyclyl, $(C_3-C_6)$cycloalkyl, $(C=O)OC_1-C_6$ alkyl, $(C=O)C_1-C_6$ alkyl or $S(O)_2R^a$;
$R^c$ and $R^{c'}$ are independently selected from: H, morpholine, piperazine, pyrrolidine, phenyl, pyridine, oxazole, pyrazole, oxadiazole, thiazole, triazole, oxopyridine, piperidine, tetrahydrofuran, dioxane, and $(C_3-C_6)$cycloalkyl, or $R^c$ and $R^{c'}$ can be taken together with the nitrogen to which they are attached to form morpholine, azetidine or pyrrolidine.

5. A compound of the Formula III,

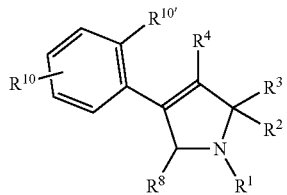

III or a pharmaceutically acceptable salt or stereoisomer thereof, wherein
a is 0 or 1;
b is 0 or 1;
m is 0, 1, or 2;
r is 0 or 1;
s is 0 or 1;
$R^1$ is selected from:
1) $(C=O)NR^cR^{c'}$;
$R^2$ is selected from:
1) phenyl,
said phenyl, is optionally substituted with one or more substituents selected from $R^{10}$;
$R^3$, $R^4$, $R^8$, and $R^9$ are independently selected from:
1) H, and
2) $C_1-C_{10}$ alkyl;
$R^{10}$ is independently selected from:
1) $C_1-C_{10}$ alkyl,
7) halo,
8) CN, and
9) OH,
said alkyl is optionally substituted with halo;

$R^{10'}$ is halogen;
$R^{11}$ is selected from:
1) $(C=O)_rO_s(C_1-C_{10})$alkyl,
2) $O_r(C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_rO_s(C_3-C_6)$cycloalkyl,
10) $(C=O)_rO_s(C_0-C_6)$alkylene-aryl,
11) $(C=O)_rO_s(C_0-C_6)$alkylene-heterocyclyl,
12) $(C=O)_rO_s(C_0-C_6)$alkylene-$N(R^b)_2$,
13) $C(O)R^a$,
14) $(C_0-C_6)$alkylene-$CO_2R^a$,
15) C(O)H,
16) $(C_0-C_6)$alkylene-$CO_2H$, and
17) $C(O)N(R^b)_2$,
18) $S(O)_mR^a$, and
19) $S(O)_2N(R^b)_2$;
said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^{12}$ and $R^{13}$ are independently selected from:
1) H,
2) $(C=O)O_bC_1-C_{10}$ alkyl,
3) $(C=O)O_bC_3-C_8$ cycloalkyl,
4) $(C=O)O_b$ aryl,
5) $(C=O)O_b$ heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl,
12) $SO_2R^a$, and
13) $(C=O)NR^b_2$,
said alkyl, cycloalkyl, aryl, heterocylyl, alkenyl, and alkynyl is optionally substituted with one, two or three substituents selected from $R^{11}$, or
$R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{11}$;
$R^a$ is $(C_1-C_6)$alkyl, $(C_3-C_6)$cycloalkyl, aryl; or heterocyclyl
$R^b$ is H, $(C_1-C_6)$alkyl, aryl, heterocyclyl, $(C_3-C_6)$cycloalkyl, $(C=O)OC_1-C_6$ alkyl, $(C=O)C_1-C_6$ alkyl or $S(O)_2R^a$;
$R^c$ and $R^{c'}$ are independently selected from: H, morpholine, piperazine, pyrrolidine, phenyl, pyridine, oxazole, pyrazole, oxadiazole, thiazole, triazole, oxopyridine, piperidine, tetrahydrofuran, dioxane, and $(C_3-C_6)$cycloalkyl,
or $R^c$ and $R^{c'}$ can be taken together with the nitrogen to which they are attached to form morpholine, azetidine or pyrrolidine.

6. The compound according to claim 4 of the Formula IV,

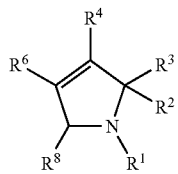

IV or a pharmaceutically acceptable salt or stereoisomer thereof, wherein
a is 0 or 1;
b is 0 or 1;
m is 0, 1, or 2;
r is 0 or 1;
s is 0 or 1;
$R^1$ is selected from:
1) $(C=O)NR^cR^{c'}$;
$R^2$ is selected from:
1) phenyl,
said phenyl, is optionally substituted with one or more substituents selected from $R^{10}$;
$R^3$, $R^4$, $R^8$, and $R^9$ are independently selected from:
1) H, and
2) $C_1-C_{10}$ alkyl;
$R^6$ is selected from:
1) phenyl,
said phenyl, is optionally substituted with one or more substituents selected from $R^{10}$;
$R^{10}$ is independently selected from:
1) $C_1-C_{10}$ alkyl,
7) halo,
8) CN, and
9) OH,
said alkyl is optionally substituted with halo;
$R^{11}$ is selected from:
1) $(C=O)_rO_s(C_1-C_{10})$alkyl,
2) $O_r(C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_rO_s(C_3-C_6)$cycloalkyl,
10) $(C=O)_rO_s(C_0-C_6)$alkylene-aryl,
11) $(C=O)_rO_s(C_0-C_6)$alkylene-heterocyclyl,
12) $(C=O)_rO_s(C_0-C_6)$alkylene-$N(R^b)_2$,
13) $C(O)R^a$,
14) $(C_0-C_6)$alkylene-$CO_2R^a$,
15) C(O)H,
16) $(C_0-C_6)$alkylene-$CO_2H$,
17) $C(O)N(R^b)_2$,
18) $S(O)_mR^a$, and
19) $S(O)_2N(R^b)_2$
said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^{12}$ and $R^{13}$ are independently selected from:
1) H,
2) $(C=O)O_bC_1-C_{10}$ alkyl,
3) $(C=O)O_bC_3-C_8$ cycloalkyl,
4) $(C=O)O_b$ aryl, 5) (C=O)O_b heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) $SO_2R^a$, and
13) $(C=O)NR^b{}_2$,
said alkyl, cycloalkyl, aryl, heterocylyl, alkenyl, and alkynyl is optionally substituted with one, two or three substituents selected from $R^{11}$, or
$R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one or more substituents selected from $R^{11}$;
$R^a$ is independently selected from: $(C_1$-$C_6)$alkyl, $(C_3$-$C_6)$ cycloalkyl, aryl; and heterocyclyl;
$R^b$ is independently selected from: H, $(C_1$-$C_6)$alkyl, aryl, heterocyclyl, $(C_3$-$C_6)$cycloalkyl, $(C=O)OC_1$-$C_6$ alkyl, $(C=O)C_1$-$C_6$ alkyl or $S(O)_2R^a$; and
$R^c$ and $R^{c'}$ are independently selected from: H, morpholine, piperazine, pyrrolidine, phenyl, pyridine, oxazole, pyrazole, oxadiazole, thiazole, triazole, oxopyridine, piperidine, tetrahydrofuran, dioxane, and $(C_3$-$C_6)$cycloalkyl, or
$R^c$ and $R^{c'}$ can be taken together with the nitrogen to which they are attached to form morpholine, azetidine or pyrrolidine.

7. The compound according to claim 6 or a pharmaceutically acceptable salt or stereoisomer thereof, wherein:
$R^2$ and $R^6$ are phenyl optionally substituted with one or two substituents selected from $R^{10}$.

8. A compound selected from:
4-(2-chloro-5-fluorophenyl)-N,N-dimethyl-2-phenyl-2,5-dihydro-1H-pyrrole-1-carboxamide;
(+)-4-(2,5-difluorophenyl)-N,N-dimethyl-2-phenyl-2,5-dihydro-1H-pyrrole-1-carboxamide;
(−)-4-(2,5-difluorophenyl)-N,N-dimethyl-2-phenyl-2,5-dihydro-1H-pyrrole-1-carboxamide;
4-(5-chloro-2-fluorophenyl)-N,N-dimethyl-2-phenyl-2,5-dihydro-1H-pyrrole-1-carboxamide;
4-(2-fluorophenyl)-N,N-dimethyl-2-phenyl-2,5-dihydro-1H-pyrrole-1-carboxamide;
4-(2-fluoro-5-methylphenyl)-N,N-dimethyl-2-phenyl-2,5-dihydro-1H-pyrrole-1-carboxamide;
4-(5-bromo-2-fluorophenyl)-N,N-dimethyl-2-phenyl-2,5-dihydro-1H-pyrrole-1-carboxamide;
4-{[4-(5-chloro-2-fluorophenyl)-2-phenyl-2,5-dihydro-1H-pyrrol-1-yl]carbonyl}morpholine;
4-{[4-(2,5-difluorophenyl)-2-phenyl-2,5-dihydro-1H-pyrrol-1-yl]carbonyl}morpholine;
N,N-dimethyl-2,4-diphenyl-2,5-dihydro-1H-pyrrole-1-carboxamide;
4-(2,5-difluorophenyl)-2-(4-fluorophenyl)-N,N-dimethyl-2,5-dihydro-1H-pyrrole-1-carboxamide;
4-(2,5-difluorophenyl)-2-(2-fluorophenyl)-N,N-dimethyl-2,5-dihydro-1H-pyrrole-1-carboxamide;
2-(3-bromophenyl)-4-(2,5-difluorophenyl)-N,N-dimethyl-2,5-dihydro-1H-pyrrole-1-carboxamide;
2-(3-aminophenyl)-4-(2,5-difluorophenyl)-N,N-dimethyl-2,5-dihydro-1H-pyrrole-1-carboxamide;
4-(2,5-difluorophenyl)-2-(3-methylphenyl)-N,N-dimethyl-2,5-dihydro-1H-pyrrole-1-carboxamide;
(2S)-4-(5-chloro-2-fluorophenyl)-N,N-dimethyl-2-phenyl-2,5-dihydro-1H-pyrrole-1-carboxamide;
4-(2-fluoro-5-isocyanophenyl)-N,N-dimethyl-2-phenyl-2,5-dihydro-1H-pyrrole-1-carboxamide;
(2S)-4-(2,5-Difluorophenyl)-N-methyl-2-phenyl-N-piperidin-4-yl-2,5-dihydro-1H-pyrrole-1-carboxamide;
(2S)-4-(2,5-Difluorophenyl)-N-methyl-2-phenyl-N-(piperidin-4-ylmethyl)-2,5-dihydro-1H-pyrrole-1-carboxamide;
(2S)-4-(5-Chloro-2-fluorophenyl)-N-methyl-2-phenyl-N-[(3R)-pyrrolidin-3-yl]-2,5-dihydro-1H-pyrrole-1-carboxamide;
(2S)-4-(5-chloro-2-fluorophenyl)-N-methyl-2-phenyl-N-piperidin-4-yl-2,5-dihydro-1H-pyrrole-1-carboxamide;
(2S)-4-(5-chloro-2-fluorophenyl)-N-methyl-2-phenyl-N-[(3S)-pyrrolidin-3-yl]-2,5-dihydro-1H-pyrrole-1-carboxamide;
(2S)-4-(2,5-difluorophenyl)-N-methyl-2-phenyl-N-pyrrolidin-3-yl-2,5-dihydro-1H-pyrrole-1-carboxamide;
(2S)-4-(2,5-difluorophenyl)-N-methyl-N-[(3S)-1-methylpyrrolidin-3-yl]-2-phenyl-2,5-dihydro-1H-pyrrole-1-carboxamide;
(2S)-4-(2,5-difluorophenyl)-N-methyl-N-[(3R)-1-methylpyrrolidin-3-yl]-2-phenyl-2,5-dihydro-1H-pyrrole-1-carboxamide;
(2S)-4-(2,5-difluorophenyl)-N-methyl-N-[(1-methyl-5-oxopyrrolidin-2-yl)methyl]-2-phenyl-2,5-dihydro-1H-pyrrole-1-carboxamide;
(2S)-4-(2,5-difluorophenyl)-N-(1,3-dioxolan-2-ylmethyl)-N-methyl-2-phenyl-2,5-dihydro-1H-pyrrole-1-carboxamide;
(2S)-4-(2,5-difluorophenyl)-N-methyl-2-phenyl-N-tetrahydrofuran-3-yl-2,5-dihydro-1H-pyrrole-1-carboxamide;
(2S)-N-(1-allylpiperidin-4-yl)-4-(2,5-difluorophenyl)-N-methyl-2-phenyl-2,5-dihydro-1H-pyrrole-1-carboxamide;
allyl 4-[{[(2S)-4-(2,5-difluorophenyl)-2-phenyl-2,5-dihydro-1H-pyrrol-1-yl]carbonyl}(methyl)amino]piperidine-1-carboxylate;
allyl 4-{[{[(2S)-4-(2,5-difluorophenyl)-2-phenyl-2,5-dihydro-1H-pyrrol-1-yl]carbonyl}(methyl)amino] methyl}piperidine-1-carboxylate;
(2S)-4-(2,5-difluorophenyl)-N-methyl-N-(1-methylpiperidin-4-yl)-2-phenyl-2,5-dihydro-1H-pyrrole-1-carboxamide;
4-(2,5-Difluorophenyl)-N-methyl-N-[(1-methylpiperidin-3-yl)methyl]-2-phenyl-2,5-dihydro-1H-pyrrole-1-carboxamide;
4-(2,5-difluorophenyl)-N-methyl-2-phenyl-N-(pyridin-3-ylmethyl)-2,5-dihydro-1H-pyrrole-1-carboxamide;
N-benzyl-4-(2,5-difluorophenyl)-N-methyl-2-phenyl-2,5-dihydro-1H-pyrrole-1-carboxamide;
4-(2,5-difluorophenyl)-N-methyl-N-[(1-methyl-1H-pyrazol-4-yl)methyl]-2-phenyl-2,5-dihydro-1H-pyrrole-1-carboxamide;
4-(2,5-difluorophenyl)-N-[2-(dimethylamino)ethyl]-N-methyl-2-phenyl-2,5-dihydro-1H-pyrrole-1-carboxamide;
4-(2,5-difluorophenyl)-N-(2-hydroxyethyl)-N-methyl-2-phenyl-2,5-dihydro-1H-pyrrole-1-carboxamide;
4-(2,5-difluorophenyl)-N-isobutyl-N-methyl-2-phenyl-2,5-dihydro-1H-pyrrole-1-carboxamide;
4-(2,5-difluorophenyl)-N-methyl-2-phenyl-N-(2-pyridin-2-ylethyl)-2,5-dihydro-1H-pyrrole-1-carboxamide;

4-(2,5-difluorophenyl)-N-(2-methoxyethyl)-N-methyl-2-phenyl-2,5-dihydro-1H-pyrrole-1-carboxamide;

4-(2,5-difluorophenyl)-N-(2,3-dihydroxypropyl)-N-methyl-2-phenyl-2,5-dihydro-1H-pyrrole-1-carboxamide;

4-(2,5-difluorophenyl)-N-methyl-2-phenyl-N-(2-phenylethyl)-2,5-dihydro-1H-pyrrole-1-carboxamide;

4-(2,5-difluorophenyl)-2-phenyl-N-propyl-2,5-dihydro-1H-pyrrole-1-carboxamide;

4-(5-chloro-2-fluorophenyl)-2-(3-hydroxyphenyl)-N-methyl-N-piperidin-4-yl-2,5-dihydro-1H-pyrrole-1-carboxamide;

4-(2,5-difluorophenyl)-2-(3-hydroxyphenyl)-N-methyl-N-piperidin-4-yl-2,5-dihydro-1H-pyrrole-1-carboxamide;

(2S)-4-(2,5-difluorophenyl)-N,N,2-trimethyl-2-phenyl-2,5-dihydro-1H-pyrrole-1-carboxamide;

(2S)-4-(5-chloro-2-fluorophenyl)-N,N,2-trimethyl-2-phenyl-2,5-dihydro-1H-pyrrole-1-carboxamide;

(2S)-4-(5-chloro-2-fluorophenyl)-2-methyl-2-phenyl-2,5-dihydro-1H-pyrrole-1-carboxamide;

(2S)-4-(5-chloro-2-fluorophenyl)-N-ethyl-2-methyl-2-phenyl-2,5-dihydro-1H-pyrrole-1-carboxamide;

N-(tert-butyl)-2-[(2S)-4-(2,5-difluorophenyl)-2-phenyl-2,5-dihydro-1H-pyrrol-1-yl]acetamide;

2-[(2S)-4-(2,5-difluorophenyl)-2-phenyl-2,5-dihydro-1H-pyrrol-1-yl]-N-isopropylacetamide;

(2S)-1-(2-azetidin-1-yl-2-oxoethyl)-4-(2,5-difluorophenyl)-2-phenyl-2,5-dihydro-1H-pyrrole;

(2S)-4-(2,5-difluorophenyl)-1-(2-oxo-2-pyrrolidin-1-ylethyl)-2-phenyl-2,5-dihydro-1H-pyrrole;

4-{[(2S)-4-(2,5-difluorophenyl)-2-phenyl-2,5-dihydro-1H-pyrrol-1-yl]acetyl}morpholine;

1-{[(2S)-4-(2,5-difluorophenyl)-2-phenyl-2,5-dihydro-1H-pyrrol-1-yl]acetyl}piperazine;

1-{[(2S)-4-(2,5-difluorophenyl)-2-phenyl-2,5-dihydro-1H-pyrrol-1-yl]acetyl}-4-methylpiperazine;

2-[(2S)-4-(2,5-difluorophenyl)-2-phenyl-2,5-dihydro-1H-pyrrol-1-yl]-N-isopropylbutanamide;

4-{2-[(2S)-4-(2,5-difluorophenyl)-2-phenyl-2,5-dihydro-1H-pyrrol-1-yl]butanoyl}morpholine;

2-[(2S)-4-(2,5-difluorophenyl)-2-phenyl-2,5-dihydro-1H-pyrrol-1-yl]-N-ethylacetamide;

N-cyclobutyl-2-[(2S)-4-(2,5-difluorophenyl)-2-phenyl-2,5-dihydro-1H-pyrrol-1-yl]acetamide;

2-[(2S)-4-(2,5-difluorophenyl)-2-phenyl-2,5-dihydro-1H-pyrrol-1-yl]-N-ethylpropanamide;

N-cyclobutyl-2-[(2S)-4-(2,5-difluorophenyl)-2-phenyl-2,5-dihydro-1H-pyrrol-1-yl]propanamide;

2-[(2S)-4-(2,5-difluorophenyl)-2-phenyl-2,5-dihydro-1H-pyrrol-1-yl]-N-methylpropanamide;

2-[(2S)-4-(2,5-difluorophenyl)-2-phenyl-2,5-dihydro-1H-pyrrol-1-yl]-N-isopropylpropanamide;

N-(tert-butyl)-2-[(2S)-4-(2,5-difluorophenyl)-2-phenyl-2,5-dihydro-1H-pyrrol-1-yl]propanamide;

4-{2-[(2S)-4-(2,5-difluorophenyl)-2-phenyl-2,5-dihydro-1H-pyrrol-1-yl]propanoyl}morpholine;

2-({(1S)-1-tert-butyl-2-[(2S)-4-(2,5-difluorophenyl)-2-phenyl-2,5-dihydro-1H-pyrrol-1-yl]-2-oxoethyl}amino)-N-isopropylacetamide;

2-(dimethylamino)ethyl(1S)-1-cyclopropyl-2-[(2S)-4-(2,5-difluorophenyl)-2-phenyl-2,5-dihydro-1H-pyrrol-1-yl]-2-oxoethylcarbamate;

1-methylpiperidin-4-yl(1S)-1-cyclopropyl-2-[(2S)-4-(2,5-difluorophenyl)-2-phenyl-2,5-dihydro-1H-pyrrol-1-yl]-2-oxoethylcarbamate;

4-(2,5-difluorophenyl)-2-(3-hydroxyphenyl)-N,N-dimethyl-2,5-dihydro-1H-pyrrole-1-carboxamide;

(2S)-4-(2,5-difluorophenyl)-2-(3-hydroxyphenyl)-N,N-dimethyl-2,5-dihydro-1H-pyrrole-1-carboxamide;

(2S)-4-(2,5-difluorophenyl)-N-(2-hydroxyethyl)-N-methyl-2-phenyl-2,5-dihydro-1H-pyrrole-1-carboxamide;

N-{[4-(2,5-difluorophenyl)-2-(3-hydroxyphenyl)-2,5-dihydro-1H-pyrrol-1-yl]carbonyl}-N-methyl-beta-alanine;

methyl N-{[4-(2,5-difluorophenyl)-2-(3-hydroxyphenyl)-2,5-dihydro-1H-pyrrol-1-yl]carbonyl}-N-methyl-beta-alaninate;

4-{[4-(2,5-difluorophenyl)-2-(3-hydroxyphenyl)-2,5-dihydro-1H-pyrrol-1-yl]acetyl}-morpholin-4-ium;

3-[4-(2,5-difluorophenyl)-1-(morpholin-4-ylcarbonyl)-2,5-dihydro-1H-pyrrol-2-yl]phenol;

(2S)-4-(2,5-difluorophenyl)-2-(3-hydroxyphenyl)-N-methyl-N-tetrahydrofuran-3-yl-2,5-dihydro-1H-pyrrole-1-carboxamide;

(2S)-4-(2,5-difluorophenyl)-2-(3-hydroxyphenyl)-N-(2-methoxyethyl)-N-methyl-2,5-dihydro-1H-pyrrole-1-carboxamide;

(2S)-4-(2,5-difluorophenyl)-2-(3-hydroxyphenyl)-N-methyl-N-tetrahydro-2H-pyran-4-yl-2,5-dihydro-1H-pyrrole-1-carboxamide;

4-(2,5-difluorophenyl)-N-[1-(2-fluoroethyl)piperidin-4-yl]-2-(3-hydroxyphenyl)-N-methyl-2,5-dihydro-1H-pyrrole-1-carboxamide;

4-[{[4-(2,5-difluorophenyl)-2-(3-hydroxyphenyl)-2,5-dihydro-1H-pyrrol-1-yl]carbonyl}(methyl)amino]piperidinium trifluoroacetate;

2-[{[4-(2,5-difluorophenyl)-2-(3-hydroxyphenyl)-2,5-dihydro-1H-pyrrol-1-yl]carbonyl}(methyl)amino]ethyl 4-methylpiperazine-1-carboxylate;

3-{4-(2,5-difluorophenyl)-1-[(4-methylpiperazin-1-yl)carbonyl]-2,5-dihydro-1H-pyrrol-2-yl}phenol;

2-[{[4-(2,5-difluorophenyl)-2-(3-hydroxyphenyl)-2,5-dihydro-1H-pyrrol-1-yl]carbonyl}(methyl)amino]ethyl morpholine-4-carboxylate;

4-(2,5-difluorophenyl)-2-(3-hydroxyphenyl)-N-methyl-N-[(1-methyl-1H-pyrazol-4-yl)methyl]-2,5-dihydro-1H-pyrrole-1-carboxamide;

4-(2,5-difluorophenyl)-2-(3-hydroxyphenyl)-N-(isoxazol-5-ylmethyl)-N-methyl-2,5-dihydro-1H-pyrrole-1-carboxamide;

2-[{[4-(2,5-difluorophenyl)-2-(3-hydroxyphenyl)-2,5-dihydro-1H-pyrrol-1-yl]carbonyl}(methyl)amino]ethyl dimethylaminocarboxylate;

2-[{[4-(2,5-difluorophenyl)-2-(3-hydroxyphenyl)-2,5-dihydro-1H-pyrrol-1-yl]carbonyl}(methyl)amino]ethyl piperidine-1-carboxylate;

4-(2,5-difluorophenyl)-2-(3-hydroxyphenyl)-N-methyl-N-[2-(2-oxopyrrolidin-1-yl)ethyl]-2,5-dihydro-1H-pyrrole-1-carboxamide;

4-(2,5-difluorophenyl)-2-(3-hydroxyphenyl)-N-methyl-N-[(5-oxo-4,5-dihydro-1H-1,2,4-triazol-3-yl)methyl]-2,5-dihydro-1H-pyrrole-1-carboxamide;

4-(2,5-difluorophenyl)-2-(3-hydroxyphenyl)-N-methyl-N-(tetrahydro-2H-pyran-4-ylmethyl)-2,5-dihydro-1H-pyrrole-1-carboxamide;

4-(2,5-difluorophenyl)-2-(3-hydroxyphenyl)-N-{[5-(methoxymethyl)-1H-pyrazol-3-yl]methyl}-N-methyl-2,5-dihydro-1H-pyrrole-1-carboxamide;

4-(2,5-difluorophenyl)-2-(3-hydroxyphenyl)-N-methyl-N-(1,3-thiazol-4-ylmethyl)-2,5-dihydro-1H-pyrrole-1-carboxamide;

4-(2,5-difluorophenyl)-2-(3-hydroxyphenyl)-N-methyl-N-[(4-methyl-1,2,5-oxadiazol-3-yl)methyl]-2,5-dihydro-1H-pyrrole-1-carboxamide;

4-(2,5-difluorophenyl)-2-(3-hydroxyphenyl)-N-methyl-
   N-(1,3-thiazol-2-ylmethyl)-2,5-dihydro-1H-pyrrole-1-
   carboxamide;
4-(2,5-difluorophenyl)-2-(3-hydroxyphenyl)-N-(isox-
   azol-3-ylmethyl)-N-methyl-2,5,-dihydro-1H-pyrrole-
   1-carboxamide;
4-(2,5-difluorophenyl)-2-(3-hydroxyphenyl)-N-methyl-
   N-[2-(1H-1,2,4-triazol-1-yl)ethyl]-2,5-dihydro-1H-
   pyrrole-1-carboxamide;
4-(2,5-difluorophenyl)-2-(3-hydroxyphenyl)-N-methyl-
   N-[2-(1H-pyrazol-1-yl)ethyl]-2,5-dihydro-1H-pyrrole-
   1-carboxamide;
4-(2,5-difluorophenyl)-2-(3-hydroxyphenyl)-N-methyl-
   N-[(1-methyl-5-oxopyrrolidin-2-yl)methyl]-2,5-dihy-
   dro-1H-pyrrole-1-carboxamide;
4-(2,5-difluorophenyl)-2-(3-hydroxyphenyl)-N-(1-isox-
   azol-3-ylethyl)-N-methyl-2,5-dihydro-1H-pyrrole-1-
   carboxamide;
4-(2,5-difluorophenyl)-N-(1,3-dioxolan-2-ylmethyl)-2-
   (3-hydroxyphenyl)-N-methyl-2,5-dihydro-1H-pyrrole-
   1-carboxamide;
4-(2,5-difluorophenyl)-N-(1,4-dioxan-2-ylmethyl)-2-(3-
   hydroxyphenyl)-N-methyl-2,5-dihydro-1H-pyrrole-1-
   carboxamide;
4-(2,5-difluorophenyl)-2-(3-hydroxyphenyl)-N-methyl-
   N-[(5-methyl-1,3,4-oxadiazol-2-yl)methyl]-2,5-dihy-
   dro-1H-pyrrole-1-carboxamide;
4-(2,5-difluorophenyl)-2-(3-hydroxyphenyl)-N-methyl-
   N-[2-(methylsulfonyl)ethyl]-2,5-dihydro-1H-pyrrole-
   1-carboxamide 2-[{[4-(2,5-difluorophenyl)-2-(3-hy-
   droxyphenyl)-2,5-dihydro-1H-pyrrol-1-yl]carbonyl}
   (methyl)amino]ethanesulfonic acid;
3-[(2S)-4-(2,5-difluorophenyl)-2-phenyl-2,5-dihydro-
   1H-pyrrol-1-yl]-N-methylpropanamide;
3-[(2S)-4-(2,5-difluorophenyl)-2-phenyl-2,5-dihydro-
   1H-pyrrol-1-yl]-N,N-dimethylpropanamide;
3-[(2S)-4-(2,5-difluorophenyl)-2-phenyl-2,5-dihydro-
   1H-pyrrol-1-yl]-N,N,2-trimethyipropanamide;
4-{3-[(2S)-4-(2,5-difluorophenyl)-2-phenyl-2,5-dihydro-
   1H-pyrrol-1-yl]propanoyl}morpholine;
1-{3-[(2S)-4-(2,5-difluorophenyl)-2-phenyl-2,5-dihydro-
   1H-pyrrol-1-yl]propanoyl}-4-(methylsulfonyl)pipera-
   zine;
1-{3-[(2S)-4-(2,5-difluorophenyl)-2-phenyl-2,5-dihydro-
   1H-pyrrol-1-yl]propanoyl}piperidin-4-ol;
or a pharmaceutically acceptable salt or stereoisomer
thereof.

9. The compound according to claim 8 which is selected from:
(−)-4-(2,5-difluorophenyl)-N,N-dimethyl-2-phenyl-2,5-
   dihydro-1H-pyrrole-1-carboxamide;
4-(5-chloro-2-fluorophenyl)-N,N-dimethyl-2-phenyl-2,5-
   dihydro-1H-pyrrole-1-carboxamide; and
(2S)-4-(2,5-difluorophenyl)-N-methyl-2-phenyl-N-pip-
   eridin-4-yl-2,5-dihydro-1H-pyrrole-1-carboxamide;
or a pharmaceutically acceptable salt or stereoisomer
thereof.

10. The compound according to claim 8 which is selected from:
(2S)-4-(2,5-difluorophenyl)-N-methyl-2-phenyl-N-pip-
   eridin-4-yl-2,5-dihydro-1H-pyrrole-1-carboxamide;
(2S)-4-(2,5-difluorophenyl)-2-(3-hydroxyphenyl)-N,N-
   dimethyl-2,5-dihydro-1H-pyrrole-1-carboxamide;
(2S)-4-(2,5-difluorophenyl)-N-methyl-N-(1-methylpip-
   eridin-4-yl)-2-phenyl-2,5-dihydro-1H-pyrrole-1-car-
   boxamide; or or a pharmaceutically acceptable salt or stereoisomer
thereof.

11. A compound selected from:
(2S)-4-(2,5-difluorophenyl)-2-(3-hydroxyphenyl)-N-me-
   thyl-N-tetrahydrofuran-3-yl-2,5-dihydro-1H-pyrrole-
   1-carboxamide;
(2S)-4-(2,5-difluorophenyl)-2-(3-hydroxyphenyl)-N-(2-
   methoxyethyl)-N-methyl-2,5-dihydro-1H-pyrrole-1-
   carboxamide;
(2S)-4-(2,5-difluorophenyl)-2-(3-hydroxyphenyl)-N-me-
   thyl-N-tetrahydro-2H-pyran-4-yl-2,5-dihydro-1H-pyr-
   role-1-carboxamide;
4-(2,5-difluorophenyl)-N-[1-(2-fluoroethyl)piperidin-4-
   yl]-2-(3-hydroxyphenyl)-N-methyl-2,5-dihydro-1H-
   pyrrole-1-carboxamide;
4-[{[4-(2,5-difluorophenyl)-2-(3-hydroxyphenyl)-2,5-di-
   hydro-1H-pyrrol-1-yl]carbonyl}(methyl)amino]piperi-
   dinium trifluoro acetate; 2-[{[4-(2,5-difluorophenyl)-2-
   (3-hydroxyphenyl)-2,5-dihydro-1H-pyrrol-1-yl]
   carbonyl}(methyl)amino]ethyl 4-methylpiperazine-1-
   carboxylate;
3-{4-(2,5-difluorophenyl)-1-[(4-methylpiperazin-1-yl)
   carbonyl]-2,5-dihydro-1H-pyrrol-2-yl}phenol;
2-[{[4-(2,5-difluorophenyl)-2-(3-hydroxyphenyl)-2,5-di-
   hydro-1H-pyrrol-1-yl]carbonyl}(methyl)amino]ethyl
   morpholine-4-carboxylate;
4-(2,5-difluorophenyl)-2-(3-hydroxyphenyl)-N-methyl-
   N-[(1-methyl-1H-pyrazol-4-yl)methyl]-2,5-dihydro-
   1H-pyrrole-1-carboxamide;
4-(2,5-difluorophenyl)-2-(3-hydroxyphenyl)-N-(isox-
   azol-5-ylmethyl)-N-methyl-2,5-dihydro-1H-pyrrole-1-
   carboxamide;
2-[{[4-(2,5-difluorophenyl)-2-(3-hydroxyphenyl)-2,5-di-
   hydro-1H-pyrrol-1-yl]carbonyl}(methyl)amino]ethyl
   dimethylaminocarboxylate;
2-[{[4-(2,5-difluorophenyl)-2-(3-hydroxyphenyl)-2,5-di-
   hydro-1H-pyrrol-1-yl]carbonyl}(methyl)amino]ethyl
   piperidine-1-carboxylate;
4-(2,5-difluorophenyl)-2-(3-hydroxyphenyl)-N-methyl-
   N-[2-(2-oxopyrrolidin-1-yl)ethyl]-2,5-dihydro-1H-
   pyrrole-1-carboxamide;
4-(2,5-difluorophenyl)-2-(3-hydroxyphenyl)-N-methyl-
   N-[(5-oxo-4,5-dihydro-1H-1,2,4-triazol-3-yl)methyl]-
   2,5-dihydro-1H-pyrrole-1-carboxamide;
4-(2,5-difluorophenyl)-2-(3-hydroxyphenyl)-N-methyl-
   N-(tetrahydro-2H-pyran-4-ylmethyl)-2,5-dihydro-1H-
   pyrrole-1-carboxamide;
4-(2,5-difluorophenyl)-2-(3-hydroxyphenyl)-N-{[5-
   (methoxymethyl)-1H-pyrazol-3-yl]methyl}-N-methyl-
   2,5-dihydro-1H-pyrrole-1-carboxamide;
4-(2,5-difluorophenyl)-2-(3-hydroxyphenyl)-N-methyl-
   N-(1,3-thiazol-4-ylmethyl)-2,5-dihydro-1H-pyrrole-1-
   carboxamide;
4-(2,5-difluorophenyl)-2-(3-hydroxyphenyl)-N-methyl-
   N-[(4-methyl-1,2,5-oxadiazol-3-yl)methyl]-2,5-dihy-
   dro-1H-pyrrole-1-carboxamide;
4-(2,5-difluorophenyl)-2-(3-hydroxyphenyl)-N-methyl-
   N-(1,3-thiazol-2-ylmethyl)-2,5-dihydro-1H-pyrrole-1-
   carboxamide;
4-(2,5-difluorophenyl)-2-(3-hydroxyphenyl)-N-(isox-
   azol-3-ylmethyl)-N-methyl-2,5-dihydro-1H-pyrrole-1-
   carboxamide;
4-(2,5-difluorophenyl)-2-(3-hydroxyphenyl)-N-methyl-
   N-[2-(1H-1,2,4-triazol-1-yl)ethyl]-2,5-dihydro-1H-
   pyrrole-1-carboxamide;

4-(2,5-difluorophenyl)-2-(3-hydroxyphenyl)-N-methyl-N-[2-(1H-pyrazol-1-yl)ethyl]-2,5-dihydro-1H-pyrrole-1-carboxamide;

4-(2,5-difluorophenyl)-2-(3-hydroxyphenyl)-N-methyl-N-[(1-methyl-5-oxopyrrolidin-2-yl)methyl]-2,5-dihydro-1H-pyrrole-1-carboxamide;

4-(2,5-difluorophenyl)-2-(3-hydroxyphenyl)-N-(1-isoxazol-3-ylethyl)-N-methyl-2,5-dihydro-1H-pyrrole-1-carboxamide;

4-(2,5-difluorophenyl)-N-(1,3-dioxolan-2-ylmethyl)-2-(3-hydroxyphenyl)-N-methyl-2,5-dihydro-1H-pyrrole-1-carboxamide;

4-(2,5-difluorophenyl)-N-(1,4-dioxan-2-ylmethyl)-2-(3-hydroxyphenyl)-N-methyl-2,5-dihydro-1H-pyrrole-1-carboxamide;

4-(2,5-difluorophenyl)-2-(3-hydroxyphenyl)-N-methyl-N-[(5-methyl-1,3,4-oxadiazol-2-yl)methyl]-2,5-dihydro-1H-pyrrole-1-carboxamide;

4-(2,5-difluorophenyl)-2-(3-hydroxyphenyl)-N-methyl-N-[2-(methylsulfonyl)ethyl]-2,5-dihydro-1H-pyrrole-1-carboxamide;

2-[{[4-(2,5-difluorophenyl)-2-(3-hydroxyphenyl)-2,5-dihydro-1H-pyrrol-1-yl]carbonyl}(methyl)amino]ethanesulfonic acid;

3-[(2S)-4-(2,5-difluorophenyl)-2-phenyl-2,5-dihydro-1H-pyrrol-1-yl]-N-methylpropanamide;

3-[(2S)-4-(2,5-difluorophenyl)-2-phenyl-2,5-dihydro-1H-pyrrol-1-yl]-N,N-dimethylpropanamide 3-[(2S)-4-(2,5-difluorophenyl)-2-phenyl-2,5-dihydro-1H-pyrrol-1-yl]-N,N,2-trimethylpropanamide;

4-{3-[(2S)-4-(2,5-difluorophenyl)-2-phenyl-2,5-dihydro-1H-pyrrol-1-yl]propanoyl}morpholine;

1-{3-[(2S)-4-(2,5-difluorophenyl)-2-phenyl-2,5-dihydro-1H-pyrrol-1-yl]propanoyl}-4-(methylsulfonyl)piperazine; and 1-{3-[(2S)-4-(2,5-difluorophenyl)-2-phenyl-2,5-dihydro-1H-pyrrol-1-yl]propanoyl}piperidin-4-ol;

or a pharmaceutically acceptable salt thereof.

12. The compound according to claim 9 which is the TFA salt of a compound selected from:

(2S)-4-(2,5-Difluorophenyl)-N-methyl-2-phenyl-N-(piperidin-4-ylmethyl)-2,5-dihydro-1H-pyrrole-1-carboxamide;

(2S)-4-(5-Chloro-2-fluorophenyl)-N-methyl-2-phenyl-N-[(3R)-pyrrolidin-3-yl]-2,5-dihydro-1H-pyrrole-1-carboxamide;

(2S)-4-(5-chloro-2-fluorophenyl)-N-methyl-2-phenyl-N-piperidin-4-yl-2,5-dihydro-1H-pyrrole-1-carboxamide;

(2S)-4-(5-chloro-2-fluorophenyl)-N-methyl-2-phenyl-N-[(3S)-pyrrolidin-3-yl]-2,5-dihydro-1H-pyrrole-1-carboxamide;

(2S)-4-(2,5-difluorophenyl)-N-methyl-2-phenyl-N-pyrrolidin-3-yl-2,5-dihydro-1H-pyrrole-1-carboxamide;

(2S)-N-(1-allylpiperidin-4-yl)-4-(2,5-difluorophenyl)-N-methyl-2-phenyl-2,5-dihydro-1H-pyrrole-1-carboxamide;

4-(2,5-Difluorophenyl)-N-methyl-N-[(1-methylpiperidin-3-yl)methyl]-2-phenyl-2,5-dihydro-1H-pyrrole-1-carboxamide;

4-(2,5-difluorophenyl)-N-methyl-2-phenyl-N-(pyridin-3-ylmethyl)-2,5-dihydro-1H-pyrrole-1-carboxamide;

4-(2,5-difluorophenyl)-N-methyl-N-[(1-methyl-1H-pyrazol-4-yl)methyl]-2-phenyl-2,5-dihydro-1H-pyrrole-1-carboxamide;

4-(2,5-difluorophenyl)-N-[2-(dimethylamino)ethyl]-N-methyl-2-phenyl-2,5-dihydro-1H-pyrrole-1-carboxamide;

4-(2,5-difluorophenyl)-N-methyl-2-phenyl-N-(2-pyridin-2-ylethyl)-2,5-dihydro-1H-pyrrole-1-carboxamide;

4-(5-chloro-2-fluorophenyl)-2-(3-hydroxyphenyl)-N-methyl-N-piperidin-4-yl-2,5-dihydro-1H-pyrrole-1-carboxamide;

4-(2,5-difluorophenyl)-2-(3-hydroxyphenyl)-N-methyl-N-piperidin-4-yl-2,5-dihydro-1H-pyrrole-1-carboxamide;

N-(tert-butyl)-2-[(2S)-4-(2,5-difluorophenyl)-2-phenyl-2,5-dihydro-1H-pyrrol-1-yl]acetamide;

2-[(2S)-4-(2,5-difluorophenyl)-2-phenyl-2,5-dihydro-1H-pyrrol-1-yl]-N-isopropylacetamide;

(2S)-1-(2-azetidin-1-yl-2-oxoethyl)-4-(2,5-difluorophenyl)-2-phenyl-2,5-dihydro-1H-pyrrole;

(2S)-4-(2,5-difluorophenyl)-1-(2-oxo-2-pyrrolidin-1-ylethyl)-2-phenyl-2,5-dihydro-1H-pyrrole;

4-{[(2S)-4-(2,5-difluorophenyl)-2-phenyl-2,5-dihydro-1H-pyrrol-1-yl]acetyl}morpholine;

1-{[(2S)-4-(2,5-difluorophenyl)-2-phenyl-2,5-dihydro-1H-pyrrol-1-yl]acetyl}piperazine;

1-{[(2S)-4-(2,5-difluorophenyl)-2-phenyl-2,5-dihydro-1H-pyrrol-1-yl]acetyl}-4-methylpiperazine;

2-[(2S)-4-(2,5-difluorophenyl)-2-phenyl-2,5-dihydro-1H-pyrrol-1-yl]-N-isopropylbutanamide;

4-{2-[(2S)-4-(2,5-difluorophenyl)-2-phenyl-2,5-dihydro-1H-pyrrol-1-yl]butanoyl}morpholine;

2-[(2S)-4-(2,5-difluorophenyl)-2-phenyl-2,5-dihydro-1H-pyrrol-1-yl]-N-ethylacetamide;

N-cyclobutyl-2-[(2S)-4-(2,5-difluorophenyl)-2-phenyl-2,5-dihydro-1H-pyrrol-1-yl]acetamide;

2-[(2S)-4-(2,5-difluorophenyl)-2-phenyl-2,5-dihydro-1H-pyrrol-1-yl]-N-ethylpropanamide;

N-cyclobutyl-2-[(2S)-4-(2,5-difluorophenyl)-2-phenyl-2,5-dihydro-1H-pyrrol-1-yl]propanamide;

2-[(2S)-4-(2,5-difluorophenyl)-2-phenyl-2,5-dihydro-1H-pyrrol-1-yl]-N-methylpropanamide;

2-[(2S)-4-(2,5-difluorophenyl)-2-phenyl-2,5-dihydro-1H-pyrrol-1-yl]-N-isopropylpropanamide;

N-(tert-butyl)-2-[(2S)-4-(2,5-difluorophenyl)-2-phenyl-2,5-dihydro-1H-pyrrol-1-yl]propanamide;

4-{2-[(2S)-4-(2,5-difluorophenyl)-2-phenyl-2,5-dihydro-1H-pyrrol-1-yl]propanoyl}morpholine;

4-{[4-(2,5-difluorophenyl)-2-(3-hydroxyphenyl)-2,5-dihydro-1H-pyrrol-1-yl]acetyl}morpholin-4-ium;

4-(2,5-difluorophenyl)-2-(3-hydroxyphenyl)-N-methyl-N-piperidin-4-yl-2,5-dihydro-1H-pyrrole-1-carboxamide;

2-[{[4-(2,5-difluorophenyl)-2-(3-hydroxyphenyl)-2,5-dihydro-1H-pyrrol-1-yl]carbonyl}(methyl)amino]ethyl-4-methylpiperazine-1-carboxylate;

3-{4-(2,5-difluorophenyl)-1-[(4-methylpiperazin-1-yl)carbonyl]-2,5-dihydro-1H-pyrrol-2-yl}phenol;

4-(2,5-difluorophenyl)-2-(3-hydroxyphenyl)-N-methyl-N-[(1-methyl-1H-pyrazol-4-yl)methyl]-2,5-dihydro-1H-pyrrole-1-carboxamide;

4-(2,5-difluoro-phenyl)-2,5-dihydro-2-(3-hydroxyphenyl)-N-methyl-N-[2-(4-methyl-1-piperazinyl)-2-oxoethyl]-H-pyrrole-1-carboxamide;

4-(2,5-difluorophenyl)-2-(3-hydroxyphenyl)-N-methyl-N-[(5-oxo-4,5-dihydro-1H-1,2,4-triazol-3-yl)methyl]-2,5-dihydro-1H-pyrrole-1-carboxamide;

4-(2,5-difluorophenyl)-2-(3-hydroxyphenyl)-N-{[5-(methoxymethyl)-1H-pyrazol-3-yl]methyl}-N-methyl-2,5-dihydro-1H-pyrrole-1-carboxamide;

4-(2,5-difluorophenyl)-2-(3-hydroxyphenyl)-N-methyl-N-(1,3-thiazol-4-ylmethyl)-2,5-dihydro-1H-pyrrole-1-carboxamide;

4-(2,5-difluorophenyl)-2-(3-hydroxyphenyl)-N-methyl-N-(1,3-thiazol-2-ylmethyl)-2,5-dihydro-1H-pyrrole-1-carboxamide;

4-(2,5-difluorophenyl)-2-(3-hydroxyphenyl)-N-methyl-N-[2-(1H-1,2,4-triazol-1-yl)ethyl]-2,5-dihydro-1H-pyrrole-1-carboxamide;

4-(2,5-difluorophenyl)-2-(3-hydroxyphenyl)-N-methyl-N-[2-(1H-pyrazol-1-yl)ethyl]-2,5-dihydro-1H-pyrrole-1-carboxamide;

3-[(2S)-4-(2,5-difluorophenyl)-2-phenyl-2,5-dihydro-1H-pyrrol-1-yl]-N-methylpropanamide;

3-[(2S)-4-(2,5-difluorophenyl)-2-phenyl-2,5-dihydro-1H-pyrrol-1-yl]-N,N-dimethylpropanamide;

3-[(2S)-4-(2,5-difluorophenyl)-2-phenyl-2,5-dihydro-1H-pyrrol-1-yl]-N,N,2-trimethyipropanamide;

4-{3-[(2S)-4-(2,5-difluorophenyl)-2-phenyl-2,5-dihydro-1H-pyrrol-1-yl]propanoyl}morpholine;

1-{3-[(2S)-4-(2,5-difluorophenyl)-2-phenyl-2,5-dihydro-1H-pyrrol-1-yl]propanoyl}-4-(methylsulfonyl)piperazine;

1-{3-[(2S)-4-(2,5-difluorophenyl)-2-phenyl-2,5-dihydro-1H-pyrrol-1-yl]propanoyl}piperidin-4-ol; and methyl 3-[(2S)-4-(2,5-difluorophenyl)-2-phenyl-2,5-dihydro-1H-pyrrol-1-yl]propanoate.

13. A pharmaceutical composition that is comprised of a compound in accordance with claim 1 and a pharmaceutically acceptable carrier.

\* \* \* \* \*